(12) United States Patent
Chen et al.

(10) Patent No.: US 11,884,947 B2
(45) Date of Patent: Jan. 30, 2024

(54) FUSION PROTEINS FOR BASE EDITING

(71) Applicant: ShanghaiTech University, Pudong New Area (CN)

(72) Inventors: Jia Chen, Shanghai (CN); Li Yang, Shanghai (CN); Xingxu Huang, Shanghai (CN); Bei Yang, Shanghai (CN); Xiao Wang, Shanghai (CN); Jianan Li, Shanghai (CN)

(73) Assignee: ShanghaiTech University, Shanghai (CN)

( * ) Notice: Subject to any disclaimer, the term of this patent is extended or adjusted under 35 U.S.C. 154(b) by 445 days.

(21) Appl. No.: 16/770,572

(22) PCT Filed: Feb. 22, 2019

(86) PCT No.: PCT/CN2019/075897
§ 371 (c)(1),
(2) Date: Jun. 5, 2020

(87) PCT Pub. No.: WO2019/161783
PCT Pub. Date: Aug. 29, 2019

(65) Prior Publication Data
US 2021/0163913 A1 Jun. 3, 2021

(30) Foreign Application Priority Data

Feb. 23, 2018 (WO) ................ PCT/CN2018/076991
Aug. 14, 2018 (WO) ................ PCT/CN2018/100411

(51) Int. Cl.
*C12N 9/78* (2006.01)
*C12N 9/22* (2006.01)
*C12N 15/11* (2006.01)
*C12N 15/90* (2006.01)
*C12N 15/01* (2006.01)

(52) U.S. Cl.
CPC ................ *C12N 9/78* (2013.01); *C12N 9/22* (2013.01); *C12N 15/01* (2013.01); *C12N 15/907* (2013.01); *C12Y 305/04* (2013.01); *C07K 2319/00* (2013.01); *C12N 2310/20* (2017.05); *C12N 2800/80* (2013.01)

(58) Field of Classification Search
CPC . C12N 9/78; C12N 9/22; C12N 15/11; C12N 15/907; C12N 2310/20; C12N 2800/80; C12N 15/102; C12N 15/62; C12Y 305/04
See application file for complete search history.

(56) References Cited

U.S. PATENT DOCUMENTS

2018/0094257 A1 * 4/2018 Wang .................... C12N 15/111

FOREIGN PATENT DOCUMENTS

| WO | WO2015099850 A1 * | 7/2015 |
| WO | 2016164889 A1 | 10/2016 |
| WO | 2017070632 A2 | 4/2017 |
| WO | 2018010516 A1 | 1/2018 |
| WO | WO2018218188 A2 * | 11/2018 |

OTHER PUBLICATIONS

European Search Report and Opinion dated Jun. 20, 2022 for EP Application No. 19757302.5. 16 pages.
Kouno, et al. Crystal structure of APOBEC3A bound to single-stranded DNA reveals structural basis for cytidine deamination and specificity. Nature Communications. Apr. 2017; 15024: 8 pages.
Logue, et al. A DNA sequence recognition loop on APOBEC3A controls substrate specificity. PLOS ONE. May 2014; 9(5):e97062.
Mitra, et al. Structural determinants of human APOBEC3A enzymatic and nucleic acid binding properties. Nucleic Acids Research, 2014, vol. 42, No. 2 1095-1110.
Shi, et al. Structural basis for targeted DNA cytosine deamination and mutagenesis by APOBEC3A and APOBEC3B. Nature Structural & Molecular Biology. Feb. 2017; 24(2):131-139.
Gehrke et al., "An APOBEC3A-Cas9 base editor with minimized bystander and off-target activities", Nature Biotechnology, vol. 36, No. 10, Jul. 30, 2018, pp. 977-986.
International Search Report and Written Opinion for PCT/CN2019/075897 dated Jun. 3, 2019, 10 pages.
Lei et al., "APOBEC3 induces mutations during repair of CRISPR-Cas9-generated DNA breaks", Nature Structural & Molecular Biology, vol. 25, No. 1, Dec. 11, 2017, pp. 45-52.
Supplementary European Search Report for EP Application No. 19757302.5 dated Dec. 3, 2021, 14 pages.
Wang et al., "Cas12a base editors induce efficient and specific editing with low DNA damage response", Cell Reports, vol. 31, No. 9, Jun. 1, 2020, pp. 107723.
Wang et al., "Efficient base editing in methylated regions with a human APOBEC3A-Cas9 fusion", Nature Biotechnology, vol. 36, No. 10, Aug. 20, 2018, p. 946-949.
Zong et al., "Efficient C-to-T base editing in plants using a fusion of nCas9 and human APOBEC3A", Nature Biotechnology, vol. 36, No. 10, Oct. 1, 2018.

* cited by examiner

*Primary Examiner* — Iqbal H Chowdhury

(74) *Attorney, Agent, or Firm* — Sheppard Mullin Richter & Hampton LLP

(57) ABSTRACT

Provided are fusion proteins that include an apolipoprotein B mRNA editing enzyme catalytic subunit 3A (APOBEC3A) and a clustered regularly interspaced short palindromic repeats (CRISPR)-associated (Cas) protein, optionally further with uracil glycosylase inhibitor (UGI). Such a fusion protein is able to conduct base editing in DNA by deaminating cytosine to uracil, even when the cytosine is in a GpC context or is methylated.

14 Claims, 21 Drawing Sheets

Specification includes a Sequence Listing.

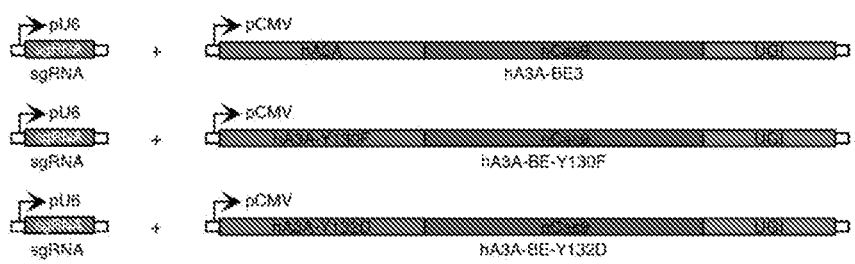
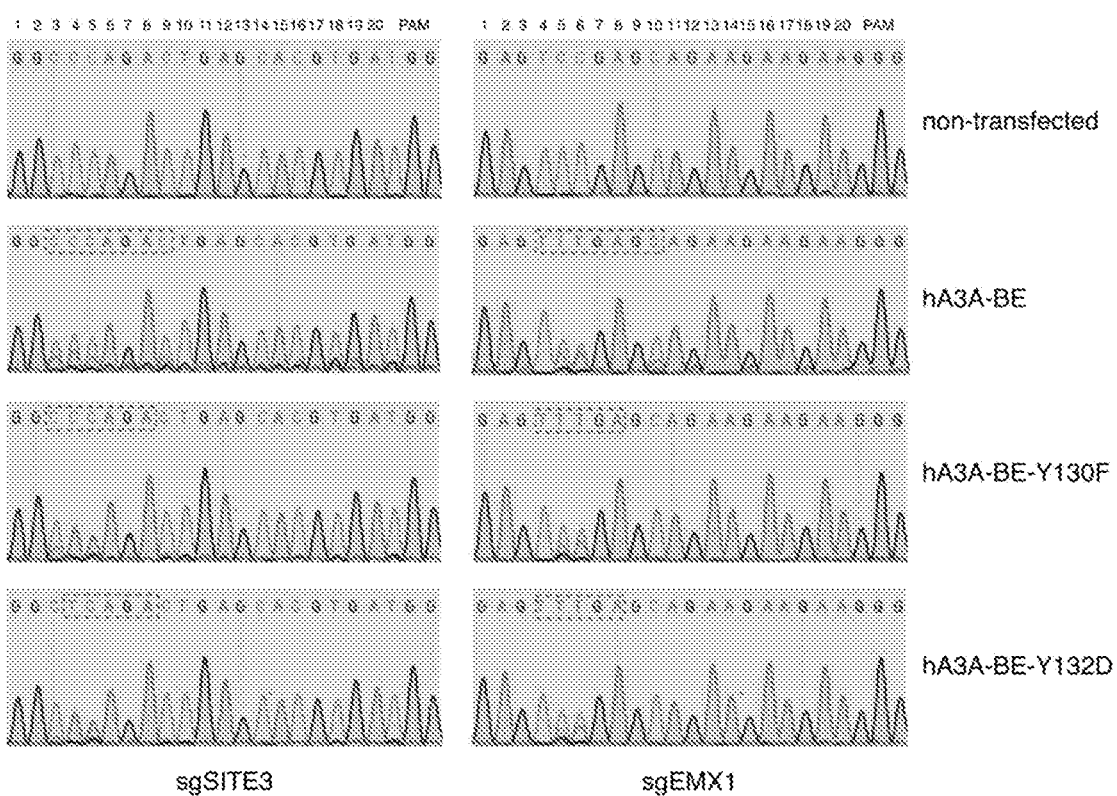
FIG. 2

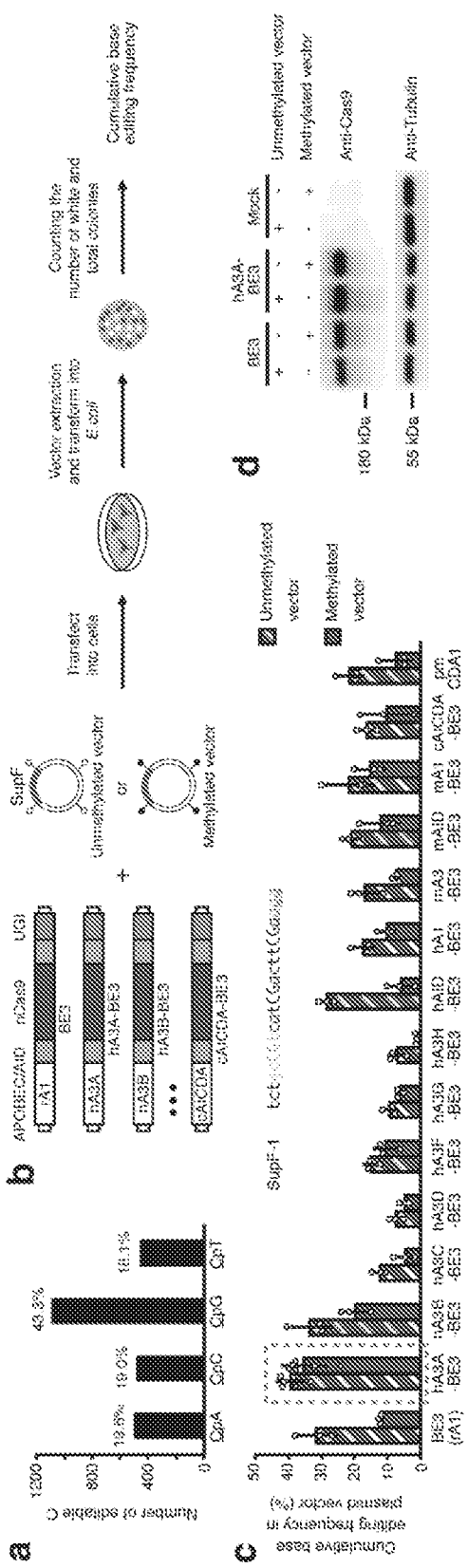
FIG. 5a-d

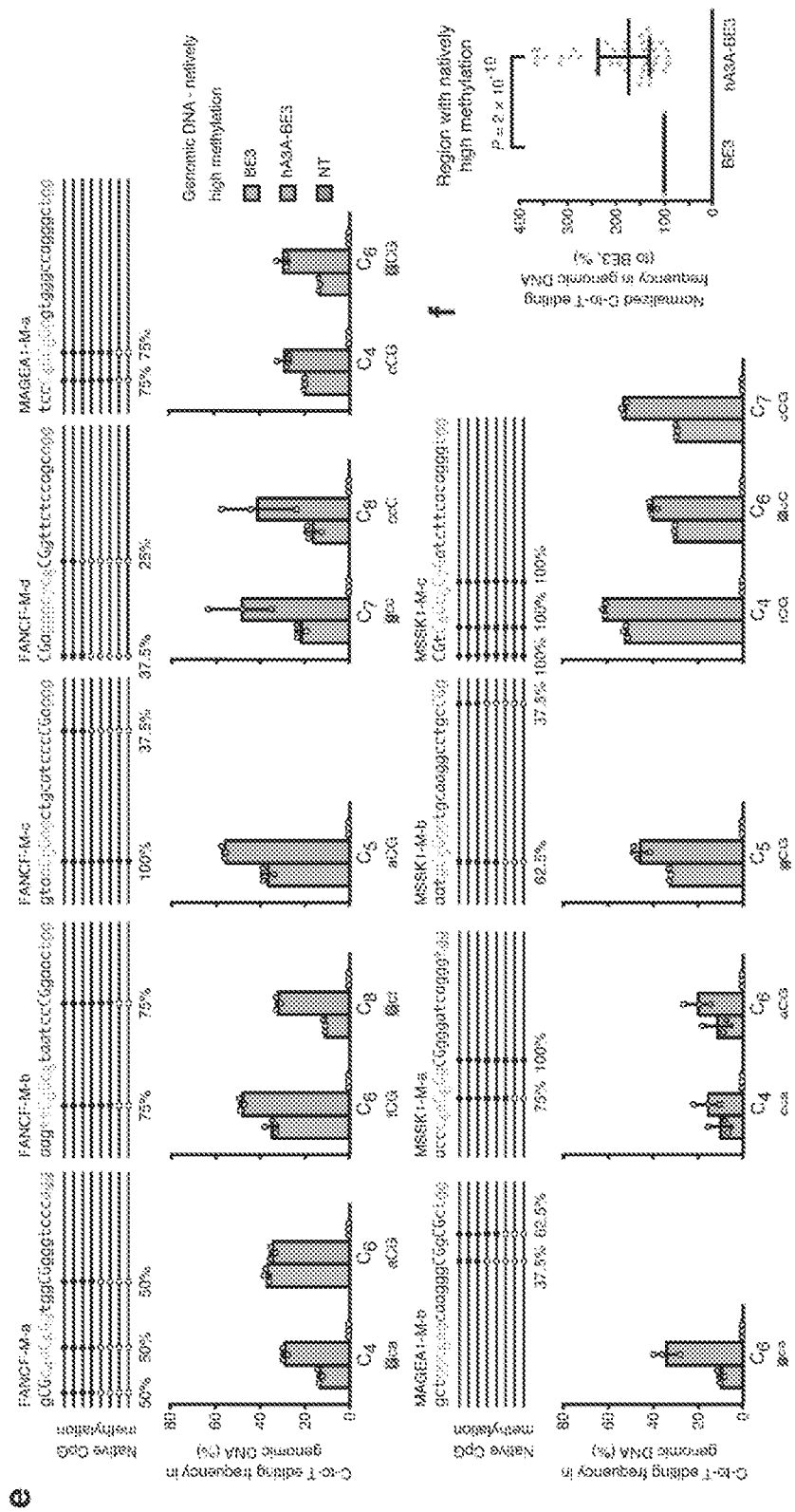
FIG. 5e-f

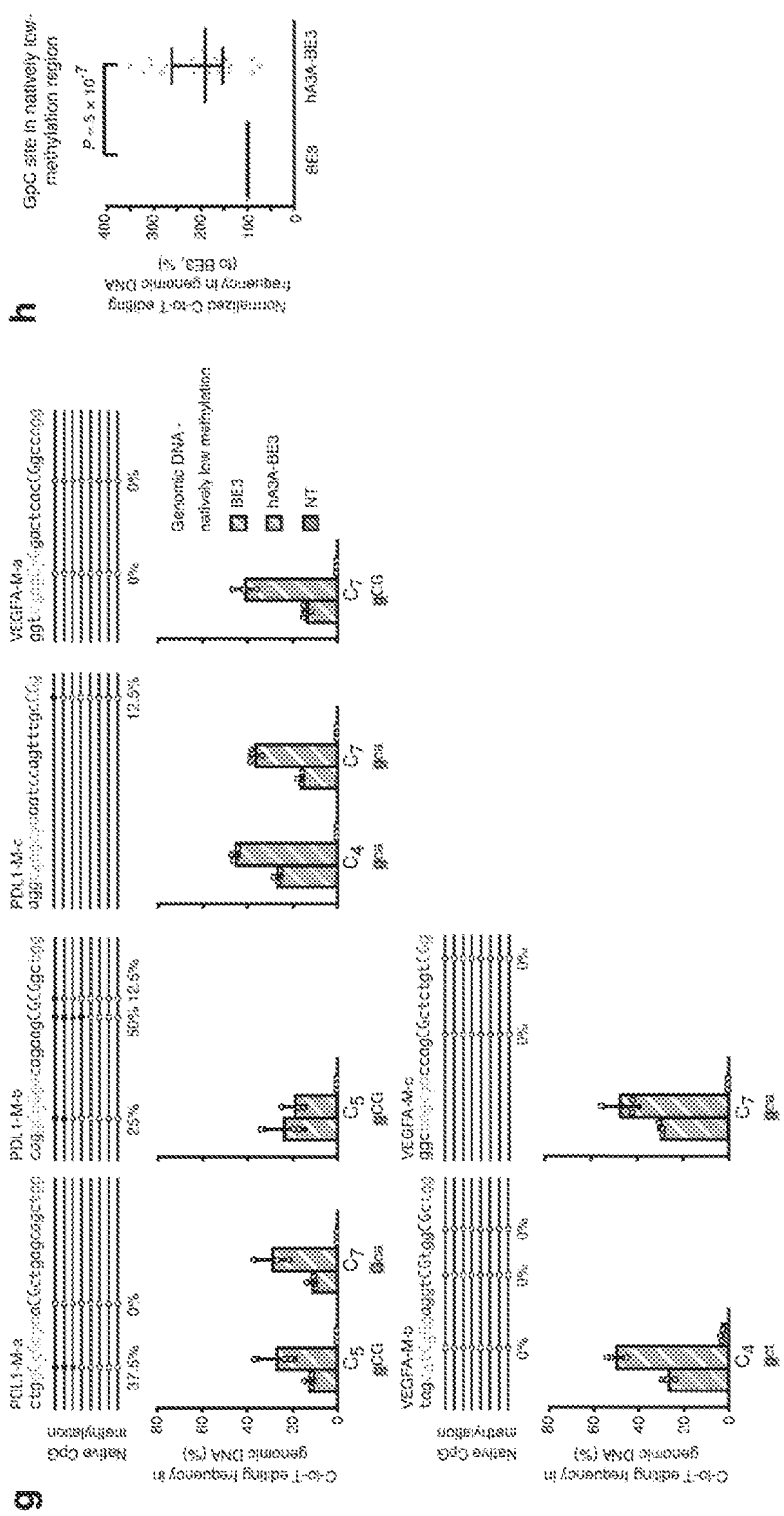
FIG. 5g-h

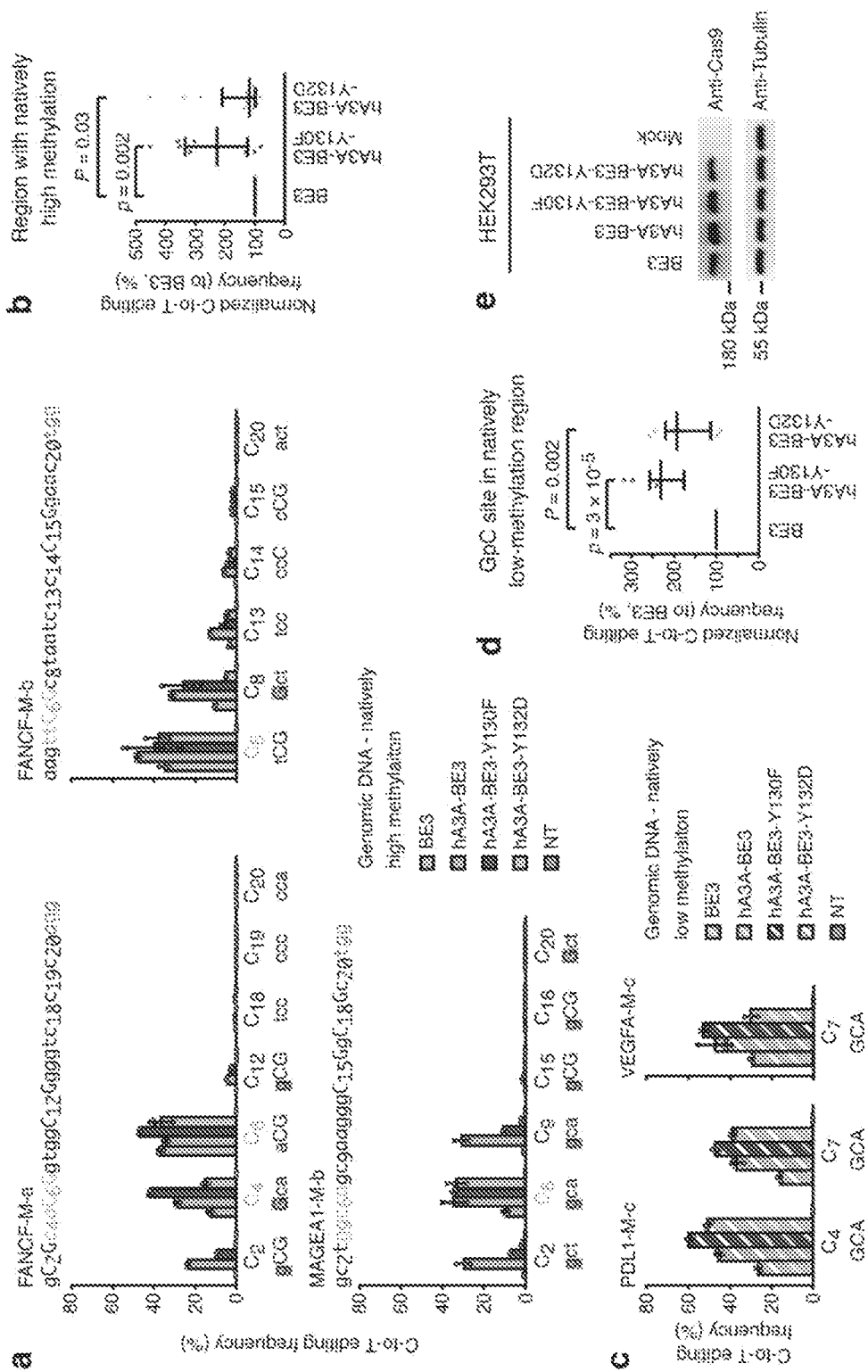
FIG. 6 a-e

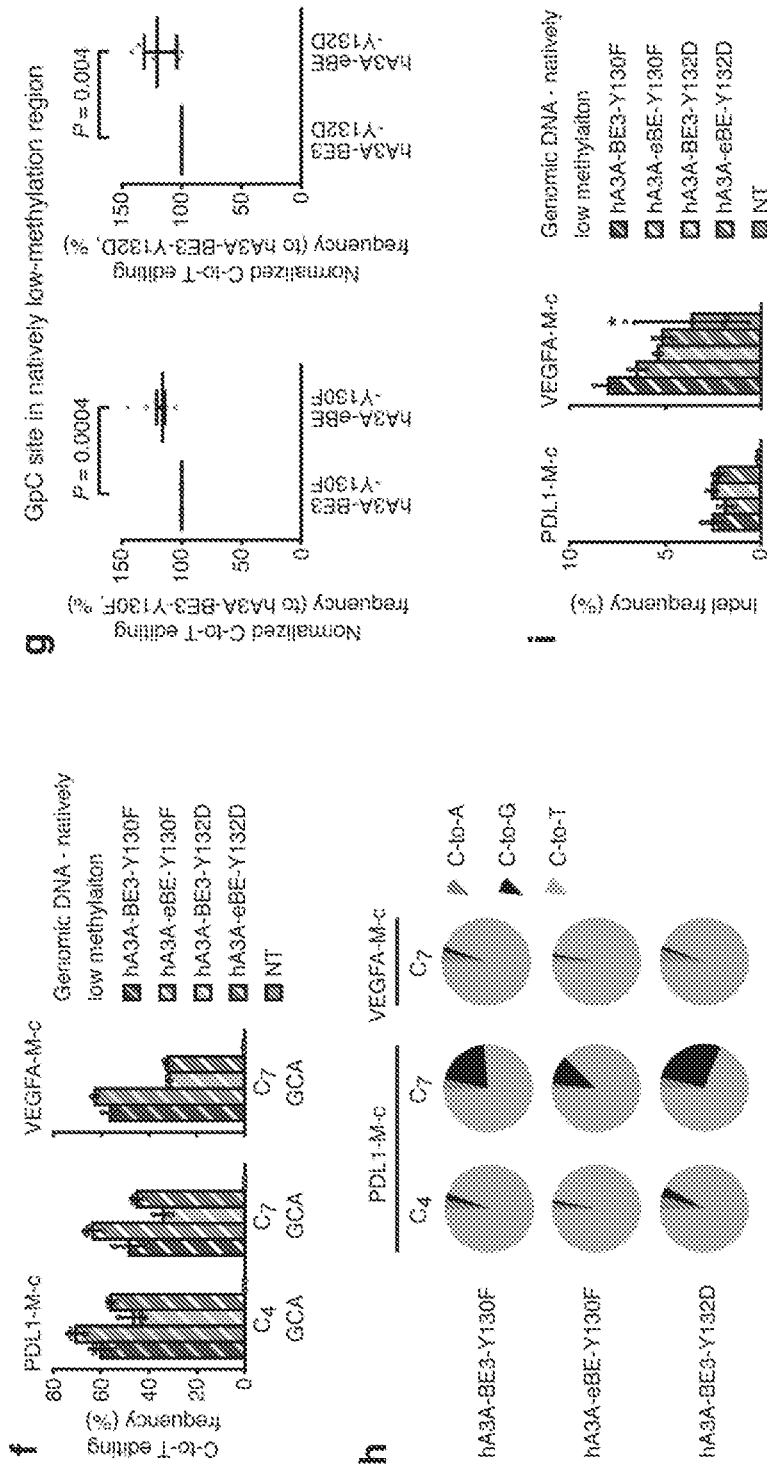
FIG. 6 f-i

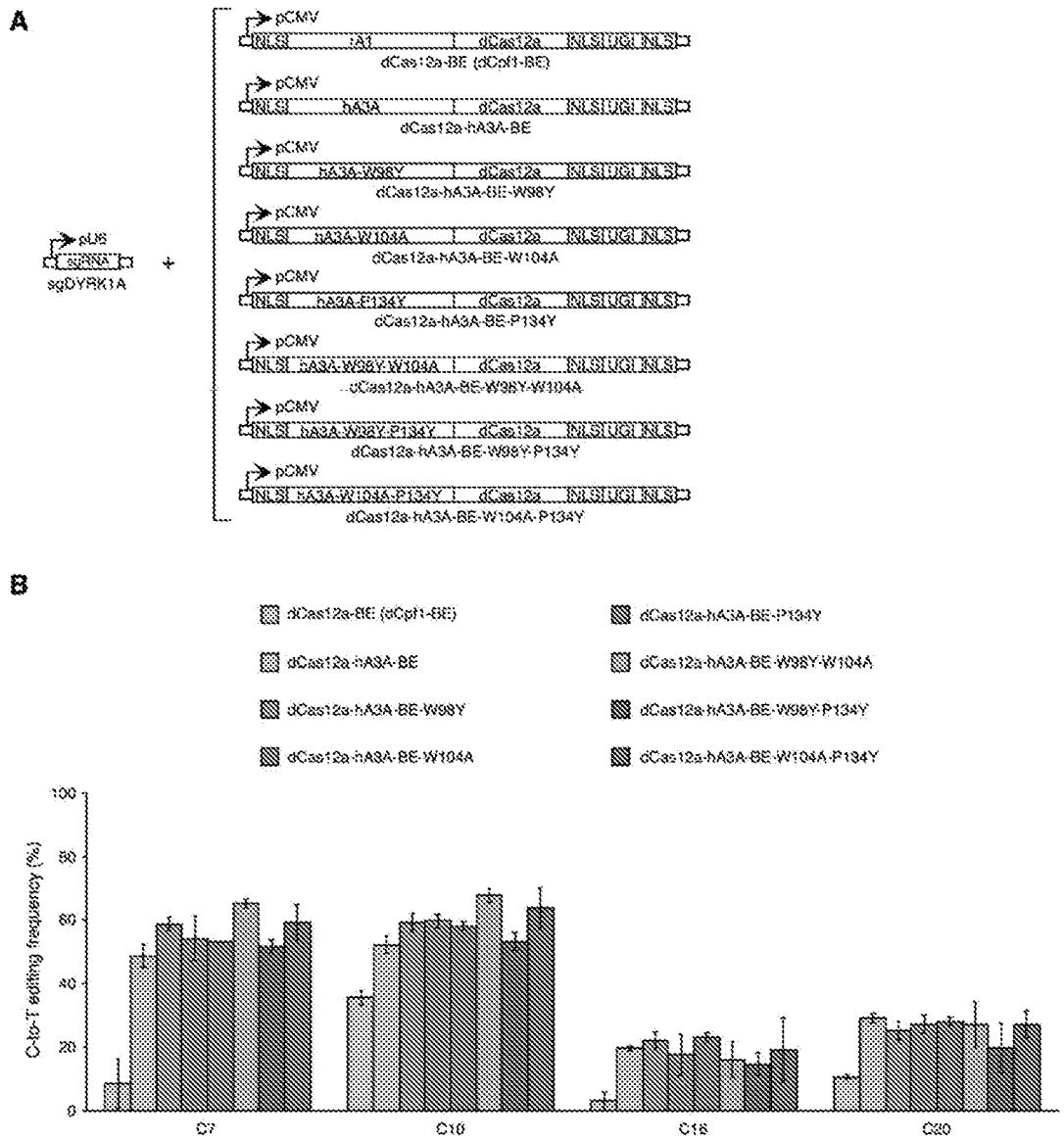
FIG. 7A-B

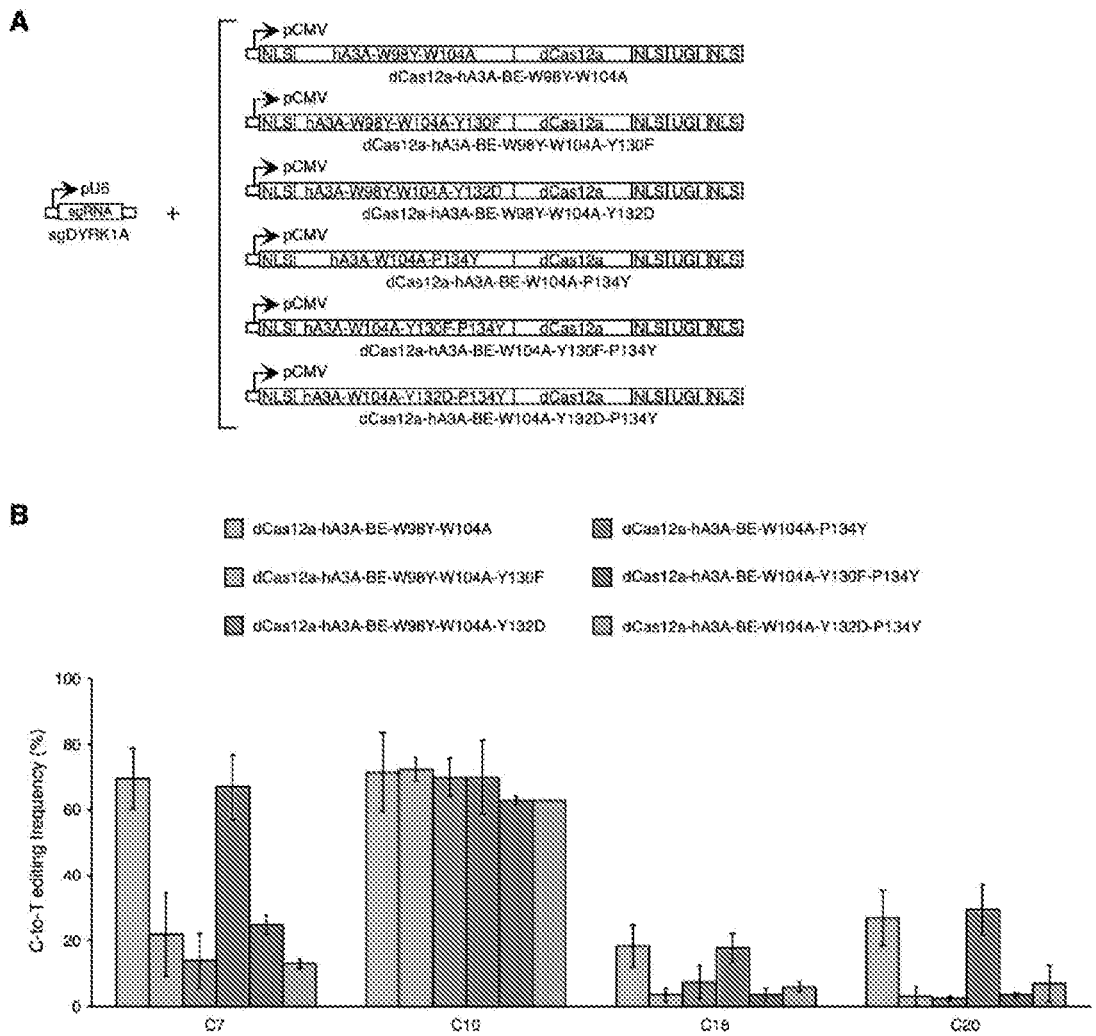
FIG. 8A-B

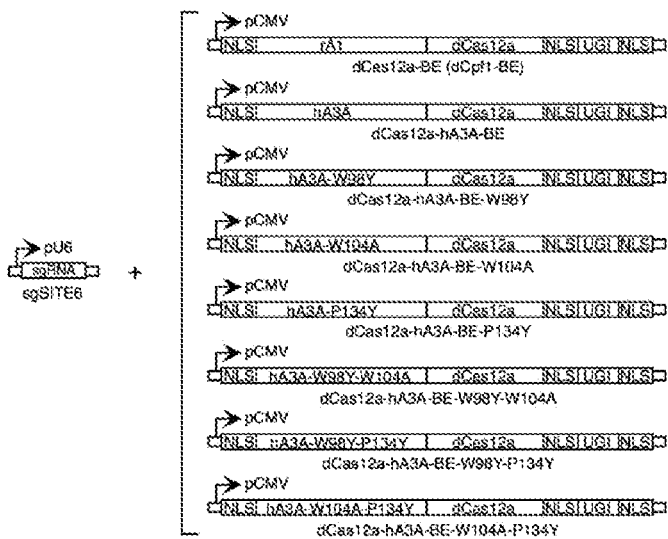
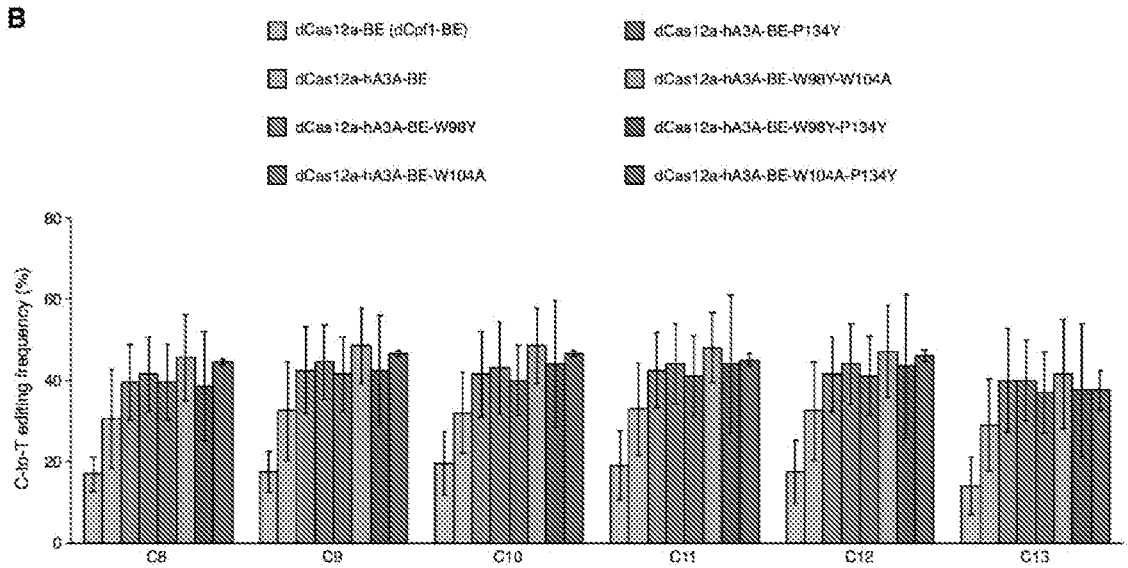
FIG. 9A-B

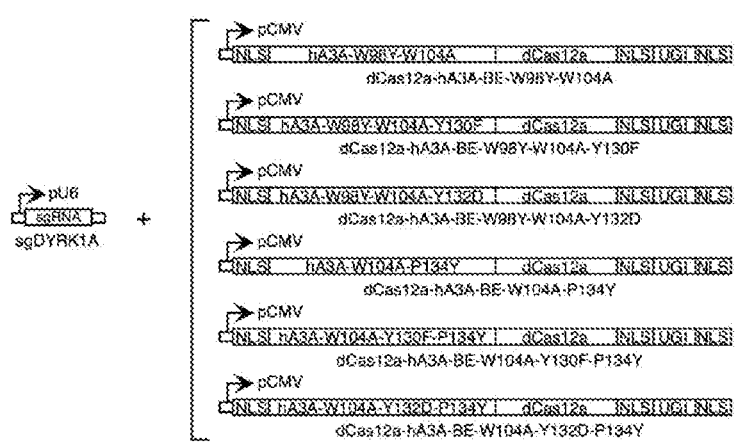
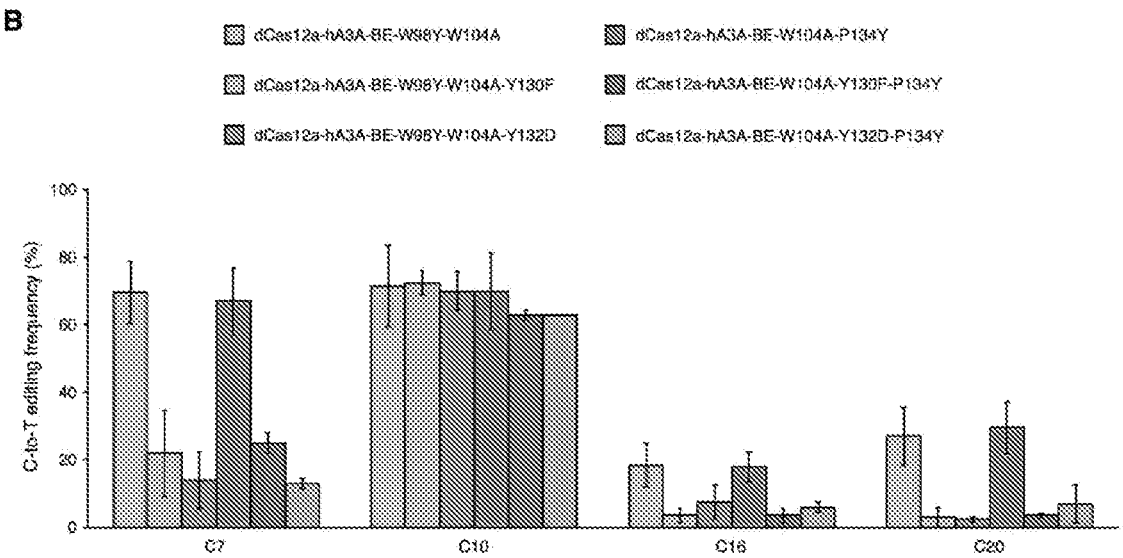
FIG. 10A-B

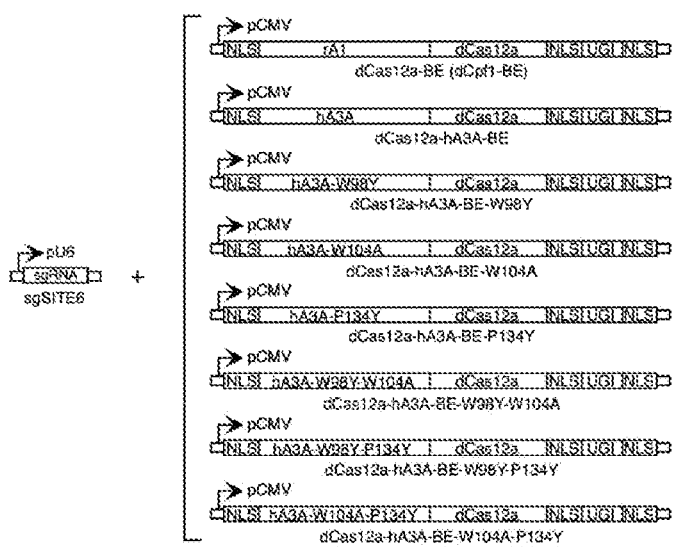
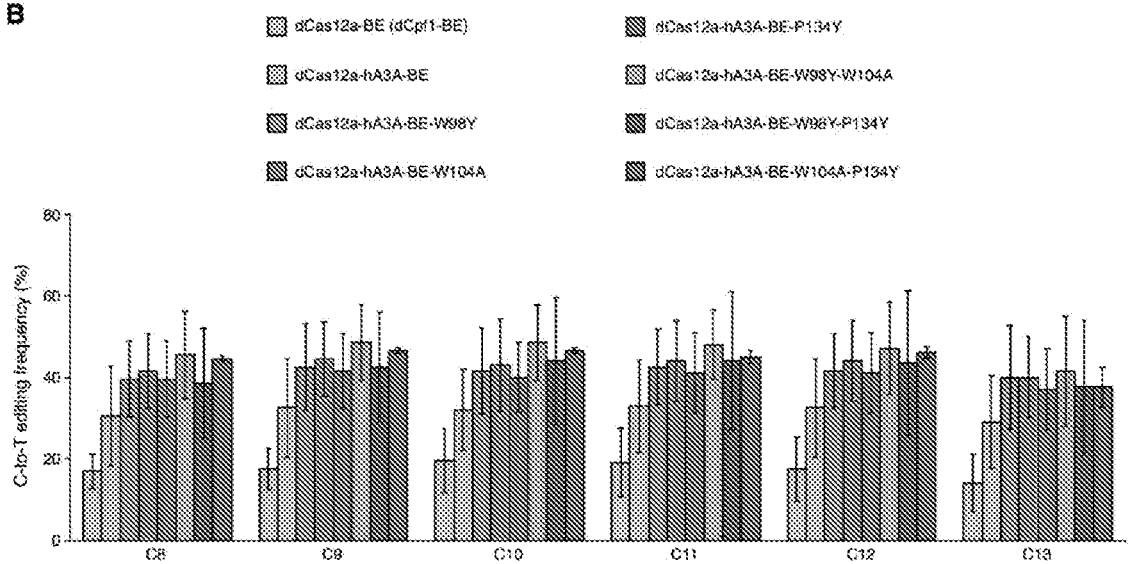
FIG. 11A-B

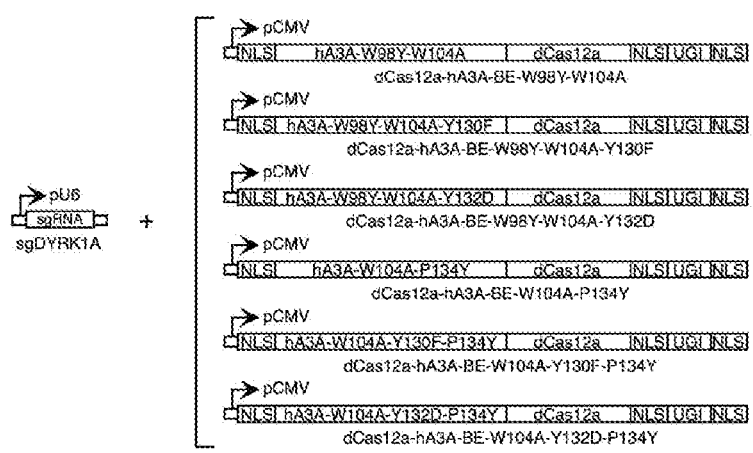
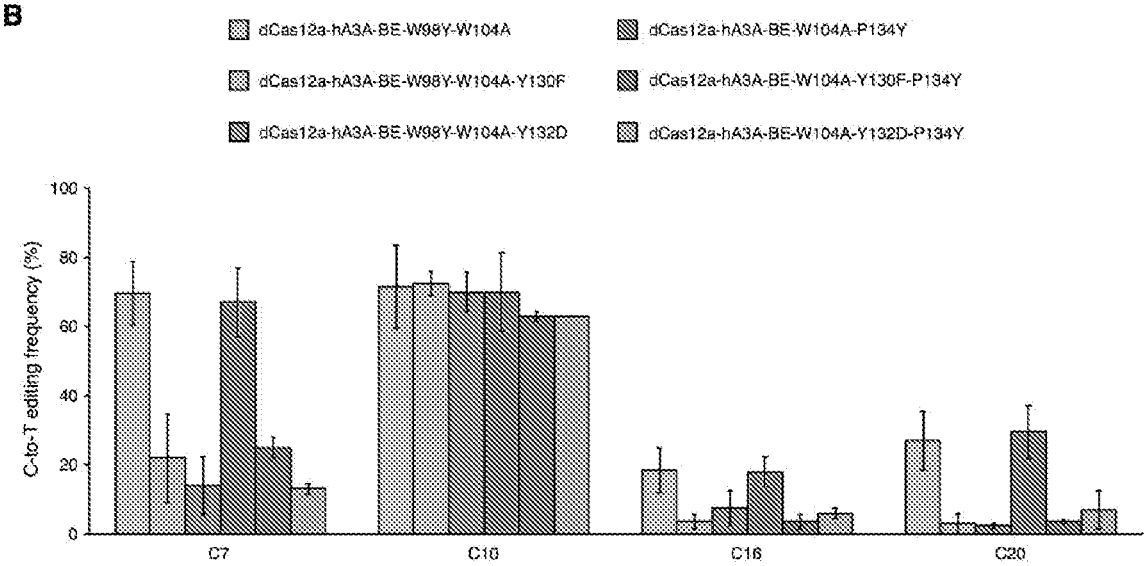
FIG. 12A-B

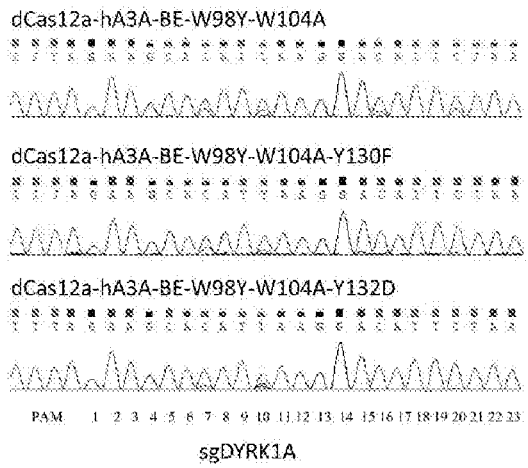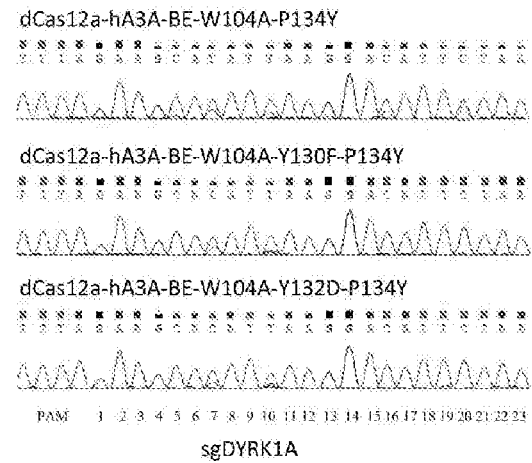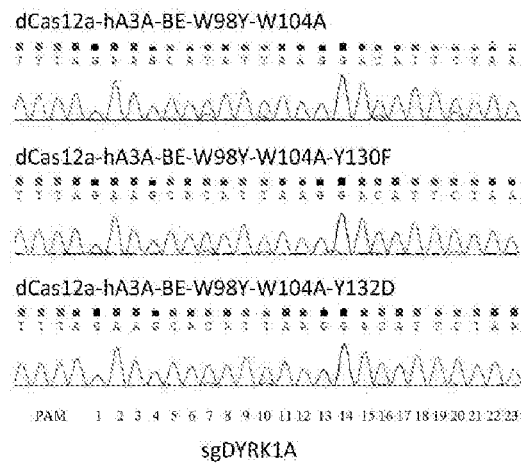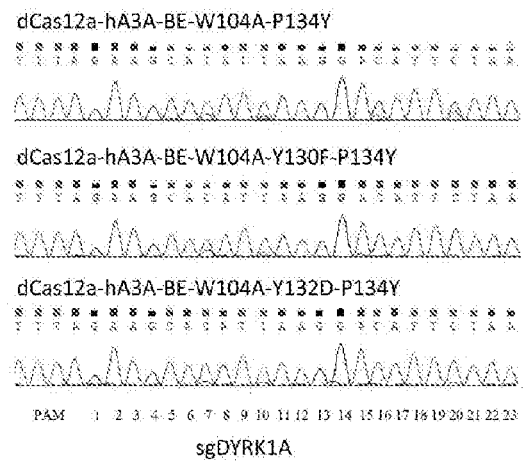
FIG. 14

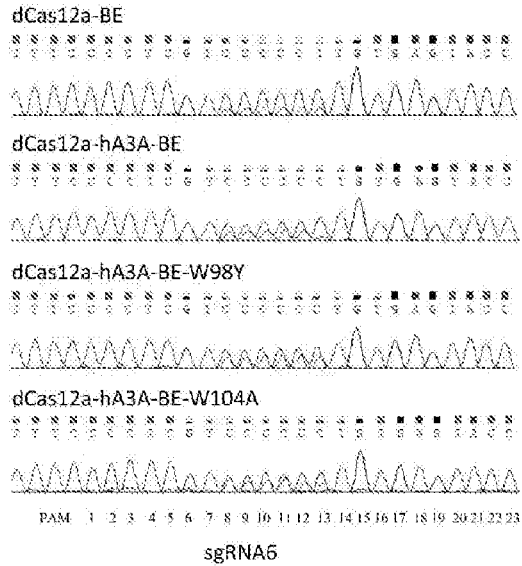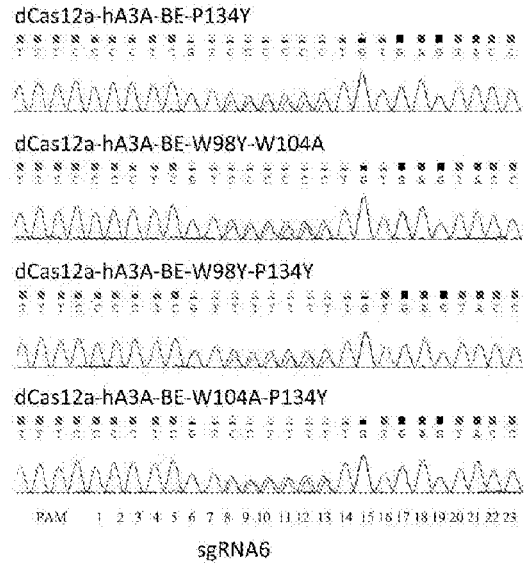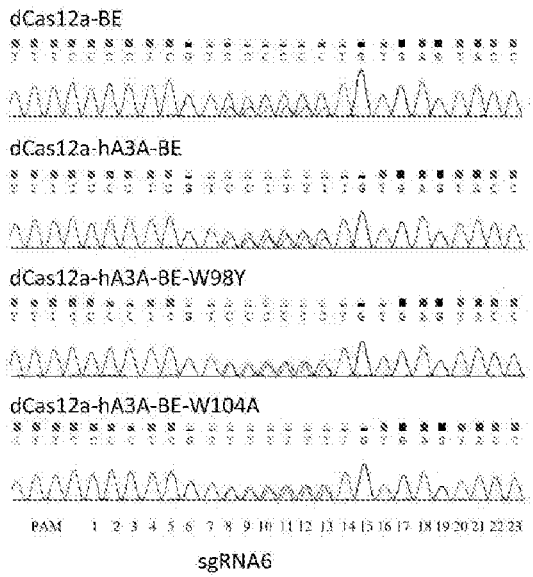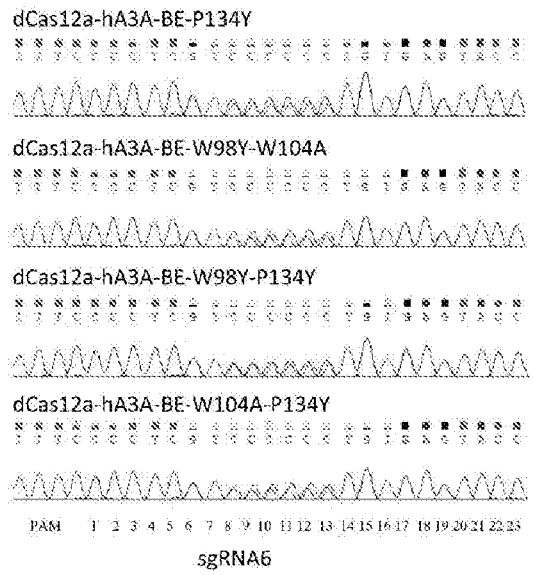
FIG. 15

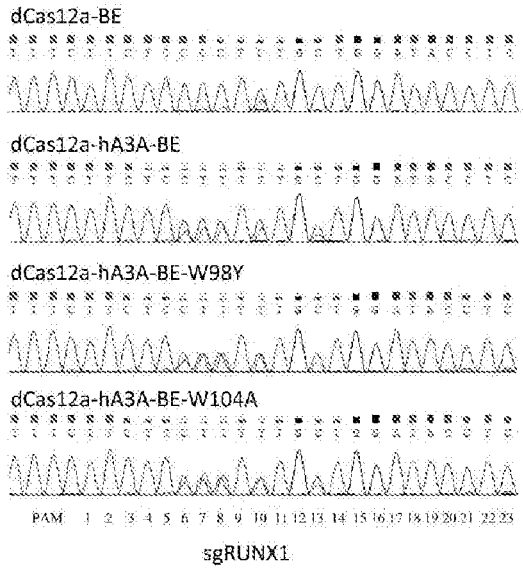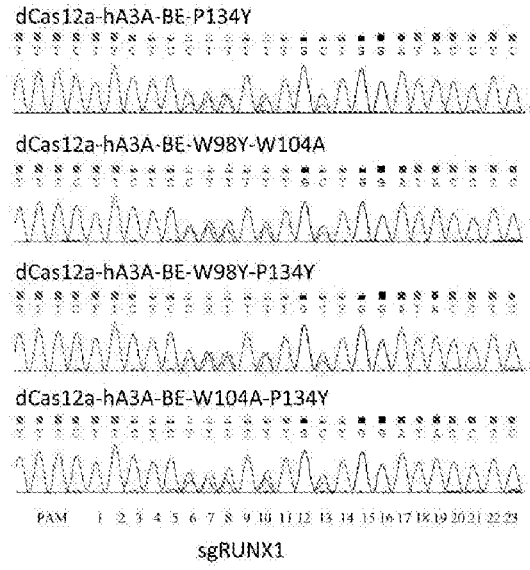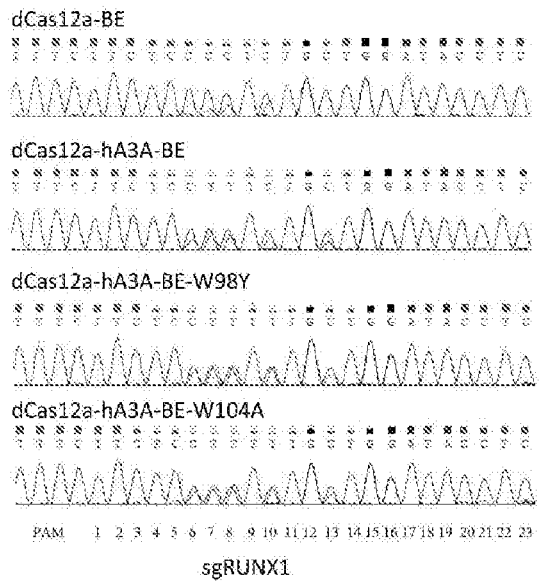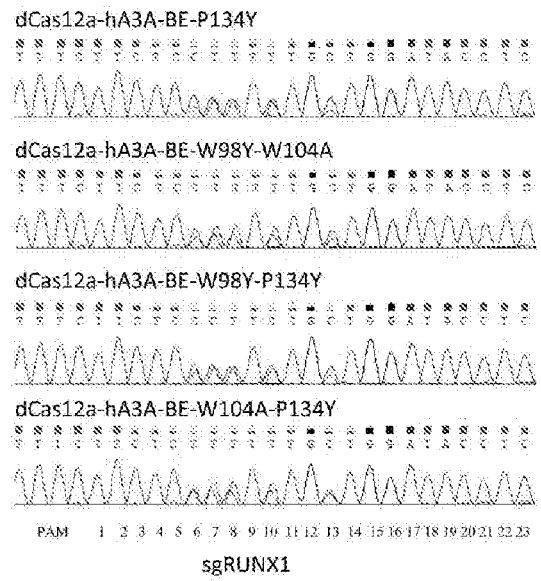
FIG. 17

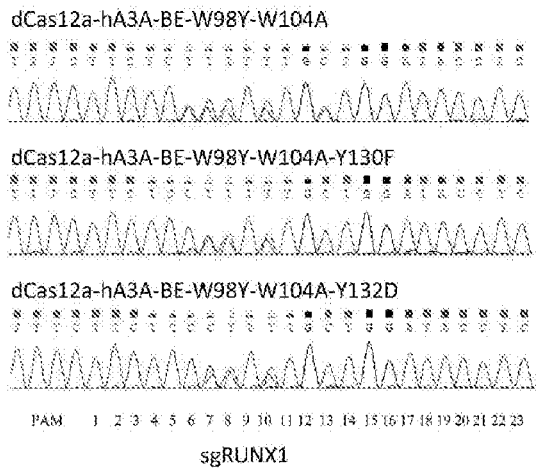
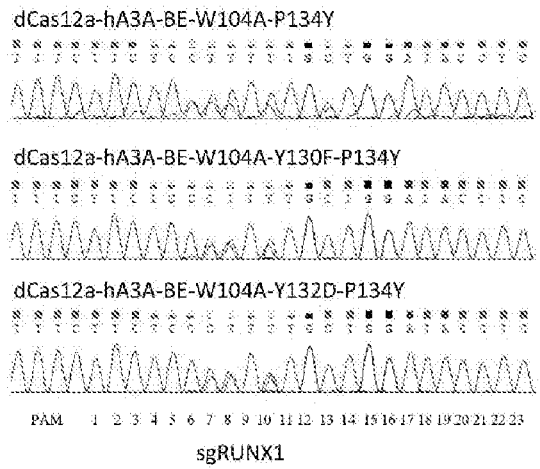
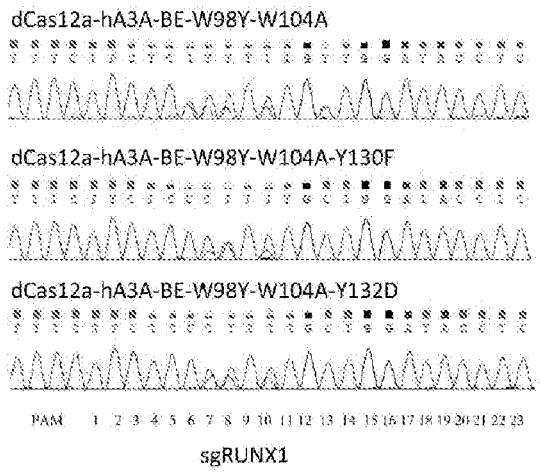
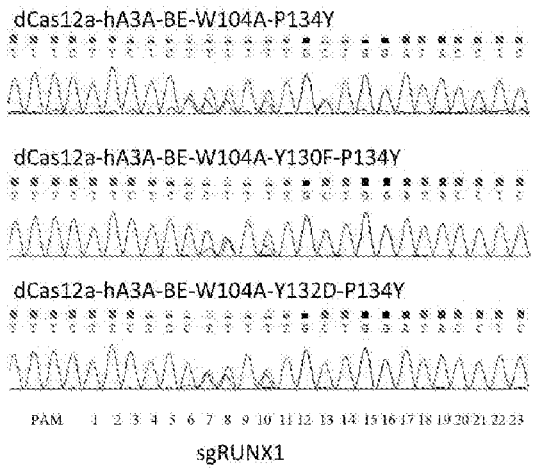
FIG. 18

FUSION PROTEINS FOR BASE EDITING

CROSS-REFERENCE TO RELATED PATENT APPLICATIONS

This application is a U.S. National Stage Application under 35 U.S.C. 371 of International Application No. PCT/CN2019/075897, filed Feb. 22, 2019, which claims priority to PCT/CN2018/100411, filed on Aug. 14, 2018 and PCT/CN2018/076991, filed on Feb. 23, 2018, the contents of all of which are incorporated herein by reference in their entirety in the present disclosure.

SEQUENCE LISTING

The instant application contains a Sequence Listing which has been submitted in ASCII format via EFS-Web and is hereby incorporated by reference in its entirety. Said ASCII copy, created on Jul. 31, 2023, is named 268973US_ST25.txt and is 341 kilobytes in size.

BACKGROUND

Genome editing is a type of genetic engineering in which DNA is inserted, deleted or replaced in the genome of a living organism using engineered nucleases (molecular scissors). Utilizing genome editing tools to genetically manipulate the genome of cells and living organism has broad application interest in life sciences research, biotechnology/agricultural technology development and most importantly pharmaceutical/clinical innovation. For example, genome editing can be used to correct driver mutations underlying genetic diseases and thereby resulting in complete cure of these diseases in a living organism; genome editing can also be applied to engineer the genome of crops, thus increasing the yield of crops and conferring crops resistance to environmental contamination or pathogen infection; likewise, microbial genome transformation through accurate genome editing is of great significance in the development of renewable bio-energy.

CRISPR/Cas (Clustered regularly interspaced short palindromic repeats/CRISPR-associated protein) system has been the most powerful genomic editing tool since its conception for its unparalleled editing efficiency, convenience and the potential applications in living organism. Directed by guide RNA (gRNA), a Cas nuclease can generate DNA double strand breaks (DSBs) at the targeted genomic sites in various cells (both cell lines and cells from living organisms). These DSBs are then repaired by the endogenous DNA repair system, which could be utilized to perform desired genome editing.

In general, two major DNA repair pathways could be activated by DSBs, non-homologous end joining (NHEJ) and homology-directed repair (HDR). NHEJ can introduce random insertions/deletions (indels) in the genomic DNA region around the DSBs, thereby leading to open reading frame (ORF) shift and ultimately gene inactivation. In contrast, when HDR is triggered, the genomic DNA sequence at target site could be replaced by the sequence of the exogenous donor DNA template through a homologous recombination mechanism, which can result in the correction of genetic mutation.

However, the practical efficiency of HDR-mediated gene correction is low (normally <5%) because the occurrence of homologous recombination is both cell type-specific and cell cycle-dependent and NHEJ is triggered more frequently than HDR is. The relatively low efficiency of HDR therefore limited the translation of CRISPR/Cas genome editing tools in the field of precision gene therapy (diseases-driven gene correction).

Base editors (BE), which integrate the CRISPR/Cas system with the APOBEC (apolipoprotein B mRNA editing enzyme, catalytic polypeptide-like) cytosine deaminase family, were recently invented that greatly enhanced the efficiency of CRISPR/Cas9-meditated gene correction. Through fusion with Cas9 nickase (nCas9), the cytosine (C) deamination activity of rat APOBEC1 (rA1) can be purposely directed to the target bases in genome and to catalyze C to Thymine (T) substitutions at these bases.

However, current rA1-based BEs cannot efficiently edit C that follows a G (i.e., C of GpC), thereby limiting the genome targeting breadth. Therefore, creating new BEs that can efficiently edit C of GpC is highly desirable. Such new BEs will enable us to perform efficient base editing in a broader genomic space of various living organisms. Importantly, the high efficiency of such BEs on C of GpC will promote clinical translation, particularly in gene therapies that involve restoring disease-related GpT-to-GpC mutations.

SUMMARY

The present disclosure demonstrates that when an apolipoprotein B mRNA editing enzyme catalytic subunit 3A (APOBEC3A or A3A) is fused to a clustered regularly interspaced short palindromic repeats (CRISPR)-associated (Cas) protein, optionally further with uracil glycosylase inhibitor (UGI), the resulting fusion protein is able to efficiently deaminate cytosine's to uracil's resulting in C to T substitution. Such base editing, surprisingly and unexpectedly, was effective even when the C follows a G (i.e., in a GpC dinucleotide context) or when the C is methylated. The editing efficiency can be further increased when the A3A includes a few tested mutations. This has significant clinical significance as cytosine methylation is common in living cells.

In conventional base editors, Cas9 is the commonly used DNA endonuclease. The Cas12a (Cpf1) has the advantage of recognizing A/T rich sequence when used together with APOBEC1 in base editors. In another surprising discovery, when APOBEC1 was replaced with A3A, the editing efficiency was greatly increased. Yet, the editing efficiency of such a Cas12a-A3A can be further increased when the A3A includes a few tested mutations.

Accordingly, in one embodiment, the present disclosure provides a fusion protein comprising a first fragment comprising an apolipoprotein B mRNA editing enzyme catalytic subunit 3A (APOBEC3A) and a second fragment comprising a clustered regularly interspaced short palindromic repeats (CRISPR)-associated (Cas) protein. In some embodiments, the fusion protein further comprises a uracil glycosylase inhibitor (UGI).

Preferably, the fusion protein has fewer than 3000, 2500, 2200, 2100, 2000, 1900, 1800, 1700, 1600, or 1500 amino acid residues in total.

In some embodiments, the APOBEC3A is a wildtype human APOBEC3A or a mutant of human APOBEC3A having a mutation selected from the group consisting of Y130F, D131Y, D131E, Y132D, W104A, W98Y, P134Y and combinations thereof, according to residue numbering in SEQ ID NO:1, wherein the mutant retains cytidine deaminase activity.

In some embodiments, the APOBEC3A is a mutant human APOBEC3A having mutations selected from the group consisting of Y130F+D131E+Y132D, Y130F+ D131Y+Y132D, W98Y+W104A, W98Y+P134Y, W104A+ P134Y, W104A+Y130F, W104A+Y132D, W98Y+W104A+ Y130F, W98Y+W104A+Y132D, W104A+Y130F+P134Y, and W104A+Y132D+P134Y, according to residue numbering in SEQ ID NO:1.

In some embodiments, the APOBEC3A comprises the amino acid sequence of SEQ ID NO:1 or has at least 90% sequence identity to amino acid residues 29-199 of SEQ ID NO:1 and retains cytidine deaminase activity. In some embodiments, the APOBEC3A comprises an amino acid sequence selected from the group consisting of SEQ ID NO:1-10 and 22-36.

In some embodiments, the Cas protein is selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, KKH SaCas9, NmeCas9, StCas9, CjCas9, AsCpf1, FnCpf1, SsCpf1, PcCpf1, BpCpf1, CmtCpf1, LbCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b, CasX, and CasY. In some embodiments, the Cas protein is a mutant of protein selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, KKH SaCas9, NmeCas9, StCas9, CjCas9, AsCpf1, FnCpf1, SsCpf1, PcCpf1, BpCpf1, CmtCpf1, LbCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b, CasX, and CasY, wherein the mutant retains the DNA-binding capability but does not introduce double strand DNA breaks. In some embodiments, the mutant is capable of introducing a nick to one of the strands of a double stranded DNA bound by the mutant. In some embodiments, the Cas protein comprises the amino acid sequence of any one of SEQ ID NO:11 and 37-39.

In some embodiments, the UGI comprises the amino acid sequence of SEQ ID NO:12 or has at least at least 90% sequence identity to SEQ ID NO:12 and retains the uracil glycosylase inhibition activity.

In some embodiments, the first fragment is at the N-terminal side of the second fragment. In some embodiments, the first fragment is at the N-terminal side of the second fragment which is at the N-terminal side of the UGI.

In some embodiments, the fusion protein further comprises a peptide linker between the first fragment and the second fragment. In some embodiments, the peptide linker has from 1 to 100 amino acid residues. In some embodiments, at least 10%, 20%, 30%, 40%, 50%, 60%, 70%, 80% or 90% of the amino acid residues of peptide linker are amino acid residues selected from the group consisting of alanine, glycine, cysteine, and serine. In some embodiments, the peptide linker has an amino acid sequence of SEQ ID NO:13 or 14. In some embodiments, the fusion protein further comprises a nuclear localization sequence.

Non-limiting examples of fusion proteins include those having an amino acid sequence selected from the group consisting of SEQ ID NO:16-20 and 40-50.

In another embodiment, a fusion protein is provided that comprises a first fragment comprising an apolipoprotein B mRNA editing enzyme catalytic subunit 3A (APOBEC3A) and a second fragment comprising a CRISPR-associated endonuclease in *Prevotella* and *Francisella* 1 (Cpf1). In some embodiments, the Cpf1 is catalytically inactive.

The Cpf1 (Cas12a) can be selected from the group consisting of AsCpf1, LbCpf1, and FnCpf1, in some embodiments. In a specific embodiment, the Cpf1 is a catalytically inactive *Lachnospiraceae bacterium* Cpf1 (dLbCpf1).

In some embodiments, the APOBEC3A is a wildtype human APOBEC3A or a mutant of human APOBEC3A having a mutation selected from the group consisting of Y130F, D131Y, D131E, Y132D, W104A, W98Y, P134Y and combinations thereof, according to residue numbering in SEQ ID NO:1, wherein the mutant retains cytidine deaminase activity.

Also provided is a polynucleotide that encodes a fusion protein of the present disclosure. Still, in another embodiment, provided is a composition comprising a fusion protein of the present disclosure and a pharmaceutically acceptable carrier. In some embodiments, the composition further comprises a guide RNA.

Methods of using the fusion proteins and compositions are also provided. In one embodiment, a method for editing a target polynucleotide is provided, comprising contacting to the target polynucleotide a fusion protein of the present disclosure and a guide RNA having at least partial sequence complementarity to the target polynucleotide, wherein the editing comprises deamination of a cytosine (C) in the target polynucleotide. In some embodiments, the C is in a GpC context. In some embodiments, the C is methylated. In some embodiments, the contacting is in vitro, ex vivo, or in vivo. In some embodiments, the method further comprises contacting to the target polynucleotide with a uracil glycosylase inhibitor (UGI) not fused to a Cas protein.

BRIEF DESCRIPTION OF THE DRAWINGS

FIG. 2A-B. Construction and performance of hA3A-BE-Y130F and hA3A-BE-Y132D. Panel A: Schematic diagram illustrating the co-expression of hA3A-BE/sgRNA, hA3A-BE-Y130F/sgRNA or hA3A-BE-Y132D/sgRNA. Panel B: Comparing to the co-expression of hA3A-BE/sgRNA, the co-expression of hA3A-BE-Y130F/sgRNA or hA3A-BE-Y132D/sgRNA induced base editing in more narrowed windows in the sgRNA targeted genomic regions (sgSITE3 and sgEMX1). Dashed boxes represent the base editing windows. Sequences as shown in panel B, from left column to right column and from top to down, are SEQ ID NO:57-64.

Figure 1:
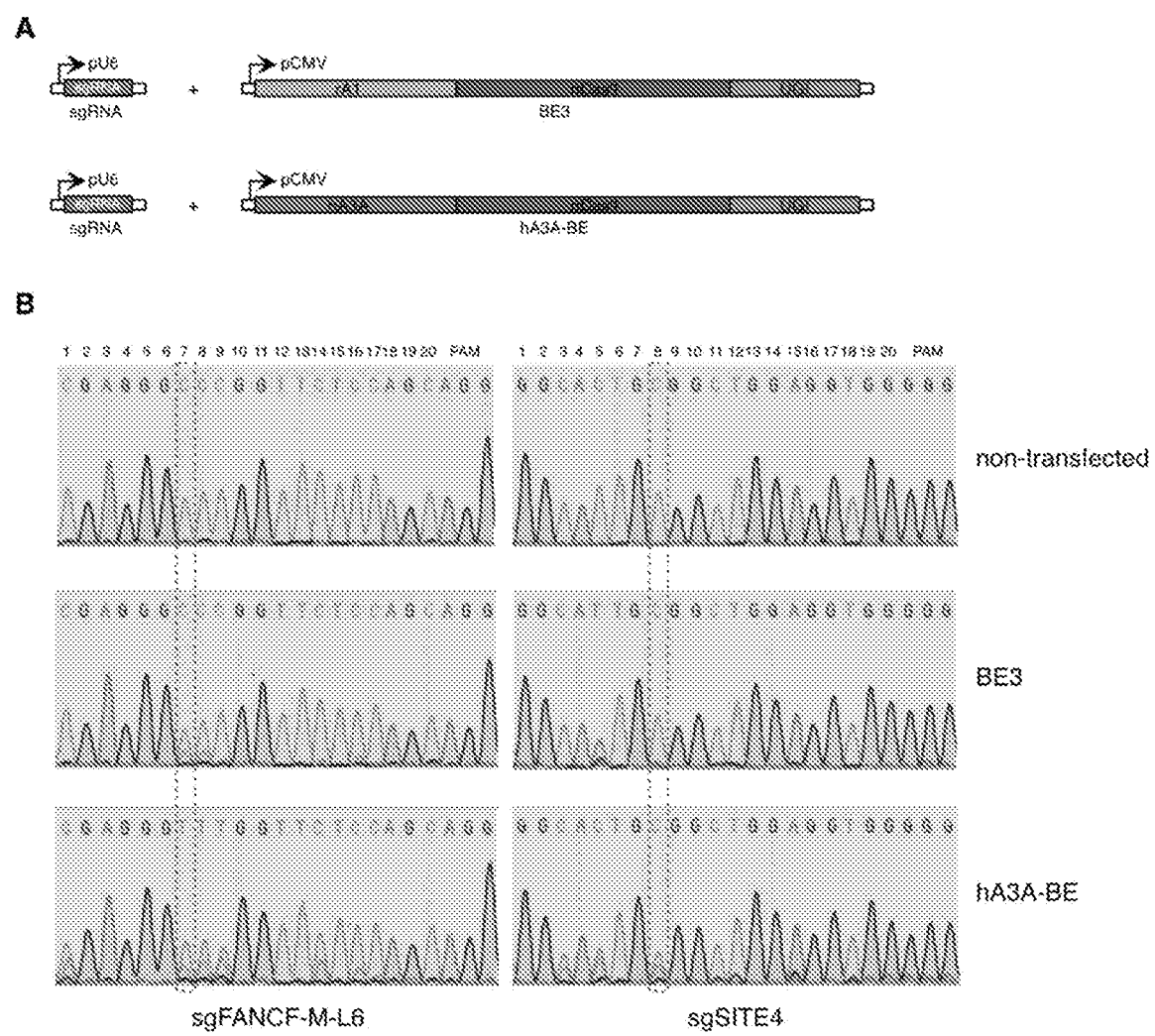
FIG. 1A-B. Construction and performance of hA3A-BE. Panel A: Schematic diagram illustrating the co-expression of BE3/sgRNA or hA3A-BE/sgRNA. Panel B: Comparing to the co-expression of BE3/sgRNA, the co-expression of hA3A-BE/sgRNA achieved more efficient base editing on the C of GpC in the sgRNA targeted genomic regions (sgFANCF-M-L6 and sgSITE4). Dashed boxes represent the cytosine's locating in the context of GpC. Sequences as shown in panel B, from left column to right column and from top to down, are SEQ ID NO:51-56.

Y132D. Panel A: Schematic diagram illustrating the co-expression of hA3A-BE/sgRNA, hA3A-BE-Y130E-D131E-Y132D/sgRNA or hA3A-BE-Y130E-D131Y-Y132D/sgRNA. Panel B: Comparing to the co-expression of hA3A-BE/sgRNA, the co-expression of hA3A-BE-Y130E-D131E-Y132D/sgRNA or hA3A-BE-Y130E-D131Y-Y132D/sgRNA induced base editing in more narrowed windows in the sgRNA targeted genomic regions (sgFANCF and sgSITE3). Dashed boxes represent the edited cytosine's. Sequences as shown in panel B, from left column to right column and from top to down, are SEQ ID NO:73-80.

FIG. 5a-h. hA3A-BE3 induces efficient base editing in methylated region and in GpC context. (a) Distribution of BE-editable T-to-C (or A-to-G) variants. Potentially editable cytosines (underlined) are sub-classified according to their 3' adjacent bases. (b) Screening of BEs for efficient base editing in a high-methylation background. A series of new BEs were constructed by fusing different APOBEC/AID deaminases with Cas9 nickase (nCas9) and uracil DNA glycosylase inhibitor (UGI). (c) Cumulative base editing frequencies induced by different BEs in unmethylated and methylated vectors. A commonly used rA1-based BE3 was chosen for comparison. Means±s.d. were from three (six for hA3A-BE3) independent experiments. (d) Immunoblots of BE3 and hA3A-BE3 co-transfected with unmethylated or methylated vectors. Tubulin was used as a loading control and immunoblot images are representative of three independent experiments. (e) Comparison of base editing efficiencies induced by BE3 and hA3A-BE3 in genomic regions with natively high levels of DNA methylation. C-to-T editing frequencies of indicated cytosines were determined individually. Target site sequences are shown with the BE3 editing window (position 4-8, setting the base distal to the PAM as position 1) in pink, PAM in cyan and CpG site in capital. Shaded gray, guanines at 5' end of editable cytosines. NT, native HEK293T cells with no treatment. (f) Statistical analysis of normalized C-to-T editing frequencies in regions with natively high levels of DNA methylation shown in (e), setting the ones induced by BE3 as 100%. n=48 samples from three independent experiments. (g) Comparison of base editing efficiencies induced by BE3 and hA3A-BE3 at C of GpC in genomic regions with natively low levels of DNA methylation. (h) Statistical analysis of normalized C-to-T editing frequencies at GpC sites in regions with natively low levels of DNA methylation shown in (g), setting the ones induced by BE3 as 100%. n=24 samples from three independent experiments. (e,g) Means±s.d. were from three independent experiments. (f,h) P value, one-tailed Student's t test. The median and interquartile range (IQR) are shown. Sequences as shown in FIG. 5e are SEQ ID NO:81-89. Sequences as shown in FIG. 5g are SEQ ID NO:90-95.

FIG. 6a-i. Improvements in hA3A-BE3. (a) Comparison of base editing efficiencies induced by BE3, hA3A-BE3, hA3A-BE3-Y130F and hA3A-BE3-Y132D in genomic regions with natively high levels of DNA methylation. Target site sequences are shown with the overlapped editing window (position 4-7) in pink, PAM in cyan and CpG site in capital. NT, native HEK293T cells with no treatment. (b) Statistical analysis of normalized C-to-T editing frequencies in the overlapped editing window shown in (a), setting the ones induced by BE3 as 100%. n=12 samples from three independent experiments. (c) Comparison of base editing efficiencies induced by BE3, hA3A-BE3, hA3A-BE3-Y130F and hA3A-BE3-Y132D at C of GpC in the overlapped editing window in genomic regions with natively low levels of DNA methylation. (d) Statistical analysis of normalized C-to-T editing frequencies shown in (c), setting the ones induced by BE3 as 100%. n=9 samples from three independent experiments. (e) Immunoblots of BEs transfected into HEK293T cells. Tubulin was used as a loading control and immunoblot images are representative of three independent experiments. (f) Comparison of base editing efficiencies induced by hA3A-BE3-Y130F, hA3A-eBE-Y130F, hA3A-BE3-Y132D and hA3A-eBE-Y132D at C of GpC in the overlapped editing window in genomic regions with natively low levels of DNA methylation. (g) Statistical analysis of normalized C-to-T editing frequencies shown in (f), setting the ones induced by hA3A-BE3-Y130F (left) or hA3A-BE3-Y132D (right) as 100%. n=9 samples from three independent experiments. (h,i) Comparison of product purity (h) and indels (i) yielded by hA3A-BE3-Y130F, hA3A-eBE-Y130F, hA3A-BE3-Y132D and hA3A-eBE-Y132D in genomic DNA regions with natively low levels of DNA methylation. Asterisk denotes an unusually high basal indel frequency (or amplification, sequencing or alignment artifact) at the examined VEGFA-M-c site in NT. (a,c,f,i) Means±s.d. were from three independent experiments. (b,d,g) P value, one-tailed Student's t test. The median and IQR are shown. Sequences as shown in FIG. 6a are SEQ ID NO:96-98.

FIGS. 7A-B and 8A-B show the vector structures of each of the tested base editors and charting showing their editing efficiencies on the target DYRK1A gene.

FIGS. 9A-B and 10A-B show the vector structures of each of the tested base editors and charting showing their editing efficiencies on the target SITE6 gene.

FIGS. 11A-B and 12A-B show the vector structures of each of the tested base editors and charting showing their editing efficiencies on the target RUNX1 gene.

Figure 13:
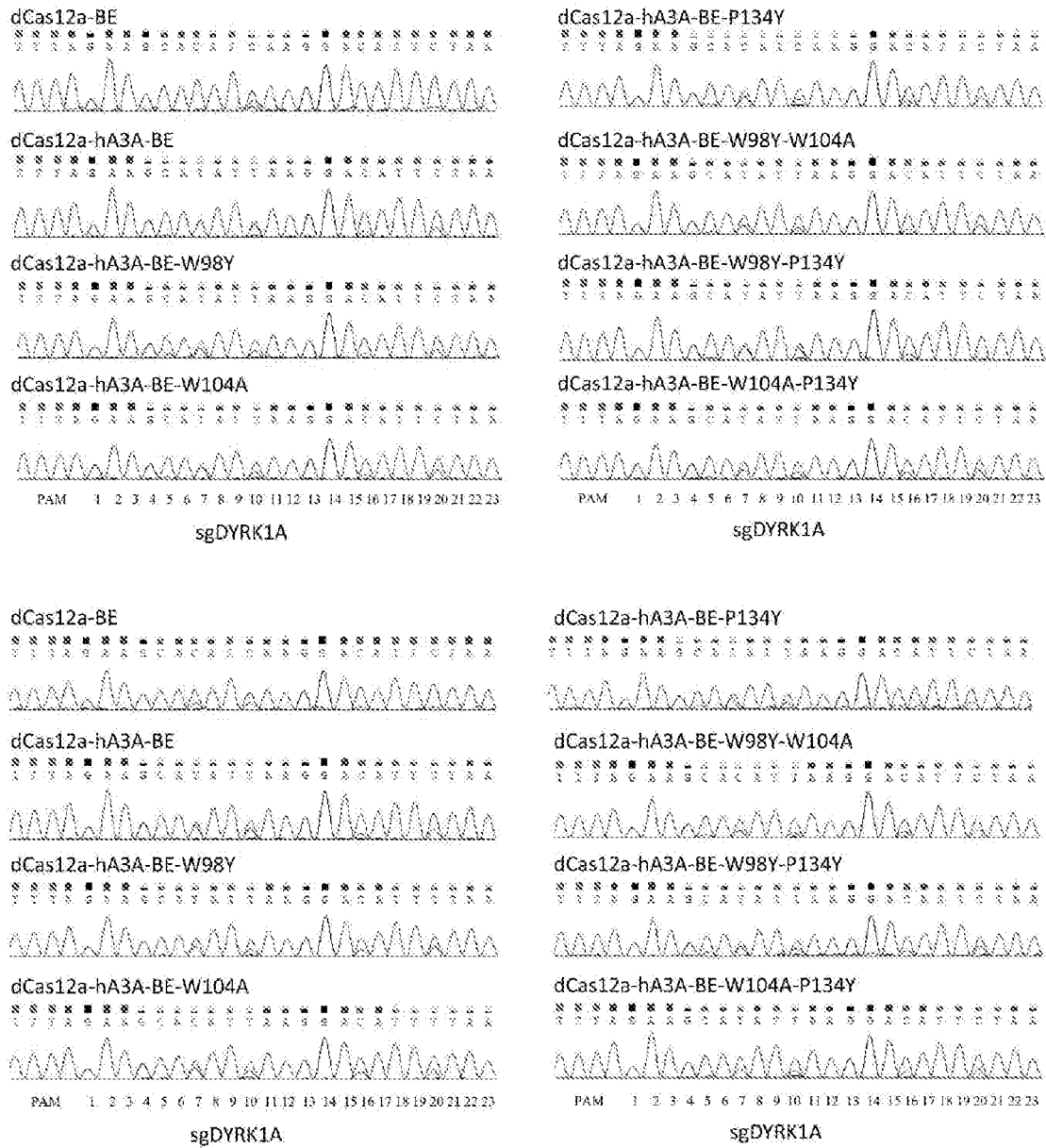
Figure 16:
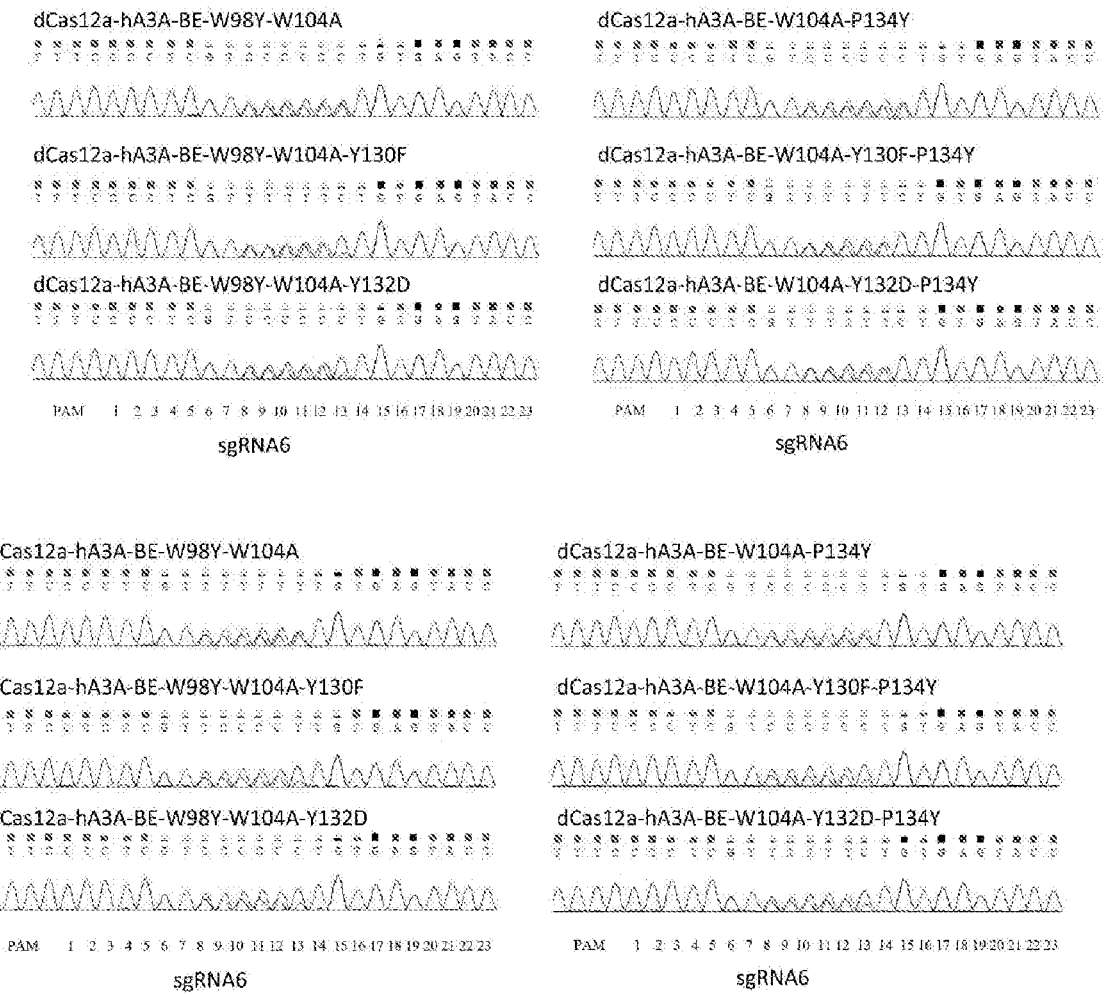

FIG. 13-18 show the sequencing results for Examples 3-5. Sequences as shown in FIG. 13, from left column to right column and from top to down, are SEQ ID NO:99-114. Sequences as shown in FIG. 14, from left column to right column and from top to down, are SEQ ID NO:115-126. Sequences as shown in FIG. 15, from left column to right column and from top to down, are SEQ ID NO:127-142. Sequences as shown in FIG. 16, from left column to right column and from top to down, are SEQ ID NO:143-156. Sequences as shown in FIG. 17, from left column to right column and from top to down, are SEQ ID NO:157-172. Sequences as shown in FIG. 18, from left column to right column and from top to down, are SEQ ID NO:173-184.

DETAILED DESCRIPTION

Definitions

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Fusion Proteins

The current rA1-based BEs (base editors) cannot efficiently edit C in methylated regions or in the context of GpC, which limits the use of base editing. The present disclosure provides fusion molecules that combine an apolipoprotein B mRNA editing enzyme catalytic subunit 3A (APOBEC3A or A3A) and a clustered regularly interspaced short palindromic repeats (CRISPR)-associated (Cas) protein, optionally further with uracil glycosylase inhibitor (UGI).

The resulting fusion protein is able to efficiently deaminate cytosine's to uracil's resulting in C to T substitution. Such base editing, surprisingly and unexpectedly, was effective even when the C follows a G (i.e., in a GpC dinucleotide context) and/or even when it is in a methylated region. This has significant clinical significance as cytosine methylation is common in living cells.

In accordance with one embodiment of the present disclosure, provided is a fusion protein comprising a first fragment comprising an apolipoprotein B mRNA editing enzyme catalytic subunit 3A (APOBEC3A) and a second fragment comprising a clustered regularly interspaced short palindromic repeats (CRISPR)-associated (Cas) protein.

APOBEC3A, also referred to as apolipoprotein B mRNA editing enzyme catalytic subunit 3A or A3A, is a protein of the APOBEC3 family found in humans, non-human primates, and some other mammals. The APOBEC3A protein lacks the zinc binding activity of other family members. In human, isoform a (NP_663745.1; SEQ ID NO:1) and isoform b (NP_001257335.1; SEQ ID NO:6) both are active, while isoform a includes a few more residues close to the N-terminus. The term "APOBEC3A" also encompasses variants and mutants that have certain level (e.g., 70%, 75%, 80%, 85%, 90%, 95%, 98%, 99%) of sequence identity to a wildtype mammalian APOBEC3A and retains its cytidine deaminating activity.

As demonstrated in the experimental examples, certain mutants (e.g., Y130F (SEQ ID NO:2), Y132D (SEQ ID NO:3), W104A (SEQ ID NO:4), D131Y (SEQ ID NO:5), D131E (SEQ ID NO:22), W98Y (SEQ ID NO:24), W104A (SEQ ID NO:25), and P134Y (SEQ ID NO:26)) even outperformed the wildtype human APOBEC3A. Furthermore, a number of tested combinations of these mutations also exhibited great performances. Moreover, although not specifically tested, the same mutations are believed to also work in the isoform b of A3A. Examples of such variants and mutants are provided in Table 1 below.

TABLE 1

Examples of APOBEC3A Sequences

| Name | Sequence | | | | | SEQ ID NO: |
|---|---|---|---|---|---|---|
| Human APOBEC3A isoform a wildtype | 1 MEASPASGPR<br>51 HRGFLHNQAK<br>101 CFSWGCAGEV<br>151 SIMTYDEFKH | HLMDPHIFTS<br>NLLCGFYGRH<br>RAFLQENTHV<br>CWDTFVDHQG | NFNNGIGRHK<br>AELRFLDLVP<br>RLRIFAARIY<br>CPFQPWDGLD | TYLCYEVERL<br>SLQLDPAQIY<br>DYDPLYKEAL<br>EHSQALSGRL | DNGTSVKMDQ<br>RVTWFISWSP<br>QMLRDAGAQV<br>RAILQNQGN | 1 |
| Human APOBEC3A isoform a Y130F | 1 MEASPASGPR<br>51 HRGFLHNQAK<br>101 CFSWGCAGEV<br>151 SIMTYDEFKH | HLMDPHIFTS<br>NLLCGFYGRH<br>RAFLQENTHV<br>CWDTFVDHQG | NFNNGIGRHK<br>AELRFLDLVP<br>RLRIFAARIF<br>CPFQPWDGLD | TYLCYEVERL<br>SLQLDPAQIY<br>DYDPLYKEAL<br>EHSQALSGRL | DNGTSVKMDQ<br>RVTWFISWSP<br>QMLRDAGAQV<br>RAILQNQGN | 2 |
| Human APOBEC3A isoform a Y132D | 1 MEASPASGPR<br>51 HRGFLHNQAK<br>101 CFSWGCAGEV<br>151 SIMTYDEFKH | HLMDPHIFTS<br>NLLCGFYGRH<br>RAFLQENTHV<br>CWDTFVDHQG | NFNNGIGRHK<br>AELRFLDLVP<br>RLRIFAARIY<br>CPFQPWDGLD | TYLCYEVERL<br>SLQLDPAQIY<br>DDDPLYKEAL<br>EHSQALSGRL | DNGTSVKMDQ<br>RVTWFISWSP<br>QMLRDAGAQV<br>RAILQNQGN | 3 |
| Human APOBEC3A isoform a W104A | 1 MEASPASGPR<br>51 HRGFLHNQAK<br>101 CFSAGCAGEV<br>151 SIMTYDEFKH | HLMDPHIFTS<br>NLLCGFYGRH<br>RAFLQENTHV<br>CWDTFVDHQG | NFNNGIGRHK<br>AELRFLDLVP<br>RLRIFAARIY<br>CPFQPWDGLD | TYLCYEVERL<br>SLQLDPAQIY<br>DYDPLYKEAL<br>EHSQALSGRL | DNGTSVKMDQ<br>RVTWFISWSP<br>QMLRDAGAQV<br>RAILQNQGN | 4 |
| Human APOBEC3A isoform a D131Y | 1 MEASPASGPR<br>51 HRGFLHNQAK<br>101 CFSWGCAGEV<br>151 SIMTYDEFKH | HLMDPHIFTS<br>NLLCGFYGRH<br>RAFLQENTHV<br>CWDTFVDHQG | NFNNGIGRHK<br>AELRFLDLVP<br>RLRIFAARIY<br>CPFQPWDGLD | TYLCYEVERL<br>SLQLDPAQIY<br>YYDPLYKEAL<br>EHSQALSGRL | DNGTSVKMDQ<br>RVTWFISWSP<br>QMLRDAGAQV<br>RAILQNQGN | 5 |
| Human APOBEC3A isoform b wildtype | 1 MEASPASGPR<br>51 RHAELRFLDL<br>101 HVRLRIFAAR<br>151 QGCPFQPWDG | HKTYLCYEVE<br>VPSLQLDPAQ<br>IYDYDPLYKE<br>LDEHSQALSG | RLDNGTSVKM<br>IYRVTWFISW<br>ALQMLRDAGA<br>RLRAILQNOG | DQHRGFLHNQ<br>SPCFSWGCAG<br>QVSIMTYDEF<br>N | AKNLLCGFYG<br>EVRAFLQENT<br>KHCWDTFVDH | 6 |
| Human APOBEC3A isoform b Y112F | 1 MEASPASGPR<br>51 RHAELRFLDL<br>101 HVRLRIFAAR<br>151 QGCPFQPWDG | HKTYLCYEVE<br>VPSLQLDPAQ<br>IFDYDPLYKE<br>LDEHSQALSG | RLDNGTSVKM<br>IYRVTWFISW<br>ALQMLRDAGA<br>RLRAILQNOG | DQHRGFLHNQ<br>SPCFSWGCAG<br>QVSIMTYDEF<br>N | AKNLLCGFYG<br>EVRAFLQENT<br>KHCWDTFVDH | 7 |

TABLE 1-continued

Examples of APOBEC3A Sequences

| Name | Sequence | SEQ ID NO: |
|---|---|---|
| Human APOBEC3A isoform b Y114D | 1 MEASPASGPR HKTYLCYEVE RLDNGTSVKM DQHRGFLHNQ AKNLLCGFYG<br>51 RHAELRFLDL VPSLQLDPAQ IYRVTWFISW SPCFSWGACG EVRAFLQENT<br>101 HVRLRIFAAR IYDDDPLYKE ALQMLRDAGA QVSIMTYDEF KHCWDTFVDH<br>151 QGCPFQPWDG LDEHSQALSG RLRAILQNQG N | 8 |
| Human APOBEC3A isoform b W86A | 1 MEASPASGPR HKTYLCYEVE RLDNGTSVKM DQHRGFLHNQ AKNLLCGFYG<br>51 RHAELRFLDL VPSLQLDPAQ IYRVTWFISW SPCFSAGCAG RVRAFLQENT<br>101 HVRLRIFAAR IYDYDPLYKE ALQMLRDAGA QVSIMTYDEF KHCWDTFVDH<br>151 QGCPFQPWDG LDEHSQALSG RLRAILQNQG N | 9 |
| Human APOBEC3A isoform b D113Y | 1 MEASPASGPR HKTYLCYEVE RLDNGTSVKM DQHRGFLHNQ AKNLLCGFYG<br>51 RHAELRFLDL VPSLQLDPAQ IYRVTWFISW SPCFSWGCAG EVRAFLQENT<br>101 HVRLRIFAAR IYYYDPLYKE ALQMLRDAGA QVSIMTYDEF KHCWDTFVDH<br>151 QGCPFQPWDG LDEHSQALSG RLRAILQNQG N | 10 |
| Human APOBEC3A isoform a Y130F – D131E – Y132D | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIF EDDPLYKEAL QMLRDAGAQV<br>151 SIMTYDEFKH CWDTFVDHQG VFPQPWDGLD EHSQALSGRL RAILQNQGN | 22 |
| Human APOBEC3A isoform a Y130F – D131Y – Y132D | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIF YDDPLYKEAL QMLRDAGAQV<br>151 SIMTYDEFKH CWDTFVDHQG CPFQPWDGLD EHSQALSGRL RAILQNQGN | 23 |
| Human APOBEC3A isoform a W98Y | 1 MEASPASGPR HLMDPHIFTS NFNNGIGRHK TYLCYEVERL DNGTSVKMDQ<br>51 HRGFLHNQAK NLLCGFYGRH AELRDLDLVP SLQLDPAQIY RVTWFISYSP<br>101 CFSWGCAGEV RAFLQENTHV RLRIFAARIY DYDPLYKEAL QMLRDAGAQV<br>150 SIMTYDEFKH CWDTFVDHQG CPFQPWDGLD EHSQALSGRL RAILQNQGN | 24 |
| Human APOBEC3A isoform a P134Y | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 VFSWGCAGEV RAFLQENTHV RLRIFAARIY DYDYLYKEAL QMLRDAGAQV<br>151 SIMTYDEFKH CWDTFVDHQG CPFQPWDGLD EHSQALSGRL RAILQNQGN | 25 |
| Human APOBEC3A isoform a W98Y + W104A | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISYSP<br>101 CFSAGCAGEV RAFLQENTHV RLRIFAARIY DYDPLYKEAL QMLRDAGAQV<br>151 SIMTYDEFKH CWDTFVDHQG CPFQPWDGLD EHSQALSGRL RAILQNQGN | 26 |
| Human APOBEC3A isoform a W98Y + P134Y | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISYSP<br>101 CFSWGCAGEV RAFLQENTHV RLRIFAARIY DYDYLYKEAL QMLRDAGAQV<br>151 SIMTYDEFKH CWDTFVDHQG VPFQPWDGLD EHSQALSGRL RAILQNQGN | 27 |
| Human APOBEC3A isoform a W104A + P134Y | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSAGCAGEV RAFLQENTHV RLRIFAARIY DYDYLYKEAL QMLRDAGAQV<br>151 SIMTYDEFKH CWDTFVDHQG CPFQPWDGLD EHSQALSGRL RAILQNQGN | 28 |
| Human APOBEC3A isoform a W98Y + W104A + Y130F | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISYSP<br>101 VFSAGCAGEV RAFLQENTHV RLRIFAARIF DYDPLYKEAL QMLRDAGAQV<br>151 SIMTYDEFKH CWDTFVDHQG CPFQPWDGLD EHSQALSGRL RAILQNQGN | 29 |
| Human APOBEC3A isoform a W98Y + W104A + Y132D | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISYSP<br>101 CFSAGCAGEV RAFLQENTHV RLRIFAARIY DDDPLYKEAL QMLRDAGAQV<br>151 SIMTYDEFKH CWDTFVDHQG VPFQPWDGLD EHSQALSGRL RAILQNQGN | 30 |
| Human APOBEC3A isoform a W104A + Y130F + P134Y | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 VFSAGCAGEV RAFLQENTHV RLRIFAARIF DYDYLYKEAL QMLRDAGAQV<br>151 SIMTYDEFKH CWDTFVDHQG CPFQPWDGLD EHSQALSGRL RAILQNQGN | 31 |
| Human APOBEC3A isoform a W104A + Y132D + P134Y | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSAGCAGEV RAFLQENTHV RLRIFAARIY DDDLYKEAL QMLRDAGAQV<br>151 SIMTYDEFKH CWDTFVDHQG CPFQPWDGLD EHSQALSGRL RAILQNQGN | 32 |

TABLE 1-continued

Examples of APOBEC3A Sequences

| Name | Sequence | SEQ ID NO: |
|---|---|---|
| Human APOBEC3A isoform a W104A + Y130F | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSAGCAGEV RAFLQENTHV RLRIFAARIF DYDPLYKEAL QMLRDAGAQV<br>151 SIMTYDEFKH CWDTFVDHQG CPFQPWDGLD EHSQALSGRL RAILQNQGN | 33 |
| Human APOBEC3A isoform a W104A + Y132D | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSAGCAGEV RAFLQENTHV RLRIFAARIY DDDPLYKEAL QMLRDAGAQV<br>151 SIMTYDEFKH CWDTFVDHQG CPFQPWDGLD EHSQALAGRL RAILQNQGN | 34 |
| Human APOBEC3A isoform b W80Y | 1 MEASPASGPR HKTYLCYEVE RLDNGTSVKM DQHRGFLHNQ AKNLLCGFYG<br>51 RHAELRFLDL VPSLQLDPAQ IYRVTWFISY SPCFSWGCAG RVRAFLQENT<br>101 HVRLRIFAAR IYDYDPLYKE ALQMLRDAGA QVSIMTYDEF KHCWDTFVDH<br>151 QGCPFQPWDG LDEHSQALSG RLRAILQNQG N | 35 |
| Human APOBEC3A isoform b P116Y | 1 MEASPASGPR HKTYLCYEVE RLDNGTSVKM DQHRGFLHNQ AKNLLCGFYG<br>51 RHAELRFLDL VPSLQLDPAQ IYRVTWFISW SPCFSWGCAG RVRAFLQENT<br>101 HVRLRIFAAR IYDYDLYKE ALQMLRDAGA QVSIMTYDEF KHCWDTFVDH<br>151 QGCPFQPWDG LDEHSQALSG RLRAILQNQG N | 36 |

In some embodiments, the APOBEC3A in the fusion protein of the present disclosure is human isoform a or a sequence having at least 70%, 75%, 80%, 85%, 90%, 95%, 98%, 99% of sequence identity to isoform a. In some embodiments, the APOBEC3A in the fusion protein of the present disclosure is human isoform b or a sequence having at least 70%, 75%, 80%, 85%, 90%, 95%, 98%, 99% of sequence identity to isoform b. In some embodiments, the APOBEC3A in the fusion protein of the present disclosure is rat APOBEC3 or a sequence having at least 70%, 75%, 80%, 85%, 90%, 95%, 98%, 99% of sequence identity to the rat APOBEC3. In some embodiments, the APOBEC3A in the fusion protein of the present disclosure is mouse APOBEC3 or a sequence having at least 70%, 75%, 80%, 85%, 90%, 95%, 98%, 99% of sequence identity to the mouse APOBEC3. In some embodiments, the sequence retains the cytidine deaminase activity.

In some embodiments, the APOBEC3A includes a Y130F mutation, according to residue numbering in SEQ ID NO:1 (the numbering would be different in human isoform b and rat and mouse sequences, but can readily be converted). In some embodiments, the APOBEC3A includes a Y132D mutation, according to residue numbering in SEQ ID NO:1. In some embodiments, the APOBEC3A includes a W104A mutation, according to residue numbering in SEQ ID NO:1. In some embodiments, the APOBEC3A includes a D131Y mutation, according to residue numbering in SEQ ID NO:1. In some embodiments, the APOBEC3A includes a D131E mutation, according to residue numbering in SEQ ID NO: 1. In some embodiments, the APOBEC3A includes a W98Y mutation, according to residue numbering in SEQ ID NO: 1. In some embodiments, the APOBEC3A includes a P134Y mutation, according to residue numbering in SEQ ID NO:1.

In some embodiments, the APOBEC3A includes mutations Y130F, D131E, and Y132D, according to residue numbering in SEQ ID NO:1 (the numbering would be different in human isoform b and rat and mouse sequences, but can readily be converted). In some embodiments, the APOBEC3A includes mutations Y130F, D131Y, and Y132D, according to residue numbering in SEQ ID NO:1. In some embodiments, the APOBEC3A includes mutations W98Y and W104A, according to residue numbering in SEQ ID NO: 1. In some embodiments, the APOBEC3A includes mutations W98Y and P134Y, according to residue numbering in SEQ ID NO:1. In some embodiments, the APOBEC3A includes mutations W104A and P134Y, according to residue numbering in SEQ ID NO:1. In some embodiments, the APOBEC3A includes mutations W98Y, W104A, and Y130F, according to residue numbering in SEQ ID NO:1. In some embodiments, the APOBEC3A includes mutations W98Y, W104A, and Y132D, according to residue numbering in SEQ ID NO:1. In some embodiments, the APOBEC3A includes mutations W104A, Y130F, and P134Y, according to residue numbering in SEQ ID NO:1. In some embodiments, the APOBEC3A includes mutations W104A, Y132D, and P134Y, according to residue numbering in SEQ ID NO:1. In some embodiments, the APOBEC3A includes mutations W104A and Y130F, according to residue numbering in SEQ ID NO: 1. In some embodiments, the APOBEC3A includes mutations W104A and Y132D, according to residue numbering in SEQ ID NO:1.

Example APOBEC3A sequences are shown in SEQ ID NO:1-10 and 22-36.

The APOBEC3A protein can allow further modifications, such as addition, deletion and/or substitutions, at other amino acid locations as well. Such modifications can be substitution at one, two or three or more positions. In one embodiment, the modification is substitution at one of the positions. Such substitutions, in some embodiments, are conservative substitutions. In some embodiments, the modified APOBEC3A protein still retains the cytidine deaminase activity. In some embodiments, the modified APOBEC3A protein retains the mutations tested in the experimental examples.

In various embodiments, the APOBEC3A can be substituted with another deaminase such as A3B (APOBEC3B), A3C (APOBEC3C), A3D (APOBEC3D), A3F (APOBEC3F), A3G (APOBEC3G), A3H (APOBEC3H), A3 (APOBEC3), and AID (AICDA).

In some embodiments, provided is a fusion protein comprising a first fragment comprising an apolipoprotein B mRNA editing enzyme catalytic subunit 3B (APOBEC3B) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3C (APOBEC3C) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3D (APOBEC3D) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3F (APOBEC3F) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3G (APOBEC3G) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3H (APOBEC3H) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit 3 (APOBEC3) and a second fragment comprising a clustered regularly interspaced short palindromic repeats (CRISPR)-associated (Cas) protein. In some embodiments, provided is a fusion protein comprising a first fragment comprising an apolipoprotein B mRNA editing enzyme catalytic subunit AID (AICDA) and a second fragment comprising a clustered regularly interspaced short palindromic repeats (CRISPR)-associated (Cas) protein.

In some embodiments, the APOBEC protein is a human protein. In some embodiments, the APOBEC protein is a mouse or rat protein. Some example APOBEC proteins are listed in the table below.

| Deaminase | Example version | NCBI Accession Nos. |
|---|---|---|
| A3B (APOBEC3B) | hA3B (human) | NP_001257340, NP_004891 |
| A3C (APOBEC3C) | hA3C (human) | NP_055323 |
| A3D (APOBEC3D) | hA3D (human) | NP_689639, NP_001350710 |
| A3F (APOBEC3F) | hA3F (human) | NP_660341, NP_001006667 |
| A3G (APOBEC3G) | hA3G (human) | NP_068594, NP_001336365, NP_001336366, NP_001336367 |
| A3H (APOBEC3H) | hA3H (human) | NP_001159474, NP_001159475, NP_001159476, and NP_861438 |
| A1 (APOBEC1) | hA1 (human) | NP_001291495, NP_001635, NP_005880 |
| | mA1 (mouse) | NP_001127863, NP_112436 |
| A3 (APOBEC3) | mA3 (mouse) | NP_001153887, NP_001333970, NP_084531 |
| AID (AICDA) | hAID (human) | NP_001317272, NP_065712 |
| | mAID (mouse) | NP_033775 |
| | cAICDA (channel catfish) | NP_001187114 |

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

The term "clustered regularly interspaced short palindromic repeats (CRISPR)-associated (Cas) protein" or simply "Cas protein" refers to RNA-guided DNA endonuclease enzymes associated with the CRISPR (Clustered Regularly Interspaced Short Palindromic Repeats) adaptive immunity system in *Streptococcus pyogenes*, as well as other bacteria. Non-limiting examples of Cas proteins include *Streptococcus pyogenes* Cas9 (SpCas9), *Staphylococcus aureus* Cas9 (SaCas9), *Acidaminococcus* sp. Cas12a (Cpf1), *Lachnospiraceae bacterium* Cas12a (Cpf1), *Francisella novicida* Cas12a (Cpf1). Additional examples are provided in Komor et al., "CRISPR-Based Technologies for the Manipulation of Eukaryotic Genomes," Cell. 2017 Jan. 12; 168(1-2):20-36.

Example Cas proteins include SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b, CasX, CasY and those provided in Table C below.

TABLE C

Example Cas Proteins

| Cas protein types | Cas proteins |
|---|---|
| Cas9 proteins | Cas 9 from *Streptococcus pyogenes* (SpCas9) |
| | Cas9 from *Staphylococcus aureus* (SaCas9) |
| | Cas9 from *Neisseria meningitidis* (NmeCas9) |
| | Cas9 from *Streptococcus thermophilus* (StCas9) |
| | Cas9 from *Campylobacter jejuni* (CjCas9) |
| Cas12a (Cpf1) proteins | Cas12a (Cpf1) from *Lachnospiraceae bacterium* Cas12a (LbCpf1) |
| | Cas12a (Cpf1) from *Acidaminococcus* sp BV3L6 (AsCpf1) |
| | Cas12a (Cpf1) from *Francisella novicida* sp BV3L6 (FnCpf1) |
| | Cas12a (Cpf1) from *Smithella* sp SC K08D17 (SsCpf1) |
| | Cas12a (Cpf1) from *Porphyromonas crevioricanis* (PcCpf1) |
| | Cas12a (Cpf1) from *Butyrivibrio proteoclasticus* (BpCpf1) |
| | Cas12a (Cpf1) from *Candidatus Methanoplasma termitum* (CmtCpf1) |
| | Cas12a (Cpf1) from *Leptospira inadai* (LiCpf1) |
| | Cas12a (Cpf1) from *Porphyromonas macacae* (PmCpf1) |
| | Cas12a (Cpf1) from *Peregrinibacteria bacterium* GW2011 WA2 33 10 (Pb3310Cpf1) |
| | Cas12a (Cpf1) from *Parcubacteria bacterium* GW2011 GWC2 44 17 (Pb4417Cpf1) |
| | Cas12a (Cpf1) from *Butyrivibrio* sp. NC3005 (BsCpf1) |
| | Cas12a (Cpf1) from *Eubacterium eligens* (EeCpf1) |
| Cas12b (C2c1) proteins | Cas12b (C2c1) *Bacillus hisashii* (BhCas12b) |
| | Cas12b (C2c1) *Bacillus hisashii* with a gain-of-function mutation (see, e.g., Strecker et al., Nature Communications 10 (article 212) (2019) |
| | Cas12b (C2c1) *Alicyclobacillus kakegawensis* (AkCas12b) |
| | Cas12b (C2c1) *Elusimicrobia bacterium* (EbCas12b) |
| | Cas12b (C2c1) *Laceyella sediminis* (Ls) (LsCas12b) |
| Cas13 proteins | Cas13d from *Ruminococcus flavefaciens* XPD3002 (RfCas13d) |
| | Cas13a from *Leptotrichia wadei* (LwaCas13a) |
| | Cas13b from *Prevotella* sp. P5-125 (PspCas13b) |
| | Cas13b from *Porphyromonas gulae* (PguCas13b) |
| | Cas13b from *Riemerella anatipestifer* (RanCas13b) |
| Engineered Cas proteins | Nickases (mutation in one nuclease domain) |
| | Catalytically inactive mutant (dCas; mutations in both of the nuclease domains) |
| | Enhanced variants with improved specificity (see, e.g., Chen et al., Nature, 550, 407-410 (2017) |

In some embodiments, the Cas protein is a mutant of protein selected from the above, wherein the mutant retains the DNA-binding capability but does not introduce double strand DNA breaks.

For example, it is known that in SpCas9, residues Asp10 and His840 are important for Cas9's catalytic (nuclease) activity. When both residues are mutated to Ala, the mutant loses the nuclease activity. In another embodiment, only the Asp10Ala mutation is made, and such a mutant protein cannot generate a double strand break; rather, a nick is generated on one of the strands. Such a mutant is also referred to as a Cas9 nickase. A non-limiting example of a Cas9 nickase is provided is SEQ ID NO: 11. Non-limiting example of a Cas12a nickase are provided is SEQ ID NO:37-39. Cas proteins also encompass mutants of known Cas proteins that have certain sequence identity (e.g., 70%, 75%, 80%, 85%, 90%, 95%, 98%, 99% or more). In some embodiments, the Cas protein retains the catalytic (nuclease) activity.

In some embodiments, the Cas protein in a fusion protein of the present disclosure is a Cas12a (Cpf1, CRISPR-associated endonuclease in *Prevotella* and *Francisella* 1) protein. In conventional base editors, Cas9 is the commonly used DNA endonuclease. The Cas12a (Cpf1) has the advantage of recognizing A/T rich sequence when used together with APOBEC1 in base editors. In another surprising discovery of the present disclosure, when APOBEC1 was replaced with A3A, the editing efficiency was greatly increased (see, e.g., Examples 3-5 and FIGS. 7B, 9B and 11B). Yet, the editing efficiency of such a Cas12a-A3A can be further increased when the A3A includes a few tested mutations (Examples 3-5 and FIGS. 7B, 9B and 11B) and the editing window such a Cas12a-A3A can be narrowed to achieve more precise editing when even more tested mutations are included in A3A (Examples 3-5 and FIGS. 8B, 10B and 12B).

In some embodiments, therefore, provided is a fusion protein comprising a first fragment comprising an apolipoprotein B mRNA editing enzyme catalytic subunit 3A (APOBEC3A) and a second fragment comprising a CRISPR-associated endonuclease in *Prevotella* and *Francisella* 1 (Cpf1). Examples of APOBEC3A, as well as its alternatives (e.g., A3B (APOBEC3B), A3C (APOBEC3C), A3D (APOBEC3D), A3F (APOBEC3F), A3G (APOBEC3G), A3H (APOBEC3H), A3 (APOBEC3), or AID (AICDA)) and biological equivalents (homologues) have been disclosed above. Non-limiting example fusion sequences are provided in SEQ ID NO:40-50.

In some embodiments, the fusion protein further comprises a uracil glycosylase inhibitor (UGI). A non-limiting example of UGI is found in *Bacillus phage* AR9 (YP_009283008.1). In some embodiments, the UGI comprises the amino acid sequence of SEQ ID NO:12 or has at least at least 90% sequence identity to SEQ ID NO:12 and retains the uracil glycosylase inhibition activity.

In some embodiments, the UGI is not fused to the fusion protein, but rather is provided separately (free UGI, not fused to a Cas protein or a cytosine deaminase) when the fusion protein is used for genomic editing. In some embodiments, the free UGI is provided with the fusion protein which also includes a UGI portion.

Preferably, a peptide linker is provided between each of the fragments in the fusion protein. In some embodiments, the peptide linker has from 1 to 100 amino acid residues (or 3-20, 4-15, without limitation). In some embodiments, at least 10%, 20%, 30%, 40%, 50%, 60%, 70%, 80% or 90% of the amino acid residues of peptide linker are amino acid residues selected from the group consisting of alanine, glycine, cysteine, and serine. In some embodiments, the peptide linker has an amino acid sequence of SEQ ID NO:13 or 14.

The APOBEC3A, Cas protein, and UGI can be arranged in any manner. However, in a preferred embodiment, APOBEC3A is placed at the N-terminal side of the Cas protein. In one embodiment, the Cas protein is placed at the N-terminal side of the UGI.

In some embodiments, the fusion protein further comprises a nuclear localization sequence such as SEQ ID NO:15.

Non-limiting examples of fusion proteins include those having an amino acid sequence selected from the group consisting of SEQ ID NO:16-20.

TABLE 2

Additional Sequences

| Name | Sequence | | | | SEQ ID NO: |
|---|---|---|---|---|---|
| Cas9-Nickase | 1 MYPYDVPDYA | SPKKKRKVEA | SDKKYSIGLA | IGTNSVGWAV | ITDEYKVPSK | 11 |
| | 51 KFKVLGNTDR | HSIKKNLIGA | LLFDSGETAE | ATRLKRTARR | RYTRRKNRIC | |
| | 101 YLQEIFSNEM | AKVDDSFFHR | LEESFLVEED | KKHERHPIFG | NIVDEVAYHE | |
| | 151 KYPTIYHLRK | KLVDSTDKAD | LRLIYLALAH | MIKFRGHFLI | EGDLNPDNSD | |
| | 201 VDKLFIQLVQ | TYNQLFEENP | INASGVDAKA | ILSARLSKSR | RLENLIAQLP | |
| | 251 GEKKNGLFGN | LIALSLGLTP | NFKSNFDLAE | DAKLQLSKDT | YDDDLDNLLA | |
| | 301 QIGDQYADLF | LAAKNLSDAI | LLSDILRVNT | EITKAPLSAS | MIKRYDEHHQ | |
| | 351 DLTLLKALVR | QQLPEKYKEI | FFDQSKNGYA | GYIDGGASQE | EFYKFEIPIL | |
| | 401 EKMDGTEELL | VKLNREDLLR | KQRTFDNGSI | PHQIHLGELH | AILRRQEDFY | |
| | 451 PFLKDNREKI | EKILTFRIPY | YVGPLARGNS | RFAWMTRKSE | ETITPWNFEE | |
| | 501 VVDKGASAQS | FIERMTNFDK | NLPNEKVLPK | HSLLYEYFTV | YNELTKVKYV | |
| | 551 TEGMRKPAFL | SGEQKKAIVD | LLFKTNRKVT | VKQLKEDYFK | KIECFDSVEI | |
| | 601 SGVEDRFNAS | LGTYHDLLKI | IKDKDFLDNE | ENEDILEDIV | LTLTLFEDRE | |
| | 651 MIEERLKTYA | HLFDDKVMKQ | KLRRRYTGWG | RLSRKLINGI | RDKQSGKTIL | |
| | 701 DFLKSDGFAN | RNFMQLIHDD | SLTFKEDIQK | AQVSGQGDSL | HEHIANLAGS | |
| | 751 PAIKKGILQT | VKVVDELVKV | MGRHKPENIV | IEMARENQTT | QKGQKNSRER | |
| | 801 MKRIEEGIKE | LGSQILKEHP | VENTQLQNEK | LYLYYLQNGR | DMYVDQELDI | |
| | 851 NRLSDYDVDH | IVPQSFLKDD | SIDNKVLTRS | DKNRGKSDNV | PSEEVVKKMK | |
| | 901 NYWRQLLNAK | LITQRKFDNL | TKAERGGLSE | LDKAGFIKRQ | LVETRQITKH | |
| | 951 VAQILDSRMN | TKYDENDKLI | REVKVITLKS | KLVSDFRKDF | QFYKVREINN | |
| | 1001 YHHAHDAYLN | AVVGTALIKK | YPKLESEFVY | GDYKVYDVRK | MIAKSEQEIG | |
| | 1051 KATAKYFFYS | NIMNFFKTEI | TLANGEIRKR | PLIETNGETG | EIVWDKGRDF | |
| | 1101 ATVRKVLSMP | QVNIVKKTEV | QTGGFSKESI | LPKRNSDKLI | ARKKDWDPKK | |
| | 1151 YGGFDSPTVA | YSVLVVAKVE | KGKSKKLKSV | KELLGITIME | RSSFEKNPID | |

TABLE 2-continued

Additional Sequences

| Name | Sequence | SEQ ID NO: |
|---|---|---|
| | 1201 FLEAKGYKEV KKDLIIKLPK YSLFELENGR KRMLASAGEL QKGNELALPS<br>1251 KYVNFLYLAS HYEKLKGSPE DNEQKQLFVE QHKHYLDEII EQISEFSKRV<br>1301 ILADANLDKV LSAYNKHRDK PIREQAENII HLFTLTNLGA PAAFKYFDTT<br>1351 IDRKRYTSTK EVLDATLIHQ SITGLYETRI DLSQLGGDSP KKKRKVEAS | |
| Uracil-DNA-glycosylase inhibitor (UGI) | 1 TNLSDIIEKE TGKQLVIQES ILMLPEEVEE VIGNKPESDI LVHTAYDEST<br>51 DENVMLLTSD APEYKPWALV IQDSNGENKI KML | 12 |
| Linker 1 | 1 SGSETPGTSE SATPES | 13 |
| Linker 2 | 1 SGGS | 14 |
| Nuclear localization sequence | 1 PKKKRKV | |
| Fusion protein 1 | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIY DYDPLYKEAL QMLRDAGAQV<br>151 SIMTYDEFKH CWDTFVDHQG CPFQPWDGLD EHSQALSGRL RAILQNQGNS<br>201 GSETPGTSES ATPESDKKYS IGLAIGTNSV GWAVITDEYK VPSKKFKVLG<br>251 NTDRHSIKKN LIGALLFDSG ETAEATRLKR TARRRYTRRK NRICYLQEIF<br>301 SNEMAKVDDS FFHRLEESFL VEEDKKHERH PIFGNIVDEV AYHEKYPTIY<br>351 HLRKKLVDST DKADLRLIYL ALAHMIKFRG HFLIEGDLNP DNSDVDKLFI<br>401 QLVQTYNQLF EENPINASGV DAKAILSARL SKSRRLENLI AQLPGEKKNG<br>451 LFGNLIALSL SLTPNFKSNF DLAEDAKLQL SKDTYDDDLD NLLAQIGDQY<br>501 ADLFLAAKNL SDAILLSDIL RVNTEITKAP LSASMIKRYD EHHQDLTLLK<br>551 ALVRQQLPEK YKEIFFDQSK NGYAGYIDGG ASQEEFYKFI KPILEKMDGT<br>601 EELLVKLNRE DLLRKQRTFD NGSIPHQIHL GELHAILRRQ EDFYPFLKDN<br>651 REKIEKILTF RIPYYVGPLA RGNSRFAWMT RKSEETITPW NFEEVVDKGA<br>701 SAQSFIERMT NFDKNLPNEK VLPKHSLLYE YFTVYNELTK VKYVTEGMRK<br>751 PAFLSGEQKK AIVDLLFKTN RKVTVKQLKE DYFKKIECFD SVEISGVEDR<br>801 FNASLGTYHD LLKIIKDKDF LDNEENEDIL EDIVLTLTLF EDREMIEERL<br>851 KTYAHLFDDK VMKQLKRRRY TGWGRLSRKL INGIRDKQSG KTILDFLKSD<br>901 GFANRNFMQL IHDDSLTFKE IDQKAQVSGQ GDSLHEHIAN LAGSPAIKKG<br>951 ILQTVKVVDE LVKVMGRHKP ENIVIEMARE NQTTQKGQKN SRERMKRIEE<br>1001 GIKELGSQIL HEKPVENTQL QNEKLYLYYL QNGRDMYVDQ ELDINRLSDY<br>1051 DVDHIVPQSF LKDDSIDNKV LTRSDKNRGK SDNVPSEEVV KKMKNYWRQL<br>1101 LNAKLITQRK FDNLTKAERG GLSELDKAGF IKRQLVETRQ ITKHVAQILD<br>1151 SRMNTKYDEN DKLIREVKVI TLKSKLVSDF RKDFQFYKVR EINNYHHAHD<br>1201 AYLNAVVGTA LIKKYPKLES EFVYGDYKVY DVRKMIAKSE QEIGKATAKY<br>1251 FFYSNIMNFF KTEITLANGE IRKRPLIETN GETGEIVWDK GRDFATVRKV<br>1301 LSMPQVNIVK KTEVQTGGFS KESILPKRNS DKLIARKKDW DPKKYGGFDS<br>1351 PTVAYSVLVV AKVEKGKSKK LKSVKELLGI TIMERSSFEK NPIDFLEAKG<br>1401 YKEVKKDLII KLPKYSLFEL ENGRKRMLAS AGELQKGNEL ALPSKYVNFL<br>1451 YLASHYEKLK GSPEDNEQKQ LFVEQHKHYL DEIIEQISEF SKRVILADAN<br>1501 LDKVLSAYNK HRDKPIREQA ENIIHLFTLT NLGAPAAFKY FDTTIDRKRY<br>1551 TSTKEVLDAT LIHQSITGLY ETRIDLSQLG GDSGGSTNLS DIIEKETGKQ<br>1601 LVIQESILML PEEVEEVIGN KPESDILVHT AYDESTDENV MLLTSDAPEY<br>1651 KPWALVIQDS NGENKIKMLS GGSPKKKRKV | 16 |
| Fusion protein 2 (Y130F) | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIF DYDPLYKEAL QMLRDAGAQV<br>151 SIMTYDEFKH VWDTFVDHQG CPFQPWDGLD EHSQALSGRL RAILQNQGNS<br>201 GSETPGTSES ATPESDKKYS IGLAIGTNSV GWAVITDEYK VPSKKFKVLG<br>251 NTDRHSIKKN LIGALLFDSG ETAEATRLKR TARRRYTRRK NRICYLQEIF<br>301 SNEMAKVDDS FFHRLEESFL VEEDKKHERH PIFGNIVDEV AYHEKYPTIY<br>351 HLRKKLVDST DKADLRLIYL ALAHMIKFRG HFLIEGDLNP DNSDVDKLFI<br>401 QLVQTYNQLF EENPINASGV DAKAILSARL SKSRRLENLI AQLPGEKKNG<br>451 LFGNLIALSL GLTPNFKSNF DLAEDAKLQL SKDTYDDDLD NLLAQIGDQY<br>501 ADLFLAAKNL SDAILLSDIL RVNTEITKAP LSASMIKRYD EHHQDLTLLK<br>551 ALVRQQLPEK YKEIFFDQSK NGYAGYIDGG ASQEEFYKFI KPILEKMDGT<br>601 EELLVKLNRE DLLRKQRTFD NGSIPHQIHL GELHAILRRQ EDFYPFLKDN<br>651 REKIEKILTF RIPYYVGPLA RGNSRFAWMT RKSEETITPW NFEEVVDKGA<br>701 SAQSFIERMT NFDKNLPNEK VLPKHSLLYE YFTVYNELTK VKYVTEGMRK<br>751 PAFLSGEQKK QIVDLLFKTN RKVTVKQLKE DYFKKIECFD SVEISGVEDR<br>801 FNASLGTYHD LLKIIKDKDF LDNEENEDIL EDIVLTLTLF EDREMIEERL<br>851 KTYAHLFDDK VMKQLKRRRY TGWGRLSRKL INGIRDKQSG KTILDFLKSD<br>901 GFANRNFMQL IHDDSLTFKE IDQKAQVSGQ GDSLHEHIAN LAGSPAIKKG<br>951 ILQTVKVVDE KVKVMGRHKP ENIVIEMARE NQTTQKGQKN SRERMKRIEE<br>1001 GIKELGSQIL KEHPVENTQL QNEKLYLYYL QNGRDMYVDQ ELDINRLSDY<br>1051 DVDHIVPQSF LKDDSIDNKV LTRSDKNRGK SDNVPSEEVV KKMKNYWRQL<br>1101 LNAKLITQRK FDNLTKAERG GLSELDKAGF IKRQLVETRQ ITKHVAQILD<br>1151 SRMNTKYDEN DKLIREVKVI TLKSKLVSDF RKDFQFYKVR EINNYHHAHD | 17 |

TABLE 2-continued

Additional Sequences

| Name | Sequence | SEQ ID NO: |
|---|---|---|
| | 1201 AYLNAVVGTA LIKKYPKLES EFVYGDYKVY DVRKMIAKSE QEIGKATAKY<br>1251 FFYSNIMNFF KTEITLANGE IRKRPLIETN GETGEIVWDK GRDFATVRKV<br>1301 LSMPQVNIVK KTEVQTGGFS KESILPKRNS DKLIARKKDW DPKKYGGFDS<br>1351 PTVAYSVLVV AKVEKGKSKK LKSVKELLGI TIMERSSFEK NPIDFLEAKG<br>1401 YKEVKKDLII KLPKYSLFEL ENGRKRMLAS AGELQKGNEL ALPSLYVNFL<br>1451 YLASHYEKLK GSPEDNEQKQ LFVEQHKHYL DEIIEQISEF SKRVILADAN<br>1501 LDKVLSAYNK HRDKPIREQA ENIIHLFTLT NLGAPAAFKY FDTTIDRKRY<br>1551 TSTKEVLDAT LIHQSITGLY ETRIDLSQLG GDSGGSTNLS DIIEKETGKQ<br>1601 LVIQESILML PEEVEEVIGN KPESDILVHT AYDESTDENV MLLTSDAPEY<br>1651 KPWALVIQDS NGENKIKMLS GGSPKKKRKV | |
| Fusion protein 3<br>(Y132D) | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIY D<u>D</u>DPLYKEAL QMLRDAGAQV<br>151 SIMTYDEFKH CWDTFVDHQG CPFQPWDGLD EHSQALSGRL RAILQNOGNS<br>201 GSETPGTSES ATPESDKKYS IGLAIGTNSV GWAVITDEYK VPSKKFKVLG<br>251 NTDRHSIKKN LIGALLFDSG ETAEATRLKR TARRRYTRRK NRICYLQEIF<br>301 SNEMAKVDDS FFHRLEESFL VEEDKKHERH PIFGNIVDEV AYHEKYPTIY<br>351 HLRKKLVDST DKADLRLIYL ALAHMIKFRG HFLIEGDLNP DNSDVDKLFI<br>401 QLVQTYNQLF EENPINASGV DAKAILSARL SKSRRLENLI AQLPGEKKNG<br>451 LFGNLIALSL GLTPNFKSNF DLAEDAKLQL SKDTYDDDLD NLLAQIGDQY<br>501 ADLFLAAKNL SDAILLSDIL RVNTEITKAP LSASMIKRYD EHHQDLTLLK<br>551 ALVRQQLPEK YKEIFFDQSK NGYAGYIDGG ASQEEFYKFI KPILEKMDGT<br>601 EELLVKLNRE DLLRKQRTFD NGSIPHQIHL GELHAILRRQ EDFYPFLKDN<br>651 REKIEKILTF RIPYYVGPLA RGNSRFAWMT RKSEETITPW NFEEVVDKGA<br>701 SAQSFIERMT NFDKNLPNEK VLPKHSLLYE YFTVYNELTK VKYVTEGMRK<br>751 PAFLSGEQKK AIVDLLFKTN RKVTVKQLKE DYFKKIECFD SVEISGVEDR<br>801 FNASLGTYHD LLKIIKDKDF LDNEENEDIL EDIVLTLTLF EDREMIEERL<br>851 KTYAHLFDDK VMKQLKRRY TGWGRLSRKL INGIRDKQSG KTILDFLKSD<br>901 GFANRNFMQL IHDDSLTFKE DIQKAQVSGQ GDSLHEHIAN LAGSPAIKKG<br>951 ILQTVKVVDE LVKVMGRHKP ENIVIEMARE NQTTQKGQKN SRERMKRIEE<br>1001 GIKELGSQIL KEHPVENTQL QNEKLYLYYL QNGRDMYVDQ ELDINRLSDY<br>1051 DVDHIVPQSF LKDDSIDNKV LTRSDKNRGK SDNVPSEEVV KKMKNYWRQL<br>1101 LNAKLITQRK FDNLTKAERG GLSELDKAGF IKRQLVETRQ ITKHVAQILD<br>1151 SRMNTKYDEN DKLIREVKVI TLKSKLVSDF RKDFQFYKVR EINNYHHAHD<br>1201 AYLNAVVGTA LIKKYPKLES EFVYGDYKVY DVRKMIAKSE QEIGKATAKY<br>1251 FFYSNIMNFF KTEITLANGE IRKRPLIETN GETGEIVWDK GRDFATVRKV<br>1301 LSMPQVNIVK KTEVQTGGFS KESILPKRNS DKLIARKKDW DPKKYGGFDS<br>1351 PTVAYSVLVV AKVEKGKSKK LKSVKELLGI TIMERSSFEK NPIDFLEAKG<br>1401 YKEVKKDLII KLPKYSLFEL ENGRKRMLAS AGELQKGNEL ALPSYVNFL<br>1451 YLASHYEKLK GSPEDNEQKQ LFVEQHKHYL DEIIEQISEF SKRVILADAN<br>1501 LDKVLSAYNK HRDKPIREQA ENIIHLFTLT NLGAPAAFKY FDTTIDRKRY<br>1551 TSTKEVLDAT LIHQSITGLY ETRIDLSQLG GDSGGSTNLS DIIEKETGKQ<br>1601 LVIQESILML PEEVEEVIGN KPESDILVHT AYDESTDENV MLLTSDAPEY<br>1651 KPWALVIQDS NGENKIKMLS GGSPKKKRKV | 18 |
| Fusion protein 4<br>(W104A) | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFS<u>A</u>GCAGEV RAFLQENTHV RLRIFAARIY DYDPLYKEAL QMLRDAGAQV<br>151 SIM<u>T</u>YDEFKH CWDTFVDHQG CPFQPWDGLD EHSQALSGRL RAILQNOGNS<br>201 GSETPGTSES ATPESDKKYS IGLAIGTNSV GWAVITDEYK VPSKKFKVLG<br>251 NTDRHSIKKN LIGALLFDSG ETAEATRLKR TARRRYTRRK NRICYLQEIF<br>301 SNEMAKVDDS FFHRLEESFL VEEDKKHERH PIFGNIVDEV AYHEKYPTIY<br>351 HLRKKLVDST DKADLRLIYL ALAHMIKFRG HFLIEGDLNP DNSDVDKLFI<br>401 QLVQTYNQLF EENPINASGV DAKAILSARL SKSRRLENLI AQLPGEKKNG<br>451 LFGNLIALSL GLTPNFKSNF DLAEDAKLQL SKDTYDDDLD NLLAQIGDQY<br>501 ADLFLAAKNL SDAILLSDIL RVNTEITKAP LSASMIKRYD EHHQDLTLLK<br>551 ALVRQQLPEK YEIKFFDQSK NGYAGYIDGG ASQEEFYKFI KPILEKMDGT<br>601 EELLVKLNRE DLLRKQRTFD NGSIPHQIHL GELHAILRRQ EDFYPFLKDN<br>651 REKIEKILTF RIPYYVGPLA RGNSRFAWMT RKSEETITPW NFEEVVDKGA<br>701 SAQSFIERMT NFDKNLPNEK VLPKHSLLYE YFTVYNELTK VKYVTEGMRK<br>751 PAFLSGEQKK AIVDLLFKTN RKVTVKQLKE DYFKKIECFD SVEISGVEDR<br>801 FNASLGTYHD LLKIIKDKDF LDNEENEDIL EDIVLTLTLF EDREMIEERL<br>851 KTYAHLFDDK VMKQLKRRY TGWGRLSRKL INGIRDKQSG KTILDFLKSD<br>901 GFANRNFMQL IHDDSLTFKE DIQKAQVSGQ GDSLHEHIAN LAGSPAIKKG<br>951 ILQTVKVVDE LVKVMGRHKP ENIVIEMARE NQTTQKGQKN SRERMKRIEE<br>1001 GIKELGSQIL KEHPVENTQL QNEKLYLYYL QNGRDMYVDQ ELDINRLSDY<br>1051 DVDHIVPQSF LKDDSIDNKV LTRSDKNRGK SDNVPSEEVV KKMKNYWRQL<br>1101 LNAKLITQRK FDNLTKAERG GLSELDKAGF IKRQLVETRQ ITKHVAQILD<br>1151 SRMNTKYDEN DKLIREVKVI TLKSKLVSDF RKDFQFYKVR EINNYHHAHD<br>1201 AYLNAVVGTA LIKKYPKLES EFVYGDYKVY DVRKMIAKSE QEIGKATAKY<br>1251 FFYSNIMNFF KTEITLANGE IRKRPLIETN GETGEIVWDK GRDFATVRKV<br>1301 LSMPQVNIVK KTEVQTGGFS KESILPKRNS DKLIARKKDW DPKKYGGFDS<br>1351 PTVAYSVLVV AKVEKGKSKK LKSVKELLGI TIMERSSFEK NPIDFLEAKG<br>1401 YKEVKKDLII KLPKYSLFEL ENGRKRMLAS AGELQKGNEL ALPSYVNFL<br>1451 YLASHYEKLK GSPEDNEQKQ LFVEQHKHYL DEIIEQISEF SKRVILADAN | 19 |

TABLE 2-continued

Additional Sequences

| Name | Sequence | SEQ ID NO: |
|---|---|---|
| | 1501 LDKVLSAYNK HRDKPIREQA ENIIHLFTLT NLGAPAAFKY FDTTIDRKRY<br>1551 TSTKEVLDAT LIHQSITGLY ETRIDLSQLG GDSGGSTNLS DIIEKETGKQ<br>1601 LVIQESILML PEEVEEVIGN KPESDILVHT AYDESTDENV MLLTSDAPEY<br>1651 KPWALVIQDS NGENKIKMLS GGSPKKKRKV | |
| Fusion protein 5 | 1 MEASPASGPR HLMDPHIFTS NFNNGIGRHK TYLCYEVERL DNGTSVKMDQ<br>51 HRGFLHNQAK NLLCGFYGRH AELRFLDLVP SLQLDPAQIY RVTWFISWSP<br>101 CFSWGCAGEV RAFLQENTHV RLRIFAARIY YDPLYKEAL QMLRDAGAQV<br>151 SIMTYDEFKH CWDTFVDHQG CPFQPWDGLD EHSQALSGRL RAILQNQGNS<br>201 GSETPGTSES ATPESDKKYS IGLAIGTNSV GWAVITDEYK VPSKKFKVLG<br>251 NTDRHSIKKN LIGALLFDSG ETAEATRLKR TARRRYTRRK NRICYLQEIF<br>301 SNEMAKVDDS FFHRLEESFL VEEDKKHERH PIFGNIVDEV AYHEKYPTIY<br>351 HLRKKLVDST DKADLRLIYL ALAHMIKFRG HFLIEGDLNP DNSDVDKLFI<br>401 QLVQTYNQLF EENPINASGV DAKAILSARL SKSRRLENLI AQLPGEKKNG<br>451 LFGNLIALSL GLTPNFKSNF DLAEDAKLQL SKDTYDDDLD NLLAQIGDQY<br>501 ADLFLAAKNL SDAILLSDIL RVNTEITKAP LSASMIKRYD EHHQDLTLLK<br>551 ALVRQQLPEK YKEIFFDQSK NGYAGYIDGG ASQEEFYKFI KPILEKMDGT<br>601 EELLVKLNRE DLLRKQRTFD NGSIPHQIHL GELHAILRRQ EDFYPFLKDN<br>651 REKIEKILTF RIPYYVGPLA RGNSRFAWMT RKSEETITPW NFEEVVDKGA<br>701 SAQSFIERMT NFDKNLPNEK VLPKHSLLYE YFTVYNELTK VKYVTEGMRK<br>751 PAFLSGEQKK AIVDLLFKTN RKVTVKQLKE DYFKKIECFD SVEISGVEDR<br>801 FNASLGTYHD LLKIIKDKDF LDNEENEDIL EDIVLTLTLF EDREMIEERL<br>851 KTYAHLFDDK VMKQLKRRRY TGWGRLSRKP INGIRDKQSG KTILDFLKSD<br>901 GFANRNFMQL IHDDSLTFKE DIQKAQVSGQ GDSLHEHIAN LAGSPAIKKG<br>951 ILQTVKVVDE LVKVMGRHKP ENIVIEMARE NQTTQKGQKN SRERMKRIEE<br>1001 GIKELGSQIL KEHPVENTQL QNEKLYLYYL QNGRDMYVDQ ELDINRLSDY<br>1051 DVDHIVPQSF LKDDSIDNKV LTRSDKNRGK SDNVPSEEVV KKMKNYWRQL<br>1101 LNAKLITQRK FDNLTKAERG GLSELDKAGF IKRQLVETRQ ITKHVAQILD<br>1151 SRMNTKYDEN DKLIREVKVI TLKSKLVSDF RKDFQFYKVR EINNYHHAHD<br>1201 AYLNAVVGTA LIKKYPKLES EFVYGDYKVY DVRKMIAKSE QEIGKATAKY<br>1251 FFYSNIMNFF KTEITLANGE IRKRPLIETN GETGEIVWDK GRDFATVRKV<br>1301 LSMPQVNIVK KTEVQTGGFS KESILPKRNS DKLIARKKDW DPKKYGGFDS<br>1351 PTVAYSVLVV AKVEKGKSKK LKSVKELLGI TIMERSSFEK NPIDFLEAKG<br>1401 YKEVKKDLII KLPKYSLFEL ENGRKRMLAS AGELQKGNEL ALPSKYVNFL<br>1451 YLASHYELKL GSPEDNEQKQ LFVEQHKHYL DEIIEQISEF SKRVILADAN<br>1501 LDKVLSAYNK HRDKPIREQA ENIIHLFTLT NLGAPAAFKY FDTTIDRKRY<br>1551 TSTKEVLDAT LIHQSITGLY ETRIDLSQLG GDSGGSTNLS DIIEKETGKQ<br>1601 LVIQESILML PEEVEEVIGN KPESDILVHT AYDESTDENV MLLTSDAPEY<br>1651 KPWALVIQDS NGENKIKMLS GGSPKKKRKV | 20 |
| DNA construct | 1 Atatgccaag tacgcccct attgacgtca atgacggtaa atggcccgcc<br>51 tggcattatg cccagtacat gaccttatgg gactttccta cttgcagta<br>101 catctacgta ttagtcatcg ctattaccat ggtgatgcgg ttttggcagt<br>151 acatcaatgg gcgtggatag cggtttgact cacggggatt tccaagtctc<br>201 caccccattg acgtcaatgg gagtttgttt tggcaccaaa atcaacggga<br>251 cttttccaaaa tgtcgtaaca actccgcccc attgacgcaa atgggcggta<br>301 ggcgtgtacg gtgggaggtc tatataagca gagctggttt agtgaaccgt<br>351 cagatccgct agagatccgg ggccgctaat acgactcact ataggagag<br>401 ccgccaccat ggaagccagc ccagcatccg ggcccagaca cttgatggat<br>451 ccacacatat tcacttccaa ctttaacaat ggcattggaa ggcataagac<br>501 ctacctgtgc tacgaagtgg agcgcctgga caatggcacc tcggtcaaga<br>551 tggaccagca caggggcttt ctacacaacc aggctaagaa tcttctctgt<br>601 ggcttttacg gccgccatgc ggagctgcgc ttcttggacc tggttccttc<br>651 tttgcagttg gacccggccc agatctacag ggtcacttgg ttcatctcct<br>701 ggagccctg cttctcctgg ggctgtgccg gggaagtgcg tgcgttcctt<br>751 caggagaaca cacacgtgag actgcgtatc ttcgctgccc gcatctatga<br>801 ttacgacccc ctatataagg aggcactgca aatgctgcgg gatgctgggg<br>851 cccaagtctc catcatgacc tacgatgaat ttaagcactg ctgggacacc<br>901 tttgtggacc accaggggatg tcccttccag ccctgggatg gactagatga<br>951 gcacagccaa gccctgagtg ggaggctgcg ggccattctc cagaatcagg<br>1001 gaaacagcgg cagcgagact cccgggacct cagagtccgc cacacccgaa<br>1051 agtgataaaa agtattctat tggtttagcc atcggcacta attccgttgg<br>1101 atgggctgtc ataaccgatg aatacaaagt accttcaaag aaatttaagg<br>1151 tgttgggaa cacagaccgt cattcgatta aaaagaatct tatcggtgcc<br>1201 ctcctattcg atagtggcga aacggcagag gcgactcgcc tgaaacgaac<br>1251 cgctcggaga aggtatacac gtcgcaagaa ccgaatatgt tacttacaag<br>1301 aaatttttag caatgagatg gccaaagttg acgattcttt ctttcaccgt<br>1351 ttggaagagt ccttccttgt cgaaggaggac aagaaacatg aacggcaccc<br>1401 catctttgga aacatagtag atgaggtggc atatcatgaa aagtacccaa<br>1451 cgatttatca cctcagaaaa agctagttta actcaactga taaagcggac<br>1501 ctgaggttaa tctacttggc ctgcccat atgataaagt tccgtgggca<br>1551 cttttctcatt gagggtgatc taaatccgga caactcggat gtcgacaaac<br>1601 tgttcatcca gttagtacaa acctataatc agttgtttga agagaaccct<br>1651 ataaatgcaa gtggcgtgga tgcgaaggct attcttagcg cccgcctctc<br>1701 taaatcccga cggctagaaa acctgatcgc acaattaccc ggagagaaga<br>1751 aaaatgggtt gttcggtaac cttatagcgc tctcactagg cctgacacca | 21 |

TABLE 2-continued

Additional Sequences

| Name | Sequence | SEQ ID NO: |
|---|---|---|
| | 1801 aattttaagt cgaacttcga cttagctgaa gatgccaaat tgcagcttag | |
| | 1851 taaggacacg tacgatgacg atctcgacaa tctactggca caaattggag | |
| | 1901 atcagtatgc ggacttattt ttggctgcca aaaaccttag cgatgcaatc | |
| | 1951 ctcctatctg acatactgag agttaatact gagattacca aggcgccgtt | |
| | 2001 atccgcttca atgatcaaaa ggtacgatga acatcaccaa gacttgacac | |
| | 2051 ttctcaaggc cctagtccgt cagcaactgc ctgagaaata taaggaaata | |
| | 2101 ttctttgatc agtcgaaaaa cgggtacgca ggttatattg acggcggagc | |
| | 2151 gagtcaagag gaattctaca agtttatcaa acccatatta gagaagatgg | |
| | 2201 atgggacgga agagttgctt gtaaaactca atcgcgaaga tctactgcga | |
| | 2251 aagcagcgga cttccgacaa cggtagcatt ccacatcaaa tccacttagg | |
| | 2301 cgaattgcat gctatactta gaaggcagga ggattttat ccgttcctca | |
| | 2351 aagacaatcg tgaaaagatt gagaaaatcc taacctttcg cataccttac | |
| | 2401 tatgtgggac ccctggcccg agggaactct cggttcgcat ggatgacaag | |
| | 2451 aaagtccgaa gaaacgatta ctccatggaa ttttgaggaa gttgtcgata | |
| | 2501 aaggtgcgtc agctcaatcg ttcatcgaga ggatgaccaa ctttgaccag | |
| | 2551 aatttaccga acgaaaaagt attgcctaag cacagtttac tttacgagta | |
| | 2601 tttcacagtg tacaatgaac tcacgaaagt taagtatgtc actgagggca | |
| | 2651 tgcgtaaacc cgcctttcta agcggagaac agaagaaagc aatagtagat | |
| | 2701 ctgttattca agaccaaccg caaagtgaca gttaagcaat tgaaagagga | |
| | 2751 ctactttaag aaaattgaat gcttcgattc tgtcgagatc tccggggtag | |
| | 2801 aagatcgatt taatgcgtca cttggtacgt atcatgacct cctaaagata | |
| | 2851 attaaagata aggacttcct ggataacgaa gagaatgaag atatcttaga | |
| | 2901 agatatagtg ttgactctta ccctctttga agatcgggaa atgattgagg | |
| | 2951 aaagactaaa aacatacgct cacctgttcg acgataaggt tatgaaacag | |
| | 3001 ttaaagaggc gtcgctatac gggctgggga cgattgtcgc ggaaacttat | |
| | 3051 caacgggata agagacaagc aaagtggtaa aactattctc gattttctaa | |
| | 3101 agagcgacgg cttcgccaat aggaacttta tgcagctgat ccatgatgac | |
| | 3151 tctttaacct tcaaagagga tatacaaaag gcacaggttt ccggacaagg | |
| | 3201 ggactcattg cacgaacata ttgcgaatct tgctggttcg ccagccatca | |
| | 3251 aaaagggcat actccagaca gtcaaagtag tggatgagct agttaaggtc | |
| | 3301 atgggacgtc acaaaccgga aacattgta atcgagatgg cacgcgaaaa | |
| | 3351 tcaaacgact cagaagggc aaaaaaacag tcgagagcgg atgaagagaa | |
| | 3401 tagaagaggg tattaaagaa ctgggcagcc agatcttaaa ggagcatcct | |
| | 3451 gtggaaaata cccaattgca gaacgagaaa ctttacctct attacctaca | |
| | 3501 aaatgaagg gacatgtatg ttgatcagga actggacata aaccgtttat | |
| | 3551 ctgattacga cgtcgatcac attgtacccc aatccttttt gaaggacgat | |
| | 3601 tcaatcgaca ataaagtgct tacacgctcg gataagaacc gagggaaaag | |
| | 3651 tgacaatgtt ccaagcgagg aagtcgtaaa gaaaatgaag aactattgag | |
| | 3701 ggcagctcct aaatgcgaaa ctgataacgc aaagaaagtt cgataactta | |
| | 3751 actaaagctg agaggggtgg cttgtctgaa cttgacaagg ccggatttat | |
| | 3801 taaacgtcag ctcgtggaaa cccgccaaat cacaaagcat gttgcacaga | |
| | 3851 tactagattc ccgaatgaat acgaaatacg acgagaacga taagctgatt | |
| | 3901 cgggaagtca agtaatcac tttaaagtca aaattggtgt cggacttcag | |
| | 3951 aaaggatttt caattctata agttaggga gataaataac taccaccatg | |
| | 4001 cgcacgacgc ttatcttaat gccgtcgtag ggaccgcact cattaagaaa | |
| | 4051 tacccgaagc tagaaagtga gtttgtgtat ggtgattaca aagtttatga | |
| | 4101 cgtccgtaag atgatcgcga aaagcgaaca ggagataggc aaggctacag | |
| | 4151 ccaaatactt cttttattct aacattatga atttctttaa gacggaaatc | |
| | 4201 actctggcaa acggagagat acgcaaacga cctttaattg aaaccaatgg | |
| | 4251 ggagacaggt gaaatcgtat gggataaggg ccgggacttc gcgacggtca | |
| | 4301 gaaaagtttt gtccatgccc caagtcaaca tagtaaagaa aactgaggtg | |
| | 4351 cagaccggag ggttttcaaa ggaatcgatt cttccaaaaa ggaatagtga | |
| | 4401 taagctcatc gctcgtaaaa aggactggga cccgaaaaag tacggtggct | |
| | 4451 tcgatagccc tacagttgcc tattctgtcc tagtagtggc aaaagttgag | |
| | 4501 aagggaaaat ccaagaaact gaagtcagtc aaagaattat tggggataac | |
| | 4551 gattatggag cgctcgtctt ttgaaaagaa ccccatcgac ttccttgagg | |
| | 4601 cgaaaggtta caaggaagta aaaaaggatc tcataattaa actaccaaag | |
| | 4651 tatagtctgt ttgagttaga aaatggccga aaacggatgt tggctagcgc | |
| | 4701 cggagagctt caaaagggga acgaactcgc actaccgtct aaatacgtga | |
| | 4751 atttcctgta tttagcgtcc cattacgaga agttgaaagg ttcacctgaa | |
| | 4801 gataacgaac agaagcaact ttttgttgag cagcacaaac attatctcga | |
| | 4851 cgaaatcata gagcaaattt cggaattcag taagagagtc atcctagctg | |
| | 4901 atgccaatct ggacaaagta ttaagcgcat acaacaagca cagggataaa | |
| | 4951 cccatacgtg agcaggcgga aaatattatc catttgttta ctcttaccaa | |
| | 5001 cctcggcgct ccagccgcat tcaagtattt tgacacaacg gattcaccaa | |
| | 5051 aacgatacac ttctaccaag gaggtgctag acgcgacact gattcaccaa | |
| | 5101 tccatcacgg gattatatga aactcggata gatttgtcac agcttgggg | |
| | 5151 tgactctggt ggttctacta atctgtcaga tattattgaa aaggagaccg | |
| | 5201 gtaagcaact ggttatccag gaatccatcc tcatgctccc agaggaggtg | |
| | 5251 gaagaagtca ttgggaacaa gccggaaagc gatatactcg tgcacaccgc | |
| | 5301 ctacgacgag agcaccgacg agaatgtcat gcttctgact agcgacgccc | |
| | 5351 ctgaatacaa gccttggcct ctggtcatac aggatagcaa cggtgagaac | |
| | 5401 aagattaaga tgctctctgg tggttctccc aagaagaaga ggaaagtcta | |
| | 5451 accggtcatc atcaccatca ccattgagtt taaacccgct gatcagcctc | |
| | 5501 gactgtgcct tctagttgcc agccatctgt tgtttgcccc tcccccgtgc | |
| | 5551 cttccttgac cctggaaggt gccactccca ctgtcctttc ctaataaaat | |

TABLE 2-continued

Additional Sequences

| Name | Sequence | SEQ ID NO: |
|---|---|---|
| | 5601 gaggaaattg catcgcattg tctgagtagg tgtcattcta ttctgggggg<br>5651 tggggtgggg caggacagca aggggagga ttgggaagac aatagcaggc<br>5701 atgctgggga tgcggtgggc tctatggctt ctgaggcgga aagaaccagc<br>5751 tggggctcga taccgtcgac ctctagctag agcttggcgt aatcatggtc<br>5801 atagctgttt cctgtgtgaa attgttatcc gctcacaatt ccacacaaca<br>5851 tacgagccgg aagcataaag tgtaaagcct agggtgccta atgagtgagc<br>5901 taactcacat taattgcgtt gcgctcactg cccgctttcc agtcgggaaa<br>5951 cctgtcgtgc cagctgcatt aatgaatcgg ccaacgcgcg gggagaggcg<br>6001 gtttgcgtat tgggcgctct tccgcttcct cgctcactga ctcgctgcgc<br>6051 tcggtcgttc ggctgcggcg agcggtatca gctcactcaa aggcggtaat<br>6101 acgttatcc acagaatcag ggataacgc aggaaagaac atgtgagcaa<br>6151 aaggccagca aaaggccagg aaccgtaaaa aggccgcgtt gctggcgttt<br>6201 ttccataggc tccgcccccc tgacgagcat cacaaaaatc gacgctcaag<br>6251 tcagaggtgg cgaaacccga caggactata aagataccag gcgtttcccc<br>6301 ctggaagctc cctcgtgcgc tctcctgttc cgaccctgcc gcttaccgga<br>6351 tacctgtccg cctttctccc ttcgggaagc gtggcgcttt ctcatagctc<br>6401 acgctgtagg tatctcagtt cggtgtaggt cgttcgctcc aagctgggct<br>6451 gtgtgcacga accccccgtt cagcccgacc gctgcgcctt atccggtaac<br>6501 tatcgtcttg agtccaaccc ggtaagacac gacttatcgc cactggcagc<br>6551 agccactggt aacaggatta gcagagcgag gtatgtaggc ggtgctacag<br>6601 agttcttgaa gtggtggcct aactacggct acactagaag aacagtattt<br>6651 ggtatctgcg ctctgctgaa gccagttacc ttcggaaaaa gagttggtag<br>6701 ctcttgatcc ggcaaacaaa ccaccgctgg tagcggtggt ttttttgttt<br>6751 gcaagcagca gattacgcgc agaaaaaaag gatctcaaga agatcctttg<br>6801 atcttttcta cggggtctga cgctcagtgg aacgaaaact cacgttaagg<br>6851 gattttggtc atgagattat caaaaaggat cttcacctag atccttttaa<br>6901 attaaaaatg aagttttaaa tcaatctaaa gtatatatga gtaaacttgg<br>6951 tctgacagtt accaatgctt aatcagtgag gcacctatct cagcgatctg<br>7001 tctatttcgt tcatccatag ttgcctgact ccccgtcgtg tagataacta<br>7051 cgatacggga gggcttacca tctggcccca gtgctgcaat gataccgcga<br>7101 gacccacgct caccggctcc agatttatca gcaataaacc agccagccgg<br>7151 aagggccgag cgcagaagtg gtcctgcaac tttatccgcc tccatccagt<br>7201 ctattaattg ttgccgggaa gctagagtaa gtagttcgcc agttaatagt<br>7251 ttgcgcaacg ttgttgccat tgctacaggc atcgtggtgt cacgctcgtc<br>7301 gtttggtatg gcttcattca gctccggttc ccaacgatca aggcgagtta<br>7351 catgatcccc catgttgtgc aaaaaagcgg ttagctcctt cggtcctccg<br>7401 atcgttgtca gaagtaagtt ggccgcagtg ttatcactca tggttatggc<br>7451 agcactgcat aattctctta ctgtcatgcc atccgtaaga tcttttcgtc<br>7501 tgactggtga gtactcaacc aagtcattct gagaatagtg tatgcggcga<br>7551 ccgagttgct cttgcccggc gtcaatacgg gataataccg cgccacatag<br>7601 cagaacttta aaagtgctca tcattggaaa acgttcttcg ggcgaaaac<br>7651 tctcaaggat cttaccgctg ttgagatcca gttcgatgta acccactcgt<br>7701 gcacccaact gatcttcagc atcttttact ttcaccagcg tttctgggtg<br>7751 agcaaaaaca ggaaggcaaa atgccgcaaa aaagggaata agggcgacac<br>7801 ggaaatgttg aatactcata ctcttccttt ttcaatatta ttgaagcatt<br>7851 tatcagggtt attgtctcat gagcggatac atatttgaat gtatttagaa<br>7901 aaataaacaa ataggggttc cgcgcacatt tccccgaaaa gtgccacctg<br>7951 acgtcgacgg atcgggagat cgatctcccg atcccctagg gtcgactctc<br>8001 agtacaatct gctctgatgc cgcatagtta agccagtatc tgctccctgc<br>8051 ttgtgtgttg gaggtcgctg agtagtgcgc gagcaaaatt taagctacaa<br>8101 caaggcaagg cttgaccgac aattgcatga agaatctgct tagggttagg<br>8151 cgttttgcgc tgcttcgcga tgtacgggcc agatatacgc gttgacattg<br>8201 attattgact agttattaat agtaatcaat tacggggtca ttagttcata<br>8251 gcccatatat ggagttccgc gttacataac ttacgtaaa tggcccgcct<br>8301 ggctgaccgc ccaacgaccc ccgcccattg acgtcaataa tgacgtatgt<br>8351 tcccatagta acgccaatag ggactttcca ttgacgtcaa tgggtggagt<br>8401 atttacggta aactgcccac ttggcagtac atcaagtgta tc | |
| Lb-dCas12a | 1 MSKLEKFTNC YSLSKTLRFK AIPVGKTQEN IDNKRLLVED EKRAEDYKGV<br>51 KKLLDRYYLS FINDVLHSIK LKNLNNYISL FRKKTRTEKE NKELENLEIN<br>101 LRKEIAKAFK GNEGYKSLFK KDIIETILPE FLDDKDEIAL VNSFNGFTTA<br>151 FTGFFDNREN MFSEEAKSTS IAFRCINENL TRYISNMDIF EKVDAIFDKH<br>201 EVQEIKEKIL NSDYDVEDFF EGEFFNFVLT QEGIDVYNAI IGGFVTESGE<br>251 KIKGLNEYIN LYNQKTKQKL PKFKPLYKQV LSDRESLSFY GEGYTSDEEV<br>301 LEVFRNTLNK NSEIFSSIKK LEKLFKNFDE YSSAGIFVKN GPAISTISKD<br>351 IFGEWNVIRD KWNAEYDDIH LKKKAVVTEK YEDDRRKSFK KIGSFSLEQL<br>401 QEYADADLSV VEKLKEIIIQ KVDEIYKVYG SSEKLFDADF VLEKSLKKND<br>451 AVVAIMKDLL DSVKSFENYI KAFFGEGKET NRDESFYGDF VLAYDILLKV<br>501 DHIYDAIRNY VTQKPYSKDK FKLYFQNPQF MGGWDKDKET DYRATILRYG<br>551 SKYYLAIMDK KYAKCLQKID KDDVNGNYEK INYKLLPGPN KMLPKVFFSK<br>601 KWMAYYNPSE DIQKIYKNGT FKKGDMFNLN DCHKLIDFFK DSISRYPKWS<br>651 NAYDFNFSET EKYKDIAGFY REVEEQGYKV SFESASKKEV DKLVEEGKLY<br>701 MFQIYNKDFS DKSHGTPNLH TMYFKLLFDE NNHGQIRLSG GAELFMRRAS<br>751 LKKEELVVHP ANSPIANKNP DNPKKTTTLS YDVYKDKRFS EDQYELHIPI<br>801 AINKCPKNIF KINTEVRVLL KHDDNPYVIG IARGERNLLY IVVVDGKGNI<br>851 VEQYSLNEII NNFNGIRIKT DYHSLLDKKE KERFEARQNW TSIENIKELK | 37 |

TABLE 2-continued

Additional Sequences

| Name | Sequence | SEQ ID NO: |
|---|---|---|
| | 901 AGYISQVVHK ICELVEKYDA VIALADLNSG FKNSRVKVEK QVYQKFEKML<br>951 IDKLNYMVDK KSNPCATGGA LKGYQITNKF ESFKSMSTQN GFIFYIPAWL<br>1001 TSKIDPSTGF VNLLKTKYTS IADSKKFISS FDRIMYVPEE DLFEFALDYK<br>1051 NFSRTDADYI KKWKLYSYGN RIRIFRNPKK NNVFDWEEVC LTSAYKELFN<br>1101 KYGINYQQGD IRALLCEQSD KAFYSSFMAL MSLMLQMRNS ITGRTDVAFL<br>1151 ISPVKNSDGI FYDSRNYEAQ ENAILPKNAD ANGAYNIARK VLWAIGQFKK<br>1201 AEDEKLDKVK IAISNKEWLE YAQTSVKHGS | |
| AsCas12a | 1 MTQFEGFTNL YQVSKTLRFE LIPQGKTLKH IQEQGFIEED KARNDHYKEL<br>51 KPIIDRIYKT YADQCLQLVQ LDWENLSAAI DSYRKEKTEE TRNALIEEQA<br>101 TYRNAIHDYF IGRTDNLTDA INKRHAEIYK GLFKAELFNG KVLKQLGTVT<br>151 TTEHENALLR SFDKFTTYFS GFYENRKNVF SAEDISTAIP HRIVQDNFPK<br>201 FKENCHIFTR LITAVPSLRE HFENVKKAIG IFVSTSIEEV FSFPFYNQLL<br>251 TQTQIDLYNQ LLGGISREAG TEKIKGLNEV LNLAIQKNDE TAHIIASLPH<br>301 RFIPLFKQIL SDRNTLSFIL EEFKSDEEVI QSFCKYKTLL RNENVLETAE<br>351 ALFNELNSID LTHIFISHKK LETISSALCD HWDTLRNALY ERRISELTGK<br>401 ITKSAKEKVQ RSLKHEDINL QEIISAAGKE LSEAFKQKTS EILSHAHAAL<br>451 DQPLPTTLKK QEEKEILKSQ LDSLLGLYHL LDWFAVDESN EVDPEFSARL<br>501 TGIKLEMEPS LSFYNKARNY ATKKPYSVEK FKLNFQMPTL ASGWDVNKEK<br>551 NNGAILFVKN GLYYLGIMPK QKGRYKALSF EPTEKTSEGF DKMYYDYFPD<br>601 AAKMIPKCST QLKAVTAHFQ THTTPILLSN NFIEPLEITK EIYDLNNPEK<br>651 EPKKFQTAYA KKTGDQKGYR EALCKWIDFT RDFLSKYTKT TSIDLSSLRP<br>701 SSQYKDLGEY YAELNPLLYH ISFQRIAEKE IMDAVETGKL YLFQIYNKDF<br>751 AKGHHGKPNL HTLYWTGLFS PENLAKTSIK LNGQAELFYR PKSRMKRMAH<br>801 RLGEKMLNKK LKDQKTPIPD TLYQELYDYV NHRLSHDLSD EARALLPNVI<br>851 TKEVSHEIIK DRRFTSDKFF FHVPITLNYQ AANSPSKFNQ RVNAYLKEHP<br>901 ETPIIGIDRG ERNLIYITVI DSTGKILEQR SLNTIQQFDY QKKLDNREKE<br>951 RVAARQAWSV VGTIKDLKQG YLSQVIHEIV DLMIHYQAVV VLENLNFGFK<br>1001 SKRTGIAEKA VYQQFEKMLI DKLNCLVLKD YPAEKVGGVL NPYQLTDQFT<br>1051 SFAKMGTQSG FLFYVPAPYT SKIDPLTGFV DPFVWKTIKN HESRKHFLEG<br>1101 FDFLHYDVKT GDFILHFKMN RNLSFQRGLP GFMPAWDIVF EKNETQFDAK<br>1151 GTPFIAGKRI VPVIENHRFT GRYRDLYPAN ELIALLEEKG IVFRDGSNIL<br>1201 PKLLENDDSH AIDTMVALIR SVLQMRNSNA ATGEDYINSP VRDLNGVCFD<br>1251 SRFQNPEWPM DADANGAYHI ALKGQLLLNH LKESKDLKLQ NGISNQDWLA<br>1301 YIQELRN | 38 |
| FnCas12a | 1 MSIYQEFVNK YSLSKTLRFE LIPQGKTLEN IKARGLILDD EKRAKDYKKA<br>51 KQIIDKYHQF FIEEILSSVC ISEDLLQNYS DVYFKLKKSD DDNLQKDFKS<br>101 AKDTIKKQIS EYIKDSEKFK NLFNQNLIDA KKGQESDLIL WLKQSKDNGI<br>151 ELFKANSDIT DIDEALEIIK SFKGWTTYFK GFHENRKNVY SSNDIPTSII<br>201 YRIVDDNLPK FLENKAKYES LKDKAPEAIN YEQIKKDLAE ELTFDIDYKT<br>251 SEVNQRVFSL DEVFEIANFN NYLNQSGITK FNTIIGGKFV NGENTKRKGI<br>301 NEYINLYSQQ INDKTLKKYK MSVLFKQILS DTESKSFVID KLEDDSDVVT<br>351 TMQSFYEQIA AFKTVEEKSI KETLSLLFDD LKAQKLDLSK IYFKNDKSLT<br>401 DLSQQVFDDY SVIGTAVLEY ITQQIAPKNL DNPSKKEQEL IAKKTEKAKY<br>451 LSLETIKLAL EEFNKHRDID KQCRFEEILA NFAAIPMIFD EIAQNKDNLA<br>501 QISIKYQNQG KKDLLQASAE DDVKAIKDLL DQTNNLLHKL KIFHISQSED<br>551 KANILDKDEH FYLVFEECYF ELANIVPLYN KIRNYITQKP YSDEKFKLNF<br>601 ENSTLANGWD KNKEPDNTAI LFIKDDKYYL GVMNKKNNKI FDDKAIKENK<br>651 GEGYKKIVYK LLPGANKMLP KVFFSAKSIK FYNPSEDILR IRNHSTHTKN<br>701 GSPQKGYEKF EFNIEDCRKF IDFYKQSISK HPEWKDFGFR FSDTQRYNSI<br>751 DEFYREVENQ GYKLTFENIS ESYIDSVVNQ GKLYLFQIYN KDFSAYSKGR<br>801 PNLHTLYWKA LFDERNLQDV VYKLNGEAEL FYRKQSIPKK ITHPAKEAIA<br>851 NKNKDNPKKE SVFEYDLIKD KRFTEDKFFF HCPITINFKS SGANKFNDEI<br>901 NLLLKEKAND VHILSIDRGE RHLAYYTLVD GKGNIIKQDT FNIIGNDRMK<br>951 TNYHDKLAAI EKDRDSARKD WKKINNIKEM KEGYLSQVVH EIAKLVIEYN<br>1001 AIVVFEDLNF GFKRGRFKVE KQVYQKLEKM LIEKLNYLVF KDNEFDKTGG<br>1051 VLRAYQLTAP FETFKKMGKQ TGIIYYVPAG FTSKICPVTG FVNQLYPKYE<br>1101 SVSKSQEFFS KFDKICYNLD KGYFEFSFDY KNFGDKAAKG KWTIASFGSR<br>1151 LINFRNSDKN HNWDTREVYP TKELEKLLKD YSIEYGHGEC IKAAICGESD<br>1201 KKFFAKLTSV LNTILQMRNS KTGTELDYLI SPVADVNGNF FDSRQAPKNM<br>1251 PQDADANGAY HIGLKGLMLL GRIKNNQEGK KLNLVIKNEE YFEFVQNRNN | 39 |
| dCas12a-hA3A-BE | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISWSPCF SWGCAGEVRA FLQENTHVRL RIFAARIYDY DPLYKEALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK | 40 |

TABLE 2-continued

Additional Sequences

| Name | Sequence | SEQ ID NO: |
|---|---|---|
| | 651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKMIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | |
| dCas12a-hA3A-<br>BE-W98Y | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISYSPCF SWGCAGEVRA FLQENTHVRL RIFAARIYDY DPLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 41 |
| dCas12a-hA3A-<br>BE-W104A | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISWSPCF SAGCAGEVRA FLQENTHVRL RIFAARIYDY DPLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL | 42 |

TABLE 2-continued

Additional Sequences

| Name | Sequence | SEQ ID NO: |
|---|---|---|
| | 1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | |
| dCas12a-hA3A-BE-P134Y | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISWSPCF SWGCAGEVRA FLQENTHVRL RIFAARIYDY DYLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 43 |
| dCas12a-hA3A-BE-W98Y-W104A | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISYSPCF SAGCAGEVRA FLQENTHVRL RIFAARIYDY DPLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 44 |

TABLE 2-continued

Additional Sequences

| Name | Sequence | SEQ ID NO: |
|---|---|---|
| dCas12a-hA3A-BE-W98Y-P134Y | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISYSPCF SWGCAGEVRA FLQENTHVRL RIFAARIYDY DYLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 45 |
| dCas12a-hA3A-BE-W104A-P134Y | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISWSPCF SAGCAGEVRA FLQENTHVRL RIFAARIYDY DYLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 46 |
| dCas12a-hA3A-BE-W98Y-W104A-Y130F | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISYSPCF SAGCAGEVRA FLQENTHVRL RIFAARIFDY DPLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY | 47 |

TABLE 2-continued

Additional Sequences

| Name | Sequence | SEQ ID NO: |
|---|---|---|
| | 501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | |
| dCas12a-hA3A-BE-<br>W98Y-W104A-Y132D | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLDPSL QLDPAQIYRV<br>101 TWFISYSPCF SAGCAGEVRA FLQENTHVRL RIFAARIYDD DPLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT<br>1001 TLSYDVYKDK RFSEDQYELH IPIAINKCPK NIFKINTEVR VLLKHDDNPY<br>1051 VIGIARGERN LLYIVVVDGK GNIVEQYSLN EIINNFNGIR IKTDYHSLLD<br>1101 KKEKERFEAR QNWTSIENIK ELKAGYISQV VHKICELVEK YDAVIALADL<br>1151 NSGFKNSRVK VEKQVYQKFE KMLIDKLNYM VDKKSNPCAT GGALKGYQIT<br>1201 NKFESFKSMS TQNGFIFYIP AWLTSKIDPS TGFVNLLKTK YTSIADSKKF<br>1251 ISSFDRIMYV PEEDLFEFAL DYKNFSRTDA DYIKKWKLYS YGNRIRIFRN<br>1301 PKKNNVFDWE EVCLTSAYKE LFNKYGINYQ QGDIRALLCE QSDKAFYSSF<br>1351 MALMSLMLQM RNSITGRTDV AFLISPVKNS DGIFYDSRNY EAQENAILPK<br>1401 NADANGAYNI ARKVLWAIGQ FKKAEDEKLD KVKIAISNKE WLEYAQTSVK<br>1451 HGSPKKKRKV SGGSTNLSDI IEKETGKQLV IQESILMLPE EVEEVIGNKP<br>1501 ESDILVHTAY DESTDENVML LTSDAPEYKP WALVIQDSNG ENKIKMLSGG<br>1551 SPKKKRKV | 48 |
| dCas12a-hA3A-BE-<br>W104A-Y130F-P134Y | 1 MPKKKRKVME ASPASGPRHL MDPHIFTSNF NNGIGRHKTY LCYEVERLDN<br>51 GTSVKMDQHR GFLHNQAKNL LCGFYGRHAE LRFLDLVPSL QLDPAQIYRV<br>101 TWFISWSPCF SAGCAGEVRA FLQENTHVRL RIFAARIFDY DYLYKRALQM<br>151 LRDAGAQVSI MTYDEFKHCW DTFVDHQGCP FQPWDGLDEH SQALSGRLRA<br>201 ILQNQGNSGS ETPGTSESAT PESMSKLEKF TNCYSLSKTL RFKAIPVGKT<br>251 QENIDNKRLL VEDEKRAEDY KGVKKLLDRY YLSFINDVLH SIKLKNLNNY<br>301 ISLFRKKTRT EKENKELENL EINLRKEIAK AFKGNEGYKS LFKKDIIETI<br>351 LPEFLDDKDE IALVNSFNGF TTAFTGFFDN RENMFSEEAK STSIAFRCIN<br>401 ENLTRYISNM DIFEKVDAIF DKHEVQEIKE KILNSDYDVE DFFEGEFFNF<br>451 VLTQEGIDVY NAIIGGFVTE SGEKIKGLNE YINLYNQKTK QKLPKFKPLY<br>501 KQVLSDRESL SFYGEGYTSD EEVLEVFRNT LNKNSEIFSS IKKLEKLFKN<br>551 FDEYSSAGIF VKNGPAISTI SKDIFGEWNV IRDKWNAEYD DIHLKKKAVV<br>601 TEKYEDDRRK SFKKIGSFSL EQLQEYADAD LSVVEKLKEI IIQKVDEIYK<br>651 VYGSSEKLFD ADFVLEKSLK KNDAVVAIMK DLLDSVKSFE NYIKAFFGEG<br>701 KETNRDESFY GDFVLAYDIL LKVDHIYDAI RNYVTQKPYS KDKFKLYFQN<br>751 PQFMGGWDKD KETDYRATIL RYGSKYYLAI MDKKYAKCLQ KIDKDDVNGN<br>801 YEKINYKLLP GPNKMLPKVF FSKKWMAYYN PSEDIQKIYK NGTFKKGDMF<br>851 NLNDCHKLID FFKDSISRYP KWSNAYDFNF SETEKYKDIA GFYREVEEQG<br>901 YKVSFESASK KEVDKLVEEG KLYMFQIYNK DFSDKSHGTP NLHTMYFKLL<br>951 FDENNHGQIR LSGGAELFMR RASLKKEELV VHPANSPIAN KNPDNPKKTT | 49 |

TABLE 2-continued

Additional Sequences

| Name | Sequence | | | | | SEQ ID NO: |
|---|---|---|---|---|---|---|
| | 1001 TLSYDVYKDK | RFSEDQYELH | IPIAINKCPK | NIFKINTEVR | VLLKHDDNPY | |
| | 1051 VIGIARGERN | LLYIVVVDGK | GNIVEQYSLN | EIINNFNGIR | IKTDYHSLLD | |
| | 1101 KKEKERFEAR | QNWTSIENIK | ELKAGYISQV | VHKICELVEK | YDAVIALADL | |
| | 1151 NSGFKNSRVK | VEKQVYQKFE | KMLIDKLNYM | VDKKSNPCAT | GGALKGYQIT | |
| | 1201 NKFESFKSMS | TQNGFIFYIP | AWLTSKIDPS | TGFVNLLKTK | YTSIADSKKF | |
| | 1251 ISSFDRIMYV | PEEDLFEFAL | DYKNFSRTDA | DYIKKWKLYS | YGNRIRIFRN | |
| | 1301 PKKNNVFDWE | EVCLTSAYKE | LFNKYGINYQ | QGDIRALLCE | QSDKAFYSSF | |
| | 1351 MALMSLMLQM | RNSITGRTDV | AFLISPVKNS | DGIFYDSRNY | EAQENAILPK | |
| | 1401 NADANGAYNI | ARKVLWAIGQ | FKKAEDEKLD | KVKIAISNKE | WLEYAQTSVK | |
| | 1451 HGSPKKKRKV | SGGSTNLSDI | IEKETGKQLV | IQESILMLPE | EVEEVIGNKP | |
| | 1501 ESDILVHTAY | DESTDENVML | LTSDAPEYKP | WALVIQDSNG | ENKIKMLSGG | |
| | 1551 SPKKKRKV | | | | | |
| dCas12a-hA3A-BE-W104A-Y132D-P134Y | 1 MPKKKRKVME | ASPASGPRHL | MDPHIFTSNF | NNGIGRHKTY | LCYEVERLDN | 50 |
| | 51 GTSVKMDQHR | GFLHNQAKNL | LCGFYGRHAE | LRFLDLVPSL | QLDPAQIYRV | |
| | 101 TWFISWSPCF | SAGCAGEVRA | FLQENTHVRL | RIFAARIYDD | DYLYKRALQM | |
| | 151 LRDAGAQVSI | MTYDEFKHCW | DTFVDHQGCP | FQPWDGLDEH | SQALSGRLRA | |
| | 201 ILQNQGNSGS | ETPGTSESAT | PESMSKLEKF | TNCYSLSKTL | RFKAIPVGKT | |
| | 251 QENIDNKRLL | VEDEKRAEDY | KGVKKLLDRY | YLSFINDVLH | SIKLKNLNNY | |
| | 301 ISLFRKKTRT | EKENKELENL | EINLRKEIAK | AFKGNEGYKS | LFKKDIIETI | |
| | 351 LPEFLDDKDE | IALVNSFNGF | TTAFTGFFDN | RENMFSEEAK | STSIAFRCIN | |
| | 401 ENLTRYISNM | DIFEKVDAIF | DKHEVQEIKE | KILNSDYDVE | DFFEGEFFNF | |
| | 451 VLTQEGIDVY | NAIIGGFVTE | SGEKIKGLNE | YINLYNQKTK | QKLPKFKPLY | |
| | 501 KQVLSDRESL | SFYGEGYTSD | EEVLEVFRNT | LNKNSEIFSS | IKKLEKLFKN | |
| | 551 FDEYSSAGIF | VKNGPAISTI | SKDIFGEWNV | IRDKWNAEYD | DIHLKKKAVV | |
| | 601 TEKYEDDRRK | SFKKIGSFSL | EQLQEYADAD | LSVVEKLKEI | IIQKVDEIYK | |
| | 651 VYGSSEKLFD | ADFVLEKSLK | KNDAVVAIMK | DLLDSVKSFE | NYIKAFFGEG | |
| | 701 KETNRDESFY | GDFVLAYDIL | LKVDHIYDAI | RNYVTQKPYS | KDKFKLYFQN | |
| | 751 PQFMGGWDKD | KETDYRATIL | RYGSKYYLAI | MDKKYAKCLQ | KIDKDDVNGN | |
| | 801 YEKINYKLLP | GPNKMLPKVF | FSKKWMAYYN | PSEDIQKIYK | NGTFKKGDMF | |
| | 851 NLNDCHKLID | FFKDSISRYP | KWSNAYDFNF | SETEKYKDIA | GFYREVEEQG | |
| | 901 YKVSFESASK | KEVDKLVEEG | KLYMFQIYNK | DFSDKSHGTP | NLHTMYFKLL | |
| | 951 FDENNHGQIR | LSGGAELFMR | RASLKKEELV | VHPANSPIAN | KNPDNPKKTT | |
| | 1001 TLSYDVYKDK | RFSEDQYELH | IPIAINKCPK | NIFKINTEVR | VLLKHDDNPY | |
| | 1051 VIGIARGERN | LLYIVVVDGK | GNIVEQYSLN | EIINNFNGIR | IKTDYHSLLD | |
| | 1101 KKEKERFEAR | QNWTSIENIK | ELKAGYISQV | VHKICELVEK | YDAVIALADL | |
| | 1151 NSGFKNSRVK | VEKQVYQKFE | KMLIDKLNYM | VDKKSNPCAT | GGALKGYQIT | |
| | 1201 NKFESFKSMS | TQNGFIFYIP | AWLTSKIDPS | TGFVNLLKTK | YTSIADSKKF | |
| | 1251 ISSFDRIMYV | PEEDLFEFAL | DYKNFSRTDA | DYIKKWKLYS | YGNRIRIFRN | |
| | 1301 PKKNNVFDWE | EVCLTSAYKE | LFNKYGINYQ | QGDIRALLCE | QSDKAFYSSF | |
| | 1351 MALMSLMLQM | RNSITGRTDV | AFLISPVKNS | DGIFYDSRNY | EAQENAILPK | |
| | 1401 NADANGAYNI | ARKVLWAIGQ | FKKAEDEKLD | KVKIAISNKE | WLEYAQTSVK | |
| | 1451 HGSPKKKRKV | SGGSTNLSDI | IEKETGKQLV | IQESILMLPE | EVEEVIGNKP | |
| | 1501 ESDILVHTAY | DESTDENVML | LTSDAPEYKP | WALVIQDSNG | ENKIKMLSGG | |
| | 1551 SPKKKRKV | | | | | |

The present disclosure also provides isolated polynucleotides or nucleic acid molecules (e.g., SEQ ID NO:21) encoding the fusion proteins, variants or derivatives thereof of the disclosure. Methods of making fusion proteins are well known in the art and described herein.

Compositions and Methods

The present disclosure also provides compositions and methods. Such compositions comprise an effective amount of a fusion protein, and an acceptable carrier. In some embodiments, the composition further includes a guide RNA that has a desired complementarity to a target DNA. Such a composition can be used for base editing in a sample.

The fusion proteins and the compositions can be used for base editing. In one embodiment, a method for editing a target polynucleotide is provided, comprising contacting to the target polynucleotide a fusion protein of the present disclosure and a guide RNA having at least partial sequence complementarity to the target polynucleotide, wherein the editing comprises deamination of a cytosine (C) in the target polynucleotide.

It is shown that the presently disclosed fusion proteins can edit cytosine at any location and in any context, such as in CpC, ApC, GpC, TpC, CpA, CpG, CpC, CpT. It is surprising and unexpected, however, that these fusion proteins can edit C in a GpC dinucleotide context, and even when the C is methylated.

The contacting between the fusion protein (and the guide RNA) and the target polynucleotide can be in vitro, in particular in a cell culture. When the contacting is ex vivo, or in vivo, the fusion proteins can exhibit clinical/therapeutic significance.

EXAMPLES

Example 1: Base Editors

Human apolipoprotein B mRNA editing enzyme catalytic subunit 3A (APOBEC3A, hA3A; SEQ ID NO:1) was included in an expression vector that further included a Cas9 nickase (SEQ ID NO:11) and a uracil-DNA-glycosylase inhibitor [*Bacillus phage* AR9] (SEQ ID NO:12). The Cas9 nickase contained a Asp10Ala mutation that inactivated its double strand nuclease activity, while allowing it to introduce a nick on one of the strands.

The fusion vector, hA3A-nCas9-UGI (hA3A-BE, SEQ ID NO:21), and a sgRNA expression vector were co-transfected into eukaryotic cells (FIG. 1A) to perform C-to-T base editing at sgRNA target site in the genome. After PCR amplification of the target genomic DNA, the C-to-T base editing efficiency at targeted site in genome were determined through Sanger DNA sequencing. As illustrated in two sgRNA target sites (sgFANCF-M-L6 and sgSITE4), efficient C-to-T base editing was executed on C of GpC through co-expressing hA3A-BE and sgRNA, as compared to co-expressing BE3 (APOBEC1-nCas9-UGI) and sgRNA (FIG. 1B, dashed box).

Next, mutations Y130F (SEQ ID NO:2) and Y132D (SEQ ID NO:3) were individually introduced into the hA3A gene in the construct, thereby generating the base editor hA3A-BE-Y130F or hA3A-BE-Y132D (FIG. 2A). The Y130F and Y132D mutations in hA3A-BE narrowed the window of base editing, and further improved the editing precision of hA3A-BE (FIG. 2B).

Figure 3:
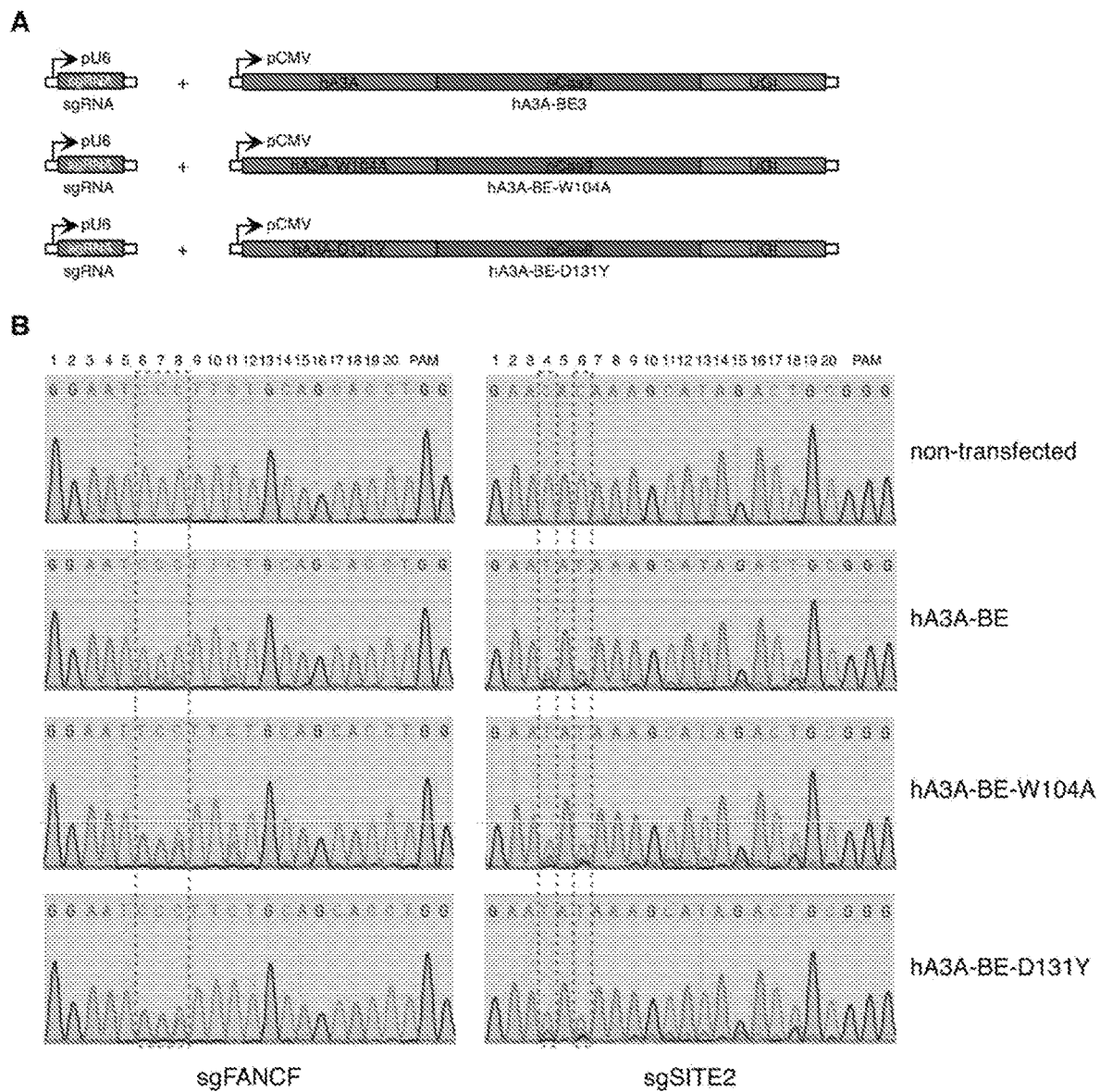
FIG. 3A-B. Construction and performance of hA3A-BE-W104A and hA3A-BE-D131Y. Panel A: Schematic diagram illustrating the co-expression of hA3A-BE/sgRNA, hA3A-BE-W104A/sgRNA or hA3A-BE-D131Y/sgRNA. Panel B: Comparing to the co-expression of hA3A-BE/sgRNA, the co-expression of hA3A-BE-W104A/sgRNA or hA3A-BE-D131Y/sgRNA induced more efficient base editing in the sgRNA targeted genomic regions (sgFANCF and sgSITE2). Dashed boxes represent the edited cytosine's. Sequences as shown in panel B, from left column to right column and from top to down, are SEQ ID NO:65-72.

Furthermore, the mutations W104A (SEQ ID NO:4) and D131Y (SEQ ID NO:5) were individually introduced into the hA3A gene of hA3A-BE, thereby generating the base editor hA3A-BE-W104A or hA3A-BE-D131Y (FIG. 3A). Both hA3A-BE-W104A and hA3A-BE-D131Y increased the efficiency of desired C to T base substitutions (FIG. 3B), achieving even higher efficiency of base editing as compared to hA3A-BE.

Figure 4:
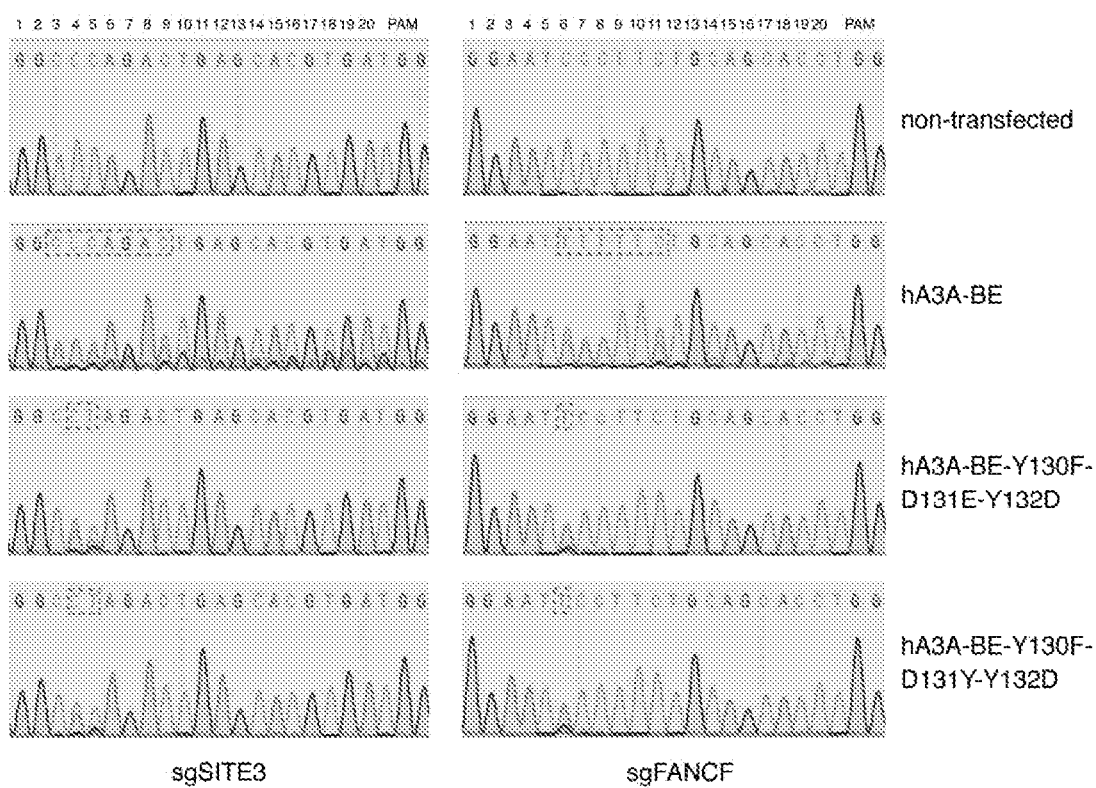
FIG. 4A-B. Construction and performance of hA3A-BE-Y130E-D131E-Y132D and hA3A-BE-Y130E-D131Y-

In a further experiment, three amino acid changes (Y130E-D131E-Y132D, SEQ ID NO:22 or Y130E-D131Y-Y132D, SEQ ID NO:23) of human APOBEC3A (hA3A) in hA3A-BE3 (FIG. 4A) were tested and it was found that these two base editors (hA3A-BE-Y130E-D131E-Y132D and hA3A-BE-Y130E-D131Y-Y132D) have more narrowed editing windows (position 4-6 in target region) and therefore higher editing precision (FIG. 4B).

Example 2: Efficient Base Editing in Methylated Regions with a Human APOBEC3A-Cas9 Fusion Base editors (BEs) enable the generation of targeted single-nucleotide mutations, but currently used rat APOBEC1-based BEs are relatively inefficient in editing cytosines in highly-methylated regions or in GpC contexts. By screening a variety of APOBEC/AID deaminases, this example shows that human APOBEC3A-conjugated BEs and versions engineered to have narrower editing windows can mediate efficient C-to-T base editing in regions with high methylation levels and GpC dinucleotide content.

Base editors (BEs), which combine a cytidine deaminase with Cas9 or Cpf1, have been successfully applied to perform targeted base editing, including C-to-T. Numerous human diseases have been reported to be driven by point mutations in genomic DNAs. With recently developed BEs, these disease-related point mutations can be potentially corrected, providing new therapeutic options. By analyzing disease-related T-to-C mutations that can be theoretically reverted to thymines by BEs, the example found that ~43% of them are on cytosines in the context of CpG dinucleotides (FIG. 5a). It is well known that C of CpG is usually methylated in mammalian cells, and methylation of C strongly suppresses cytidine deamination catalyzed by some APOBEC/AID deaminases. This example shows that CpG dinucleotide methylation hinders the C-to-T base editing by current BEs and has successfully developed BEs for efficient C-to-T base editing in highly methylated regions.

Methods and Materials
Plasmid Construction
Primer sets (hA3A_PCR_F/hA3A_PCR_R) were used to amplify the fragment Human_APOBEC3A with template pUC57-Human_APOBEC3A (synthesized by Genscript). Then the fragment Human_APOBEC3A was cloned into the SacI and SmaI linearized pCMV-BE3 (addgene, 73021) with plasmid recombination kit Clone Express® (Vazyme, C112-02) to generate the hA3A-BE3 expression vector pCMV-hAPOBEC3A-XTEN-D10A-SGGS-UGI-SGGS-NLS. hA3B-BE3, hA3C-BE3, hA3D-BE3, hA3F-BE3, hA3G-BE3, hA3H-BE3, hAID-BE3, hA1-BE3, mA3-BE3, mAID-BE3, mA1-BE3, cAICDA-BE3, expression vectors were constructed with the same strategy. The pmCDA1 expression vector pcDNA3.1_pCMV-nCas-PmCDA1-ugi pH1-gRNA (HPRT) was purchased from Addgene (79620).

Primer sets (SupF_PCR_F/SupF_PCR_R) were used to amplify the fragment SupF with template shuttle vector pSP189. Then the fragment SupF was cloned into pEASY-ZERO-BLUNT (TransGen Biotech, CB501) to generate the vector pEASY-SupF-ZERO-BLUNT.

Oligonucleotides SupF_sg1_FOR/SupF_sg1_REV and SupF_sg2_FOR/SupF_sg2_REV were annealed and ligated into BsaI linearized pGL3-U6-sgRNA-PGK-puromycin (addgene, 51133) to generate the sgRNA expression vectors psgSupF-1 and psgSupF-2 that target the SupF gene in pEASY-SupF-ZERO-BLUNT.

Two primer sets (hA3A_PCR_F/hA3A_Y130F_PCR_R) (hA3A_Y130F_PCR_F/hA3A_PCR_R) were used to amplify the Y130E-containing fragment hA3A-Y130F. Then the fragment was cloned into the ApaI and SmaI linearized hA3A-BE3 expression vector to generate the hA3A-BE3-Y130F expression vector pCMV-hAPOBEC3A_Y130E-XTEN-D10A-SGGS-UGI-SGGS-NLS. hA3A-BE3-D131Y, hA3A-BE3-Y132D, hA3A-BE3-C101S and hA3A-BE3-C106S expression vectors were constructed with the same strategy.

Primer sets (hA3A_PCR_F/hA3A_PCR_R) were used to amplify the fragment Human_APOBEC3A_Y130F with template hA3A-BE3-Y130F. Then the fragment Human_APOBEC3A_Y130F was cloned into the SacI and SmaI linearized pCMV-eBE-S3[19] to generate the hA3A-eBE-Y130F expression vector pCMV-hAPOBEC3A_Y130F-XTEN-D10A-SGGS-UGI-SGGS-NLS-T2A-UGI-NLS-P2A-UGI-NLS-T2A-UGI-NLS.
hA3A-eBE-Y132D expression vector was constructed by the similar way.

Oligonucleotides hEMX1_FOR/hEMX1_REV were annealed and ligated into BsaI linearized pGL3-U6-sgRNA-PGK-puromycin to generate sgEMX1 expression vector psgEMX1. Other sgRNA expression vectors were constructed with the same strategy.

Antibodies
Antibodies were purchased from the following sources: against alpha-tubulin (T6199)—Sigma; against Cas9 (ab204448)—Abcam.

Immunoblotting Analysis
Protein samples were incubated at 95° C. for 20 min, separated by SDS-PAGE in sample loading buffer and proteins were transferred to nitrocellulose membranes (Thermo Fisher Scientific). After blocking with TBST (25 mM Tris pH 8.0, 150 mM NaCl, and 0.1% Tween 20) containing 5% (w/v) nonfat dry milk for 2 h, the membrane was reacted overnight with indicated primary antibody. After extensive washing, the membranes were reacted with HRP-conjugated secondary antibodies for 1 h. Reactive bands were developed in ECL (Thermo Fisher Scientific) and detected with Amersham Imager 600.

Cell Culture and Transfection
HEK293T cells from ATCC were maintained in DMEM (10566, Gibco/Thermo Fisher Scientific)+10% FBS (16000-

044, Gibco/Thermo Fisher Scientific) and regularly tested to exclude *Mycoplasma* contamination.

The dCas9-Suntag-TetCD system was used to induce targeted demethylation of the genomic regions with natively high levels of methylation, e.g., FANCF, MAGEA1 and MSSK1 regions. The dCas9-DNMT3a-DNMT3l system was used to induce targeted methylation of the genomic regions with natively low levels of methylation, e.g., VEGFA and PDL1 regions. HEK293T cells were transfected by using LIPOFECTAMINE 2000 (Life, Invitrogen) with 3 μg pCAG-scFvGCN4sfGFPTET1CD (synthesized by Genscript) and 1 μg sgRNA expression vector or with 3 μg dCas9-DNMT3a-DNMT3l (synthesized by Genscript) and 1 μg sgRNA expression vector. Blasticidin (10 μg/ml, Sigma, 15205) and puromycin (1 μg/ml, Merck, 540411) were added 24 h after transfection. One week later, a portion of cells were collected to determine DNA methylation level and others were stored in liquid nitrogen for base editing. The sgRNAs used to induce genomic DNA methylation/demethylation are the ones used to induce base editing.

For base editing in genomic DNA, HEK293T cells were seeded in a 24-well plate at a density of $1.6 \times 10^5$ per well and transfected with 200 μl serum-free Opti-MEM that contained 5.04 μl LIPOFECTAMINE LTX (Life, Invitrogen), 1.68 μl LIPOFECTAMINE plus (Life, Invitrogen), 1 μg BE3 expression vector (or hA3A-BE3, hA3A-BE3-Y130F, hA3A-BE3-D131Y, hA3A-BE3-Y132D, hA3A-BE3-C101S, hA3A-BE3-C106S, hA3A-eBE-Y130F, hA3A-eBE-Y132D expression vector) and 0.68 μg sgRNA expression vector. After 72 hr, the genomic DNA was extracted from the cells with QuickExtract™ DNA Extraction Solution (QE09050, Epicentre) or the cells were lysed in 2×SDS loading buffer for western blot.

For base editing in plasmid vector, 293T cells were seeded in a 6-well plate at a density of $3 \times 10^5$ per well and transfected with 500 μl serum-free Opti-MEM that contained 4 μl LIPOFECTAMINE LTX (Life, Invitrogen), 2 μl LIPOFECTAMINE plus (Life, Invitrogen), 1 μg BE3 expression vector (or hA3A-BE3, hA3B-BE3, hA3C-BE3, hA3D-BE3, hA3F-BE3, hA3G-BE3, hA3H-BE3, hAID-BE3, hA1-BE3, mA3-BE3, mAID-BE3, mA1-BE3, cAICDA-BE3 or pmCDA1 expression vector) and 0.5 μg sgRNA expression vector. After 24 hr, these cells were transfected with 500 μl serum-free Opti-MEM that contained 4 μl LIPOFECTAMINE LTX, 2 μl LIPOFECTAMINE plus and 1.5 μg un-methylated (or methylated) pEASY-SupF-ZERO-BLUNT. After 48 hr, the plasmids were extracted from the cells with TIANprep Mini Plasmid Kit (DP103-A, TIANGEN) or the cells were lysed in 2×SDS loading buffer for western blot.

Bisulfite Sequencing Analysis

Genomic DNA was isolated and treated with bisulfite according to the instruction of EZ DNA methylation-direct Kit (Zymo Research, D5021). The bisulfite-treated DNA was PCR-amplified with Taq™ Hot Start Version (Takara, R007B). The PCR products were ligated into T-Vector pMDTM19 (Takara, 3271). Eight clones were picked out and sequenced by Sanger sequencing (Genewiz). The primers used for bisulfite PCR were listed in Supplementary Table 2.

Plasmid DNA Methylation

For in vitro methylation, 1 μl CpG methyltransferase (M.SssI, Life, EM0821) was used to methylate 2 μl plasmid DNA in a 20 μl reaction. After in vitro methylation, pEASY-SupF-ZERO-BLUNT was restricted with BstUI (NEB, R0518S) to determine the methylation level.

Blue/White Colony Screening

The plasmids extracted from transfected cells were transformed into *E. coli* strain MBM7070 ($lacZ^{aug\_amber}$), which were grown on LB plates containing 50 μg/ml kanamycin, 1 mM IPTG and 0.03% Bluo-gal (Life, Invitrogen) at 37° C. overnight and then at room temperature for another day (for maximal color development). The cumulative base editing frequency is calculated by dividing the number of white colonies with the number of total colonies.

DNA Library Preparation and Sequencing

Target genomic sites were PCR amplified by high-fidelity DNA polymerase PrimeSTAR HS (Clonetech) with primers flanking each examined sgRNA target site. The PCR primers used to amplify target genomic sequences were listed in Supplementary Table 2. Indexed DNA libraries were prepared by using the TruSeq ChIP Sample Preparation Kit (Illumina) with some minor modifications. Briefly, the PCR products were fragmented by Covaris 5220 and then amplified by using the TruSeq ChIP Sample Preparation Kit (Illumina). After being quantitated with Qubit High-Sensitivity DNA kit (Life, Invitrogen), PCR products with different tags were pooled together for deep sequencing by using the Illumina NextSeq 500 (2×150) or Hiseq X Ten (2×150) at CAS-MPG Partner Institute for Computational Biology Omics Core, Shanghai, China. Raw read qualities were evaluated by FastQC. For paired-end sequencing, only R1 reads were used. Adaptor sequences and read sequences on both ends with Phred quality score lower than 28 were trimmed. Trimmed reads were then mapped with the BWA-MEM algorithm (BWA v0.7.9a) to target sequences. After being piled up with samtools (v0.1.18), indels and base substitutions were further calculated.

Indel Frequency Calculation

Indels were estimated in the aligned regions spanning from upstream eight nucleotides of the target site to downstream 19 nucleotides of PAM sites (50 bp). Indel frequencies were subsequently calculated by dividing reads containing at least one inserted and/or deleted nucleotide by all the mapped reads at the same region.

Base Substitution Calculation

Base substitutions were selected at each position of the examined sgRNA target sites that mapped with at least 1,000 independent reads, and obvious base substitutions were only observed at the targeted base editing sites. Base substitution frequencies were calculated by dividing base substitution reads by total reads.

Calculation of BE-Targetable Genetic Variants

The single nucleotide variants (SNVs) from NCBI ClinVar database were overlapped with the pathogenic human allele sequence from NCBI dbSNP database to calculate the pathogenic T-to-C and A-to-G mutations. In 3,089 pathogenic T-to-C or A-to-G mutations, 2,499 are potentially editable by SpCas9-BE3, SaCas9-BE3, dLbCpf1-BE or xCas9-BE3 with nearby PAM sequences. These 2,499 BE-targetable SNVs are further sub-classified according to their 3' adjacent base preferences, i.e., CpA, CpC, CpG and CpT (FIG. 5a).

Statistical Analysis

P values were calculated from one-tailed Student's t test in this study.

Data Availability

The deep-sequencing data from this study are deposited in the NCBI Gene Expression Omnibus (accession no. GSE114999) and the National Omics Data Encyclopedia (accession no. OEP000030).

Results

This example first examined the base editing efficiency of a commonly used BE, the rat APOBEC1 (rA1)-based BE3, in human cells having either increased or decreased levels of methylation. When DNA methylation was promoted by DNMT3 in regions with native low methylation levels, editing frequencies by BE3 decreased. In addition, when DNA methylation was reduced by TET1 in regions with native high methylation levels, BE3-induced editing frequencies increased accordingly. These results suggest that the canonical rA1-based BE3 is less efficient in editing cytosines embedded in highly methylated genomic regions. Notably, C-to-T editing was suppressed by DNA methylation at both CpG and flanking non-CpG sites (median decrement~28%, $P=2\times10^{-8}$ for CpG sites and ~51%, $P=7\times10^{40}$ for flanking non-CpG sites). APOBECs deaminate cytidines on single-stranded DNA in a processive manner. CpG methylation may affect the sliding of APOBEC and therefore impairs its binding on the flanking non-CpG sites for deamination.

To screen for efficient base editing in high-methylation background, a series of BEs was obtained by fusing Cas9 nickase with fifteen different APOBEC/AID deaminases (FIG. 5b). This example tested these BEs then in an *E. coli*-derived vector system (FIG. 5b), which has been previously used to probe mutations. In unmethylated vectors, these BEs showed varied levels of base editing. The BEs containing human APOBEC3A (hA3A-BE3, mean editing frequency~39%), human APOBEC3B (hA3B-BE3, mean editing frequency~33%) or human AID (hAID-BE3, mean editing frequency~28%) mediated base editing at levels that are comparable to BE3 (mean editing frequency~31%) (FIG. 5c). Whereas in methylated vectors, only hA3A-BE3 induced efficient base editing (mean editing frequency~35%), compared to relatively low editing efficiencies induced by BE3 (mean editing frequency~12%) or other examined BEs (mean editing frequencies~1%-20%) (FIG. 5c). Of note, protein products of hA3A-BE3, BE3 and other examined BEs are comparable (FIG. 5d).

Similar to the observation in *E. coli*-derived vectors, hA3A-BE3 exhibited significantly higher base editing frequencies than rA1-based BE3 in all tested genomic regions, either those with a native high-methylation background (median~1.7-fold, $P=2\times10^{-10}$, FIG. 5e,f) or those with an induced high-methylation condition (median~1.8-fold, $P=5\times10^{-4}$). Thus, using hA3A as the deaminase module in BE could generally achieve high base editing efficiency in genomic regions with high methylation levels.

The base editing on cytosines in a GpC context was observed to be generally inefficient by rA1-based BEs. While, this example found that hA3A-BE3 could induce efficient base editing on most of cyto sines at GpC sites in both endogenously and induced high-methylation backgrounds (FIG. 5e). This example further compared their editing efficiencies under both endogenously and induced low-methylation backgrounds and observed a similar superiority of hA3A-BE3 over BE3 on editing cytosines in the GpC context (FIG. 5g,h). Statistical analysis confirmed that the base editing efficiency induced by hA3A-BE3 was significantly higher than that induced by BE3 on cytosines in the GpC context in either high—(median~2.3-fold, $P=1\times10^{-5}$) or low—(median~1.8-fold, $P=6\times10^{-9}$) methylation conditions. Notably, hA3A-BE3-mediated base editing was as efficient as BE3 at cytosines in non-GpC contexts in all tested low-methylation regions (median~1.1-fold, P=0.045). This example also found that hA3A-BE3 yielded less non-C-to-T conversion than BE3 in both high—(median~97% by hA3A-BE3 comparing to ~94% by BE3, $P=3\times10$) and low-methylation regions (median~92% by hA3A-BE3 comparing to ~90% by BE3, $P=4\times10^{-6}$). Both BE3 and hA3A-BE3 induced less non-C-to-T conversion at CpG sites with high methylation status than at CpG sites with low methylation status (median~95% vs~90%, $P=3\times10^{-5}$ for BE3 and median~95% vs~92%, $P=5\times10^{-4}$ for hA3A-BE3). This example also found that hA3A-BE3 induced higher indel frequencies than BE3 (median~2 in both high- and low-methylation regions). Such an increase may be caused by the high deaminase activity of hA3A, which can trigger downstream DNA repair pathways to generate DNA double strand breaks.

The results suggest that hA3A-BE3 can efficiently induce base editing in a broader scope (FIG. 5). However, the editing window of hA3A-BE3 is wider (~12 nt, position 2-13 in the sgRNA target site) than that of BE3 (~5 nt, position 4-8). As the wide editing window of hA3A-BE3 may result from the high deaminase activity of hA3A, mutations in hA3A that can reduce deaminase activity might correspondingly narrow the editing window of hA3A-BE3. Designated mutations (Y130F, D131Y or Y132D) successfully narrowed the editing window with little effect on the base editing efficiency, whereas mutations in the zinc-coordination motif almost completely eliminated the deaminase activity (C101S and C106S).

This example then focused on two engineered hA3A-BE3s (hA3A-BE3-Y130F and hA3A-BE3-Y132D), which have similar editing windows (position 3-8 for hA3A-BE3-Y130F and position 3-7 for hA3A-BE3-Y132D) as BE3 (position 4-8). In highly-methylated regions, hA3A-BE3-Y130F and hA3A-BE3-Y132D induced higher editing efficiencies than BE3 at all editable sites in overlapping editing windows (position 4-7) (FIG. 6a, cytosines in pink and FIG. 6b, median~2.3 fold, P=0.002 for hA3A-BE3-Y130F and median~1.2 fold, P=0.03 for hA3A-BE3-Y132D). For cytosines outside of overlapping editing windows, hA3A-BE3-Y132D induced C-to-T editing frequencies similar to BE3 while hA3A-BE3-Y130F induced higher editing frequencies (FIG. 6a, cytosines in black). Similar to the original hA3A-BE3, both engineered hA3A-BE3-Y130F and hA3A-BE3-Y132D edited cytosines in GpC contexts more efficiently than BE3 in overlapping editing windows (FIG. 6c,d, median~2.3 fold, $P=3\times10^{-5}$ for hA3A-BE3-Y130F and median~1.9 fold, P=0.002 for hA3A-BE3-Y132D). Protein expression levels of hA3A-BE3-Y130F and hA3A-BE3-Y132D were very similar to that of BE3 (FIG. 6e), though the two engineered hA3A-BEs induced higher C-to-T editing efficiencies (FIG. 6b,d). In terms of product purity, we found that hA3A-BE3-Y130F yielded less non-C-to-T conversion (median~96.3% by hA3A-BE3-Y130F comparing to ~95.6% by BE3, P=0.03 in high-methylation regions, median~92% by hA3A-BE3-Y130F comparing to ~90% by BE3, P=0.002 in low-methylation regions) but more indels (median~2.1 fold, P=0.0002 in high-methylation regions, median~1.3 fold in low-methylation regions, P=0.12) than BE3. The product purity induced by hA3A-BE3-Y132D was higher than BE3 in native low-methylation regions (median~93% by hA3A-BE3-Y132D comparing to ~90% by BE3, P=0.001), but lower in native high-methylation regions (median~94.9% by hA3A-BE3-Y132D comparing to ~95.6% by BE3, P=0.03). Nevertheless, indel frequencies induced by hA3A-BE3-Y132D were comparable to those induced by BE3 at all tested sites (median~1.2 fold in both high- and low-methylation regions).

To further enhance C-to-T base editing system, three copies of the 2A-uracil DNA glycosylase inhibitor (UGI) sequence were fused to the C-terminus of hA3A-BE3-Y130F and hA3A-BE3-Y132D to develop hA3A-eBE-Y130F and hA3A-eBE-Y132D. In low-methylation regions, hA3A-eBE-Y130F and hA3A-eBE-Y132D induced significantly higher editing efficiencies (FIG. 6f,g, median~1.2 fold, P=0.0004 for hA3A-eBE-Y130F and median~1.2 fold, P=0.004 for hA3A-eBE-Y132D), higher product purity (FIG. 6h, median~96% by hA3A-eBE-Y130F comparing to ~94% by hA3A-BE3-Y130F, P=0.006 and median~96% by hA3A-eBE-Y132D comparing to ~92% by hA3A-BE3-Y132D, P=0.004) and lower indel frequencies (FIG. 6i, median decrement~21%, P=4×10$^{-5}$ for hA3A-eBE-Y130F and median decrement~9%, P=0.03 for hA3A-eBE-Y132D) than hA3A-BE3-Y130F and hA3A-BE3-Y132D, respectively. In high-methylation regions, hA3A-eBE-Y130F and hA3A-eBE-Y132D induced significantly higher product purity (median~97% by hA3A-eBE-Y130F comparing to ~95% by hA3A-BE3-Y130F, P=0.003 and median~97% by hA3A-eBE-Y132D comparing to ~95% by hA3A-BE3-Y132D, P=0.003) and lower indel frequencies (median decrement~23%, P=2×10$^{-7}$ for hA3A-eBE-Y130F and median decrement~21%, P=4×10$^{-5}$ for hA3A-eBE-Y132D) than hA3A-BE3-Y130F and hA3A-BE3-Y132D, respectively, though editing efficiencies remained the same (median~1 fold for hA3A-eBE-Y130F and hA3A-eBE-Y132D). Together, these results indicated that hA3A-BE3-Y130F, hA3A-BE3-Y132D, hA3A-eBE-Y130F and hA3A-eBE-Y132D can mediate highly efficient base editing in narrowed editing windows compared to the original hA3A-BE3 in all examined contexts.

Here, this example demonstrates that hA3A-BE3 and its engineered forms, can comprehensively induce efficient base editing in all examined contexts, including both methylated DNA regions and GpC dinucleotides. It is contemplated that hA3A can also be conjugated with other Cas proteins to further expand the scope of base editing.

Example 3. Gene Editing of Human DYRK1A with dCas12a-hA3A Base Editors

This example tested base editors that combined a Cas12a (Cpf1) and various mutant human A3A proteins.

Methods

Construction of dCas12a-hA3A-BE Expression Vector pUC57-hA3A (synthesized by Genscript Biotechnology Co., Ltd.) was used as a template, using suitable primers. PCR was carried out to obtain the coding sequence of hA3A, and a fragment homologous to the linearized vector at both ends was subjected to gel electrophoresis purification. After purification by gel electrophoresis, the fragment was recombined into the linearized dCas12a-BE vector produced by SacI and SmaI by plasmid recombinant kit Clone Express® to obtain expression vector dCas12a-hA3A-BE.

Construction of dCas12a-hA3A-BE-W98Y Expression Vector

Using dCas12a-hA3A-BE as a template, two PCR products with a W98Y mutation and a homology arm, and a homologous segment with a linearized vector. After purification by gel electrophoresis, the two fragments were simultaneously recombined into the linearized dCas12a-hA3A-BE vector generated by ApaI and SmaI using plasmid recombinant kit Clone Express® to obtain expression vector dCas12a-hA3A-BE-W98Y.

Likewise, expression vectors dCas12a-hA3A-BE-W104A, dCas12a-hA3A-BE-P134Y, dCas12a-hA3A-BE-W98Y-W104A, dCas12a-hA3A-BE-W98Y-P134Y, dCas12a-hA3A-BE-W104A-P134Y, dCas12a-hA3A-BE-W98Y-W104A-Y130F, dCas12a-hA3A-BE-W98Y-W104A-Y132D, dCas12a-hA3A-BE-W104A-Y130E-P134Y, and dCas12a-hA3A-BE-W104A-Y132D-P134Y. Relevant sequences are shown in Tables 1 and 2.

Construction of gRNA Expression Plasmid

The nucleotide sequence was annealed to primers and the annealed product was ligated into the gRNA expression vector pLb-Cas12a-pGL3-U6-sgRNAdigested with restriction endonuclease BsaI using T4 DNA ligase. gRNA expression plasmid sgDYRK1A targeting human DYRK1A site was obtained.

Eukaryotic Cell Transfection

The sgDYRK1A and each of dCas12a-hA3A-BE, dCas12a-hA3A-BE-W98Y, dCas12a-hA3A-BE-W104A, dCas12a-hA3A-BE-P134Y, dCas12a-hA3A-BE-W98Y-W104A, dCas12a-hA3A-BE-W98Y-P134Y, dCas12a-hA3A-BE-W104A-P134Y, dCas12a-hA3A-BE-W98Y-W104A-Y130F, dCas12a-hA3A-BE-W98Y-W104A-Y132D, dCas12a-hA3A-BE-W104A-Y130E-P134Y, dCas12a-hA3A-BE-W104A-Y132D-P134Y were mixed into 200 μl Opti-MEM at a ratio of 0.68 ug: 1 μg, added with 1.68 μl of LIPOFECTAMINE plus, and 5.04 μl of LIPOFECTAMINE LTX was added, and allowed to stand at room temperature for 5 minutes. 500 μl DMEM (+10% FBS) medium was add for 24-well plates and transfected HEK293T cells 160,000. After 12 h, replaced with fresh medium containing 1% double antibody (cyanin). The cells were harvested after 60 hours of incubation.

EditR Analysis of Sanger Sequencing Results

DNA sanger sequencing results were analyzed using EditR software (moriaritylab.shinyapps.io/editr_v10/). EditR is a web version of the sanger sequencing result analysis software developed in 2018 (Kluesner M G, Nedveck D A, Lahr W S, et al. EditR: A Method to Quantify Base Editing from Sanger Sequencing [J]. The CRISPR Journal, 2018, 1(3): 239-250.). EditR is a simple, accurate and efficient analytical tool for processing the sequencing results of DNA samples based on the sgRNA sequence by using the sanger sequencing signal, and finally outputting the base editing efficiency at the sgRNA target site.

The sequencing results are shown FIGS. 11 and 12. The EditR analysis results are presented in FIGS. 7 and 8. When fused to the conventional cytosine deaminase, A1 (APOBEC1), Cas12a (cpf1) exhibited poor efficiency (see, e.g., FIG. 7B, the first column in each group). The combination with the hA3A wild-type protein greatly increased the editing efficiency (see, e.g., the second column). Interestingly, the A3A mutation W98Y, W104A, P134Y or the combination of each two further increased the editing efficiency (FIG. 7). Also, the editing window such a Cas12a-A3A can be narrowed to achieve more precise editing when the mutation Y130F or Y132D is further included in A3A (FIG. 8).

Example 4. Gene Editing of Human SITE6 with dCas12a-hA3A Base Editors

This example tested various indicated base editors with the human gene SITE6.

The experimental procedure is similar to Example 3. The sequencing results are shown in detail in FIGS. 15 and 16 (two replicates of experimental data). The EditR analysis results are shown in FIGS. 9 and 10. Like in Example 3, the Cas12a-A3A editor had greater editing efficiency than the Cas12a-A1 and the A3A mutation W98Y, W104A, P134Y or the combination of each two further increased the editing efficiency (FIG. 9). Also, the editing window such a Cas12a-

A3A can be narrowed to achieve more precise editing when the mutation Y130F or Y132D is further included in A3A (FIG. 10).

Example 5. Gene Editing of Human RUNX1 with dCas12a-hA3A Base Editors

This example tested various indicated base editors with the human gene RUNX1.

The experimental procedure is similar to Example 3. The sequencing results are shown in detail in FIGS. 17 and 18 (two replicates of experimental data). The EditR analysis results are shown in FIGS. 11 and 12. Like in Example 3, the Cas12a-A3A editor had greater editing efficiency than the Cas12a-rA1, and the A3A mutation W98Y, W104A, P134Y or the combination of each two further increased the editing efficiency (FIG. 11). Also, the editing window such a Cas12a-A3A can be narrowed to achieve more precise editing when the mutation Y130F or Y132D is further included in A3A (FIG. 12).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

SEQUENCE LISTING

```
<160> NUMBER OF SEQ ID NOS: 184

<210> SEQ ID NO 1
<211> LENGTH: 199
<212> TYPE: PRT
<213> ORGANISM: Artificial Sequence
<220> FEATURE:
<223> OTHER INFORMATION: Synthetic

<400> SEQUENCE: 1

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 2
<211> LENGTH: 199
```

```
<212> TYPE: PRT
<213> ORGANISM: Artificial Sequence
<220> FEATURE:
<223> OTHER INFORMATION: Synthetic

<400> SEQUENCE: 2

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Phe Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 3
<211> LENGTH: 199
<212> TYPE: PRT
<213> ORGANISM: Artificial Sequence
<220> FEATURE:
<223> OTHER INFORMATION: Synthetic

<400> SEQUENCE: 3

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125
```

Ile Tyr Asp Asp Asp Pro Leu Tyr Lys Glu Ala Leu Gln Met Leu Arg
            130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 4
<211> LENGTH: 199
<212> TYPE: PRT
<213> ORGANISM: Artificial Sequence
<220> FEATURE:
<223> OTHER INFORMATION: Synthetic

<400> SEQUENCE: 4

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 5
<211> LENGTH: 199
<212> TYPE: PRT
<213> ORGANISM: Artificial Sequence
<220> FEATURE:
<223> OTHER INFORMATION: Synthetic

<400> SEQUENCE: 5

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr

```
                    20                  25                  30
Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Tyr Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 6
<211> LENGTH: 181
<212> TYPE: PRT
<213> ORGANISM: Artificial Sequence
<220> FEATURE:
<223> OTHER INFORMATION: Synthetic

<400> SEQUENCE: 6

Met Glu Ala Ser Pro Ala Ser Gly Pro Arg His Lys Thr Tyr Leu Cys
 1               5                  10                  15

Tyr Glu Val Glu Arg Leu Asp Asn Gly Thr Ser Val Lys Met Asp Gln
                20                  25                  30

His Arg Gly Phe Leu His Asn Gln Ala Lys Asn Leu Leu Cys Gly Phe
            35                  40                  45

Tyr Gly Arg His Ala Glu Leu Arg Phe Leu Asp Leu Val Pro Ser Leu
        50                  55                  60

Gln Leu Asp Pro Ala Gln Ile Tyr Arg Val Thr Trp Phe Ile Ser Trp
 65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110

Asp Tyr Asp Pro Leu Tyr Lys Glu Ala Leu Gln Met Leu Arg Asp Ala
        115                 120                 125

Gly Ala Gln Val Ser Ile Met Thr Tyr Asp Glu Phe Lys His Cys Trp
    130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
```

```
                180

<210> SEQ ID NO 7
<211> LENGTH: 181
<212> TYPE: PRT
<213> ORGANISM: Artificial Sequence
<220> FEATURE:
<223> OTHER INFORMATION: Synthetic

<400> SEQUENCE: 7

Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45

Tyr Gly Arg His Ala Glu Leu Arg Phe Leu Asp Leu Val Pro Ser Leu
    50                  55                  60

Gln Leu Asp Pro Ala Gln Ile Tyr Arg Val Thr Trp Phe Ile Ser Trp
65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Phe
            100                 105                 110

Asp Tyr Asp Pro Leu Tyr Lys Glu Ala Leu Gln Met Leu Arg Asp Ala
        115                 120                 125

Gly Ala Gln Val Ser Ile Met Thr Tyr Asp Glu Phe Lys His Cys Trp
    130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180

<210> SEQ ID NO 8
<211> LENGTH: 181
<212> TYPE: PRT
<213> ORGANISM: Artificial Sequence
<220> FEATURE:
<223> OTHER INFORMATION: Synthetic

<400> SEQUENCE: 8

Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45

Tyr Gly Arg His Ala Glu Leu Arg Phe Leu Asp Val Pro Ser Leu
    50                  55                  60

Gln Leu Asp Pro Ala Gln Ile Tyr Arg Val Thr Trp Phe Ile Ser Trp
65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110
```

```
Asp Asp Asp Pro Leu Tyr Lys Glu Ala Leu Gln Met Leu Arg Asp Ala
            115                 120                 125

Gly Ala Gln Val Ser Ile Met Thr Tyr Asp Glu Phe Lys His Cys Trp
        130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180
```

<210> SEQ ID NO 9
<211> LENGTH: 181
<212> TYPE: PRT
<213> ORGANISM: Artificial Sequence
<220> FEATURE:
<223> OTHER INFORMATION: Synthetic

<400> SEQUENCE: 9

```
Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45

Tyr Gly Arg His Ala Glu Leu Arg Phe Leu Asp Leu Val Pro Ser Leu
    50                  55                  60

Gln Leu Asp Pro Ala Gln Ile Tyr Arg Val Thr Trp Phe Ile Ser Trp
65                  70                  75                  80

Ser Pro Cys Phe Ser Ala Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110

Asp Tyr Asp Pro Leu Tyr Lys Glu Ala Leu Gln Met Leu Arg Asp Ala
        115                 120                 125

Gly Ala Gln Val Ser Ile Met Thr Tyr Asp Glu Phe Lys His Cys Trp
    130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180
```

<210> SEQ ID NO 10
<211> LENGTH: 181
<212> TYPE: PRT
<213> ORGANISM: Artificial Sequence
<220> FEATURE:
<223> OTHER INFORMATION: Synthetic

<400> SEQUENCE: 10

```
Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45
```

```
Tyr Gly Arg His Ala Glu Leu Arg Phe Leu Asp Leu Val Pro Ser Leu
 50                  55                  60

Gln Leu Asp Pro Ala Gln Ile Tyr Arg Val Thr Trp Phe Ile Ser Trp
 65                  70                  75                  80

Ser Pro Cys Phe Ser Trp Gly Cys Ala Gly Glu Val Arg Ala Phe Leu
                 85                  90                  95

Gln Glu Asn Thr His Val Arg Leu Arg Ile Phe Ala Ala Arg Ile Tyr
            100                 105                 110

Tyr Tyr Asp Pro Leu Tyr Lys Glu Ala Leu Gln Met Leu Arg Asp Ala
        115                 120                 125

Gly Ala Gln Val Ser Ile Met Thr Tyr Asp Glu Phe Lys His Cys Trp
130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180

<210> SEQ ID NO 11
<211> LENGTH: 1399
<212> TYPE: PRT
<213> ORGANISM: Artificial Sequence
<220> FEATURE:
<223> OTHER INFORMATION: Synthetic

<400> SEQUENCE: 11

Met Tyr Pro Tyr Asp Val Pro Asp Tyr Ala Ser Pro Lys Lys Lys Arg
 1               5                  10                  15

Lys Val Glu Ala Ser Asp Lys Lys Tyr Ser Ile Gly Leu Ala Ile Gly
             20                  25                  30

Thr Asn Ser Val Gly Trp Ala Val Ile Thr Asp Glu Tyr Lys Val Pro
         35                  40                  45

Ser Lys Lys Phe Lys Val Leu Gly Asn Thr Asp Arg His Ser Ile Lys
 50                  55                  60

Lys Asn Leu Ile Gly Ala Leu Leu Phe Asp Ser Gly Glu Thr Ala Glu
 65                  70                  75                  80

Ala Thr Arg Leu Lys Arg Thr Ala Arg Arg Arg Tyr Thr Arg Arg Lys
                 85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
210                 215                 220
```

```
Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
            245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
            275                 280                 285

Asp Thr Tyr Asp Asp Leu Asp Asn Leu Leu Ala Gln Ile Gly Asp
            290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
            355                 360                 365

Glu Ile Phe Phe Asp Gln Ser Lys Asn Gly Tyr Ala Gly Tyr Ile Asp
370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
            435                 440                 445

Phe Tyr Pro Phe Leu Lys Asp Asn Arg Glu Lys Ile Glu Lys Ile Leu
            450                 455                 460

Thr Phe Arg Ile Pro Tyr Tyr Val Gly Pro Leu Ala Arg Gly Asn Ser
465                 470                 475                 480

Arg Phe Ala Trp Met Thr Arg Lys Ser Glu Glu Thr Ile Thr Pro Trp
                485                 490                 495

Asn Phe Glu Glu Val Val Asp Lys Gly Ala Ser Ala Gln Ser Phe Ile
            500                 505                 510

Glu Arg Met Thr Asn Phe Asp Lys Asn Leu Pro Asn Glu Lys Val Leu
            515                 520                 525

Pro Lys His Ser Leu Leu Tyr Glu Tyr Phe Thr Val Tyr Asn Glu Leu
            530                 535                 540

Thr Lys Val Lys Tyr Val Thr Glu Gly Met Arg Lys Pro Ala Phe Leu
545                 550                 555                 560

Ser Gly Glu Gln Lys Lys Ala Ile Val Asp Leu Leu Phe Lys Thr Asn
                565                 570                 575

Arg Lys Val Thr Val Lys Gln Leu Lys Glu Asp Tyr Phe Lys Lys Ile
            580                 585                 590

Glu Cys Phe Asp Ser Val Glu Ile Ser Gly Val Glu Asp Arg Phe Asn
            595                 600                 605

Ala Ser Leu Gly Thr Tyr His Asp Leu Leu Lys Ile Ile Lys Asp Lys
            610                 615                 620

Asp Phe Leu Asp Asn Glu Glu Asn Glu Asp Ile Leu Glu Asp Ile Val
625                 630                 635                 640
```

-continued

Leu Thr Leu Thr Leu Phe Glu Asp Arg Glu Met Ile Glu Glu Arg Leu
                645                 650                 655

Lys Thr Tyr Ala His Leu Phe Asp Asp Lys Val Met Lys Gln Leu Lys
        660                 665                 670

Arg Arg Arg Tyr Thr Gly Trp Gly Arg Leu Ser Arg Lys Leu Ile Asn
    675                 680                 685

Gly Ile Arg Asp Lys Gln Ser Gly Lys Thr Ile Leu Asp Phe Leu Lys
690                 695                 700

Ser Asp Gly Phe Ala Asn Arg Asn Phe Met Gln Leu Ile His Asp Asp
705                 710                 715                 720

Ser Leu Thr Phe Lys Glu Asp Ile Gln Lys Ala Gln Val Ser Gly Gln
            725                 730                 735

Gly Asp Ser Leu His Glu His Ile Ala Asn Leu Ala Gly Ser Pro Ala
                740                 745                 750

Ile Lys Lys Gly Ile Leu Gln Thr Val Lys Val Val Asp Glu Leu Val
                755                 760                 765

Lys Val Met Gly Arg His Lys Pro Glu Asn Ile Val Ile Glu Met Ala
770                 775                 780

Arg Glu Asn Gln Thr Thr Gln Lys Gly Gln Lys Asn Ser Arg Glu Arg
785                 790                 795                 800

Met Lys Arg Ile Glu Glu Gly Ile Lys Glu Leu Gly Ser Gln Ile Leu
            805                 810                 815

Lys Glu His Pro Val Glu Asn Thr Gln Leu Gln Asn Glu Lys Leu Tyr
                820                 825                 830

Leu Tyr Tyr Leu Gln Asn Gly Arg Asp Met Tyr Val Asp Gln Glu Leu
        835                 840                 845

Asp Ile Asn Arg Leu Ser Asp Tyr Asp Val Asp His Ile Val Pro Gln
850                 855                 860

Ser Phe Leu Lys Asp Asp Ser Ile Asp Asn Lys Val Leu Thr Arg Ser
865                 870                 875                 880

Asp Lys Asn Arg Gly Lys Ser Asp Asn Val Pro Ser Glu Glu Val Val
                885                 890                 895

Lys Lys Met Lys Asn Tyr Trp Arg Gln Leu Leu Asn Ala Lys Leu Ile
            900                 905                 910

Thr Gln Arg Lys Phe Asp Asn Leu Thr Lys Ala Glu Arg Gly Gly Leu
        915                 920                 925

Ser Glu Leu Asp Lys Ala Gly Phe Ile Lys Arg Gln Leu Val Glu Thr
930                 935                 940

Arg Gln Ile Thr Lys His Val Ala Gln Ile Leu Asp Ser Arg Met Asn
945                 950                 955                 960

Thr Lys Tyr Asp Glu Asn Asp Lys Leu Ile Arg Glu Val Lys Val Ile
            965                 970                 975

Thr Leu Lys Ser Lys Leu Val Ser Asp Phe Arg Lys Asp Phe Gln Phe
        980                 985                 990

Tyr Lys Val Arg Glu Ile Asn Asn Tyr His His Ala His Asp Ala Tyr
    995                 1000                1005

Leu Asn Ala Val Val Gly Thr Ala Leu Ile Lys Lys Tyr Pro Lys
    1010                1015                1020

Leu Glu Ser Glu Phe Val Tyr Gly Asp Tyr Lys Val Tyr Asp Val
    1025                1030                1035

Arg Lys Met Ile Ala Lys Ser Glu Gln Glu Ile Gly Lys Ala Thr
    1040                1045                1050

Ala Lys Tyr Phe Phe Tyr Ser Asn Ile Met Asn Phe Phe Lys Thr

```
                 1055                1060                1065
Glu Ile Thr Leu Ala Asn Gly Glu Ile Arg Lys Arg Pro Leu Ile
         1070                1075                1080

Glu Thr Asn Gly Glu Thr Gly Glu Ile Val Trp Asp Lys Gly Arg
     1085                1090                1095

Asp Phe Ala Thr Val Arg Lys Val Leu Ser Met Pro Gln Val Asn
     1100                1105                1110

Ile Val Lys Lys Thr Glu Val Gln Thr Gly Gly Phe Ser Lys Glu
     1115                1120                1125

Ser Ile Leu Pro Lys Arg Asn Ser Asp Lys Leu Ile Ala Arg Lys
     1130                1135                1140

Lys Asp Trp Asp Pro Lys Lys Tyr Gly Gly Phe Asp Ser Pro Thr
     1145                1150                1155

Val Ala Tyr Ser Val Leu Val Ala Lys Val Glu Lys Gly Lys
     1160                1165                1170

Ser Lys Lys Leu Lys Ser Val Lys Glu Leu Leu Gly Ile Thr Ile
     1175                1180                1185

Met Glu Arg Ser Ser Phe Glu Lys Asn Pro Ile Asp Phe Leu Glu
     1190                1195                1200

Ala Lys Gly Tyr Lys Glu Val Lys Lys Asp Leu Ile Ile Lys Leu
     1205                1210                1215

Pro Lys Tyr Ser Leu Phe Glu Leu Glu Asn Gly Arg Lys Arg Met
     1220                1225                1230

Leu Ala Ser Ala Gly Glu Leu Gln Lys Gly Asn Glu Leu Ala Leu
     1235                1240                1245

Pro Ser Lys Tyr Val Asn Phe Leu Tyr Leu Ala Ser His Tyr Glu
     1250                1255                1260

Lys Leu Lys Gly Ser Pro Glu Asp Asn Glu Gln Lys Gln Leu Phe
     1265                1270                1275

Val Glu Gln His Lys His Tyr Leu Asp Glu Ile Ile Glu Gln Ile
     1280                1285                1290

Ser Glu Phe Ser Lys Arg Val Ile Leu Ala Asp Ala Asn Leu Asp
     1295                1300                1305

Lys Val Leu Ser Ala Tyr Asn Lys His Arg Asp Lys Pro Ile Arg
     1310                1315                1320

Glu Gln Ala Glu Asn Ile Ile His Leu Phe Thr Leu Thr Asn Leu
     1325                1330                1335

Gly Ala Pro Ala Ala Phe Lys Tyr Phe Asp Thr Thr Ile Asp Arg
     1340                1345                1350

Lys Arg Tyr Thr Ser Thr Lys Glu Val Leu Asp Ala Thr Leu Ile
     1355                1360                1365

His Gln Ser Ile Thr Gly Leu Tyr Glu Thr Arg Ile Asp Leu Ser
     1370                1375                1380

Gln Leu Gly Gly Asp Ser Pro Lys Lys Lys Arg Lys Val Glu Ala
     1385                1390                1395

Ser
```

<210> SEQ ID NO 12
<211> LENGTH: 83
<212> TYPE: PRT
<213> ORGANISM: Artificial Sequence
<220> FEATURE:
<223> OTHER INFORMATION: Synthetic

<400> SEQUENCE: 12

```
Thr Asn Leu Ser Asp Ile Ile Glu Lys Glu Thr Gly Lys Gln Leu Val
1               5                   10                  15

Ile Gln Glu Ser Ile Leu Met Leu Pro Glu Val Glu Val Ile
                20                  25                  30

Gly Asn Lys Pro Glu Ser Asp Ile Leu Val His Thr Ala Tyr Asp Glu
            35                  40                  45

Ser Thr Asp Glu Asn Val Met Leu Leu Thr Ser Asp Ala Pro Glu Tyr
50                  55                  60

Lys Pro Trp Ala Leu Val Ile Gln Asp Ser Asn Gly Glu Asn Lys Ile
65                  70                  75                  80

Lys Met Leu
```

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

```
Ser Gly Ser Glu Thr Pro Gly Thr Ser Glu Ser Ala Thr Pro Glu Ser
1               5                   10                  15
```

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

```
Ser Gly Gly Ser
1
```

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

```
Pro Lys Lys Lys Arg Lys Val
1               5
```

<210> SEQ ID NO 16
<211> LENGTH: 1680
<212> TYPE: PRT
<213> ORGANISM: Artificial Sequence
<220> FEATURE:
<223> OTHER INFORMATION: Synthetic

<400> SEQUENCE: 16

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60
```

```
Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn Ser Gly Ser Glu Thr Pro Gly Thr Ser
        195                 200                 205

Glu Ser Ala Thr Pro Glu Ser Asp Lys Lys Tyr Ser Ile Gly Leu Ala
210                 215                 220

Ile Gly Thr Asn Ser Val Gly Trp Ala Val Ile Thr Asp Glu Tyr Lys
225                 230                 235                 240

Val Pro Ser Lys Lys Phe Lys Val Leu Gly Asn Thr Asp Arg His Ser
                245                 250                 255

Ile Lys Lys Asn Leu Ile Gly Ala Leu Leu Phe Asp Ser Gly Glu Thr
            260                 265                 270

Ala Glu Ala Thr Arg Leu Lys Arg Thr Ala Arg Arg Arg Tyr Thr Arg
        275                 280                 285

Arg Lys Asn Arg Ile Cys Tyr Leu Gln Glu Ile Phe Ser Asn Glu Met
290                 295                 300

Ala Lys Val Asp Asp Ser Phe Phe His Arg Leu Glu Glu Ser Phe Leu
305                 310                 315                 320

Val Glu Glu Asp Lys Lys His Glu Arg His Pro Ile Phe Gly Asn Ile
                325                 330                 335

Val Asp Glu Val Ala Tyr His Glu Lys Tyr Pro Thr Ile Tyr His Leu
            340                 345                 350

Arg Lys Lys Leu Val Asp Ser Thr Asp Lys Ala Asp Leu Arg Leu Ile
        355                 360                 365

Tyr Leu Ala Leu Ala His Met Ile Lys Phe Arg Gly His Phe Leu Ile
370                 375                 380

Glu Gly Asp Leu Asn Pro Asp Asn Ser Asp Val Asp Lys Leu Phe Ile
385                 390                 395                 400

Gln Leu Val Gln Thr Tyr Asn Gln Leu Phe Glu Glu Asn Pro Ile Asn
                405                 410                 415

Ala Ser Gly Val Asp Ala Lys Ala Ile Leu Ser Ala Arg Leu Ser Lys
            420                 425                 430

Ser Arg Arg Leu Glu Asn Leu Ile Ala Gln Leu Pro Gly Glu Lys Lys
        435                 440                 445

Asn Gly Leu Phe Gly Asn Leu Ile Ala Leu Ser Leu Gly Leu Thr Pro
450                 455                 460

Asn Phe Lys Ser Asn Phe Asp Leu Ala Glu Asp Ala Lys Leu Gln Leu
465                 470                 475                 480

Ser Lys Asp Thr Tyr Asp Asp Asp Leu Asp Asn Leu Leu Ala Gln Ile
```

```
            485                 490                 495
Gly Asp Gln Tyr Ala Asp Leu Phe Leu Ala Ala Lys Asn Leu Ser Asp
                500                 505                 510

Ala Ile Leu Leu Ser Asp Ile Leu Arg Val Asn Thr Glu Ile Thr Lys
            515                 520                 525

Ala Pro Leu Ser Ala Ser Met Ile Lys Arg Tyr Asp Glu His His Gln
        530                 535                 540

Asp Leu Thr Leu Leu Lys Ala Leu Val Arg Gln Gln Leu Pro Glu Lys
545                 550                 555                 560

Tyr Lys Glu Ile Phe Phe Asp Gln Ser Lys Asn Gly Tyr Ala Gly Tyr
                565                 570                 575

Ile Asp Gly Gly Ala Ser Gln Glu Glu Phe Tyr Lys Phe Ile Lys Pro
            580                 585                 590

Ile Leu Glu Lys Met Asp Gly Thr Glu Glu Leu Leu Val Lys Leu Asn
        595                 600                 605

Arg Glu Asp Leu Leu Arg Lys Gln Arg Thr Phe Asp Asn Gly Ser Ile
    610                 615                 620

Pro His Gln Ile His Leu Gly Glu Leu His Ala Ile Leu Arg Arg Gln
625                 630                 635                 640

Glu Asp Phe Tyr Pro Phe Leu Lys Asp Asn Arg Glu Lys Ile Glu Lys
                645                 650                 655

Ile Leu Thr Phe Arg Ile Pro Tyr Tyr Val Gly Pro Leu Ala Arg Gly
            660                 665                 670

Asn Ser Arg Phe Ala Trp Met Thr Arg Lys Ser Glu Glu Thr Ile Thr
        675                 680                 685

Pro Trp Asn Phe Glu Glu Val Val Asp Lys Gly Ala Ser Ala Gln Ser
690                 695                 700

Phe Ile Glu Arg Met Thr Asn Phe Asp Lys Asn Leu Pro Asn Glu Lys
705                 710                 715                 720

Val Leu Pro Lys His Ser Leu Leu Tyr Glu Tyr Phe Thr Val Tyr Asn
                725                 730                 735

Glu Leu Thr Lys Val Lys Tyr Val Thr Glu Gly Met Arg Lys Pro Ala
            740                 745                 750

Phe Leu Ser Gly Glu Gln Lys Lys Ala Ile Val Asp Leu Leu Phe Lys
        755                 760                 765

Thr Asn Arg Lys Val Thr Val Lys Gln Leu Lys Glu Asp Tyr Phe Lys
        770                 775                 780

Lys Ile Glu Cys Phe Asp Ser Val Glu Ile Ser Gly Val Glu Asp Arg
785                 790                 795                 800

Phe Asn Ala Ser Leu Gly Thr Tyr His Asp Leu Leu Lys Ile Ile Lys
                805                 810                 815

Asp Lys Asp Phe Leu Asp Asn Glu Glu Asn Glu Asp Ile Leu Glu Asp
            820                 825                 830

Ile Val Leu Thr Leu Thr Leu Phe Glu Asp Arg Glu Met Ile Glu Glu
        835                 840                 845

Arg Leu Lys Thr Tyr Ala His Leu Phe Asp Asp Lys Val Met Lys Gln
        850                 855                 860

Leu Lys Arg Arg Arg Tyr Thr Gly Trp Gly Arg Leu Ser Arg Lys Leu
865                 870                 875                 880

Ile Asn Gly Ile Arg Asp Lys Gln Ser Gly Lys Thr Ile Leu Asp Phe
                885                 890                 895

Leu Lys Ser Asp Gly Phe Ala Asn Arg Asn Phe Met Gln Leu Ile His
            900                 905                 910
```

```
Asp Asp Ser Leu Thr Phe Lys Glu Asp Ile Gln Lys Ala Gln Val Ser
        915                 920                 925

Gly Gln Gly Asp Ser Leu His Glu His Ile Ala Asn Leu Ala Gly Ser
930                 935                 940

Pro Ala Ile Lys Lys Gly Ile Leu Gln Thr Val Lys Val Val Asp Glu
945                 950                 955                 960

Leu Val Lys Val Met Gly Arg His Lys Pro Glu Asn Ile Val Ile Glu
            965                 970                 975

Met Ala Arg Glu Asn Gln Thr Thr Gln Lys Gly Gln Lys Asn Ser Arg
            980                 985                 990

Glu Arg Met Lys Arg Ile Glu Glu  Gly Ile Lys Glu Leu  Gly Ser Gln
            995                 1000                1005

Ile Leu  Lys Glu His Pro Val  Glu Asn Thr Gln Leu  Gln Asn Glu
1010                1015                1020

Lys Leu  Tyr Leu Tyr Tyr Leu  Gln Asn Gly Arg Asp  Met Tyr Val
1025                1030                1035

Asp Gln  Glu Leu Asp Ile Asn  Arg Leu Ser Asp Tyr  Asp Val Asp
1040                1045                1050

His Ile  Val Pro Gln Ser Phe  Leu Lys Asp Asp Ser  Ile Asp Asn
1055                1060                1065

Lys Val  Leu Thr Arg Ser Asp  Lys Asn Arg Gly Lys  Ser Asp Asn
1070                1075                1080

Val Pro  Ser Glu Glu Val Val  Lys Lys Met Lys Asn  Tyr Trp Arg
1085                1090                1095

Gln Leu  Leu Asn Ala Lys Leu  Ile Thr Gln Arg Lys  Phe Asp Asn
1100                1105                1110

Leu Thr  Lys Ala Glu Arg Gly  Gly Leu Ser Glu Leu  Asp Lys Ala
1115                1120                1125

Gly Phe  Ile Lys Arg Gln Leu  Val Glu Thr Arg Gln  Ile Thr Lys
1130                1135                1140

His Val  Ala Gln Ile Leu Asp  Ser Arg Met Asn Thr  Lys Tyr Asp
1145                1150                1155

Glu Asn  Asp Lys Leu Ile Arg  Glu Val Lys Val Ile  Thr Leu Lys
1160                1165                1170

Ser Lys  Leu Val Ser Asp Phe  Arg Lys Asp Phe Gln  Phe Tyr Lys
1175                1180                1185

Val Arg  Glu Ile Asn Asn Tyr  His His Ala His Asp  Ala Tyr Leu
1190                1195                1200

Asn Ala  Val Val Gly Thr Ala  Leu Ile Lys Lys Tyr  Pro Lys Leu
1205                1210                1215

Glu Ser  Glu Phe Val Tyr Gly  Asp Tyr Lys Val Tyr  Asp Val Arg
1220                1225                1230

Lys Met  Ile Ala Lys Ser Glu  Gln Glu Ile Gly Lys  Ala Thr Ala
1235                1240                1245

Lys Tyr  Phe Phe Tyr Ser Asn  Ile Met Asn Phe Phe  Lys Thr Glu
1250                1255                1260

Ile Thr  Leu Ala Asn Gly Glu  Ile Arg Lys Arg Pro  Leu Ile Glu
1265                1270                1275

Thr Asn  Gly Glu Thr Gly Glu  Ile Val Trp Asp Lys  Gly Arg Asp
1280                1285                1290

Phe Ala  Thr Val Arg Lys Val  Leu Ser Met Pro Gln  Val Asn Ile
1295                1300                1305
```

```
Val Lys Lys Thr Glu Val Gln Thr Gly Gly Phe Ser Lys Glu Ser
    1310                1315                1320

Ile Leu Pro Lys Arg Asn Ser Asp Lys Leu Ile Ala Arg Lys Lys
    1325                1330                1335

Asp Trp Asp Pro Lys Lys Tyr Gly Gly Phe Asp Ser Pro Thr Val
    1340                1345                1350

Ala Tyr Ser Val Leu Val Val Ala Lys Val Glu Lys Gly Lys Ser
    1355                1360                1365

Lys Lys Leu Lys Ser Val Lys Glu Leu Leu Gly Ile Thr Ile Met
    1370                1375                1380

Glu Arg Ser Ser Phe Glu Lys Asn Pro Ile Asp Phe Leu Glu Ala
    1385                1390                1395

Lys Gly Tyr Lys Glu Val Lys Lys Asp Leu Ile Ile Lys Leu Pro
    1400                1405                1410

Lys Tyr Ser Leu Phe Glu Leu Glu Asn Gly Arg Lys Arg Met Leu
    1415                1420                1425

Ala Ser Ala Gly Glu Leu Gln Lys Gly Asn Glu Leu Ala Leu Pro
    1430                1435                1440

Ser Lys Tyr Val Asn Phe Leu Tyr Leu Ala Ser His Tyr Glu Lys
    1445                1450                1455

Leu Lys Gly Ser Pro Glu Asp Asn Glu Gln Lys Gln Leu Phe Val
    1460                1465                1470

Glu Gln His Lys His Tyr Leu Asp Glu Ile Ile Glu Gln Ile Ser
    1475                1480                1485

Glu Phe Ser Lys Arg Val Ile Leu Ala Asp Ala Asn Leu Asp Lys
    1490                1495                1500

Val Leu Ser Ala Tyr Asn Lys His Arg Asp Lys Pro Ile Arg Glu
    1505                1510                1515

Gln Ala Glu Asn Ile Ile His Leu Phe Thr Leu Thr Asn Leu Gly
    1520                1525                1530

Ala Pro Ala Ala Phe Lys Tyr Phe Asp Thr Thr Ile Asp Arg Lys
    1535                1540                1545

Arg Tyr Thr Ser Thr Lys Glu Val Leu Asp Ala Thr Leu Ile His
    1550                1555                1560

Gln Ser Ile Thr Gly Leu Tyr Glu Thr Arg Ile Asp Leu Ser Gln
    1565                1570                1575

Leu Gly Gly Asp Ser Gly Gly Ser Thr Asn Leu Ser Asp Ile Ile
    1580                1585                1590

Glu Lys Glu Thr Gly Lys Gln Leu Val Ile Gln Glu Ser Ile Leu
    1595                1600                1605

Met Leu Pro Glu Glu Val Glu Glu Val Ile Gly Asn Lys Pro Glu
    1610                1615                1620

Ser Asp Ile Leu Val His Thr Ala Tyr Asp Glu Ser Thr Asp Glu
    1625                1630                1635

Asn Val Met Leu Leu Thr Ser Asp Ala Pro Glu Tyr Lys Pro Trp
    1640                1645                1650

Ala Leu Val Ile Gln Asp Ser Asn Gly Glu Asn Lys Ile Lys Met
    1655                1660                1665

Leu Ser Gly Gly Ser Pro Lys Lys Lys Arg Lys Val
    1670                1675                1680

<210> SEQ ID NO 17
<211> LENGTH: 1680
<212> TYPE: PRT
```

<213> ORGANISM: Artificial Sequence
<220> FEATURE:
<223> OTHER INFORMATION: Synthetic

<400> SEQUENCE: 17

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Phe Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn Ser Gly Ser Glu Thr Pro Gly Thr Ser
        195                 200                 205

Glu Ser Ala Thr Pro Glu Ser Asp Lys Lys Tyr Ser Ile Gly Leu Ala
    210                 215                 220

Ile Gly Thr Asn Ser Val Gly Trp Ala Val Ile Thr Asp Glu Tyr Lys
225                 230                 235                 240

Val Pro Ser Lys Lys Phe Lys Val Leu Gly Asn Thr Asp Arg His Ser
                245                 250                 255

Ile Lys Lys Asn Leu Ile Gly Ala Leu Leu Phe Asp Ser Gly Glu Thr
            260                 265                 270

Ala Glu Ala Thr Arg Leu Lys Arg Thr Ala Arg Arg Arg Tyr Thr Arg
        275                 280                 285

Arg Lys Asn Arg Ile Cys Tyr Leu Gln Glu Ile Phe Ser Asn Glu Met
    290                 295                 300

Ala Lys Val Asp Asp Ser Phe Phe His Arg Leu Glu Glu Ser Phe Leu
305                 310                 315                 320

Val Glu Glu Asp Lys Lys His Glu Arg His Pro Ile Phe Gly Asn Ile
                325                 330                 335

Val Asp Glu Val Ala Tyr His Glu Lys Tyr Pro Thr Ile Tyr His Leu
            340                 345                 350

Arg Lys Lys Leu Val Asp Ser Thr Asp Lys Ala Asp Leu Arg Leu Ile
        355                 360                 365

Tyr Leu Ala Leu Ala His Met Ile Lys Phe Arg Gly His Phe Leu Ile
    370                 375                 380

Glu Gly Asp Leu Asn Pro Asp Asn Ser Asp Val Asp Lys Leu Phe Ile
```

-continued

```
385                 390                 395                 400
Gln Leu Val Gln Thr Tyr Asn Gln Leu Phe Glu Glu Asn Pro Ile Asn
                405                 410                 415

Ala Ser Gly Val Asp Ala Lys Ala Ile Leu Ser Ala Arg Leu Ser Lys
                420                 425                 430

Ser Arg Arg Leu Glu Asn Leu Ile Ala Gln Leu Pro Gly Glu Lys Lys
                435                 440                 445

Asn Gly Leu Phe Gly Asn Leu Ile Ala Leu Ser Leu Gly Leu Thr Pro
450                 455                 460

Asn Phe Lys Ser Asn Phe Asp Leu Ala Glu Asp Ala Lys Leu Gln Leu
465                 470                 475                 480

Ser Lys Asp Thr Tyr Asp Asp Leu Asp Asn Leu Leu Ala Gln Ile
                485                 490                 495

Gly Asp Gln Tyr Ala Asp Leu Phe Leu Ala Ala Lys Asn Leu Ser Asp
                500                 505                 510

Ala Ile Leu Leu Ser Asp Ile Leu Arg Val Asn Thr Glu Ile Thr Lys
                515                 520                 525

Ala Pro Leu Ser Ala Ser Met Ile Lys Arg Tyr Asp Glu His His Gln
530                 535                 540

Asp Leu Thr Leu Leu Lys Ala Leu Val Arg Gln Gln Leu Pro Glu Lys
545                 550                 555                 560

Tyr Lys Glu Ile Phe Phe Asp Gln Ser Lys Asn Gly Tyr Ala Gly Tyr
                565                 570                 575

Ile Asp Gly Gly Ala Ser Gln Glu Glu Phe Tyr Lys Phe Ile Lys Pro
                580                 585                 590

Ile Leu Glu Lys Met Asp Gly Thr Glu Glu Leu Leu Val Lys Leu Asn
                595                 600                 605

Arg Glu Asp Leu Leu Arg Lys Gln Arg Thr Phe Asp Asn Gly Ser Ile
                610                 615                 620

Pro His Gln Ile His Leu Gly Glu Leu His Ala Ile Leu Arg Arg Gln
625                 630                 635                 640

Glu Asp Phe Tyr Pro Phe Leu Lys Asp Asn Arg Glu Lys Ile Glu Lys
                645                 650                 655

Ile Leu Thr Phe Arg Ile Pro Tyr Tyr Val Gly Pro Leu Ala Arg Gly
                660                 665                 670

Asn Ser Arg Phe Ala Trp Met Thr Arg Lys Ser Glu Glu Thr Ile Thr
                675                 680                 685

Pro Trp Asn Phe Glu Glu Val Val Asp Lys Gly Ala Ser Ala Gln Ser
690                 695                 700

Phe Ile Glu Arg Met Thr Asn Phe Asp Lys Asn Leu Pro Asn Glu Lys
705                 710                 715                 720

Val Leu Pro Lys His Ser Leu Leu Tyr Glu Tyr Phe Thr Val Tyr Asn
                725                 730                 735

Glu Leu Thr Lys Val Lys Tyr Val Thr Glu Gly Met Arg Lys Pro Ala
                740                 745                 750

Phe Leu Ser Gly Glu Gln Lys Lys Ala Ile Val Asp Leu Leu Phe Lys
                755                 760                 765

Thr Asn Arg Lys Val Thr Val Lys Gln Leu Lys Glu Asp Tyr Phe Lys
                770                 775                 780

Lys Ile Glu Cys Phe Asp Ser Val Glu Ile Ser Gly Val Glu Asp Arg
785                 790                 795                 800

Phe Asn Ala Ser Leu Gly Thr Tyr His Asp Leu Leu Lys Ile Ile Lys
                805                 810                 815
```

```
Asp Lys Asp Phe Leu Asp Asn Glu Glu Asn Glu Asp Ile Leu Glu Asp
            820                 825                 830

Ile Val Leu Thr Leu Thr Leu Phe Glu Asp Arg Glu Met Ile Glu Glu
            835                 840                 845

Arg Leu Lys Thr Tyr Ala His Leu Phe Asp Asp Lys Val Met Lys Gln
            850                 855                 860

Leu Lys Arg Arg Arg Tyr Thr Gly Trp Gly Arg Leu Ser Arg Lys Leu
865                 870                 875                 880

Ile Asn Gly Ile Arg Asp Lys Gln Ser Gly Lys Thr Ile Leu Asp Phe
            885                 890                 895

Leu Lys Ser Asp Gly Phe Ala Asn Arg Asn Phe Met Gln Leu Ile His
            900                 905                 910

Asp Asp Ser Leu Thr Phe Lys Glu Asp Ile Gln Lys Ala Gln Val Ser
            915                 920                 925

Gly Gln Gly Asp Ser Leu His Glu His Ile Ala Asn Leu Ala Gly Ser
            930                 935                 940

Pro Ala Ile Lys Lys Gly Ile Leu Gln Thr Val Lys Val Val Asp Glu
945                 950                 955                 960

Leu Val Lys Val Met Gly Arg His Lys Pro Glu Asn Ile Val Ile Glu
            965                 970                 975

Met Ala Arg Glu Asn Gln Thr Thr Gln Lys Gly Gln Lys Asn Ser Arg
            980                 985                 990

Glu Arg Met Lys Arg Ile Glu Glu  Gly Ile Lys Glu Leu  Gly Ser Gln
            995                 1000                1005

Ile Leu  Lys Glu His Pro Val  Glu Asn Thr Gln Leu  Gln Asn Glu
    1010                1015                1020

Lys Leu  Tyr Leu Tyr Tyr Leu  Gln Asn Gly Arg Asp  Met Tyr Val
    1025                1030                1035

Asp Gln  Glu Leu Asp Ile Asn  Arg Leu Ser Asp Tyr  Asp Val Asp
    1040                1045                1050

His Ile  Val Pro Gln Ser Phe  Leu Lys Asp Asp Ser  Ile Asp Asn
    1055                1060                1065

Lys Val  Leu Thr Arg Ser Asp  Lys Asn Arg Gly Lys  Ser Asp Asn
    1070                1075                1080

Val Pro  Ser Glu Glu Val Val  Lys Lys Met Lys Asn  Tyr Trp Arg
    1085                1090                1095

Gln Leu  Leu Asn Ala Lys Leu  Ile Thr Gln Arg Lys  Phe Asp Asn
    1100                1105                1110

Leu Thr  Lys Ala Glu Arg Gly  Gly Leu Ser Glu Leu  Asp Lys Ala
    1115                1120                1125

Gly Phe  Ile Lys Arg Gln Leu  Val Glu Thr Arg Gln  Ile Thr Lys
    1130                1135                1140

His Val  Ala Gln Ile Leu Asp  Ser Arg Met Asn Thr  Lys Tyr Asp
    1145                1150                1155

Glu Asn  Asp Lys Leu Ile Arg  Glu Val Lys Val Ile  Thr Leu Lys
    1160                1165                1170

Ser Lys  Leu Val Ser Asp Phe  Arg Lys Asp Phe Gln  Phe Tyr Lys
    1175                1180                1185

Val Arg  Glu Ile Asn Asn Tyr  His His Ala His Asp  Ala Tyr Leu
    1190                1195                1200

Asn Ala  Val Val Gly Thr Ala  Leu Ile Lys Lys Tyr  Pro Lys Leu
    1205                1210                1215
```

-continued

```
Glu Ser Glu Phe Val Tyr Gly Asp Tyr Lys Val Tyr Asp Val Arg
    1220            1225            1230

Lys Met Ile Ala Lys Ser Glu Gln Glu Ile Gly Lys Ala Thr Ala
    1235            1240            1245

Lys Tyr Phe Phe Tyr Ser Asn Ile Met Asn Phe Phe Lys Thr Glu
    1250            1255            1260

Ile Thr Leu Ala Asn Gly Glu Ile Arg Lys Arg Pro Leu Ile Glu
    1265            1270            1275

Thr Asn Gly Glu Thr Gly Glu Ile Val Trp Asp Lys Gly Arg Asp
    1280            1285            1290

Phe Ala Thr Val Arg Lys Val Leu Ser Met Pro Gln Val Asn Ile
    1295            1300            1305

Val Lys Lys Thr Glu Val Gln Thr Gly Gly Phe Ser Lys Glu Ser
    1310            1315            1320

Ile Leu Pro Lys Arg Asn Ser Asp Lys Leu Ile Ala Arg Lys Lys
    1325            1330            1335

Asp Trp Asp Pro Lys Lys Tyr Gly Gly Phe Asp Ser Pro Thr Val
    1340            1345            1350

Ala Tyr Ser Val Leu Val Val Ala Lys Val Glu Lys Gly Lys Ser
    1355            1360            1365

Lys Lys Leu Lys Ser Val Lys Glu Leu Leu Gly Ile Thr Ile Met
    1370            1375            1380

Glu Arg Ser Ser Phe Glu Lys Asn Pro Ile Asp Phe Leu Glu Ala
    1385            1390            1395

Lys Gly Tyr Lys Glu Val Lys Lys Asp Leu Ile Ile Lys Leu Pro
    1400            1405            1410

Lys Tyr Ser Leu Phe Glu Leu Glu Asn Gly Arg Lys Arg Met Leu
    1415            1420            1425

Ala Ser Ala Gly Glu Leu Gln Lys Gly Asn Glu Leu Ala Leu Pro
    1430            1435            1440

Ser Lys Tyr Val Asn Phe Leu Tyr Leu Ala Ser His Tyr Glu Lys
    1445            1450            1455

Leu Lys Gly Ser Pro Glu Asp Asn Glu Gln Lys Gln Leu Phe Val
    1460            1465            1470

Glu Gln His Lys His Tyr Leu Asp Glu Ile Ile Glu Gln Ile Ser
    1475            1480            1485

Glu Phe Ser Lys Arg Val Ile Leu Ala Asp Ala Asn Leu Asp Lys
    1490            1495            1500

Val Leu Ser Ala Tyr Asn Lys His Arg Asp Lys Pro Ile Arg Glu
    1505            1510            1515

Gln Ala Glu Asn Ile Ile His Leu Phe Thr Leu Thr Asn Leu Gly
    1520            1525            1530

Ala Pro Ala Ala Phe Lys Tyr Phe Asp Thr Thr Ile Asp Arg Lys
    1535            1540            1545

Arg Tyr Thr Ser Thr Lys Glu Val Leu Asp Ala Thr Leu Ile His
    1550            1555            1560

Gln Ser Ile Thr Gly Leu Tyr Glu Thr Arg Ile Asp Leu Ser Gln
    1565            1570            1575

Leu Gly Gly Asp Ser Gly Gly Ser Thr Asn Leu Ser Asp Ile Ile
    1580            1585            1590

Glu Lys Glu Thr Gly Lys Gln Leu Val Ile Gln Glu Ser Ile Leu
    1595            1600            1605

Met Leu Pro Glu Glu Val Glu Glu Val Ile Gly Asn Lys Pro Glu
```

```
                    1610                1615               1620

Ser Asp Ile Leu Val His Thr Ala Tyr Asp Glu Ser Thr Asp Glu
    1625                1630               1635

Asn Val Met Leu Leu Thr Ser Asp Ala Pro Glu Tyr Lys Pro Trp
    1640                1645               1650

Ala Leu Val Ile Gln Asp Ser Asn Gly Glu Asn Lys Ile Lys Met
    1655                1660               1665

Leu Ser Gly Gly Ser Pro Lys Lys Lys Arg Lys Val
    1670                1675               1680

<210> SEQ ID NO 18
<211> LENGTH: 1680
<212> TYPE: PRT
<213> ORGANISM: Artificial Sequence
<220> FEATURE:
<223> OTHER INFORMATION: Synthetic

<400> SEQUENCE: 18

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Asp Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn Ser Gly Ser Glu Thr Pro Gly Thr Ser
        195                 200                 205

Glu Ser Ala Thr Pro Glu Ser Asp Lys Lys Tyr Ser Ile Gly Leu Ala
    210                 215                 220

Ile Gly Thr Asn Ser Val Gly Trp Ala Val Ile Thr Asp Glu Tyr Lys
225                 230                 235                 240

Val Pro Ser Lys Lys Phe Lys Val Leu Gly Asn Thr Asp Arg His Ser
                245                 250                 255

Ile Lys Lys Asn Leu Ile Gly Ala Leu Leu Phe Asp Ser Gly Glu Thr
            260                 265                 270

Ala Glu Ala Thr Arg Leu Lys Arg Thr Ala Arg Arg Arg Tyr Thr Arg
        275                 280                 285

Arg Lys Asn Arg Ile Cys Tyr Leu Gln Glu Ile Phe Ser Asn Glu Met
```

```
              290                 295                 300
Ala Lys Val Asp Asp Ser Phe Phe His Arg Leu Glu Glu Ser Phe Leu
305                 310                 315                 320

Val Glu Glu Asp Lys Lys His Glu Arg His Pro Ile Phe Gly Asn Ile
                325                 330                 335

Val Asp Glu Val Ala Tyr His Glu Lys Tyr Pro Thr Ile Tyr His Leu
                340                 345                 350

Arg Lys Lys Leu Val Asp Ser Thr Asp Lys Ala Asp Leu Arg Leu Ile
                355                 360                 365

Tyr Leu Ala Leu Ala His Met Ile Lys Phe Arg Gly His Phe Leu Ile
370                 375                 380

Glu Gly Asp Leu Asn Pro Asp Asn Ser Asp Val Asp Lys Leu Phe Ile
385                 390                 395                 400

Gln Leu Val Gln Thr Tyr Asn Gln Leu Phe Glu Glu Asn Pro Ile Asn
                405                 410                 415

Ala Ser Gly Val Asp Ala Lys Ala Ile Leu Ser Ala Arg Leu Ser Lys
                420                 425                 430

Ser Arg Arg Leu Glu Asn Leu Ile Ala Gln Leu Pro Gly Glu Lys Lys
                435                 440                 445

Asn Gly Leu Phe Gly Asn Leu Ile Ala Leu Ser Leu Gly Leu Thr Pro
                450                 455                 460

Asn Phe Lys Ser Asn Phe Asp Leu Ala Glu Asp Ala Lys Leu Gln Leu
465                 470                 475                 480

Ser Lys Asp Thr Tyr Asp Asp Asp Leu Asp Asn Leu Leu Ala Gln Ile
                485                 490                 495

Gly Asp Gln Tyr Ala Asp Leu Phe Leu Ala Ala Lys Asn Leu Ser Asp
                500                 505                 510

Ala Ile Leu Leu Ser Asp Ile Leu Arg Val Asn Thr Glu Ile Thr Lys
                515                 520                 525

Ala Pro Leu Ser Ala Ser Met Ile Lys Arg Tyr Asp Glu His His Gln
                530                 535                 540

Asp Leu Thr Leu Leu Lys Ala Leu Val Arg Gln Gln Leu Pro Glu Lys
545                 550                 555                 560

Tyr Lys Glu Ile Phe Phe Asp Gln Ser Lys Asn Gly Tyr Ala Gly Tyr
                565                 570                 575

Ile Asp Gly Gly Ala Ser Gln Glu Glu Phe Tyr Lys Phe Ile Lys Pro
                580                 585                 590

Ile Leu Glu Lys Met Asp Gly Thr Glu Glu Leu Leu Val Lys Leu Asn
                595                 600                 605

Arg Glu Asp Leu Leu Arg Lys Gln Arg Thr Phe Asp Asn Gly Ser Ile
                610                 615                 620

Pro His Gln Ile His Leu Gly Glu Leu His Ala Ile Leu Arg Arg Gln
625                 630                 635                 640

Glu Asp Phe Tyr Pro Phe Leu Lys Asp Asn Arg Glu Lys Ile Glu Lys
                645                 650                 655

Ile Leu Thr Phe Arg Ile Pro Tyr Tyr Val Gly Pro Leu Ala Arg Gly
                660                 665                 670

Asn Ser Arg Phe Ala Trp Met Thr Arg Lys Ser Glu Glu Thr Ile Thr
                675                 680                 685

Pro Trp Asn Phe Glu Glu Val Val Asp Lys Gly Ala Ser Ala Gln Ser
                690                 695                 700

Phe Ile Glu Arg Met Thr Asn Phe Asp Lys Asn Leu Pro Asn Glu Lys
705                 710                 715                 720
```

-continued

```
Val Leu Pro Lys His Ser Leu Tyr Glu Tyr Phe Thr Val Tyr Asn
            725                 730                 735
Glu Leu Thr Lys Val Lys Tyr Val Thr Glu Gly Met Arg Lys Pro Ala
            740                 745                 750
Phe Leu Ser Gly Glu Gln Lys Lys Ala Ile Val Asp Leu Leu Phe Lys
            755                 760                 765
Thr Asn Arg Lys Val Thr Val Lys Gln Leu Lys Glu Asp Tyr Phe Lys
        770                 775                 780
Lys Ile Glu Cys Phe Asp Ser Val Glu Ile Ser Gly Val Glu Asp Arg
785                 790                 795                 800
Phe Asn Ala Ser Leu Gly Thr Tyr His Asp Leu Leu Lys Ile Ile Lys
                805                 810                 815
Asp Lys Asp Phe Leu Asp Asn Glu Glu Asn Glu Asp Ile Leu Glu Asp
                820                 825                 830
Ile Val Leu Thr Leu Thr Leu Phe Glu Asp Arg Glu Met Ile Glu Glu
                835                 840                 845
Arg Leu Lys Thr Tyr Ala His Leu Phe Asp Asp Lys Val Met Lys Gln
850                 855                 860
Leu Lys Arg Arg Arg Tyr Thr Gly Trp Gly Arg Leu Ser Arg Lys Leu
865                 870                 875                 880
Ile Asn Gly Ile Arg Asp Lys Gln Ser Gly Lys Thr Ile Leu Asp Phe
                885                 890                 895
Leu Lys Ser Asp Gly Phe Ala Asn Arg Asn Phe Met Gln Leu Ile His
                900                 905                 910
Asp Asp Ser Leu Thr Phe Lys Glu Asp Ile Gln Lys Ala Gln Val Ser
            915                 920                 925
Gly Gln Gly Asp Ser Leu His Glu His Ile Ala Asn Leu Ala Gly Ser
            930                 935                 940
Pro Ala Ile Lys Lys Gly Ile Leu Gln Thr Val Lys Val Val Asp Glu
945                 950                 955                 960
Leu Val Lys Val Met Gly Arg His Lys Pro Glu Asn Ile Val Ile Glu
                965                 970                 975
Met Ala Arg Glu Asn Gln Thr Thr Gln Lys Gly Gln Lys Asn Ser Arg
            980                 985                 990
Glu Arg Met Lys Arg Ile Glu Glu  Gly Ile Lys Glu Leu  Gly Ser Gln
            995                 1000                1005
Ile Leu Lys Glu His Pro Val  Glu Asn Thr Gln Leu  Gln Asn Glu
        1010                1015                1020
Lys Leu Tyr Leu Tyr Tyr Leu  Gln Asn Gly Arg Asp  Met Tyr Val
        1025                1030                1035
Asp Gln Glu Leu Asp Ile Asn  Arg Leu Ser Asp Tyr  Asp Val Asp
        1040                1045                1050
His Ile Val Pro Gln Ser Phe  Leu Lys Asp Asp Ser  Ile Asp Asn
        1055                1060                1065
Lys Val Leu Thr Arg Ser Asp  Lys Asn Arg Gly Lys  Ser Asp Asn
        1070                1075                1080
Val Pro Ser Glu Glu Val Val  Lys Lys Met Lys Asn  Tyr Trp Arg
        1085                1090                1095
Gln Leu Leu Asn Ala Lys Leu  Ile Thr Gln Arg Lys  Phe Asp Asn
        1100                1105                1110
Leu Thr Lys Ala Glu Arg Gly  Gly Leu Ser Glu Leu  Asp Lys Ala
        1115                1120                1125
```

```
Gly Phe Ile Lys Arg Gln Leu Val Glu Thr Arg Gln Ile Thr Lys
1130                1135                1140

His Val Ala Gln Ile Leu Asp Ser Arg Met Asn Thr Lys Tyr Asp
1145                1150                1155

Glu Asn Asp Lys Leu Ile Arg Glu Val Lys Val Ile Thr Leu Lys
1160                1165                1170

Ser Lys Leu Val Ser Asp Phe Arg Lys Asp Phe Gln Phe Tyr Lys
1175                1180                1185

Val Arg Glu Ile Asn Asn Tyr His His Ala His Asp Ala Tyr Leu
1190                1195                1200

Asn Ala Val Val Gly Thr Ala Leu Ile Lys Lys Tyr Pro Lys Leu
1205                1210                1215

Glu Ser Glu Phe Val Tyr Gly Asp Tyr Lys Val Tyr Asp Val Arg
1220                1225                1230

Lys Met Ile Ala Lys Ser Glu Gln Glu Ile Gly Lys Ala Thr Ala
1235                1240                1245

Lys Tyr Phe Phe Tyr Ser Asn Ile Met Asn Phe Phe Lys Thr Glu
1250                1255                1260

Ile Thr Leu Ala Asn Gly Glu Ile Arg Lys Arg Pro Leu Ile Glu
1265                1270                1275

Thr Asn Gly Glu Thr Gly Glu Ile Val Trp Asp Lys Gly Arg Asp
1280                1285                1290

Phe Ala Thr Val Arg Lys Val Leu Ser Met Pro Gln Val Asn Ile
1295                1300                1305

Val Lys Lys Thr Glu Val Gln Thr Gly Gly Phe Ser Lys Glu Ser
1310                1315                1320

Ile Leu Pro Lys Arg Asn Ser Asp Lys Leu Ile Ala Arg Lys Lys
1325                1330                1335

Asp Trp Asp Pro Lys Lys Tyr Gly Gly Phe Asp Ser Pro Thr Val
1340                1345                1350

Ala Tyr Ser Val Leu Val Val Ala Lys Val Glu Lys Gly Lys Ser
1355                1360                1365

Lys Lys Leu Lys Ser Val Lys Glu Leu Leu Gly Ile Thr Ile Met
1370                1375                1380

Glu Arg Ser Ser Phe Glu Lys Asn Pro Ile Asp Phe Leu Glu Ala
1385                1390                1395

Lys Gly Tyr Lys Glu Val Lys Lys Asp Leu Ile Ile Lys Leu Pro
1400                1405                1410

Lys Tyr Ser Leu Phe Glu Leu Glu Asn Gly Arg Lys Arg Met Leu
1415                1420                1425

Ala Ser Ala Gly Glu Leu Gln Lys Gly Asn Glu Leu Ala Leu Pro
1430                1435                1440

Ser Lys Tyr Val Asn Phe Leu Tyr Leu Ala Ser His Tyr Glu Lys
1445                1450                1455

Leu Lys Gly Ser Pro Glu Asp Asn Glu Gln Lys Gln Leu Phe Val
1460                1465                1470

Glu Gln His Lys His Tyr Leu Asp Glu Ile Ile Glu Gln Ile Ser
1475                1480                1485

Glu Phe Ser Lys Arg Val Ile Leu Ala Asp Ala Asn Leu Asp Lys
1490                1495                1500

Val Leu Ser Ala Tyr Asn Lys His Arg Asp Lys Pro Ile Arg Glu
1505                1510                1515

Gln Ala Glu Asn Ile Ile His Leu Phe Thr Leu Thr Asn Leu Gly
```

```
                    1520                1525                1530
Ala Pro Ala Ala Phe Lys Tyr Phe Asp Thr Thr Ile Asp Arg Lys
        1535                1540                1545
Arg Tyr Thr Ser Thr Lys Glu Val Leu Asp Ala Thr Leu Ile His
        1550                1555                1560
Gln Ser Ile Thr Gly Leu Tyr Glu Thr Arg Ile Asp Leu Ser Gln
        1565                1570                1575
Leu Gly Gly Asp Ser Gly Gly Ser Thr Asn Leu Ser Asp Ile Ile
        1580                1585                1590
Glu Lys Glu Thr Gly Lys Gln Leu Val Ile Gln Glu Ser Ile Leu
        1595                1600                1605
Met Leu Pro Glu Glu Val Glu Val Ile Gly Asn Lys Pro Glu
        1610                1615                1620
Ser Asp Ile Leu Val His Thr Ala Tyr Asp Glu Ser Thr Asp Glu
        1625                1630                1635
Asn Val Met Leu Leu Thr Ser Asp Ala Pro Glu Tyr Lys Pro Trp
        1640                1645                1650
Ala Leu Val Ile Gln Asp Ser Asn Gly Glu Asn Lys Ile Lys Met
        1655                1660                1665
Leu Ser Gly Gly Ser Pro Lys Lys Lys Arg Lys Val
        1670                1675                1680

<210> SEQ ID NO 19
<211> LENGTH: 1680
<212> TYPE: PRT
<213> ORGANISM: Artificial Sequence
<220> FEATURE:
<223> OTHER INFORMATION: Synthetic

<400> SEQUENCE: 19

Met Glu Ala Ser Pro Ala Ser Gly Pro Arg His Leu Met Asp Pro His
1               5                   10                  15
Ile Phe Thr Ser Asn Phe Asn Asn Gly Ile Gly Arg His Lys Thr Tyr
                20                  25                  30
Leu Cys Tyr Glu Val Glu Arg Leu Asp Asn Gly Thr Ser Val Lys Met
            35                  40                  45
Asp Gln His Arg Gly Phe Leu His Asn Gln Ala Lys Asn Leu Leu Cys
        50                  55                  60
Gly Phe Tyr Gly Arg His Ala Glu Leu Arg Phe Leu Asp Leu Val Pro
65                  70                  75                  80
Ser Leu Gln Leu Asp Pro Ala Gln Ile Tyr Arg Val Thr Trp Phe Ile
                85                  90                  95
Ser Trp Ser Pro Cys Phe Ser Ala Gly Cys Ala Gly Glu Val Arg Ala
            100                 105                 110
Phe Leu Gln Glu Asn Thr His Val Arg Leu Arg Ile Phe Ala Ala Arg
        115                 120                 125
Ile Tyr Asp Tyr Asp Pro Leu Tyr Lys Glu Ala Leu Gln Met Leu Arg
    130                 135                 140
Asp Ala Gly Ala Gln Val Ser Ile Met Thr Tyr Asp Glu Phe Lys His
145                 150                 155                 160
Cys Trp Asp Thr Phe Val Asp His Gln Gly Cys Pro Phe Gln Pro Trp
                165                 170                 175
Asp Gly Leu Asp Glu His Ser Gln Ala Leu Ser Gly Arg Leu Arg Ala
            180                 185                 190
Ile Leu Gln Asn Gln Gly Asn Ser Gly Ser Glu Thr Pro Gly Thr Ser
```

```
            195                 200                 205
Glu Ser Ala Thr Pro Glu Ser Asp Lys Lys Tyr Ser Ile Gly Leu Ala
210                 215                 220

Ile Gly Thr Asn Ser Val Gly Trp Ala Val Ile Thr Asp Glu Tyr Lys
225                 230                 235                 240

Val Pro Ser Lys Lys Phe Lys Val Leu Gly Asn Thr Asp Arg His Ser
                245                 250                 255

Ile Lys Lys Asn Leu Ile Gly Ala Leu Leu Phe Asp Ser Gly Glu Thr
                260                 265                 270

Ala Glu Ala Thr Arg Leu Lys Arg Thr Ala Arg Arg Tyr Thr Arg
            275                 280                 285

Arg Lys Asn Arg Ile Cys Tyr Leu Gln Glu Ile Phe Ser Asn Glu Met
            290                 295                 300

Ala Lys Val Asp Asp Ser Phe Phe His Arg Leu Glu Glu Ser Phe Leu
305                 310                 315                 320

Val Glu Glu Asp Lys Lys His Glu Arg His Pro Ile Phe Gly Asn Ile
                325                 330                 335

Val Asp Glu Val Ala Tyr His Glu Lys Tyr Pro Thr Ile Tyr His Leu
                340                 345                 350

Arg Lys Lys Leu Val Asp Ser Thr Asp Lys Ala Asp Leu Arg Leu Ile
            355                 360                 365

Tyr Leu Ala Leu Ala His Met Ile Lys Phe Arg Gly His Phe Leu Ile
370                 375                 380

Glu Gly Asp Leu Asn Pro Asp Asn Ser Asp Val Asp Lys Leu Phe Ile
385                 390                 395                 400

Gln Leu Val Gln Thr Tyr Asn Gln Leu Phe Glu Glu Asn Pro Ile Asn
                405                 410                 415

Ala Ser Gly Val Asp Ala Lys Ala Ile Leu Ser Ala Arg Leu Ser Lys
                420                 425                 430

Ser Arg Arg Leu Glu Asn Leu Ile Ala Gln Leu Pro Gly Glu Lys Lys
            435                 440                 445

Asn Gly Leu Phe Gly Asn Leu Ile Ala Leu Ser Leu Gly Leu Thr Pro
450                 455                 460

Asn Phe Lys Ser Asn Phe Asp Leu Ala Glu Asp Ala Lys Leu Gln Leu
465                 470                 475                 480

Ser Lys Asp Thr Tyr Asp Asp Asp Leu Asp Asn Leu Leu Ala Gln Ile
                485                 490                 495

Gly Asp Gln Tyr Ala Asp Leu Phe Leu Ala Ala Lys Asn Leu Ser Asp
                500                 505                 510

Ala Ile Leu Leu Ser Asp Ile Leu Arg Val Asn Thr Glu Ile Thr Lys
            515                 520                 525

Ala Pro Leu Ser Ala Ser Met Ile Lys Arg Tyr Asp Glu His His Gln
            530                 535                 540

Asp Leu Thr Leu Leu Lys Ala Leu Val Arg Gln Gln Leu Pro Glu Lys
545                 550                 555                 560

Tyr Lys Glu Ile Phe Phe Asp Gln Ser Lys Asn Gly Tyr Ala Gly Tyr
                565                 570                 575

Ile Asp Gly Gly Ala Ser Gln Glu Glu Phe Tyr Lys Phe Ile Lys Pro
                580                 585                 590

Ile Leu Glu Lys Met Asp Gly Thr Glu Glu Leu Leu Val Lys Leu Asn
            595                 600                 605

Arg Glu Asp Leu Leu Arg Lys Gln Arg Thr Phe Asp Asn Gly Ser Ile
610                 615                 620
```

```
Pro His Gln Ile His Leu Gly Glu Leu His Ala Ile Leu Arg Arg Gln
625                 630                 635                 640

Glu Asp Phe Tyr Pro Phe Leu Lys Asp Asn Arg Glu Lys Ile Glu Lys
                645                 650                 655

Ile Leu Thr Phe Arg Ile Pro Tyr Tyr Val Gly Pro Leu Ala Arg Gly
            660                 665                 670

Asn Ser Arg Phe Ala Trp Met Thr Arg Lys Ser Glu Glu Thr Ile Thr
        675                 680                 685

Pro Trp Asn Phe Glu Glu Val Val Asp Lys Gly Ala Ser Ala Gln Ser
690                 695                 700

Phe Ile Glu Arg Met Thr Asn Phe Asp Lys Asn Leu Pro Asn Glu Lys
705                 710                 715                 720

Val Leu Pro Lys His Ser Leu Leu Tyr Glu Tyr Phe Thr Val Tyr Asn
                725                 730                 735

Glu Leu Thr Lys Val Lys Tyr Val Thr Glu Gly Met Arg Lys Pro Ala
            740                 745                 750

Phe Leu Ser Gly Glu Gln Lys Lys Ala Ile Val Asp Leu Leu Phe Lys
        755                 760                 765

Thr Asn Arg Lys Val Thr Val Lys Gln Leu Lys Glu Asp Tyr Phe Lys
770                 775                 780

Lys Ile Glu Cys Phe Asp Ser Val Glu Ile Ser Gly Val Glu Asp Arg
785                 790                 795                 800

Phe Asn Ala Ser Leu Gly Thr Tyr His Asp Leu Leu Lys Ile Ile Lys
                805                 810                 815

Asp Lys Asp Phe Leu Asp Asn Glu Glu Asn Glu Asp Ile Leu Glu Asp
            820                 825                 830

Ile Val Leu Thr Leu Thr Leu Phe Glu Asp Arg Glu Met Ile Glu Glu
        835                 840                 845

Arg Leu Lys Thr Tyr Ala His Leu Phe Asp Asp Lys Val Met Lys Gln
850                 855                 860

Leu Lys Arg Arg Arg Tyr Thr Gly Trp Gly Arg Leu Ser Arg Lys Leu
865                 870                 875                 880

Ile Asn Gly Ile Arg Asp Lys Gln Ser Gly Lys Thr Ile Leu Asp Phe
                885                 890                 895

Leu Lys Ser Asp Gly Phe Ala Asn Arg Asn Phe Met Gln Leu Ile His
            900                 905                 910

Asp Asp Ser Leu Thr Phe Lys Glu Asp Ile Gln Lys Ala Gln Val Ser
        915                 920                 925

Gly Gln Gly Asp Ser Leu His Glu His Ile Ala Asn Leu Ala Gly Ser
930                 935                 940

Pro Ala Ile Lys Lys Gly Ile Leu Gln Thr Val Lys Val Val Asp Glu
945                 950                 955                 960

Leu Val Lys Val Met Gly Arg His Lys Pro Glu Asn Ile Val Ile Glu
                965                 970                 975

Met Ala Arg Glu Asn Gln Thr Thr Gln Lys Gly Gln Lys Asn Ser Arg
            980                 985                 990

Glu Arg Met Lys Arg Ile Glu Glu Gly Ile Lys Glu Leu Gly Ser Gln
        995                 1000                1005

Ile Leu Lys Glu His Pro Val Glu Asn Thr Gln Leu Gln Asn Glu
    1010                1015                1020

Lys Leu Tyr Leu Tyr Tyr Leu Gln Asn Gly Arg Asp Met Tyr Val
    1025                1030                1035
```

-continued

```
Asp Gln Glu Leu Asp Ile Asn Arg Leu Ser Asp Tyr Asp Val Asp
    1040                1045                1050

His Ile Val Pro Gln Ser Phe Leu Lys Asp Asp Ser Ile Asp Asn
    1055                1060                1065

Lys Val Leu Thr Arg Ser Asp Lys Asn Arg Gly Lys Ser Asp Asn
    1070                1075                1080

Val Pro Ser Glu Glu Val Val Lys Lys Met Lys Asn Tyr Trp Arg
    1085                1090                1095

Gln Leu Leu Asn Ala Lys Leu Ile Thr Gln Arg Lys Phe Asp Asn
    1100                1105                1110

Leu Thr Lys Ala Glu Arg Gly Gly Leu Ser Glu Leu Asp Lys Ala
    1115                1120                1125

Gly Phe Ile Lys Arg Gln Leu Val Glu Thr Arg Gln Ile Thr Lys
    1130                1135                1140

His Val Ala Gln Ile Leu Asp Ser Arg Met Asn Thr Lys Tyr Asp
    1145                1150                1155

Glu Asn Asp Lys Leu Ile Arg Glu Val Lys Val Ile Thr Leu Lys
    1160                1165                1170

Ser Lys Leu Val Ser Asp Phe Arg Lys Asp Phe Gln Phe Tyr Lys
    1175                1180                1185

Val Arg Glu Ile Asn Asn Tyr His His Ala His Asp Ala Tyr Leu
    1190                1195                1200

Asn Ala Val Val Gly Thr Ala Leu Ile Lys Lys Tyr Pro Lys Leu
    1205                1210                1215

Glu Ser Glu Phe Val Tyr Gly Asp Tyr Lys Val Tyr Asp Val Arg
    1220                1225                1230

Lys Met Ile Ala Lys Ser Glu Gln Glu Ile Gly Lys Ala Thr Ala
    1235                1240                1245

Lys Tyr Phe Phe Tyr Ser Asn Ile Met Asn Phe Phe Lys Thr Glu
    1250                1255                1260

Ile Thr Leu Ala Asn Gly Glu Ile Arg Lys Arg Pro Leu Ile Glu
    1265                1270                1275

Thr Asn Gly Glu Thr Gly Glu Ile Val Trp Asp Lys Gly Arg Asp
    1280                1285                1290

Phe Ala Thr Val Arg Lys Val Leu Ser Met Pro Gln Val Asn Ile
    1295                1300                1305

Val Lys Lys Thr Glu Val Gln Thr Gly Gly Phe Ser Lys Glu Ser
    1310                1315                1320

Ile Leu Pro Lys Arg Asn Ser Asp Lys Leu Ile Ala Arg Lys Lys
    1325                1330                1335

Asp Trp Asp Pro Lys Lys Tyr Gly Gly Phe Asp Ser Pro Thr Val
    1340                1345                1350

Ala Tyr Ser Val Leu Val Val Ala Lys Val Glu Lys Gly Lys Ser
    1355                1360                1365

Lys Lys Leu Lys Ser Val Lys Glu Leu Leu Gly Ile Thr Ile Met
    1370                1375                1380

Glu Arg Ser Ser Phe Glu Lys Asn Pro Ile Asp Phe Leu Glu Ala
    1385                1390                1395

Lys Gly Tyr Lys Glu Val Lys Lys Asp Leu Ile Ile Lys Leu Pro
    1400                1405                1410

Lys Tyr Ser Leu Phe Glu Leu Glu Asn Gly Arg Lys Arg Met Leu
    1415                1420                1425

Ala Ser Ala Gly Glu Leu Gln Lys Gly Asn Glu Leu Ala Leu Pro
```

```
      1430                1435                1440

Ser Lys Tyr Val Asn Phe Leu Tyr Leu Ala Ser His Tyr Glu Lys
      1445                1450                1455

Leu Lys Gly Ser Pro Glu Asp Asn Glu Gln Lys Gln Leu Phe Val
      1460                1465                1470

Glu Gln His Lys His Tyr Leu Asp Glu Ile Ile Glu Gln Ile Ser
      1475                1480                1485

Glu Phe Ser Lys Arg Val Ile Leu Ala Asp Ala Asn Leu Asp Lys
      1490                1495                1500

Val Leu Ser Ala Tyr Asn Lys His Arg Asp Lys Pro Ile Arg Glu
      1505                1510                1515

Gln Ala Glu Asn Ile Ile His Leu Phe Thr Leu Thr Asn Leu Gly
      1520                1525                1530

Ala Pro Ala Ala Phe Lys Tyr Phe Asp Thr Thr Ile Asp Arg Lys
      1535                1540                1545

Arg Tyr Thr Ser Thr Lys Glu Val Leu Asp Ala Thr Leu Ile His
      1550                1555                1560

Gln Ser Ile Thr Gly Leu Tyr Glu Thr Arg Ile Asp Leu Ser Gln
      1565                1570                1575

Leu Gly Gly Asp Ser Gly Gly Ser Thr Asn Leu Ser Asp Ile Ile
      1580                1585                1590

Glu Lys Glu Thr Gly Lys Gln Leu Val Ile Gln Glu Ser Ile Leu
      1595                1600                1605

Met Leu Pro Glu Glu Val Glu Val Ile Gly Asn Lys Pro Glu
      1610                1615                1620

Ser Asp Ile Leu Val His Thr Ala Tyr Asp Glu Ser Thr Asp Glu
      1625                1630                1635

Asn Val Met Leu Leu Thr Ser Asp Ala Pro Glu Tyr Lys Pro Trp
      1640                1645                1650

Ala Leu Val Ile Gln Asp Ser Asn Gly Glu Asn Lys Ile Lys Met
      1655                1660                1665

Leu Ser Gly Gly Ser Pro Lys Lys Lys Arg Lys Val
      1670                1675                1680

<210> SEQ ID NO 20
<211> LENGTH: 1680
<212> TYPE: PRT
<213> ORGANISM: Artificial Sequence
<220> FEATURE:
<223> OTHER INFORMATION: Synthetic

<400> SEQUENCE: 20

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
```

```
            100                 105                 110
Phe Leu Gln Glu Asn Thr His Val Arg Leu Arg Ile Phe Ala Ala Arg
            115                 120                 125

Ile Tyr Tyr Tyr Asp Pro Leu Tyr Lys Glu Ala Leu Gln Met Leu Arg
            130                 135             140

Asp Ala Gly Ala Gln Val Ser Ile Met Thr Tyr Asp Glu Phe Lys His
145                     150                 155                 160

Cys Trp Asp Thr Phe Val Asp His Gln Gly Cys Pro Phe Gln Pro Trp
                    165                 170                 175

Asp Gly Leu Asp Glu His Ser Gln Ala Leu Ser Gly Arg Leu Arg Ala
                180                 185                 190

Ile Leu Gln Asn Gln Gly Asn Ser Gly Ser Glu Thr Pro Gly Thr Ser
            195                 200                 205

Glu Ser Ala Thr Pro Glu Ser Asp Lys Lys Tyr Ser Ile Gly Leu Ala
            210                 215                 220

Ile Gly Thr Asn Ser Val Gly Trp Ala Val Ile Thr Asp Glu Tyr Lys
225                 230                 235                 240

Val Pro Ser Lys Lys Phe Lys Val Leu Gly Asn Thr Asp Arg His Ser
                    245                 250                 255

Ile Lys Lys Asn Leu Ile Gly Ala Leu Leu Phe Asp Ser Gly Glu Thr
                260                 265                 270

Ala Glu Ala Thr Arg Leu Lys Arg Thr Ala Arg Arg Tyr Thr Arg
                275                 280                 285

Arg Lys Asn Arg Ile Cys Tyr Leu Gln Glu Ile Phe Ser Asn Glu Met
            290                 295                 300

Ala Lys Val Asp Asp Ser Phe Phe His Arg Leu Glu Glu Ser Phe Leu
305                 310                 315                 320

Val Glu Glu Asp Lys Lys His Glu Arg His Pro Ile Phe Gly Asn Ile
                    325                 330                 335

Val Asp Glu Val Ala Tyr His Glu Lys Tyr Pro Thr Ile Tyr His Leu
                340                 345                 350

Arg Lys Lys Leu Val Asp Ser Thr Asp Lys Ala Asp Leu Arg Leu Ile
            355                 360                 365

Tyr Leu Ala Leu Ala His Met Ile Lys Phe Arg Gly His Phe Leu Ile
            370                 375                 380

Glu Gly Asp Leu Asn Pro Asp Asn Ser Asp Val Asp Lys Leu Phe Ile
385                 390                 395                 400

Gln Leu Val Gln Thr Tyr Asn Gln Leu Phe Glu Glu Asn Pro Ile Asn
                    405                 410                 415

Ala Ser Gly Val Asp Ala Lys Ala Ile Leu Ser Ala Arg Leu Ser Lys
                420                 425                 430

Ser Arg Arg Leu Glu Asn Leu Ile Ala Gln Leu Pro Gly Glu Lys Lys
            435                 440                 445

Asn Gly Leu Phe Gly Asn Leu Ile Ala Leu Ser Leu Gly Leu Thr Pro
            450                 455                 460

Asn Phe Lys Ser Asn Phe Asp Leu Ala Glu Asp Ala Lys Leu Gln Leu
465                 470                 475                 480

Ser Lys Asp Thr Tyr Asp Asp Leu Asp Asn Leu Leu Ala Gln Ile
                    485                 490                 495

Gly Asp Gln Tyr Ala Asp Leu Phe Leu Ala Ala Lys Asn Leu Ser Asp
                500                 505                 510

Ala Ile Leu Leu Ser Asp Ile Leu Arg Val Asn Thr Glu Ile Thr Lys
            515                 520                 525
```

```
Ala Pro Leu Ser Ala Ser Met Ile Lys Arg Tyr Asp Glu His His Gln
            530                 535                 540

Asp Leu Thr Leu Leu Lys Ala Leu Val Arg Gln Gln Leu Pro Glu Lys
545                 550                 555                 560

Tyr Lys Glu Ile Phe Phe Asp Gln Ser Lys Asn Gly Tyr Ala Gly Tyr
                565                 570                 575

Ile Asp Gly Gly Ala Ser Gln Glu Glu Phe Tyr Lys Phe Ile Lys Pro
            580                 585                 590

Ile Leu Glu Lys Met Asp Gly Thr Glu Glu Leu Leu Val Lys Leu Asn
            595                 600                 605

Arg Glu Asp Leu Leu Arg Lys Gln Arg Thr Phe Asp Asn Gly Ser Ile
610                 615                 620

Pro His Gln Ile His Leu Gly Glu Leu His Ala Ile Leu Arg Arg Gln
625                 630                 635                 640

Glu Asp Phe Tyr Pro Phe Leu Lys Asp Asn Arg Glu Lys Ile Glu Lys
                645                 650                 655

Ile Leu Thr Phe Arg Ile Pro Tyr Tyr Val Gly Pro Leu Ala Arg Gly
            660                 665                 670

Asn Ser Arg Phe Ala Trp Met Thr Arg Lys Ser Glu Glu Thr Ile Thr
            675                 680                 685

Pro Trp Asn Phe Glu Glu Val Val Asp Lys Gly Ala Ser Ala Gln Ser
690                 695                 700

Phe Ile Glu Arg Met Thr Asn Phe Asp Lys Asn Leu Pro Asn Glu Lys
705                 710                 715                 720

Val Leu Pro Lys His Ser Leu Leu Tyr Glu Tyr Phe Thr Val Tyr Asn
                725                 730                 735

Glu Leu Thr Lys Val Lys Tyr Val Thr Glu Gly Met Arg Lys Pro Ala
            740                 745                 750

Phe Leu Ser Gly Glu Gln Lys Lys Ala Ile Val Asp Leu Leu Phe Lys
            755                 760                 765

Thr Asn Arg Lys Val Thr Val Lys Gln Leu Lys Glu Asp Tyr Phe Lys
770                 775                 780

Lys Ile Glu Cys Phe Asp Ser Val Glu Ile Ser Gly Val Glu Asp Arg
785                 790                 795                 800

Phe Asn Ala Ser Leu Gly Thr Tyr His Asp Leu Leu Lys Ile Ile Lys
                805                 810                 815

Asp Lys Asp Phe Leu Asp Asn Glu Glu Asn Glu Asp Ile Leu Glu Asp
            820                 825                 830

Ile Val Leu Thr Leu Thr Leu Phe Glu Asp Arg Glu Met Ile Glu Glu
            835                 840                 845

Arg Leu Lys Thr Tyr Ala His Leu Phe Asp Asp Lys Val Met Lys Gln
850                 855                 860

Leu Lys Arg Arg Arg Tyr Thr Gly Trp Gly Arg Leu Ser Arg Lys Leu
865                 870                 875                 880

Ile Asn Gly Ile Arg Asp Lys Gln Ser Gly Lys Thr Ile Leu Asp Phe
                885                 890                 895

Leu Lys Ser Asp Gly Phe Ala Asn Arg Asn Phe Met Gln Leu Ile His
            900                 905                 910

Asp Asp Ser Leu Thr Phe Lys Glu Asp Ile Gln Lys Ala Gln Val Ser
            915                 920                 925

Gly Gln Gly Asp Ser Leu His Glu His Ile Ala Asn Leu Ala Gly Ser
930                 935                 940
```

-continued

```
Pro Ala Ile Lys Lys Gly Ile Leu Gln Thr Val Lys Val Val Asp Glu
945                 950                 955                 960

Leu Val Lys Val Met Gly Arg His Lys Pro Glu Asn Ile Val Ile Glu
            965                 970                 975

Met Ala Arg Glu Asn Gln Thr Thr Gln Lys Gly Gln Lys Asn Ser Arg
            980                 985                 990

Glu Arg Met Lys Arg Ile Glu Glu Gly Ile Lys Glu Leu Gly Ser Gln
            995                 1000                1005

Ile Leu Lys Glu His Pro Val Glu Asn Thr Gln Leu Gln Asn Glu
    1010                1015                1020

Lys Leu Tyr Leu Tyr Tyr Leu Gln Asn Gly Arg Asp Met Tyr Val
    1025                1030                1035

Asp Gln Glu Leu Asp Ile Asn Arg Leu Ser Asp Tyr Asp Val Asp
    1040                1045                1050

His Ile Val Pro Gln Ser Phe Leu Lys Asp Asp Ser Ile Asp Asn
    1055                1060                1065

Lys Val Leu Thr Arg Ser Asp Lys Asn Arg Gly Lys Ser Asp Asn
    1070                1075                1080

Val Pro Ser Glu Glu Val Val Lys Lys Met Lys Asn Tyr Trp Arg
    1085                1090                1095

Gln Leu Leu Asn Ala Lys Leu Ile Thr Gln Arg Lys Phe Asp Asn
    1100                1105                1110

Leu Thr Lys Ala Glu Arg Gly Gly Leu Ser Glu Leu Asp Lys Ala
    1115                1120                1125

Gly Phe Ile Lys Arg Gln Leu Val Glu Thr Arg Gln Ile Thr Lys
    1130                1135                1140

His Val Ala Gln Ile Leu Asp Ser Arg Met Asn Thr Lys Tyr Asp
    1145                1150                1155

Glu Asn Asp Lys Leu Ile Arg Glu Val Lys Val Ile Thr Leu Lys
    1160                1165                1170

Ser Lys Leu Val Ser Asp Phe Arg Lys Asp Phe Gln Phe Tyr Lys
    1175                1180                1185

Val Arg Glu Ile Asn Asn Tyr His His Ala His Asp Ala Tyr Leu
    1190                1195                1200

Asn Ala Val Val Gly Thr Ala Leu Ile Lys Lys Tyr Pro Lys Leu
    1205                1210                1215

Glu Ser Glu Phe Val Tyr Gly Asp Tyr Lys Val Tyr Asp Val Arg
    1220                1225                1230

Lys Met Ile Ala Lys Ser Glu Gln Glu Ile Gly Lys Ala Thr Ala
    1235                1240                1245

Lys Tyr Phe Phe Tyr Ser Asn Ile Met Asn Phe Phe Lys Thr Glu
    1250                1255                1260

Ile Thr Leu Ala Asn Gly Glu Ile Arg Lys Arg Pro Leu Ile Glu
    1265                1270                1275

Thr Asn Gly Glu Thr Gly Glu Ile Val Trp Asp Lys Gly Arg Asp
    1280                1285                1290

Phe Ala Thr Val Arg Lys Val Leu Ser Met Pro Gln Val Asn Ile
    1295                1300                1305

Val Lys Lys Thr Glu Val Gln Thr Gly Gly Phe Ser Lys Glu Ser
    1310                1315                1320

Ile Leu Pro Lys Arg Asn Ser Asp Lys Leu Ile Ala Arg Lys Lys
    1325                1330                1335

Asp Trp Asp Pro Lys Lys Tyr Gly Gly Phe Asp Ser Pro Thr Val
```

Ala Tyr Ser Val Leu Val Ala Lys Val Glu Lys Gly Lys Ser
1355                1360                1365

Lys Lys Leu Lys Ser Val Lys Glu Leu Leu Gly Ile Thr Ile Met
1370                1375                1380

Glu Arg Ser Ser Phe Glu Lys Asn Pro Ile Asp Phe Leu Glu Ala
1385                1390                1395

Lys Gly Tyr Lys Glu Val Lys Lys Asp Leu Ile Ile Lys Leu Pro
1400                1405                1410

Lys Tyr Ser Leu Phe Glu Leu Glu Asn Gly Arg Lys Arg Met Leu
1415                1420                1425

Ala Ser Ala Gly Glu Leu Gln Lys Gly Asn Glu Leu Ala Leu Pro
1430                1435                1440

Ser Lys Tyr Val Asn Phe Leu Tyr Leu Ala Ser His Tyr Glu Lys
1445                1450                1455

Leu Lys Gly Ser Pro Glu Asp Asn Glu Gln Lys Gln Leu Phe Val
1460                1465                1470

Glu Gln His Lys His Tyr Leu Asp Glu Ile Ile Glu Gln Ile Ser
1475                1480                1485

Glu Phe Ser Lys Arg Val Ile Leu Ala Asp Ala Asn Leu Asp Lys
1490                1495                1500

Val Leu Ser Ala Tyr Asn Lys His Arg Asp Lys Pro Ile Arg Glu
1505                1510                1515

Gln Ala Glu Asn Ile Ile His Leu Phe Thr Leu Thr Asn Leu Gly
1520                1525                1530

Ala Pro Ala Ala Phe Lys Tyr Phe Asp Thr Thr Ile Asp Arg Lys
1535                1540                1545

Arg Tyr Thr Ser Thr Lys Glu Val Leu Asp Ala Thr Leu Ile His
1550                1555                1560

Gln Ser Ile Thr Gly Leu Tyr Glu Thr Arg Ile Asp Leu Ser Gln
1565                1570                1575

Leu Gly Gly Asp Ser Gly Gly Ser Thr Asn Leu Ser Asp Ile Ile
1580                1585                1590

Glu Lys Glu Thr Gly Lys Gln Leu Val Ile Gln Glu Ser Ile Leu
1595                1600                1605

Met Leu Pro Glu Glu Val Glu Glu Val Ile Gly Asn Lys Pro Glu
1610                1615                1620

Ser Asp Ile Leu Val His Thr Ala Tyr Asp Glu Ser Thr Asp Glu
1625                1630                1635

Asn Val Met Leu Leu Thr Ser Asp Ala Pro Glu Tyr Lys Pro Trp
1640                1645                1650

Ala Leu Val Ile Gln Asp Ser Asn Gly Glu Asn Lys Ile Lys Met
1655                1660                1665

Leu Ser Gly Gly Ser Pro Lys Lys Lys Arg Lys Val
1670                1675                1680

<210> SEQ ID NO 21
<211> LENGTH: 8442
<212> TYPE: DNA
<213> ORGANISM: Artificial Sequence
<220> FEATURE:
<223> OTHER INFORMATION: Synthetic

<400> SEQUENCE: 21
atatgccaag tacgccccct attgacgtca atgacggtaa atggcccgcc tggcattatg     60

| | |
|---|---|
| cccagtacat gaccttatgg gactttccta cttggcagta catctacgta ttagtcatcg | 120 |
| ctattaccat ggtgatgcgg ttttggcagt acatcaatgg gcgtggatag cggtttgact | 180 |
| cacgggatt tccaagtctc caccccattg acgtcaatgg gagtttgttt tggcaccaaa | 240 |
| atcaacggga ctttccaaaa tgtcgtaaca actccgcccc attgacgcaa atgggcggta | 300 |
| ggcgtgtacg gtgggaggtc tatataagca gagctggttt agtgaaccgt cagatccgct | 360 |
| agagatccgc ggccgctaat acgactcact atagggagag ccgccaccat ggaagccagc | 420 |
| ccagcatccg ggcccagaca cttgatggat ccacacatat tcacttccaa cttaacaat | 480 |
| ggcattggaa ggcataagac ctacctgtgc tacgaagtgg agcgcctgga caatggcacc | 540 |
| tcggtcaaga tggaccagca caggggcttt ctacacaacc aggctaagaa tcttctctgt | 600 |
| ggcttttacg gccgccatgc ggagctgcgc ttcttggacc tggttccttc tttgcagttg | 660 |
| gacccggccc agatctacag ggtcacttgg ttcatctcct ggagcccctg cttctcctgg | 720 |
| ggctgtgccg gggaagtgcg tgcgttcctt caggagaaca cacacgtgag actgcgtatc | 780 |
| ttcgctgccc gcatctatga ttacgacccc ctatataagg aggcactgca aatgctgcgg | 840 |
| gatgctgggg cccaagtctc catcatgacc tacgatgaat ttaagcactg ctgggacacc | 900 |
| tttgtggacc accagggatg tccccttccag ccctgggatg gactagatga gcacagccaa | 960 |
| gccctgagtg ggaggctgcg ggccattctc cagaatcagg gaaacagcgg cagcgagact | 1020 |
| cccgggacct cagagtccgc cacacccgaa agtgataaaa agtattctat ggtttagcc | 1080 |
| atcggcacta attccgttgg atgggctgtc ataaccgatg aatacaaagt accttcaaag | 1140 |
| aaatttaagg tgttggggaa cacagaccgt cattcgatta aaaagaatct tatcggtgcc | 1200 |
| ctcctattcg atagtggcga aacggcgagg gcgactcgcc tgaaacgaac cgctcggaga | 1260 |
| aggtatacac gtcgcaagaa ccgaatatgt tacttacaag aaattttag caatgagatg | 1320 |
| gccaaagttg acgattcttt cttcaccgt ttggaagagt ccttccttgt cgaagaggac | 1380 |
| aagaaacatg aacggcaccc catctttgga aacatagtag atgaggtggc atatcatgaa | 1440 |
| aagtacccaa cgatttatca cctcagaaaa aagctagttg actcaactga taaagcggac | 1500 |
| ctgaggttaa tctacttggc tcttgcccat atgataaagt ccgtgggca ctttctcatt | 1560 |
| gagggtgatc taaatccgga caactcggat gtcgacaaac tgttcatcca gttagtacaa | 1620 |
| acctataatc agttgtttga agagaaccct ataaatgcaa gtggcgtgga tgcgaaggct | 1680 |
| attcttagcg cccgcctctc taaatcccga cggctagaaa acctgatcgc acaattaccc | 1740 |
| ggagagaaga aaaatgggtt gttcggtaac cttatagcgc tctcactagg cctgacacca | 1800 |
| aattttaagt cgaacttcga cttagctgaa gatgccaaat tgcagcttag taaggacacg | 1860 |
| tacgatgacg atctcgacaa tctactggca caaattggag atcagtatgc ggacttattt | 1920 |
| ttggctgcca aaaaccttag cgatgcaatc ctcctatctg acatactgag agttaatact | 1980 |
| gagattacca aggcgccgtt atccgcttca atgatcaaaa ggtacgatga acatcaccaa | 2040 |
| gacttgacac ttctcaaggc cctagtccgt cagcaactgc ctgagaaata taaggaaata | 2100 |
| ttctttgatc agtcgaaaaa cgggtacgca ggttatattg acggcggagc gagtcaagag | 2160 |
| gaattctaca gtttatcaa acccatatta gagaagatga tgggacgga agagttgctt | 2220 |
| gtaaaactca atcgcgaaga tctactgcga aagcagcgga cttcgacaa cggtagcatt | 2280 |
| ccacatcaaa tccacttagg cgaattgcat gctatactta gaaggcagga ggattttat | 2340 |
| ccgttcctca aagacaatcg tgaaaagatt gagaaaatcc taaccttcg catacctac | 2400 |

```
tatgtgggac ccctggcccg agggaactct cggttcgcat ggatgacaag aaagtccgaa    2460
gaaacgatta ctccatggaa ttttgaggaa gttgtcgata aggtgcgtc agctcaatcg     2520 ttcatcgaga ggatgaccaa ctttgacaag aatttaccga acgaaaaagt attgcctaag    2580
cacagtttac tttacgagta tttcacagtg tacaatgaac tcacgaaagt taagtatgtc    2640
actgagggca tgcgtaaacc cgcctttcta agcggagaac agaagaaagc aatagtagat    2700
ctgttattca agaccaaccg caaagtgaca gttaagcaat tgaaagagga ctactttaag    2760
aaaattgaat gcttcgattc tgtcgagatc tccggggtag aagatcgatt taatgcgtca    2820
cttggtacgt atcatgacct cctaaagata attaaagata aggacttcct ggataacgaa    2880
gagaatgaag atatcttaga agatatagtg ttgactctta ccctctttga agatcgggaa    2940
atgattgagg aaagactaaa acatacgct cacctgttcg acgataaggt tatgaaacag     3000
ttaaagaggc gtcgctatac gggctgggga cgattgtcgc ggaaacttat caacgggata    3060
agagacaagc aaagtggtaa aactattctc gattttctaa agagcgacgg cttcgccaat    3120
aggaacttta tgcagctgat ccatgatgac tctttaacct tcaaagagga tatacaaaag    3180
gcacaggttt ccggacaagg ggactcattg cacgaacata ttgcgaatct tgctggttcg    3240
ccagccatca aaagggcat actccagaca gtcaaagtag tggatgagct agttaaggtc     3300
atgggacgtc acaaaccgga aaacattgta atcgagatgg cacgcgaaaa tcaaacgact    3360
cagaaggggc aaaaaaacag tcgagagcgg atgaagagaa tagaagaggg tattaaagaa    3420
ctgggcagcc agatcttaaa ggagcatcct gtggaaaata cccaattgca gaacgagaaa    3480 cttttacctct attacctaca aaatggaagg gacatgtatg ttgatcagga actggacata    3540
aaccgtttat ctgattacga cgtcgatcac attgtacccc aatccttttt gaaggacgat    3600
tcaatcgaca ataaagtgct tacacgctcg gataagaacc gagggaaaag tgacaatgtt    3660
ccaagcgagg aagtcgtaaa gaaaatgaag aactattggc ggcagctcct aaatgcgaaa    3720
ctgataacgc aaagaaagtt cgataactta actaaagctg agaggggtgg cttgtctgaa    3780
cttgacaagg ccggatttat taaacgtcag ctcgtggaaa cccgccaaat cacaaagcat    3840
gttgcacaga tactagattc ccgaatgaat acgaaatacg acgagaacga taagctgatt    3900
cgggaagtca agtaatcac tttaaagtca aaattggtgt cggacttcag aaaggatttt    3960
caattctata aagttaggga gataaataac taccaccatg cgcacgacgc ttatcttaat    4020
gccgtcgtag ggaccgcact cattaagaaa tacccgaagc tagaaagtga gtttgtgtat    4080
ggtgattaca agtttatga cgtccgtaag atgatcgcga aaagcgaaca ggagataggc     4140
aaggctacag ccaaatactt cttttattct aacattatga atttctttaa gacggaaatc    4200
actctggcaa acgagagat acgcaaacga ccttttaattg aaaccaatgg ggagacaggt    4260
gaaatcgtat gggataaggg ccgggacttc gcgacggtga gaaaagtttt gtccatgccc    4320
caagtcaaca tagtaaagaa aactgaggtg cagaccggag ggttttcaaa ggaatcgatt    4380
cttccaaaaa ggaatagtga taagctcatc gctcgtaaaa aggactggga cccgaaaaag    4440
tacggtggct tcgatagccc tacagttgcc tattctgtcc tagtagtggc aaaagttgag    4500
aagggaaaat ccaagaaact gaagtcagtc aaagaattat tggggataac gattatggag    4560
cgctcgtctt ttgaaaagaa ccccatcgac ttccttgagg cgaaaggtta caaggaagta    4620
aaaaaggatc tcataattaa actaccaaag tatagtctgt ttgagttaga aaatggccga    4680
aaacggatgt tggctagcgc cggagagctt caaaagggga cgaactcgc actaccgtct     4740 aaatacgtga atttcctgta tttagcgtcc cattacgaga agttgaaagg ttcacctgaa    4800
```

```
gataacgaac agaagcaact ttttgttgag cagcacaaac attatctcga cgaaatcata   4860
gagcaaattt cggaattcag taagagagtc atcctagctg atgccaatct ggacaaagta   4920
ttaagcgcat acaacaagca cagggataaa cccatacgtg agcaggcgga aaatattatc   4980
catttgttta ctcttaccaa cctcggcgct ccagccgcat tcaagtattt tgacacaacg   5040
atagatcgca aacgatacac ttctaccaag gaggtgctag acgcgacact gattcaccaa   5100
tccatcacgg gattatatga aactcggata gatttgtcac agcttggggg tgactctggt   5160
ggttctacta atctgtcaga tattattgaa aaggagaccg gtaagcaact ggttatccag   5220
gaatccatcc tcatgctccc agaggaggtg aagaagtca ttgggaacaa gccggaaagc   5280
gatatactcg tgcacaccgc ctacgacgag agcaccgacg agaatgtcat gcttctgact   5340
agcgacgccc tgaatacaa gcctgggct ctggtcatac aggatagcaa cggtgagaac   5400
aagattaaga tgctctctgg tggttctccc aagaagaaga ggaaagtcta accggtcatc   5460
atcaccatca ccattgagtt taaacccgct gatcagcctc gactgtgcct tctagttgcc   5520
agccatctgt tgtttgcccc tcccccgtgc cttccttgac cctggaaggt gccactccca   5580
ctgtcctttc ctaataaaat gaggaaattg catcgcattg tctgagtagg tgtcattcta   5640
ttctgggggg tggggtgggg caggacagca aggggagga ttgggaagac aatagcaggc   5700
atgctgggga tgcggtgggc tctatggctt ctgaggcgga agaaccagc tggggctcga   5760
taccgtcgac ctctagctag agcttggcgt aatcatggtc atagctgttt cctgtgtgaa   5820
attgttatcc gctcacaatt ccacacaaca tacgagccgg aagcataaag tgtaaagcct   5880
agggtgccta atgagtgagc taactcacat taattgcgtt gcgctcactg cccgctttcc   5940
agtcgggaaa cctgtcgtgc cagctgcatt aatgaatcgg ccaacgcgcg gggagaggcg   6000
gtttgcgtat tgggcgctct tccgcttcct cgctcactga ctcgctgcgc tcggtcgttc   6060
ggctgcggcg agcggtatca gctcactcaa aggcggtaat acggttatcc acagaatcag   6120
gggataacgc aggaaagaac atgtgagcaa aaggccagca aaaggccagg aaccgtaaaa   6180
aggccgcgtt gctggcgttt ttccataggc tccgccccc tgacgagcat cacaaaaatc   6240
gacgctcaag tcagaggtgg cgaaacccga caggactata aagataccag gcgtttcccc   6300
ctggaagctc cctcgtgcgc tctcctgttc cgaccctgcc gcttaccgga tacctgtccg   6360
cctttctccc ttcgggaagc gtggcgcttt ctcatagctc acgctgtagg tatctcagtt   6420
cggtgtaggt cgttcgctcc aagctgggct gtgtgcacga acccccgtt cagcccgacc   6480
gctgcgcctt atccggtaac tatcgtcttg agtccaaccc ggtaagacac gacttatcgc   6540
cactggcagc agccactggt aacaggatta gcagagcgag gtatgtaggc ggtgctacag   6600
agttcttgaa gtggtggcct aactacggct acactagaag aacagtattt ggtatctgcg   6660
ctctgctgaa gccagttacc ttcggaaaaa gagttggtag ctcttgatcc ggcaaacaaa   6720
ccaccgctgg tagcggtggt ttttttgttt gcaagcagca gattacgcgc agaaaaaaag   6780
gatctcaaga agatcctttg atcttttcta cggggtctga cgctcagtgg aacgaaaact   6840
cacgttaagg gattttggtc atgagattat caaaaaggat cttcacctag atcctttaa   6900
attaaaaatg aagttttaaa tcaatctaaa gtatatatga gtaaacttgg tctgacagtt   6960
accaatgctt aatcagtgag gcacctatct cagcgatctg tctatttcgt tcatccatag   7020
ttgcctgact ccccgtcgtg tagataacta cgatacggga gggcttacca tctgccccca   7080
gtgctgcaat gataccgcga gacccacgct caccggctcc agatttatca gcaataaacc   7140
```

| | |
|---|---|
| agccagccgg aagggccgag cgcagaagtg gtcctgcaac tttatccgcc tccatccagt | 7200 |
| ctattaattg ttgccgggaa gctagagtaa gtagttcgcc agttaatagt ttgcgcaacg | 7260 |
| ttgttgccat tgctacaggc atcgtggtgt cacgctcgtc gtttggtatg gcttcattca | 7320 |
| gctccggttc ccaacgatca aggcgagtta catgatcccc catgttgtgc aaaaaagcgg | 7380 |
| ttagctcctt cggtcctccg atcgttgtca gaagtaagtt ggccgcagtg ttatcactca | 7440 |
| tggttatggc agcactgcat aattctctta ctgtcatgcc atccgtaaga tgcttttctg | 7500 |
| tgactggtga gtactcaacc aagtcattct gagaatagtg tatgcggcga ccgagttgct | 7560 |
| cttgcccggc gtcaatacgg gataataccg cgccacatag cagaacttta aaagtgctca | 7620 |
| tcattggaaa acgttcttcg gggcgaaaac tctcaaggat cttaccgctg ttgagatcca | 7680 |
| gttcgatgta acccactcgt gcacccaact gatcttcagc atcttttact ttcaccagcg | 7740 |
| tttctgggtg agcaaaaaca ggaaggcaaa atgccgcaaa aaagggaata agggcgacac | 7800 |
| ggaaatgttg aatactcata ctcttccttt tcaatatta ttgaagcatt tatcagggtt | 7860 |
| attgtctcat gagcggatac atatttgaat gtatttagaa aaataaacaa ataggggttc | 7920 |
| cgcgcacatt tccccgaaaa gtgccacctg acgtcgacgg atcgggagat cgatctcccg | 7980 |
| atcccctagg gtcgactctc agtacaatct gctctgatgc cgcatagtta agccagtatc | 8040 |
| tgctccctgc ttgtgtgttg gaggtcgctg agtagtgcgc gagcaaaatt taagctacaa | 8100 |
| caaggcaagg cttgaccgac aattgcatga agaatctgct tagggttagg cgttttgcgc | 8160 |
| tgcttcgcga tgtacgggcc agatatacgc gttgacattg attattgact agttattaat | 8220 |
| agtaatcaat tacggggtca ttagttcata gcccatatat ggagttccgc gttacataac | 8280 |
| ttacggtaaa tggcccgcct ggctgaccgc ccaacgaccc ccgcccattg acgtcaataa | 8340 |
| tgacgtatgt tcccatagta acgccaatag ggactttcca ttgacgtcaa tgggtggagt | 8400 |
| atttacggta aactgcccac ttggcagtac atcaagtgta tc | 8442 |

<210> SEQ ID NO 22
<211> LENGTH: 199
<212> TYPE: PRT
<213> ORGANISM: Artificial Sequence
<220> FEATURE:
<223> OTHER INFORMATION: Synthetic

<400> SEQUENCE: 22

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Phe Glu Asp Asp Pro Leu Tyr Lys Glu Ala Leu Gln Met Leu Arg

```
                130                 135                 140
Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 23
<211> LENGTH: 199
<212> TYPE: PRT
<213> ORGANISM: Artificial Sequence
<220> FEATURE:
<223> OTHER INFORMATION: Synthetic

<400> SEQUENCE: 23

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Phe Tyr Asp Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 24
<211> LENGTH: 199
<212> TYPE: PRT
<213> ORGANISM: Artificial Sequence
<220> FEATURE:
<223> OTHER INFORMATION: Synthetic

<400> SEQUENCE: 24

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30
```

```
Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
     50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Tyr Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 25
<211> LENGTH: 199
<212> TYPE: PRT
<213> ORGANISM: Artificial Sequence
<220> FEATURE:
<223> OTHER INFORMATION: Synthetic

<400> SEQUENCE: 25

```
Met Glu Ala Ser Pro Ala Ser Gly Pro Arg His Leu Met Asp Pro His
 1               5                  10                  15

Ile Phe Thr Ser Asn Phe Asn Asn Gly Ile Gly Arg His Lys Thr Tyr
             20                  25                  30

Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
     50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Tyr Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190
```

Ile Leu Gln Asn Gln Gly Asn
        195

<210> SEQ ID NO 26
<211> LENGTH: 199
<212> TYPE: PRT
<213> ORGANISM: Artificial Sequence
<220> FEATURE:
<223> OTHER INFORMATION: Synthetic

<400> SEQUENCE: 26

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Tyr Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 27
<211> LENGTH: 199
<212> TYPE: PRT
<213> ORGANISM: Artificial Sequence
<220> FEATURE:
<223> OTHER INFORMATION: Synthetic

<400> SEQUENCE: 27

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Tyr Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
            115                 120                 125

Ile Tyr Asp Tyr Asp Tyr Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
            165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 28
<211> LENGTH: 199
<212> TYPE: PRT
<213> ORGANISM: Artificial Sequence
<220> FEATURE:
<223> OTHER INFORMATION: Synthetic

<400> SEQUENCE: 28

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
            85                  90                  95

Ser Trp Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
            115                 120                 125

Ile Tyr Asp Tyr Asp Tyr Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
            165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 29
<211> LENGTH: 199
<212> TYPE: PRT
<213> ORGANISM: Artificial Sequence
<220> FEATURE:
<223> OTHER INFORMATION: Synthetic

```
<400> SEQUENCE: 29

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Tyr Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Phe Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 30
<211> LENGTH: 199
<212> TYPE: PRT
<213> ORGANISM: Artificial Sequence
<220> FEATURE:
<223> OTHER INFORMATION: Synthetic

<400> SEQUENCE: 30

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Tyr Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Asp Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
```

145              150              155              160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 31
<211> LENGTH: 199
<212> TYPE: PRT
<213> ORGANISM: Artificial Sequence
<220> FEATURE:
<223> OTHER INFORMATION: Synthetic

<400> SEQUENCE: 31

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Phe Asp Tyr Asp Tyr Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 32
<211> LENGTH: 199
<212> TYPE: PRT
<213> ORGANISM: Artificial Sequence
<220> FEATURE:
<223> OTHER INFORMATION: Synthetic

<400> SEQUENCE: 32

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

```
Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Ala Gly Cys Ala Gly Glu Val Arg Ala
               100                 105                 110

Phe Leu Gln Glu Asn Thr His Val Arg Leu Arg Ile Phe Ala Ala Arg
           115                 120                 125

Ile Tyr Asp Asp Asp Tyr Leu Tyr Lys Glu Ala Leu Gln Met Leu Arg
   130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
               165                 170                 175

Asp Gly Leu Asp Glu His Ser Gln Ala Leu Ser Gly Arg Leu Arg Ala
               180                 185                 190

Ile Leu Gln Asn Gln Gly Asn
       195
```

<210> SEQ ID NO 33
<211> LENGTH: 199
<212> TYPE: PRT
<213> ORGANISM: Artificial Sequence
<220> FEATURE:
<223> OTHER INFORMATION: Synthetic

<400> SEQUENCE: 33

```
Met Glu Ala Ser Pro Ala Ser Gly Pro Arg His Leu Met Asp Pro His
  1               5                  10                  15

Ile Phe Thr Ser Asn Phe Asn Asn Gly Ile Gly Arg His Lys Thr Tyr
                 20                  25                  30

Leu Cys Tyr Glu Val Glu Arg Leu Asp Asn Gly Thr Ser Val Lys Met
             35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Ala Gly Cys Ala Gly Glu Val Arg Ala
               100                 105                 110

Phe Leu Gln Glu Asn Thr His Val Arg Leu Arg Ile Phe Ala Ala Arg
           115                 120                 125

Ile Phe Asp Tyr Asp Pro Leu Tyr Lys Glu Ala Leu Gln Met Leu Arg
   130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
               165                 170                 175

Asp Gly Leu Asp Glu His Ser Gln Ala Leu Ser Gly Arg Leu Arg Ala
               180                 185                 190

Ile Leu Gln Asn Gln Gly Asn
       195
```

<210> SEQ ID NO 34
<211> LENGTH: 199
<212> TYPE: PRT
<213> ORGANISM: Artificial Sequence
<220> FEATURE:
<223> OTHER INFORMATION: Synthetic

<400> SEQUENCE: 34

```
Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Ala Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 35
<211> LENGTH: 181
<212> TYPE: PRT
<213> ORGANISM: Artificial Sequence
<220> FEATURE:
<223> OTHER INFORMATION: Synthetic

<400> SEQUENCE: 35

```
Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45

Tyr Gly Arg His Ala Glu Leu Arg Phe Leu Asp Leu Val Pro Ser Leu
    50                  55                  60

Gln Leu Asp Pro Ala Gln Ile Tyr Arg Val Thr Trp Phe Ile Ser Tyr
65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110
```

```
Asp Tyr Asp Pro Leu Tyr Lys Glu Ala Leu Gln Met Leu Arg Asp Ala
            115                 120                 125

Gly Ala Gln Val Ser Ile Met Thr Tyr Asp Glu Phe Lys His Cys Trp
        130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180

<210> SEQ ID NO 36
<211> LENGTH: 181
<212> TYPE: PRT
<213> ORGANISM: Artificial Sequence
<220> FEATURE:
<223> OTHER INFORMATION: Synthetic

<400> SEQUENCE: 36

Met Glu Ala Ser Pro Ala Ser Gly Pro Arg His Lys Thr Tyr Leu Cys
1               5                   10                  15

Tyr Glu Val Glu Arg Leu Asp Asn Gly Thr Ser Val Lys Met Asp Gln
            20                  25                  30

His Arg Gly Phe Leu His Asn Gln Ala Lys Asn Leu Leu Cys Gly Phe
        35                  40                  45

Tyr Gly Arg His Ala Glu Leu Arg Phe Leu Asp Leu Val Pro Ser Leu
    50                  55                  60

Gln Leu Asp Pro Ala Gln Ile Tyr Arg Val Thr Trp Phe Ile Ser Trp
65                  70                  75                  80

Ser Pro Cys Phe Ser Trp Gly Cys Ala Gly Glu Val Arg Ala Phe Leu
                85                  90                  95

Gln Glu Asn Thr His Val Arg Leu Arg Ile Phe Ala Ala Arg Ile Tyr
            100                 105                 110

Asp Tyr Asp Tyr Leu Tyr Lys Glu Ala Leu Gln Met Leu Arg Asp Ala
            115                 120                 125

Gly Ala Gln Val Ser Ile Met Thr Tyr Asp Glu Phe Lys His Cys Trp
        130                 135                 140

Asp Thr Phe Val Asp His Gln Gly Cys Pro Phe Gln Pro Trp Asp Gly
145                 150                 155                 160

Leu Asp Glu His Ser Gln Ala Leu Ser Gly Arg Leu Arg Ala Ile Leu
                165                 170                 175

Gln Asn Gln Gly Asn
            180

<210> SEQ ID NO 37
<211> LENGTH: 1230
<212> TYPE: PRT
<213> ORGANISM: Artificial Sequence
<220> FEATURE:
<223> OTHER INFORMATION: Synthetic

<400> SEQUENCE: 37

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
```

```
                35                  40                  45
Gly Val Lys Lys Leu Leu Asp Arg Tyr Tyr Leu Ser Phe Ile Asn Asp
 50                  55                  60

Val Leu His Ser Ile Lys Leu Lys Asn Leu Asn Asn Tyr Ile Ser Leu
 65                  70                  75                  80

Phe Arg Lys Lys Thr Arg Thr Glu Lys Asn Lys Glu Leu Glu Asn
                 85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
                115                 120                 125

Pro Glu Phe Leu Asp Asp Lys Asp Glu Ile Ala Leu Val Asn Ser Phe
                130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
                195                 200                 205

Ile Leu Asn Ser Asp Tyr Asp Val Glu Asp Phe Phe Glu Gly Glu Phe
                210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
                275                 280                 285

Phe Tyr Gly Glu Gly Tyr Thr Ser Asp Glu Glu Val Leu Glu Val Phe
                290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
                355                 360                 365

Ile His Leu Lys Lys Lys Ala Val Val Thr Glu Lys Tyr Glu Asp Asp
                370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
450                 455                 460
```

Ser Phe Glu Asn Tyr Ile Lys Ala Phe Phe Gly Gly Lys Glu Thr
465                 470                 475                 480

Asn Arg Asp Glu Ser Phe Tyr Gly Asp Phe Val Leu Ala Tyr Asp Ile
            485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
                515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
        610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
        690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
        770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Ala
            820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Ile Asn Asn Phe Asn
        850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Ala Asp Leu Asn
    915                 920                 925

Ser Gly Phe Lys Asn Ser Arg Val Lys Val Glu Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Ala Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Gly Ser
    1220                1225                1230

<210> SEQ ID NO 38
<211> LENGTH: 1307
<212> TYPE: PRT
<213> ORGANISM: Artificial Sequence
<220> FEATURE:
<223> OTHER INFORMATION: Synthetic

<400> SEQUENCE: 38

-continued

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
        130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
```

-continued

```
                420                 425                 430
Glu Ala Phe Lys Gln Lys Thr Ser Glu Ile Leu Ser His Ala His Ala
            435                 440                 445
Ala Leu Asp Gln Pro Leu Pro Thr Thr Leu Lys Lys Gln Glu Glu Lys
        450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
                485                 490                 495
Ser Ala Arg Leu Thr Gly Ile Lys Leu Glu Met Glu Pro Ser Leu Ser
            500                 505                 510
Phe Tyr Asn Lys Ala Arg Asn Tyr Ala Thr Lys Lys Pro Tyr Ser Val
        515                 520                 525
Glu Lys Phe Lys Leu Asn Phe Gln Met Pro Thr Leu Ala Ser Gly Trp
        530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
        595                 600                 605
Ser Thr Gln Leu Lys Ala Val Thr Ala His Phe Gln Thr His Thr Thr
        610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
        675                 680                 685
Lys Thr Thr Ser Ile Asp Leu Ser Ser Leu Arg Pro Ser Ser Gln Tyr
        690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
        755                 760                 765
Phe Ser Pro Glu Asn Leu Ala Lys Thr Ser Ile Lys Leu Asn Gly Gln
        770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
        835                 840                 845
```

-continued

Val Ile Thr Lys Glu Val Ser His Glu Ile Ile Lys Asp Arg Arg Phe
850                 855                 860

Thr Ser Asp Lys Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
                915                 920                 925

Gln Arg Ser Leu Asn Thr Ile Gln Gln Phe Asp Tyr Gln Lys Lys Leu
                930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys Ser Lys Arg Thr Gly Ile Ala Glu
                995                1000                1005

Lys Ala Val Tyr Gln Gln Phe Glu Lys Met Leu Ile Asp Lys Leu
1010                1015                1020

Asn Cys Leu Val Leu Lys Asp Tyr Pro Ala Glu Lys Val Gly Gly
1025                1030                1035

Val Leu Asn Pro Tyr Gln Leu Thr Asp Gln Phe Thr Ser Phe Ala
1040                1045                1050

Lys Met Gly Thr Gln Ser Gly Phe Leu Phe Tyr Val Pro Ala Pro
1055                1060                1065

Tyr Thr Ser Lys Ile Asp Pro Leu Thr Gly Phe Val Asp Pro Phe
1070                1075                1080

Val Trp Lys Thr Ile Lys Asn His Glu Ser Arg Lys His Phe Leu
1085                1090                1095

Glu Gly Phe Asp Phe Leu His Tyr Asp Val Lys Thr Gly Asp Phe
1100                1105                1110

Ile Leu His Phe Lys Met Asn Arg Asn Leu Ser Phe Gln Arg Gly
1115                1120                1125

Leu Pro Gly Phe Met Pro Ala Trp Asp Ile Val Phe Glu Lys Asn
1130                1135                1140

Glu Thr Gln Phe Asp Ala Lys Gly Thr Pro Phe Ile Ala Gly Lys
1145                1150                1155

Arg Ile Val Pro Val Ile Glu Asn His Arg Phe Thr Gly Arg Tyr
1160                1165                1170

Arg Asp Leu Tyr Pro Ala Asn Glu Leu Ile Ala Leu Leu Glu Glu
1175                1180                1185

Lys Gly Ile Val Phe Arg Asp Gly Ser Asn Ile Leu Pro Lys Leu
1190                1195                1200

Leu Glu Asn Asp Asp Ser His Ala Ile Asp Thr Met Val Ala Leu
1205                1210                1215

Ile Arg Ser Val Leu Gln Met Arg Asn Ser Asn Ala Ala Thr Gly
1220                1225                1230

Glu Asp Tyr Ile Asn Ser Pro Val Arg Asp Leu Asn Gly Val Cys
1235                1240                1245

```
Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 39
<211> LENGTH: 1300
<212> TYPE: PRT
<213> ORGANISM: Artificial Sequence
<220> FEATURE:
<223> OTHER INFORMATION: Synthetic

<400> SEQUENCE: 39

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300
```

```
Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
```

```
              725                 730                 735
Phe Gly Phe Arg Phe Ser Asp Thr Gln Arg Tyr Asn Ser Ile Asp Glu
              740                 745                 750
Phe Tyr Arg Glu Val Glu Asn Gln Gly Tyr Lys Leu Thr Phe Glu Asn
              755                 760                 765
Ile Ser Glu Ser Tyr Ile Asp Ser Val Val Asn Gln Gly Lys Leu Tyr
              770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
              805                 810                 815
Leu Gln Asp Val Val Tyr Lys Leu Asn Gly Glu Ala Glu Leu Phe Tyr
              820                 825                 830
Arg Lys Gln Ser Ile Pro Lys Lys Ile Thr His Pro Ala Lys Glu Ala
              835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
              885                 890                 895
Asn Asp Glu Ile Asn Leu Leu Leu Lys Glu Lys Ala Asn Asp Val His
              900                 905                 910
Ile Leu Ser Ile Asp Arg Gly Glu Arg His Leu Ala Tyr Tyr Thr Leu
              915                 920                 925
Val Asp Gly Lys Gly Asn Ile Ile Lys Gln Asp Thr Phe Asn Ile Ile
930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
              965                 970                 975
Ile Lys Glu Met Lys Glu Gly Tyr Leu Ser Gln Val Val His Glu Ile
              980                 985                 990
Ala Lys Leu Val Ile Glu Tyr Asn Ala Ile Val Val Phe Glu Asp Leu
              995                1000                1005
Asn Phe Gly Phe Lys Arg Gly Arg Phe Lys Val Glu Lys Gln Val
              1010                1015                1020
Tyr Gln Lys Leu Glu Lys Met Leu Ile Glu Lys Leu Asn Tyr Leu
              1025                1030                1035
Val Phe Lys Asp Asn Glu Phe Asp Lys Thr Gly Gly Val Leu Arg
              1040                1045                1050
Ala Tyr Gln Leu Thr Ala Pro Phe Glu Thr Phe Lys Lys Met Gly
              1055                1060                1065
Lys Gln Thr Gly Ile Ile Tyr Tyr Val Pro Ala Gly Phe Thr Ser
              1070                1075                1080
Lys Ile Cys Pro Val Thr Gly Phe Val Asn Gln Leu Tyr Pro Lys
              1085                1090                1095
Tyr Glu Ser Val Ser Lys Ser Gln Glu Phe Phe Ser Lys Phe Asp
              1100                1105                1110
Lys Ile Cys Tyr Asn Leu Asp Lys Gly Tyr Phe Glu Phe Ser Phe
              1115                1120                1125
Asp Tyr Lys Asn Phe Gly Asp Lys Ala Ala Lys Gly Lys Trp Thr
              1130                1135                1140
```

```
Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300
```

<210> SEQ ID NO 40
<211> LENGTH: 1558
<212> TYPE: PRT
<213> ORGANISM: Artificial Sequence
<220> FEATURE:
<223> OTHER INFORMATION: Synthetic

<400> SEQUENCE: 40

```
Met Pro Lys Lys Arg Lys Val Met Glu Ala Ser Pro Ala Ser Gly
1               5                   10                  15

Pro Arg His Leu Met Asp Pro His Ile Phe Thr Ser Asn Phe Asn
                20                  25                  30

Gly Ile Gly Arg His Lys Thr Tyr Leu Cys Tyr Glu Val Glu Arg Leu
                35                  40                  45

Asp Asn Gly Thr Ser Val Lys Met Asp Gln His Arg Gly Phe Leu His
50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Trp Ser Pro Cys Phe Ser Trp
                100                 105                 110

Gly Cys Ala Gly Glu Val Arg Ala Phe Leu Gln Glu Asn Thr His Val
                115                 120                 125

Arg Leu Arg Ile Phe Ala Ala Arg Ile Tyr Asp Tyr Asp Pro Leu Tyr
                130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
                180                 185                 190
```

```
Ala Leu Ser Gly Arg Leu Arg Ala Ile Leu Gln Asn Gln Gly Asn Ser
            195                 200                 205

Gly Ser Glu Thr Pro Gly Thr Ser Glu Ser Ala Thr Pro Glu Ser Met
210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
                260                 265                 270

Val Lys Lys Leu Leu Asp Arg Tyr Tyr Leu Ser Phe Ile Asn Asp Val
            275                 280                 285

Leu His Ser Ile Lys Leu Lys Asn Leu Asn Asn Tyr Ile Ser Leu Phe
        290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
            340                 345                 350

Glu Phe Leu Asp Asp Lys Asp Glu Ile Ala Leu Val Asn Ser Phe Asn
        355                 360                 365

Gly Phe Thr Thr Ala Phe Thr Gly Phe Phe Asp Asn Arg Glu Asn Met
    370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
                420                 425                 430

Leu Asn Ser Asp Tyr Asp Val Glu Asp Phe Phe Glu Gly Glu Phe Phe
            435                 440                 445

Asn Phe Val Leu Thr Gln Glu Gly Ile Asp Val Tyr Asn Ala Ile Ile
        450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Glu Val Leu Glu Val Phe Arg
        515                 520                 525

Asn Thr Leu Asn Lys Asn Ser Glu Ile Phe Ser Ser Ile Lys Lys Leu
    530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
        595                 600                 605
```

-continued

Arg Lys Ser Phe Lys Lys Ile Gly Ser Phe Ser Leu Glu Gln Leu Gln
610             615                 620

Glu Tyr Ala Asp Ala Asp Leu Ser Val Val Glu Lys Leu Lys Glu Ile
625             630                 635                 640

Ile Ile Gln Lys Val Asp Glu Ile Tyr Lys Val Tyr Gly Ser Ser Glu
            645                 650                 655

Lys Leu Phe Asp Ala Asp Phe Val Leu Glu Lys Ser Leu Lys Lys Asn
            660                 665                 670

Asp Ala Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
690             695                 700

Arg Asp Glu Ser Phe Tyr Gly Asp Phe Val Leu Ala Tyr Asp Ile Leu
705             710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
                740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
770             775                 780

Tyr Ala Lys Cys Leu Gln Lys Ile Asp Lys Asp Val Asn Gly Asn
785             790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
            820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
850             855                 860

Ser Ile Ser Arg Tyr Pro Lys Trp Ser Asn Ala Tyr Asp Phe Asn Phe
865             870                 875                 880

Ser Glu Thr Glu Lys Tyr Lys Asp Ile Ala Gly Phe Tyr Arg Glu Val
            885                 890                 895

Glu Glu Gln Gly Tyr Lys Val Ser Phe Glu Ser Ala Ser Lys Lys Glu
            900                 905                 910

Val Asp Lys Leu Val Glu Gly Lys Leu Tyr Met Phe Gln Ile Tyr
            915                 920                 925

Asn Lys Asp Phe Ser Asp Lys Ser His Gly Thr Pro Asn Leu His Thr
930             935                 940

Met Tyr Phe Lys Leu Leu Phe Asp Glu Asn Asn His Gly Gln Ile Arg
945             950                 955                 960

Leu Ser Gly Gly Ala Glu Leu Phe Met Arg Arg Ala Ser Leu Lys Lys
            965                 970                 975

Glu Glu Leu Val Val His Pro Ala Asn Ser Pro Ile Ala Asn Lys Asn
            980                 985                 990

Pro Asp Asn Pro Lys Lys Thr Thr Thr Leu Ser Tyr Asp Val Tyr Lys
            995                 1000                1005

Asp Lys Arg Phe Ser Glu Asp Gln Tyr Glu Leu His Ile Pro Ile
    1010                1015                1020

Ala Ile Asn Lys Cys Pro Lys Asn Ile Phe Lys Ile Asn Thr Glu

```
                   1025                1030                1035

Val Arg Val Leu Leu Lys His Asp Asp Asn Pro Tyr Val Ile Gly
                   1040                1045                1050

Ile Ala Arg Gly Glu Arg Asn Leu Leu Tyr Ile Val Val Val Asp
                   1055                1060                1065

Gly Lys Gly Asn Ile Val Glu Gln Tyr Ser Leu Asn Glu Ile Ile
                   1070                1075                1080

Asn Asn Phe Asn Gly Ile Arg Ile Lys Thr Asp Tyr His Ser Leu
                   1085                1090                1095

Leu Asp Lys Lys Glu Lys Glu Arg Phe Glu Ala Arg Gln Asn Trp
                   1100                1105                1110

Thr Ser Ile Glu Asn Ile Lys Glu Leu Lys Ala Gly Tyr Ile Ser
                   1115                1120                1125

Gln Val Val His Lys Ile Cys Glu Leu Val Glu Lys Tyr Asp Ala
                   1130                1135                1140

Val Ile Ala Leu Ala Asp Leu Asn Ser Gly Phe Lys Asn Ser Arg
                   1145                1150                1155

Val Lys Val Glu Lys Gln Val Tyr Gln Lys Phe Glu Lys Met Leu
                   1160                1165                1170

Ile Asp Lys Leu Asn Tyr Met Val Asp Lys Lys Ser Asn Pro Cys
                   1175                1180                1185

Ala Thr Gly Gly Ala Leu Lys Gly Tyr Gln Ile Thr Asn Lys Phe
                   1190                1195                1200

Glu Ser Phe Lys Ser Met Ser Thr Gln Asn Gly Phe Ile Phe Tyr
                   1205                1210                1215

Ile Pro Ala Trp Leu Thr Ser Lys Ile Asp Pro Ser Thr Gly Phe
                   1220                1225                1230

Val Asn Leu Leu Lys Thr Lys Tyr Thr Ser Ile Ala Asp Ser Lys
                   1235                1240                1245

Lys Phe Ile Ser Ser Phe Asp Arg Ile Met Tyr Val Pro Glu Glu
                   1250                1255                1260

Asp Leu Phe Glu Phe Ala Leu Asp Tyr Lys Asn Phe Ser Arg Thr
                   1265                1270                1275

Asp Ala Asp Tyr Ile Lys Lys Trp Lys Leu Tyr Ser Tyr Gly Asn
                   1280                1285                1290

Arg Ile Arg Ile Phe Arg Asn Pro Lys Lys Asn Asn Val Phe Asp
                   1295                1300                1305

Trp Glu Glu Val Cys Leu Thr Ser Ala Tyr Lys Glu Leu Phe Asn
                   1310                1315                1320

Lys Tyr Gly Ile Asn Tyr Gln Gln Gly Asp Ile Arg Ala Leu Leu
                   1325                1330                1335

Cys Glu Gln Ser Asp Lys Ala Phe Tyr Ser Ser Phe Met Ala Leu
                   1340                1345                1350

Met Ser Leu Met Leu Gln Met Arg Asn Ser Ile Thr Gly Arg Thr
                   1355                1360                1365

Asp Val Ala Phe Leu Ile Ser Pro Val Lys Asn Ser Asp Gly Ile
                   1370                1375                1380

Phe Tyr Asp Ser Arg Asn Tyr Glu Ala Gln Glu Asn Ala Ile Leu
                   1385                1390                1395

Pro Lys Asn Ala Asp Ala Asn Gly Ala Tyr Asn Ile Ala Arg Lys
                   1400                1405                1410

Val Leu Trp Ala Ile Gly Gln Phe Lys Lys Ala Glu Asp Glu Lys
                   1415                1420                1425
```

Leu Asp Lys Val Lys Ile Ala Ile Ser Asn Lys Glu Trp Leu Glu
    1430                1435                1440

Tyr Ala Gln Thr Ser Val Lys His Gly Ser Pro Lys Lys Lys Arg
    1445                1450                1455

Lys Val Ser Gly Gly Ser Thr Asn Leu Ser Asp Ile Ile Glu Lys
    1460                1465                1470

Glu Thr Gly Lys Gln Leu Val Ile Gln Glu Ser Ile Leu Met Leu
    1475                1480                1485

Pro Glu Glu Val Glu Glu Val Ile Gly Asn Lys Pro Glu Ser Asp
    1490                1495                1500

Ile Leu Val His Thr Ala Tyr Asp Glu Ser Thr Asp Glu Asn Val
    1505                1510                1515

Met Leu Leu Thr Ser Asp Ala Pro Glu Tyr Lys Pro Trp Ala Leu
    1520                1525                1530

Val Ile Gln Asp Ser Asn Gly Glu Asn Lys Ile Lys Met Leu Ser
    1535                1540                1545

Gly Gly Ser Pro Lys Lys Lys Arg Lys Val
    1550                1555

<210> SEQ ID NO 41
<211> LENGTH: 1558
<212> TYPE: PRT
<213> ORGANISM: Artificial Sequence
<220> FEATURE:
<223> OTHER INFORMATION: Synthetic

<400> SEQUENCE: 41

Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
        50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Tyr Ser Pro Cys Phe Ser Trp
            100                 105                 110

Gly Cys Ala Gly Glu Val Arg Ala Phe Leu Gln Glu Asn Thr His Val
        115                 120                 125

Arg Leu Arg Ile Phe Ala Ala Arg Ile Tyr Asp Tyr Asp Pro Leu Tyr
    130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
        195                 200                 205

Gly Ser Glu Thr Pro Gly Thr Ser Glu Ser Ala Thr Pro Glu Ser Met
    210                 215                 220

```
Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
            245                 250                 255

Lys Arg Leu Leu Val Glu Asp Glu Lys Arg Ala Glu Asp Tyr Lys Gly
        260                 265                 270

Val Lys Lys Leu Leu Asp Arg Tyr Tyr Leu Ser Phe Ile Asn Asp Val
    275                 280                 285

Leu His Ser Ile Lys Leu Lys Asn Leu Asn Asn Tyr Ile Ser Leu Phe
290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
            325                 330                 335

Gly Tyr Lys Ser Leu Phe Lys Lys Asp Ile Ile Glu Thr Ile Leu Pro
        340                 345                 350

Glu Phe Leu Asp Asp Lys Asp Glu Ile Ala Leu Val Asn Ser Phe Asn
    355                 360                 365

Gly Phe Thr Thr Ala Phe Thr Gly Phe Phe Asp Asn Arg Glu Asn Met
370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
            405                 410                 415

Asp Ala Ile Phe Asp Lys His Glu Val Gln Glu Ile Lys Glu Lys Ile
        420                 425                 430

Leu Asn Ser Asp Tyr Asp Val Asp Phe Phe Glu Gly Glu Phe Phe
    435                 440                 445

Asn Phe Val Leu Thr Gln Glu Gly Ile Asp Val Tyr Asn Ala Ile Ile
450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
            485                 490                 495

Lys Pro Leu Tyr Lys Gln Val Leu Ser Asp Arg Glu Ser Leu Ser Phe
        500                 505                 510

Tyr Gly Glu Gly Tyr Thr Ser Asp Glu Glu Val Leu Glu Val Phe Arg
    515                 520                 525

Asn Thr Leu Asn Lys Asn Ser Glu Ile Phe Ser Ser Ile Lys Lys Leu
530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
            565                 570                 575

Glu Trp Asn Val Ile Arg Asp Lys Trp Asn Ala Glu Tyr Asp Asp Ile
        580                 585                 590

His Leu Lys Lys Lys Ala Val Val Thr Glu Lys Tyr Glu Asp Asp Arg
    595                 600                 605

Arg Lys Ser Phe Lys Lys Ile Gly Ser Phe Ser Leu Glu Gln Leu Gln
610                 615                 620

Glu Tyr Ala Asp Ala Asp Leu Ser Val Val Glu Lys Leu Lys Glu Ile
625                 630                 635                 640
```

```
Ile Ile Gln Lys Val Asp Glu Ile Tyr Lys Val Tyr Gly Ser Ser Glu
            645                 650                 655

Lys Leu Phe Asp Ala Asp Phe Val Leu Glu Lys Ser Leu Lys Lys Asn
        660                 665                 670

Asp Ala Val Ala Ile Met Lys Asp Leu Leu Asp Ser Val Lys Ser
        675                 680                 685

Phe Glu Asn Tyr Ile Lys Ala Phe Phe Gly Glu Gly Lys Glu Thr Asn
        690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
            740                 745                 750

Phe Met Gly Gly Trp Asp Lys Asp Lys Glu Thr Asp Tyr Arg Ala Thr
        755                 760                 765

Ile Leu Arg Tyr Gly Ser Lys Tyr Tyr Leu Ala Ile Met Asp Lys Lys
        770                 775                 780

Tyr Ala Lys Cys Leu Gln Lys Ile Asp Lys Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Asn Pro Ser
            820                 825                 830

Glu Asp Ile Gln Lys Ile Tyr Lys Asn Gly Thr Phe Lys Lys Gly Asp
        835                 840                 845

Met Phe Asn Leu Asn Asp Cys His Lys Leu Ile Asp Phe Phe Lys Asp
        850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
            900                 905                 910

Val Asp Lys Leu Val Glu Glu Gly Lys Leu Tyr Met Phe Gln Ile Tyr
        915                 920                 925

Asn Lys Asp Phe Ser Asp Lys Ser His Gly Thr Pro Asn Leu His Thr
        930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
            980                 985                 990

Pro Asp Asn Pro Lys Lys Thr Thr Thr Leu Ser Tyr Asp Val Tyr Lys
        995                 1000                1005

Asp Lys Arg Phe Ser Glu Asp Gln Tyr Glu Leu His Ile Pro Ile
        1010                1015                1020

Ala Ile Asn Lys Cys Pro Lys Asn Ile Phe Lys Ile Asn Thr Glu
        1025                1030                1035

Val Arg Val Leu Leu Lys His Asp Asp Asn Pro Tyr Val Ile Gly
        1040                1045                1050

Ile Ala Arg Gly Glu Arg Asn Leu Leu Tyr Ile Val Val Val Asp
```

-continued

```
            1055                1060                1065
Gly Lys Gly Asn Ile Val Glu Gln Tyr Ser Leu Asn Glu Ile Ile
            1070                1075                1080
Asn Asn Phe Asn Gly Ile Arg Ile Lys Thr Asp Tyr His Ser Leu
            1085                1090                1095
Leu Asp Lys Lys Glu Lys Glu Arg Phe Glu Ala Arg Gln Asn Trp
            1100                1105                1110
Thr Ser Ile Glu Asn Ile Lys Glu Leu Lys Ala Gly Tyr Ile Ser
            1115                1120                1125
Gln Val Val His Lys Ile Cys Glu Leu Val Glu Lys Tyr Asp Ala
            1130                1135                1140
Val Ile Ala Leu Ala Asp Leu Asn Ser Gly Phe Lys Asn Ser Arg
            1145                1150                1155
Val Lys Val Glu Lys Gln Val Tyr Gln Lys Phe Glu Lys Met Leu
            1160                1165                1170
Ile Asp Lys Leu Asn Tyr Met Val Asp Lys Lys Ser Asn Pro Cys
            1175                1180                1185
Ala Thr Gly Gly Ala Leu Lys Gly Tyr Gln Ile Thr Asn Lys Phe
            1190                1195                1200
Glu Ser Phe Lys Ser Met Ser Thr Gln Asn Gly Phe Ile Phe Tyr
            1205                1210                1215
Ile Pro Ala Trp Leu Thr Ser Lys Ile Asp Pro Ser Thr Gly Phe
            1220                1225                1230
Val Asn Leu Leu Lys Thr Lys Tyr Thr Ser Ile Ala Asp Ser Lys
            1235                1240                1245
Lys Phe Ile Ser Ser Phe Asp Arg Ile Met Tyr Val Pro Glu Glu
            1250                1255                1260
Asp Leu Phe Glu Phe Ala Leu Asp Tyr Lys Asn Phe Ser Arg Thr
            1265                1270                1275
Asp Ala Asp Tyr Ile Lys Lys Trp Lys Leu Tyr Ser Tyr Gly Asn
            1280                1285                1290
Arg Ile Arg Ile Phe Arg Asn Pro Lys Lys Asn Asn Val Phe Asp
            1295                1300                1305
Trp Glu Glu Val Cys Leu Thr Ser Ala Tyr Lys Glu Leu Phe Asn
            1310                1315                1320
Lys Tyr Gly Ile Asn Tyr Gln Gln Gly Asp Ile Arg Ala Leu Leu
            1325                1330                1335
Cys Glu Gln Ser Asp Lys Ala Phe Tyr Ser Ser Phe Met Ala Leu
            1340                1345                1350
Met Ser Leu Met Leu Gln Met Arg Asn Ser Ile Thr Gly Arg Thr
            1355                1360                1365
Asp Val Ala Phe Leu Ile Ser Pro Val Lys Asn Ser Asp Gly Ile
            1370                1375                1380
Phe Tyr Asp Ser Arg Asn Tyr Glu Ala Gln Glu Asn Ala Ile Leu
            1385                1390                1395
Pro Lys Asn Ala Asp Ala Asn Gly Ala Tyr Asn Ile Ala Arg Lys
            1400                1405                1410
Val Leu Trp Ala Ile Gly Gln Phe Lys Lys Ala Glu Asp Glu Lys
            1415                1420                1425
Leu Asp Lys Val Lys Ile Ala Ile Ser Asn Lys Glu Trp Leu Glu
            1430                1435                1440
Tyr Ala Gln Thr Ser Val Lys His Gly Ser Pro Lys Lys Lys Arg
            1445                1450                1455
```

-continued

Lys Val Ser Gly Gly Ser Thr Asn Leu Ser Asp Ile Ile Glu Lys
1460                1465                1470

Glu Thr Gly Lys Gln Leu Val Ile Gln Glu Ser Ile Leu Met Leu
    1475                1480                1485

Pro Glu Glu Val Glu Val Ile Gly Asn Lys Pro Glu Ser Asp
1490                1495                1500

Ile Leu Val His Thr Ala Tyr Asp Glu Ser Thr Asp Glu Asn Val
1505                1510                1515

Met Leu Leu Thr Ser Asp Ala Pro Glu Tyr Lys Pro Trp Ala Leu
    1520                1525                1530

Val Ile Gln Asp Ser Asn Gly Glu Asn Lys Ile Lys Met Leu Ser
    1535                1540                1545

Gly Gly Ser Pro Lys Lys Lys Arg Lys Val
    1550                1555

<210> SEQ ID NO 42
<211> LENGTH: 1558
<212> TYPE: PRT
<213> ORGANISM: Artificial Sequence
<220> FEATURE:
<223> OTHER INFORMATION: Synthetic

<400> SEQUENCE: 42

Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
        50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Trp Ser Pro Cys Phe Ser Ala
                100                 105                 110

Gly Cys Ala Gly Glu Val Arg Ala Phe Leu Gln Glu Asn Thr His Val
            115                 120                 125

Arg Leu Arg Ile Phe Ala Ala Arg Ile Tyr Asp Tyr Asp Pro Leu Tyr
        130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
        195                 200                 205

Gly Ser Glu Thr Pro Gly Thr Ser Glu Ser Ala Thr Pro Glu Ser Met
    210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

```
Lys Arg Leu Leu Val Glu Asp Glu Lys Arg Ala Glu Asp Tyr Lys Gly
            260                 265                 270

Val Lys Lys Leu Leu Asp Arg Tyr Tyr Leu Ser Phe Ile Asn Asp Val
        275                 280                 285

Leu His Ser Ile Lys Leu Lys Asn Leu Asn Asn Tyr Ile Ser Leu Phe
    290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
            340                 345                 350

Glu Phe Leu Asp Asp Lys Asp Glu Ile Ala Leu Val Asn Ser Phe Asn
        355                 360                 365

Gly Phe Thr Thr Ala Phe Thr Gly Phe Phe Asp Asn Arg Glu Asn Met
    370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
            420                 425                 430

Leu Asn Ser Asp Tyr Asp Val Glu Asp Phe Phe Glu Gly Glu Phe Phe
        435                 440                 445

Asn Phe Val Leu Thr Gln Glu Gly Ile Asp Val Tyr Asn Ala Ile Ile
    450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Glu Val Leu Glu Val Phe Arg
        515                 520                 525

Asn Thr Leu Asn Lys Asn Ser Glu Ile Phe Ser Ser Ile Lys Lys Leu
    530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
        595                 600                 605

Arg Lys Ser Phe Lys Lys Ile Gly Ser Phe Ser Leu Glu Gln Leu Gln
    610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
            660                 665                 670
```

```
Asp Ala Val Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
            725                 730                 735

Lys Pro Tyr Ser Lys Asp Lys Phe Leu Tyr Phe Gln Asn Pro Gln
            740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
            770                 775                 780

Tyr Ala Lys Cys Leu Gln Lys Ile Asp Lys Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
            820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
                900                 905                 910

Val Asp Lys Leu Val Glu Glu Gly Lys Leu Tyr Met Phe Gln Ile Tyr
            915                 920                 925

Asn Lys Asp Phe Ser Asp Lys Ser His Gly Thr Pro Asn Leu His Thr
930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
            980                 985                 990

Pro Asp Asn Pro Lys Lys Thr Thr Thr Leu Ser Tyr Asp Val Tyr Lys
            995                 1000                1005

Asp Lys Arg Phe Ser Glu Asp Gln Tyr Glu Leu His Ile Pro Ile
            1010                1015                1020

Ala Ile Asn Lys Cys Pro Lys Asn Ile Phe Lys Ile Asn Thr Glu
            1025                1030                1035

Val Arg Val Leu Leu Lys His Asp Asp Asn Pro Tyr Val Ile Gly
            1040                1045                1050

Ile Ala Arg Gly Glu Arg Asn Leu Leu Tyr Ile Val Val Val Asp
            1055                1060                1065

Gly Lys Gly Asn Ile Val Glu Gln Tyr Ser Leu Asn Glu Ile Ile
            1070                1075                1080

Asn Asn Phe Asn Gly Ile Arg Ile Lys Thr Asp Tyr His Ser Leu
```

-continued

```
             1085                1090                1095

Leu Asp Lys Lys Glu Lys Glu Arg Phe Glu Ala Arg Gln Asn Trp
        1100                1105                1110

Thr Ser Ile Glu Asn Ile Lys Glu Leu Lys Ala Gly Tyr Ile Ser
        1115                1120                1125

Gln Val Val His Lys Ile Cys Glu Leu Val Glu Lys Tyr Asp Ala
        1130                1135                1140

Val Ile Ala Leu Ala Asp Leu Asn Ser Gly Phe Lys Asn Ser Arg
        1145                1150                1155

Val Lys Val Glu Lys Gln Val Tyr Gln Lys Phe Glu Lys Met Leu
        1160                1165                1170

Ile Asp Lys Leu Asn Tyr Met Val Asp Lys Lys Ser Asn Pro Cys
        1175                1180                1185

Ala Thr Gly Gly Ala Leu Lys Gly Tyr Gln Ile Thr Asn Lys Phe
        1190                1195                1200

Glu Ser Phe Lys Ser Met Ser Thr Gln Asn Gly Phe Ile Phe Tyr
        1205                1210                1215

Ile Pro Ala Trp Leu Thr Ser Lys Ile Asp Pro Ser Thr Gly Phe
        1220                1225                1230

Val Asn Leu Leu Lys Thr Lys Tyr Thr Ser Ile Ala Asp Ser Lys
        1235                1240                1245

Lys Phe Ile Ser Ser Phe Asp Arg Ile Met Tyr Val Pro Glu Glu
        1250                1255                1260

Asp Leu Phe Glu Phe Ala Leu Asp Tyr Lys Asn Phe Ser Arg Thr
        1265                1270                1275

Asp Ala Asp Tyr Ile Lys Lys Trp Lys Leu Tyr Ser Tyr Gly Asn
        1280                1285                1290

Arg Ile Arg Ile Phe Arg Asn Pro Lys Lys Asn Asn Val Phe Asp
        1295                1300                1305

Trp Glu Glu Val Cys Leu Thr Ser Ala Tyr Lys Glu Leu Phe Asn
        1310                1315                1320

Lys Tyr Gly Ile Asn Tyr Gln Gln Gly Asp Ile Arg Ala Leu Leu
        1325                1330                1335

Cys Glu Gln Ser Asp Lys Ala Phe Tyr Ser Ser Phe Met Ala Leu
        1340                1345                1350

Met Ser Leu Met Leu Gln Met Arg Asn Ser Ile Thr Gly Arg Thr
        1355                1360                1365

Asp Val Ala Phe Leu Ile Ser Pro Val Lys Asn Ser Asp Gly Ile
        1370                1375                1380

Phe Tyr Asp Ser Arg Asn Tyr Glu Ala Gln Glu Asn Ala Ile Leu
        1385                1390                1395

Pro Lys Asn Ala Asp Ala Asn Gly Ala Tyr Asn Ile Ala Arg Lys
        1400                1405                1410

Val Leu Trp Ala Ile Gly Gln Phe Lys Lys Ala Glu Asp Glu Lys
        1415                1420                1425

Leu Asp Lys Val Lys Ile Ala Ile Ser Asn Lys Glu Trp Leu Glu
        1430                1435                1440

Tyr Ala Gln Thr Ser Val Lys His Gly Ser Pro Lys Lys Lys Arg
        1445                1450                1455

Lys Val Ser Gly Gly Ser Thr Asn Leu Ser Asp Ile Ile Glu Lys
        1460                1465                1470

Glu Thr Gly Lys Gln Leu Val Ile Gln Glu Ser Ile Leu Met Leu
        1475                1480                1485
```

```
Pro Glu Glu Val Glu Glu Val Ile Gly Asn Lys Pro Glu Ser Asp
    1490                1495                1500

Ile Leu Val His Thr Ala Tyr Asp Glu Ser Thr Asp Glu Asn Val
    1505                1510                1515

Met Leu Leu Thr Ser Asp Ala Pro Glu Tyr Lys Pro Trp Ala Leu
    1520                1525                1530

Val Ile Gln Asp Ser Asn Gly Glu Asn Lys Ile Lys Met Leu Ser
    1535                1540                1545

Gly Gly Ser Pro Lys Lys Lys Arg Lys Val
    1550                1555

<210> SEQ ID NO 43
<211> LENGTH: 1558
<212> TYPE: PRT
<213> ORGANISM: Artificial Sequence
<220> FEATURE:
<223> OTHER INFORMATION: Synthetic

<400> SEQUENCE: 43

Met Pro Lys Lys Arg Lys Val Met Glu Ala Ser Pro Ala Ser Gly
1               5                   10                  15

Pro Arg His Leu Met Asp Pro His Ile Phe Thr Ser Asn Phe Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
    50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Trp Ser Pro Cys Phe Ser Trp
            100                 105                 110

Gly Cys Ala Gly Glu Val Arg Ala Phe Leu Gln Glu Asn Thr His Val
            115                 120                 125

Arg Leu Arg Ile Phe Ala Ala Arg Ile Tyr Asp Tyr Asp Tyr Leu Tyr
        130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
            195                 200                 205

Gly Ser Glu Thr Pro Gly Thr Ser Glu Ser Ala Thr Pro Glu Ser Met
        210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
            260                 265                 270

Val Lys Lys Leu Leu Asp Arg Tyr Tyr Leu Ser Phe Ile Asn Asp Val
        275                 280                 285
```

```
Leu His Ser Ile Lys Leu Lys Asn Leu Asn Asn Tyr Ile Ser Leu Phe
    290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
            340                 345                 350

Glu Phe Leu Asp Asp Lys Asp Glu Ile Ala Leu Val Asn Ser Phe Asn
        355                 360                 365

Gly Phe Thr Thr Ala Phe Thr Gly Phe Phe Asp Asn Arg Glu Asn Met
    370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
            420                 425                 430

Leu Asn Ser Asp Tyr Asp Val Glu Asp Phe Phe Glu Gly Glu Phe Phe
        435                 440                 445

Asn Phe Val Leu Thr Gln Glu Gly Ile Asp Val Tyr Asn Ala Ile Ile
    450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Glu Val Leu Glu Val Phe Arg
        515                 520                 525

Asn Thr Leu Asn Lys Asn Ser Glu Ile Phe Ser Ser Ile Lys Lys Leu
    530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
        595                 600                 605

Arg Lys Ser Phe Lys Lys Ile Gly Ser Phe Ser Leu Glu Gln Leu Gln
    610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
            660                 665                 670

Asp Ala Val Val Ala Ile Met Lys Asp Leu Leu Asp Ser Val Lys Ser
        675                 680                 685

Phe Glu Asn Tyr Ile Lys Ala Phe Phe Gly Glu Gly Lys Glu Thr Asn
    690                 695                 700
```

-continued

```
Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
            725                 730                 735

Lys Pro Tyr Ser Lys Asp Lys Phe Lys Leu Tyr Phe Gln Asn Pro Gln
            740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
            770                 775                 780

Tyr Ala Lys Cys Leu Gln Lys Ile Asp Lys Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Asn Pro Ser
            820                 825                 830

Glu Asp Ile Gln Lys Ile Tyr Lys Asn Gly Thr Phe Lys Lys Gly Asp
                835                 840                 845

Met Phe Asn Leu Asn Asp Cys His Lys Leu Ile Asp Phe Phe Lys Asp
850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
                900                 905                 910

Val Asp Lys Leu Val Glu Glu Gly Lys Leu Tyr Met Phe Gln Ile Tyr
                915                 920                 925

Asn Lys Asp Phe Ser Asp Lys Ser His Gly Thr Pro Asn Leu His Thr
930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
                980                 985                 990

Pro Asp Asn Pro Lys Lys Thr Thr Thr Leu Ser Tyr Asp Val Tyr Lys
            995                 1000                1005

Asp Lys Arg Phe Ser Glu Asp Gln Tyr Glu Leu His Ile Pro Ile
    1010                1015                1020

Ala Ile Asn Lys Cys Pro Lys Asn Ile Phe Lys Ile Asn Thr Glu
    1025                1030                1035

Val Arg Val Leu Leu Lys His Asp Asp Asn Pro Tyr Val Ile Gly
    1040                1045                1050

Ile Ala Arg Gly Glu Arg Asn Leu Leu Tyr Ile Val Val Val Asp
    1055                1060                1065

Gly Lys Gly Asn Ile Val Glu Gln Tyr Ser Leu Asn Glu Ile Ile
    1070                1075                1080

Asn Asn Phe Asn Gly Ile Arg Ile Lys Thr Asp Tyr His Ser Leu
    1085                1090                1095

Leu Asp Lys Lys Glu Lys Glu Arg Phe Glu Ala Arg Gln Asn Trp
    1100                1105                1110

Thr Ser Ile Glu Asn Ile Lys Glu Leu Lys Ala Gly Tyr Ile Ser
```

-continued

```
            1115                1120                1125

Gln Val Val His Lys Ile Cys Glu Leu Val Lys Tyr Asp Ala
        1130                1135                1140

Val Ile Ala Leu Ala Asp Leu Asn Ser Gly Phe Lys Asn Ser Arg
        1145                1150                1155

Val Lys Val Glu Lys Gln Val Tyr Gln Lys Phe Glu Lys Met Leu
        1160                1165                1170

Ile Asp Lys Leu Asn Tyr Met Val Asp Lys Lys Ser Asn Pro Cys
        1175                1180                1185

Ala Thr Gly Gly Ala Leu Lys Gly Tyr Gln Ile Thr Asn Lys Phe
        1190                1195                1200

Glu Ser Phe Lys Ser Met Ser Thr Gln Asn Gly Phe Ile Phe Tyr
        1205                1210                1215

Ile Pro Ala Trp Leu Thr Ser Lys Ile Asp Pro Ser Thr Gly Phe
        1220                1225                1230

Val Asn Leu Leu Lys Thr Lys Tyr Thr Ser Ile Ala Asp Ser Lys
        1235                1240                1245

Lys Phe Ile Ser Ser Phe Asp Arg Ile Met Tyr Val Pro Glu Glu
        1250                1255                1260

Asp Leu Phe Glu Phe Ala Leu Asp Tyr Lys Asn Phe Ser Arg Thr
        1265                1270                1275

Asp Ala Asp Tyr Ile Lys Lys Trp Lys Leu Tyr Ser Tyr Gly Asn
        1280                1285                1290

Arg Ile Arg Ile Phe Arg Asn Pro Lys Lys Asn Val Phe Asp
        1295                1300                1305

Trp Glu Glu Val Cys Leu Thr Ser Ala Tyr Lys Glu Leu Phe Asn
        1310                1315                1320

Lys Tyr Gly Ile Asn Tyr Gln Gln Gly Asp Ile Arg Ala Leu Leu
        1325                1330                1335

Cys Glu Gln Ser Asp Lys Ala Phe Tyr Ser Ser Phe Met Ala Leu
        1340                1345                1350

Met Ser Leu Met Leu Gln Met Arg Asn Ser Ile Thr Gly Arg Thr
        1355                1360                1365

Asp Val Ala Phe Leu Ile Ser Pro Val Lys Asn Ser Asp Gly Ile
        1370                1375                1380

Phe Tyr Asp Ser Arg Asn Tyr Glu Ala Gln Glu Asn Ala Ile Leu
        1385                1390                1395

Pro Lys Asn Ala Asp Ala Asn Gly Ala Tyr Asn Ile Ala Arg Lys
        1400                1405                1410

Val Leu Trp Ala Ile Gly Gln Phe Lys Lys Ala Glu Asp Glu Lys
        1415                1420                1425

Leu Asp Lys Val Lys Ile Ala Ile Ser Asn Lys Glu Trp Leu Glu
        1430                1435                1440

Tyr Ala Gln Thr Ser Val Lys His Gly Ser Pro Lys Lys Lys Arg
        1445                1450                1455

Lys Val Ser Gly Gly Ser Thr Asn Leu Ser Asp Ile Ile Glu Lys
        1460                1465                1470

Glu Thr Gly Lys Gln Leu Val Ile Gln Glu Ser Ile Leu Met Leu
        1475                1480                1485

Pro Glu Glu Val Glu Glu Val Ile Gly Asn Lys Pro Glu Ser Asp
        1490                1495                1500

Ile Leu Val His Thr Ala Tyr Asp Glu Ser Thr Asp Glu Asn Val
        1505                1510                1515
```

-continued

```
Met Leu Leu Thr Ser Asp Ala Pro Glu Tyr Lys Pro Trp Ala Leu
    1520                1525                1530

Val Ile Gln Asp Ser Asn Gly Glu Asn Lys Ile Lys Met Leu Ser
1535                1540                1545

Gly Gly Ser Pro Lys Lys Arg Lys Val
    1550                1555

<210> SEQ ID NO 44
<211> LENGTH: 1558
<212> TYPE: PRT
<213> ORGANISM: Artificial Sequence
<220> FEATURE:
<223> OTHER INFORMATION: Synthetic

<400> SEQUENCE: 44

Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
        50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Tyr Ser Pro Cys Phe Ser Ala
            100                 105                 110

Gly Cys Ala Gly Glu Val Arg Ala Phe Leu Gln Glu Asn Thr His Val
        115                 120                 125

Arg Leu Arg Ile Phe Ala Ala Arg Ile Tyr Asp Tyr Asp Pro Leu Tyr
    130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
        195                 200                 205

Gly Ser Glu Thr Pro Gly Thr Ser Glu Ser Ala Thr Pro Glu Ser Met
    210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
            260                 265                 270

Val Lys Lys Leu Leu Asp Arg Tyr Tyr Leu Ser Phe Ile Asn Asp Val
        275                 280                 285

Leu His Ser Ile Lys Leu Lys Asn Leu Asn Asn Tyr Ile Ser Leu Phe
    290                 295                 300

Arg Lys Lys Thr Arg Thr Glu Lys Glu Asn Lys Glu Leu Glu Asn Leu
305                 310                 315                 320
```

```
Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
                340                 345                 350

Glu Phe Leu Asp Asp Lys Asp Glu Ile Ala Leu Val Asn Ser Phe Asn
                355                 360                 365

Gly Phe Thr Thr Ala Phe Thr Gly Phe Phe Asp Asn Arg Glu Asn Met
            370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
                420                 425                 430

Leu Asn Ser Asp Tyr Asp Val Glu Asp Phe Phe Glu Gly Glu Phe Phe
                435                 440                 445

Asn Phe Val Leu Thr Gln Glu Gly Ile Asp Val Tyr Asn Ala Ile Ile
        450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
                500                 505                 510

Tyr Gly Glu Gly Tyr Thr Ser Asp Glu Glu Val Leu Glu Val Phe Arg
            515                 520                 525

Asn Thr Leu Asn Lys Asn Ser Glu Ile Phe Ser Ser Ile Lys Lys Leu
        530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
        595                 600                 605

Arg Lys Ser Phe Lys Lys Ile Gly Ser Phe Ser Leu Glu Gln Leu Gln
610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
                660                 665                 670

Asp Ala Val Val Ala Ile Met Lys Asp Leu Leu Asp Ser Val Lys Ser
                675                 680                 685

Phe Glu Asn Tyr Ile Lys Ala Phe Phe Gly Glu Gly Lys Glu Thr Asn
            690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735
```

```
Lys Pro Tyr Ser Lys Asp Lys Phe Lys Leu Tyr Phe Gln Asn Pro Gln
                740                 745                 750

Phe Met Gly Gly Trp Asp Lys Asp Lys Glu Thr Asp Tyr Arg Ala Thr
        755                 760                 765

Ile Leu Arg Tyr Gly Ser Lys Tyr Tyr Leu Ala Ile Met Asp Lys Lys
    770                 775                 780

Tyr Ala Lys Cys Leu Gln Lys Ile Asp Lys Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
                820                 825                 830

Glu Asp Ile Gln Lys Ile Tyr Lys Asn Gly Thr Phe Lys Lys Gly Asp
                835                 840                 845

Met Phe Asn Leu Asn Asp Cys His Lys Leu Ile Asp Phe Phe Lys Asp
    850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
                900                 905                 910

Val Asp Lys Leu Val Glu Gly Lys Leu Tyr Met Phe Gln Ile Tyr
                915                 920                 925

Asn Lys Asp Phe Ser Asp Lys Ser His Gly Thr Pro Asn Leu His Thr
                930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
                980                 985                 990

Pro Asp Asn Pro Lys Lys Thr Thr Thr Leu Ser Tyr Asp Val Tyr Lys
                995                 1000                1005

Asp Lys Arg Phe Ser Glu Asp Gln Tyr Glu Leu His Ile Pro Ile
    1010                1015                1020

Ala Ile Asn Lys Cys Pro Lys Asn Ile Phe Lys Ile Asn Thr Glu
    1025                1030                1035

Val Arg Val Leu Leu Lys His Asp Asp Asn Pro Tyr Val Ile Gly
    1040                1045                1050

Ile Ala Arg Gly Glu Arg Asn Leu Leu Tyr Ile Val Val Val Asp
    1055                1060                1065

Gly Lys Gly Asn Ile Val Glu Gln Tyr Ser Leu Asn Glu Ile Ile
    1070                1075                1080

Asn Asn Phe Asn Gly Ile Arg Ile Lys Thr Asp Tyr His Ser Leu
    1085                1090                1095

Leu Asp Lys Lys Glu Lys Glu Arg Phe Glu Ala Arg Gln Asn Trp
    1100                1105                1110

Thr Ser Ile Glu Asn Ile Lys Glu Leu Lys Ala Gly Tyr Ile Ser
    1115                1120                1125

Gln Val Val His Lys Ile Cys Glu Leu Val Glu Lys Tyr Asp Ala
    1130                1135                1140

Val Ile Ala Leu Ala Asp Leu Asn Ser Gly Phe Lys Asn Ser Arg
```

```
            1145                1150                1155

Val Lys Val Glu Lys Gln Val Tyr Gln Lys Phe Glu Lys Met Leu
            1160                1165                1170

Ile Asp Lys Leu Asn Tyr Met Val Asp Lys Lys Ser Asn Pro Cys
            1175                1180                1185

Ala Thr Gly Gly Ala Leu Lys Gly Tyr Gln Ile Thr Asn Lys Phe
            1190                1195                1200

Glu Ser Phe Lys Ser Met Ser Thr Gln Asn Gly Phe Ile Phe Tyr
            1205                1210                1215

Ile Pro Ala Trp Leu Thr Ser Lys Ile Asp Pro Ser Thr Gly Phe
            1220                1225                1230

Val Asn Leu Leu Lys Thr Lys Tyr Thr Ser Ile Ala Asp Ser Lys
            1235                1240                1245

Lys Phe Ile Ser Ser Phe Asp Arg Ile Met Tyr Val Pro Glu Glu
            1250                1255                1260

Asp Leu Phe Glu Phe Ala Leu Asp Tyr Lys Asn Phe Ser Arg Thr
            1265                1270                1275

Asp Ala Asp Tyr Ile Lys Lys Trp Lys Leu Tyr Ser Tyr Gly Asn
            1280                1285                1290

Arg Ile Arg Ile Phe Arg Asn Pro Lys Lys Asn Asn Val Phe Asp
            1295                1300                1305

Trp Glu Glu Val Cys Leu Thr Ser Ala Tyr Lys Glu Leu Phe Asn
            1310                1315                1320

Lys Tyr Gly Ile Asn Tyr Gln Gln Gly Asp Ile Arg Ala Leu Leu
            1325                1330                1335

Cys Glu Gln Ser Asp Lys Ala Phe Tyr Ser Ser Phe Met Ala Leu
            1340                1345                1350

Met Ser Leu Met Leu Gln Met Arg Asn Ser Ile Thr Gly Arg Thr
            1355                1360                1365

Asp Val Ala Phe Leu Ile Ser Pro Val Lys Asn Ser Asp Gly Ile
            1370                1375                1380

Phe Tyr Asp Ser Arg Asn Tyr Glu Ala Gln Glu Asn Ala Ile Leu
            1385                1390                1395

Pro Lys Asn Ala Asp Ala Asn Gly Ala Tyr Asn Ile Ala Arg Lys
            1400                1405                1410

Val Leu Trp Ala Ile Gly Gln Phe Lys Lys Ala Glu Asp Glu Lys
            1415                1420                1425

Leu Asp Lys Val Lys Ile Ala Ile Ser Asn Lys Glu Trp Leu Glu
            1430                1435                1440

Tyr Ala Gln Thr Ser Val Lys His Gly Ser Pro Lys Lys Lys Arg
            1445                1450                1455

Lys Val Ser Gly Gly Ser Thr Asn Leu Ser Asp Ile Ile Glu Lys
            1460                1465                1470

Glu Thr Gly Lys Gln Leu Val Ile Gln Glu Ser Ile Leu Met Leu
            1475                1480                1485

Pro Glu Glu Val Glu Glu Val Ile Gly Asn Lys Pro Glu Ser Asp
            1490                1495                1500

Ile Leu Val His Thr Ala Tyr Asp Glu Ser Thr Asp Glu Asn Val
            1505                1510                1515

Met Leu Leu Thr Ser Asp Ala Pro Glu Tyr Lys Pro Trp Ala Leu
            1520                1525                1530

Val Ile Gln Asp Ser Asn Gly Glu Asn Lys Ile Lys Met Leu Ser
            1535                1540                1545
```

Gly Gly Ser Pro Lys Lys Lys Arg Lys Val
        1550            1555

<210> SEQ ID NO 45
<211> LENGTH: 1558
<212> TYPE: PRT
<213> ORGANISM: Artificial Sequence
<220> FEATURE:
<223> OTHER INFORMATION: Synthetic

<400> SEQUENCE: 45

Met Pro Lys Lys Arg Lys Val Met Glu Ala Ser Pro Ala Ser Gly
1               5                   10                  15

Pro Arg His Leu Met Asp Pro His Ile Phe Thr Ser Asn Phe Asn
                20                  25                  30

Gly Ile Gly Arg His Lys Thr Tyr Leu Cys Tyr Glu Val Glu Arg Leu
                35                  40                  45

Asp Asn Gly Thr Ser Val Lys Met Asp Gln His Arg Gly Phe Leu His
50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Tyr Ser Pro Cys Phe Ser Trp
                100                 105                 110

Gly Cys Ala Gly Glu Val Arg Ala Phe Leu Gln Glu Asn Thr His Val
                115                 120                 125

Arg Leu Arg Ile Phe Ala Ala Arg Ile Tyr Asp Tyr Asp Tyr Leu Tyr
                130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
                180                 185                 190

Ala Leu Ser Gly Arg Leu Arg Ala Ile Leu Gln Asn Gln Gly Asn Ser
                195                 200                 205

Gly Ser Glu Thr Pro Gly Thr Ser Glu Ser Ala Thr Pro Glu Ser Met
                210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
                260                 265                 270

Val Lys Lys Leu Leu Asp Arg Tyr Tyr Leu Ser Phe Ile Asn Asp Val
                275                 280                 285

Leu His Ser Ile Lys Leu Lys Asn Leu Asn Asn Tyr Ile Ser Leu Phe
                290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
                340                 345                 350

```
Glu Phe Leu Asp Asp Lys Asp Glu Ile Ala Leu Val Asn Ser Phe Asn
            355                 360                 365

Gly Phe Thr Thr Ala Phe Thr Gly Phe Phe Asp Asn Arg Glu Asn Met
        370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
                420                 425                 430

Leu Asn Ser Asp Tyr Asp Val Glu Asp Phe Phe Glu Gly Glu Phe Phe
            435                 440                 445

Asn Phe Val Leu Thr Gln Glu Gly Ile Asp Val Tyr Asn Ala Ile Ile
            450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Glu Val Leu Glu Val Phe Arg
            515                 520                 525

Asn Thr Leu Asn Lys Asn Ser Glu Ile Phe Ser Ser Ile Lys Lys Leu
            530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
            595                 600                 605

Arg Lys Ser Phe Lys Lys Ile Gly Ser Phe Ser Leu Glu Gln Leu Gln
            610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
                660                 665                 670

Asp Ala Val Val Ala Ile Met Lys Asp Leu Leu Asp Ser Val Lys Ser
                675                 680                 685

Phe Glu Asn Tyr Ile Lys Ala Phe Phe Gly Glu Gly Lys Glu Thr Asn
            690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
                740                 745                 750

Phe Met Gly Gly Trp Asp Lys Asp Lys Glu Thr Asp Tyr Arg Ala Thr
            755                 760                 765
```

```
Ile Leu Arg Tyr Gly Ser Lys Tyr Tyr Leu Ala Ile Met Asp Lys Lys
770                 775                 780

Tyr Ala Lys Cys Leu Gln Lys Ile Asp Lys Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
                820                 825                 830

Glu Asp Ile Gln Lys Ile Tyr Lys Asn Gly Thr Phe Lys Lys Gly Asp
                835                 840                 845

Met Phe Asn Leu Asn Asp Cys His Lys Leu Ile Asp Phe Phe Lys Asp
850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
                900                 905                 910

Val Asp Lys Leu Val Glu Glu Gly Lys Leu Tyr Met Phe Gln Ile Tyr
                915                 920                 925

Asn Lys Asp Phe Ser Lys Ser His Gly Thr Pro Asn Leu His Thr
930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
                980                 985                 990

Pro Asp Asn Pro Lys Lys Thr Thr Thr Leu Ser Tyr Asp Val Tyr Lys
                995             1000                1005

Asp Lys Arg Phe Ser Glu Asp Gln Tyr Glu Leu His Ile Pro Ile
    1010                1015                1020

Ala Ile Asn Lys Cys Pro Asn Ile Phe Lys Ile Asn Thr Glu
    1025                1030                1035

Val Arg Val Leu Leu Lys His Asp Asp Asn Pro Tyr Val Ile Gly
    1040                1045                1050

Ile Ala Arg Gly Glu Arg Asn Leu Leu Tyr Ile Val Val Asp
    1055                1060                1065

Gly Lys Gly Asn Ile Val Glu Gln Tyr Ser Leu Asn Glu Ile Ile
    1070                1075                1080

Asn Asn Phe Asn Gly Ile Arg Ile Lys Thr Asp Tyr His Ser Leu
    1085                1090                1095

Leu Asp Lys Lys Glu Lys Glu Arg Phe Glu Ala Arg Gln Asn Trp
    1100                1105                1110

Thr Ser Ile Glu Asn Ile Lys Glu Leu Lys Ala Gly Tyr Ile Ser
    1115                1120                1125

Gln Val Val His Lys Ile Cys Glu Leu Val Glu Lys Tyr Asp Ala
    1130                1135                1140

Val Ile Ala Leu Ala Asp Leu Asn Ser Gly Phe Lys Asn Ser Arg
    1145                1150                1155

Val Lys Val Glu Lys Gln Val Tyr Gln Lys Phe Glu Lys Met Leu
    1160                1165                1170

Ile Asp Lys Leu Asn Tyr Met Val Asp Lys Lys Ser Asn Pro Cys
```

```
                1175                1180                1185

Ala Thr Gly Gly Ala Leu Lys Gly Tyr Gln Ile Thr Asn Lys Phe
            1190                1195                1200

Glu Ser Phe Lys Ser Met Ser Thr Gln Asn Gly Phe Ile Phe Tyr
            1205                1210                1215

Ile Pro Ala Trp Leu Thr Ser Lys Ile Asp Pro Ser Thr Gly Phe
            1220                1225                1230

Val Asn Leu Leu Lys Thr Lys Tyr Thr Ser Ile Ala Asp Ser Lys
            1235                1240                1245

Lys Phe Ile Ser Ser Phe Asp Arg Ile Met Tyr Val Pro Glu Glu
            1250                1255                1260

Asp Leu Phe Glu Phe Ala Leu Asp Tyr Lys Asn Phe Ser Arg Thr
            1265                1270                1275

Asp Ala Asp Tyr Ile Lys Lys Trp Lys Leu Tyr Ser Tyr Gly Asn
            1280                1285                1290

Arg Ile Arg Ile Phe Arg Asn Pro Lys Lys Asn Val Phe Asp
            1295                1300                1305

Trp Glu Glu Val Cys Leu Thr Ser Ala Tyr Lys Glu Leu Phe Asn
            1310                1315                1320

Lys Tyr Gly Ile Asn Tyr Gln Gln Gly Asp Ile Arg Ala Leu Leu
            1325                1330                1335

Cys Glu Gln Ser Asp Lys Ala Phe Tyr Ser Ser Phe Met Ala Leu
            1340                1345                1350

Met Ser Leu Met Leu Gln Met Arg Asn Ser Ile Thr Gly Arg Thr
            1355                1360                1365

Asp Val Ala Phe Leu Ile Ser Pro Val Lys Asn Ser Asp Gly Ile
            1370                1375                1380

Phe Tyr Asp Ser Arg Asn Tyr Glu Ala Gln Glu Asn Ala Ile Leu
            1385                1390                1395

Pro Lys Asn Ala Asp Ala Asn Gly Ala Tyr Asn Ile Ala Arg Lys
            1400                1405                1410

Val Leu Trp Ala Ile Gly Gln Phe Lys Lys Ala Glu Asp Glu Lys
            1415                1420                1425

Leu Asp Lys Val Lys Ile Ala Ile Ser Asn Lys Glu Trp Leu Glu
            1430                1435                1440

Tyr Ala Gln Thr Ser Val Lys His Gly Ser Pro Lys Lys Lys Arg
            1445                1450                1455

Lys Val Ser Gly Gly Ser Thr Asn Leu Ser Asp Ile Ile Glu Lys
            1460                1465                1470

Glu Thr Gly Lys Gln Leu Val Ile Gln Glu Ser Ile Leu Met Leu
            1475                1480                1485

Pro Glu Glu Val Glu Glu Val Ile Gly Asn Lys Pro Glu Ser Asp
            1490                1495                1500

Ile Leu Val His Thr Ala Tyr Asp Glu Ser Thr Asp Glu Asn Val
            1505                1510                1515

Met Leu Leu Thr Ser Asp Ala Pro Glu Tyr Lys Pro Trp Ala Leu
            1520                1525                1530

Val Ile Gln Asp Ser Asn Gly Glu Asn Lys Ile Lys Met Leu Ser
            1535                1540                1545

Gly Gly Ser Pro Lys Lys Lys Arg Lys Val
            1550                1555

<210> SEQ ID NO 46
```

<211> LENGTH: 1558
<212> TYPE: PRT
<213> ORGANISM: Artificial Sequence
<220> FEATURE:
<223> OTHER INFORMATION: Synthetic

<400> SEQUENCE: 46

```
Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
            20                  25                  30

Gly Ile Gly Arg His Lys Thr Tyr Leu Cys Tyr Glu Val Glu Arg Leu
        35                  40                  45

Asp Asn Gly Thr Ser Val Lys Met Asp Gln His Arg Gly Phe Leu His
    50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Trp Ser Pro Cys Phe Ser Ala
            100                 105                 110

Gly Cys Ala Gly Glu Val Arg Ala Phe Leu Gln Glu Asn Thr His Val
        115                 120                 125

Arg Leu Arg Ile Phe Ala Ala Arg Ile Tyr Asp Tyr Asp Tyr Leu Tyr
    130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
        195                 200                 205

Gly Ser Glu Thr Pro Gly Thr Ser Glu Ser Ala Thr Pro Glu Ser Met
    210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
            260                 265                 270

Val Lys Lys Leu Leu Asp Arg Tyr Tyr Leu Ser Phe Ile Asn Asp Val
        275                 280                 285

Leu His Ser Ile Lys Leu Lys Asn Leu Asn Asn Tyr Ile Ser Leu Phe
    290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Glu Thr Ile Leu Pro
            340                 345                 350

Glu Phe Leu Asp Asp Lys Asp Glu Ile Ala Leu Val Asn Ser Phe Asn
        355                 360                 365

Gly Phe Thr Thr Ala Phe Thr Gly Phe Phe Asp Asn Arg Glu Asn Met
    370                 375                 380
```

```
Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
            405                 410                 415

Asp Ala Ile Phe Asp Lys His Glu Val Gln Glu Ile Lys Glu Lys Ile
        420                 425                 430

Leu Asn Ser Asp Tyr Asp Val Glu Asp Phe Phe Glu Gly Glu Phe Phe
    435                 440                 445

Asn Phe Val Leu Thr Gln Glu Gly Ile Asp Val Tyr Asn Ala Ile Ile
450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Val Leu Glu Val Phe Arg
        515                 520                 525

Asn Thr Leu Asn Lys Asn Ser Glu Ile Phe Ser Ser Ile Lys Lys Leu
530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
    595                 600                 605

Arg Lys Ser Phe Lys Lys Ile Gly Ser Phe Ser Leu Glu Gln Leu Gln
        610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
            660                 665                 670

Asp Ala Val Val Ala Ile Met Lys Asp Leu Leu Asp Ser Val Lys Ser
        675                 680                 685

Phe Glu Asn Tyr Ile Lys Ala Phe Phe Gly Glu Gly Lys Glu Thr Asn
    690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
            740                 745                 750

Phe Met Gly Gly Trp Asp Lys Asp Lys Glu Thr Asp Tyr Arg Ala Thr
        755                 760                 765

Ile Leu Arg Tyr Gly Ser Lys Tyr Tyr Leu Ala Ile Met Asp Lys Lys
    770                 775                 780

Tyr Ala Lys Cys Leu Gln Lys Ile Asp Lys Asp Asp Val Asn Gly Asn
785                 790                 795                 800
```

```
Tyr Glu Lys Ile Asn Tyr Lys Leu Leu Pro Gly Pro Asn Lys Met Leu
            805                 810                 815

Pro Lys Val Phe Phe Ser Lys Lys Trp Met Ala Tyr Tyr Asn Pro Ser
            820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
            850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
            885                 890                 895

Glu Glu Gln Gly Tyr Lys Val Ser Phe Glu Ser Ala Ser Lys Lys Glu
            900                 905                 910

Val Asp Lys Leu Val Glu Gly Lys Leu Tyr Met Phe Gln Ile Tyr
            915                 920                 925

Asn Lys Asp Phe Ser Asp Lys Ser His Gly Thr Pro Asn Leu His Thr
            930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
            980                 985                 990

Pro Asp Asn Pro Lys Lys Thr Thr Thr Leu Ser Tyr Asp Val Tyr Lys
            995                 1000                1005

Asp Lys Arg Phe Ser Glu Asp Gln Tyr Glu Leu His Ile Pro Ile
            1010                1015                1020

Ala Ile Asn Lys Cys Pro Lys Asn Ile Phe Lys Ile Asn Thr Glu
            1025                1030                1035

Val Arg Val Leu Leu Lys His Asp Asp Asn Pro Tyr Val Ile Gly
            1040                1045                1050

Ile Ala Arg Gly Glu Arg Asn Leu Leu Tyr Ile Val Val Val Asp
            1055                1060                1065

Gly Lys Gly Asn Ile Val Glu Gln Tyr Ser Leu Asn Glu Ile Ile
            1070                1075                1080

Asn Asn Phe Asn Gly Ile Arg Ile Lys Thr Asp Tyr His Ser Leu
            1085                1090                1095

Leu Asp Lys Lys Glu Lys Glu Arg Phe Glu Ala Arg Gln Asn Trp
            1100                1105                1110

Thr Ser Ile Glu Asn Ile Lys Glu Leu Lys Ala Gly Tyr Ile Ser
            1115                1120                1125

Gln Val Val His Lys Ile Cys Glu Leu Val Glu Lys Tyr Asp Ala
            1130                1135                1140

Val Ile Ala Leu Ala Asp Leu Asn Ser Gly Phe Lys Asn Ser Arg
            1145                1150                1155

Val Lys Val Glu Lys Gln Val Tyr Gln Lys Phe Glu Lys Met Leu
            1160                1165                1170

Ile Asp Lys Leu Asn Tyr Met Val Asp Lys Lys Ser Asn Pro Cys
            1175                1180                1185

Ala Thr Gly Gly Ala Leu Lys Gly Tyr Gln Ile Thr Asn Lys Phe
            1190                1195                1200

Glu Ser Phe Lys Ser Met Ser Thr Gln Asn Gly Phe Ile Phe Tyr
```

1205                1210                1215

Ile Pro Ala Trp Leu Thr Ser Lys Ile Asp Pro Ser Thr Gly Phe
    1220                1225                1230

Val Asn Leu Leu Lys Thr Lys Tyr Thr Ser Ile Ala Asp Ser Lys
    1235                1240                1245

Lys Phe Ile Ser Ser Phe Asp Arg Ile Met Tyr Val Pro Glu Glu
    1250                1255                1260

Asp Leu Phe Glu Phe Ala Leu Asp Tyr Lys Asn Phe Ser Arg Thr
    1265                1270                1275

Asp Ala Asp Tyr Ile Lys Lys Trp Lys Leu Tyr Ser Tyr Gly Asn
    1280                1285                1290

Arg Ile Arg Ile Phe Arg Asn Pro Lys Lys Asn Asn Val Phe Asp
    1295                1300                1305

Trp Glu Glu Val Cys Leu Thr Ser Ala Tyr Lys Glu Leu Phe Asn
    1310                1315                1320

Lys Tyr Gly Ile Asn Tyr Gln Gln Gly Asp Ile Arg Ala Leu Leu
    1325                1330                1335

Cys Glu Gln Ser Asp Lys Ala Phe Tyr Ser Ser Phe Met Ala Leu
    1340                1345                1350

Met Ser Leu Met Leu Gln Met Arg Asn Ser Ile Thr Gly Arg Thr
    1355                1360                1365

Asp Val Ala Phe Leu Ile Ser Pro Val Lys Asn Ser Asp Gly Ile
    1370                1375                1380

Phe Tyr Asp Ser Arg Asn Tyr Glu Ala Gln Glu Asn Ala Ile Leu
    1385                1390                1395

Pro Lys Asn Ala Asp Ala Asn Gly Ala Tyr Asn Ile Ala Arg Lys
    1400                1405                1410

Val Leu Trp Ala Ile Gly Gln Phe Lys Lys Ala Glu Asp Glu Lys
    1415                1420                1425

Leu Asp Lys Val Lys Ile Ala Ile Ser Asn Lys Glu Trp Leu Glu
    1430                1435                1440

Tyr Ala Gln Thr Ser Val Lys His Gly Ser Pro Lys Lys Lys Arg
    1445                1450                1455

Lys Val Ser Gly Gly Ser Thr Asn Leu Ser Asp Ile Ile Glu Lys
    1460                1465                1470

Glu Thr Gly Lys Gln Leu Val Ile Gln Glu Ser Ile Leu Met Leu
    1475                1480                1485

Pro Glu Glu Val Glu Glu Val Ile Gly Asn Lys Pro Glu Ser Asp
    1490                1495                1500

Ile Leu Val His Thr Ala Tyr Asp Glu Ser Thr Asp Glu Asn Val
    1505                1510                1515

Met Leu Leu Thr Ser Asp Ala Pro Glu Tyr Lys Pro Trp Ala Leu
    1520                1525                1530

Val Ile Gln Asp Ser Asn Gly Glu Asn Lys Ile Lys Met Leu Ser
    1535                1540                1545

Gly Gly Ser Pro Lys Lys Lys Arg Lys Val
    1550                1555

<210> SEQ ID NO 47
<211> LENGTH: 1558
<212> TYPE: PRT
<213> ORGANISM: Artificial Sequence
<220> FEATURE:
<223> OTHER INFORMATION: Synthetic

<400> SEQUENCE: 47

```
Met Pro Lys Lys Arg Lys Val Met Glu Ala Ser Pro Ala Ser Gly
1               5                   10                  15

Pro Arg His Leu Met Asp Pro His Ile Phe Thr Ser Asn Phe Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln
                85                  90                  95

Ile Tyr Arg Val Thr Trp Phe Ile Ser Tyr Ser Pro Cys Phe Ser Ala
                100                 105                 110

Gly Cys Ala Gly Glu Val Arg Ala Phe Leu Gln Glu Asn Thr His Val
            115                 120                 125

Arg Leu Arg Ile Phe Ala Ala Arg Ile Phe Asp Tyr Asp Pro Leu Tyr
    130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
    195                 200                 205

Gly Ser Glu Thr Pro Gly Thr Ser Glu Ser Ala Thr Pro Glu Ser Met
210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
                260                 265                 270

Val Lys Lys Leu Leu Asp Arg Tyr Tyr Leu Ser Phe Ile Asn Asp Val
                275                 280                 285

Leu His Ser Ile Lys Leu Lys Asn Leu Asn Asn Tyr Ile Ser Leu Phe
290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
                340                 345                 350

Glu Phe Leu Asp Asp Lys Asp Glu Ile Ala Leu Val Asn Ser Phe Asn
                355                 360                 365

Gly Phe Thr Thr Ala Phe Thr Gly Phe Phe Asp Asn Arg Glu Asn Met
            370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415
```

```
Asp Ala Ile Phe Asp Lys His Glu Val Gln Glu Ile Lys Glu Lys Ile
            420                 425                 430

Leu Asn Ser Asp Tyr Asp Val Glu Asp Phe Phe Gly Glu Phe Phe
            435                 440                 445

Asn Phe Val Leu Thr Gln Glu Gly Ile Asp Val Tyr Asn Ala Ile Ile
            450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
            485                 490                 495

Lys Pro Leu Tyr Lys Gln Val Leu Ser Asp Arg Glu Ser Leu Ser Phe
            500                 505                 510

Tyr Gly Glu Gly Tyr Thr Ser Asp Glu Glu Val Leu Glu Val Phe Arg
            515                 520                 525

Asn Thr Leu Asn Lys Asn Ser Glu Ile Phe Ser Ser Ile Lys Lys Leu
            530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
            565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
            595                 600                 605

Arg Lys Ser Phe Lys Lys Ile Gly Ser Phe Ser Leu Glu Gln Leu Gln
            610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
            645                 650                 655

Lys Leu Phe Asp Ala Asp Phe Val Leu Glu Lys Ser Leu Lys Lys Asn
            660                 665                 670

Asp Ala Val Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
            690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
            725                 730                 735

Lys Pro Tyr Ser Lys Asp Lys Phe Lys Leu Tyr Phe Gln Asn Pro Gln
            740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
            770                 775                 780

Tyr Ala Lys Cys Leu Gln Lys Ile Asp Lys Asp Asp Val Asn Gly Asn
785                 790                 795                 800

Tyr Glu Lys Ile Asn Tyr Lys Leu Leu Pro Gly Pro Asn Lys Met Leu
            805                 810                 815

Pro Lys Val Phe Phe Ser Lys Lys Trp Met Ala Tyr Tyr Asn Pro Ser
            820                 825                 830
```

-continued

Glu Asp Ile Gln Lys Ile Tyr Lys Asn Gly Thr Phe Lys Gly Asp
835                 840                 845

Met Phe Asn Leu Asn Asp Cys His Lys Leu Ile Asp Phe Phe Lys Asp
850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
            900                 905                 910

Val Asp Lys Leu Val Glu Glu Gly Lys Leu Tyr Met Phe Gln Ile Tyr
            915                 920                 925

Asn Lys Asp Phe Ser Lys Ser His Gly Thr Pro Asn Leu His Thr
930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
            980                 985                 990

Pro Asp Asn Pro Lys Lys Thr Thr Thr Leu Ser Tyr Asp Val Tyr Lys
            995                 1000                1005

Asp Lys Arg Phe Ser Glu Asp Gln Tyr Glu Leu His Ile Pro Ile
    1010                1015                1020

Ala Ile Asn Lys Cys Pro Lys Asn Ile Phe Lys Ile Asn Thr Glu
    1025                1030                1035

Val Arg Val Leu Leu Lys His Asp Asp Asn Pro Tyr Val Ile Gly
    1040                1045                1050

Ile Ala Arg Gly Glu Arg Asn Leu Leu Tyr Ile Val Val Val Asp
    1055                1060                1065

Gly Lys Gly Asn Ile Val Glu Gln Tyr Ser Leu Asn Glu Ile Ile
    1070                1075                1080

Asn Asn Phe Asn Gly Ile Arg Ile Lys Thr Asp Tyr His Ser Leu
    1085                1090                1095

Leu Asp Lys Lys Glu Lys Glu Arg Phe Glu Ala Arg Gln Asn Trp
    1100                1105                1110

Thr Ser Ile Glu Asn Ile Lys Glu Leu Lys Ala Gly Tyr Ile Ser
    1115                1120                1125

Gln Val Val His Lys Ile Cys Glu Leu Val Glu Lys Tyr Asp Ala
    1130                1135                1140

Val Ile Ala Leu Ala Asp Leu Asn Ser Gly Phe Lys Asn Ser Arg
    1145                1150                1155

Val Lys Val Glu Lys Gln Val Tyr Gln Lys Phe Glu Lys Met Leu
    1160                1165                1170

Ile Asp Lys Leu Asn Tyr Met Val Asp Lys Lys Ser Asn Pro Cys
    1175                1180                1185

Ala Thr Gly Gly Ala Leu Lys Gly Tyr Gln Ile Thr Asn Lys Phe
    1190                1195                1200

Glu Ser Phe Lys Ser Met Ser Thr Gln Asn Gly Phe Ile Phe Tyr
    1205                1210                1215

Ile Pro Ala Trp Leu Thr Ser Lys Ile Asp Pro Ser Thr Gly Phe
    1220                1225                1230

Val Asn Leu Leu Lys Thr Lys Tyr Thr Ser Ile Ala Asp Ser Lys

```
                   1235                1240                1245

Lys Phe Ile Ser Ser Phe Asp Arg Ile Met Tyr Val Pro Glu Glu
        1250                1255                1260

Asp Leu Phe Glu Phe Ala Leu Asp Tyr Lys Asn Phe Ser Arg Thr
        1265                1270                1275

Asp Ala Asp Tyr Ile Lys Lys Trp Lys Leu Tyr Ser Tyr Gly Asn
        1280                1285                1290

Arg Ile Arg Ile Phe Arg Asn Pro Lys Lys Asn Val Phe Asp
        1295                1300                1305

Trp Glu Glu Val Cys Leu Thr Ser Ala Tyr Lys Glu Leu Phe Asn
        1310                1315                1320

Lys Tyr Gly Ile Asn Tyr Gln Gln Gly Asp Ile Arg Ala Leu Leu
        1325                1330                1335

Cys Glu Gln Ser Asp Lys Ala Phe Tyr Ser Phe Met Ala Leu
        1340                1345                1350

Met Ser Leu Met Leu Gln Met Arg Asn Ser Ile Thr Gly Arg Thr
        1355                1360                1365

Asp Val Ala Phe Leu Ile Ser Pro Val Lys Asn Ser Asp Gly Ile
        1370                1375                1380

Phe Tyr Asp Ser Arg Asn Tyr Glu Ala Gln Glu Asn Ala Ile Leu
        1385                1390                1395

Pro Lys Asn Ala Asp Ala Asn Gly Ala Tyr Asn Ile Ala Arg Lys
        1400                1405                1410

Val Leu Trp Ala Ile Gly Gln Phe Lys Lys Ala Glu Asp Glu Lys
        1415                1420                1425

Leu Asp Lys Val Lys Ile Ala Ile Ser Asn Lys Glu Trp Leu Glu
        1430                1435                1440

Tyr Ala Gln Thr Ser Val Lys His Gly Ser Pro Lys Lys Lys Arg
        1445                1450                1455

Lys Val Ser Gly Gly Ser Thr Asn Leu Ser Asp Ile Ile Glu Lys
        1460                1465                1470

Glu Thr Gly Lys Gln Leu Val Ile Gln Glu Ser Ile Leu Met Leu
        1475                1480                1485

Pro Glu Glu Val Glu Glu Val Ile Gly Asn Lys Pro Glu Ser Asp
        1490                1495                1500

Ile Leu Val His Thr Ala Tyr Asp Glu Ser Thr Asp Glu Asn Val
        1505                1510                1515

Met Leu Leu Thr Ser Asp Ala Pro Glu Tyr Lys Pro Trp Ala Leu
        1520                1525                1530

Val Ile Gln Asp Ser Asn Gly Glu Asn Lys Ile Lys Met Leu Ser
        1535                1540                1545

Gly Gly Ser Pro Lys Lys Lys Arg Lys Val
        1550                1555

<210> SEQ ID NO 48
<211> LENGTH: 1558
<212> TYPE: PRT
<213> ORGANISM: Artificial Sequence
<220> FEATURE:
<223> OTHER INFORMATION: Synthetic

<400> SEQUENCE: 48

Met Pro Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
```

```
            20                  25                  30
Gly Ile Gly Arg His Lys Thr Tyr Leu Cys Tyr Glu Val Glu Arg Leu
         35                  40                  45
Asp Asn Gly Thr Ser Val Lys Met Asp Gln His Arg Gly Phe Leu His
 50                  55                  60
Asn Gln Ala Lys Asn Leu Leu Cys Gly Phe Tyr Gly Arg His Ala Glu
 65                  70                  75                  80
Leu Arg Phe Leu Asp Leu Val Pro Ser Leu Gln Leu Asp Pro Ala Gln
                 85                  90                  95
Ile Tyr Arg Val Thr Trp Phe Ile Ser Tyr Ser Pro Cys Phe Ser Ala
            100                 105                 110
Gly Cys Ala Gly Glu Val Arg Ala Phe Leu Gln Glu Asn Thr His Val
            115                 120                 125
Arg Leu Arg Ile Phe Ala Ala Arg Ile Tyr Asp Asp Pro Leu Tyr
            130                 135                 140
Lys Glu Ala Leu Gln Met Leu Arg Asp Ala Gly Ala Gln Val Ser Ile
145                 150                 155                 160
Met Thr Tyr Asp Glu Phe Lys His Cys Trp Asp Thr Phe Val Asp His
                 165                 170                 175
Gln Gly Cys Pro Phe Gln Pro Trp Asp Gly Leu Asp Glu His Ser Gln
            180                 185                 190
Ala Leu Ser Gly Arg Leu Arg Ala Ile Leu Gln Asn Gln Gly Asn Ser
            195                 200                 205
Gly Ser Glu Thr Pro Gly Thr Ser Glu Ser Ala Thr Pro Glu Ser Met
            210                 215                 220
Ser Lys Leu Glu Lys Phe Thr Asn Cys Tyr Ser Leu Ser Lys Thr Leu
225                 230                 235                 240
Arg Phe Lys Ala Ile Pro Val Gly Lys Thr Gln Glu Asn Ile Asp Asn
                 245                 250                 255
Lys Arg Leu Leu Val Glu Asp Glu Lys Arg Ala Glu Asp Tyr Lys Gly
            260                 265                 270
Val Lys Lys Leu Leu Asp Arg Tyr Tyr Leu Ser Phe Ile Asn Asp Val
            275                 280                 285
Leu His Ser Ile Lys Leu Lys Asn Leu Asn Asn Tyr Ile Ser Leu Phe
            290                 295                 300
Arg Lys Lys Thr Arg Thr Glu Lys Glu Asn Lys Glu Leu Glu Asn Leu
305                 310                 315                 320
Glu Ile Asn Leu Arg Lys Glu Ile Ala Lys Ala Phe Lys Gly Asn Glu
                 325                 330                 335
Gly Tyr Lys Ser Leu Phe Lys Lys Asp Ile Ile Glu Thr Ile Leu Pro
            340                 345                 350
Glu Phe Leu Asp Asp Lys Asp Glu Ile Ala Leu Val Asn Ser Phe Asn
            355                 360                 365
Gly Phe Thr Thr Ala Phe Thr Gly Phe Phe Asp Asn Arg Glu Asn Met
            370                 375                 380
Phe Ser Glu Glu Ala Lys Ser Thr Ser Ile Ala Phe Arg Cys Ile Asn
385                 390                 395                 400
Glu Asn Leu Thr Arg Tyr Ile Ser Asn Met Asp Ile Phe Glu Lys Val
                 405                 410                 415
Asp Ala Ile Phe Asp Lys His Glu Val Gln Glu Ile Lys Glu Lys Ile
            420                 425                 430
Leu Asn Ser Asp Tyr Asp Val Glu Asp Phe Phe Glu Gly Glu Phe Phe
            435                 440                 445
```

```
Asn Phe Val Leu Thr Gln Glu Gly Ile Asp Val Tyr Asn Ala Ile Ile
            450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                    485                 490                 495

Lys Pro Leu Tyr Lys Gln Val Leu Ser Asp Arg Glu Ser Leu Ser Phe
                500                 505                 510

Tyr Gly Glu Gly Tyr Thr Ser Asp Glu Glu Val Leu Glu Val Phe Arg
            515                 520                 525

Asn Thr Leu Asn Lys Asn Ser Glu Ile Phe Ser Ser Ile Lys Lys Leu
530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
                580                 585                 590

His Leu Lys Lys Lys Ala Val Val Thr Glu Lys Tyr Glu Asp Asp Arg
            595                 600                 605

Arg Lys Ser Phe Lys Lys Ile Gly Ser Phe Ser Leu Glu Gln Leu Gln
            610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
                660                 665                 670

Asp Ala Val Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                    725                 730                 735

Lys Pro Tyr Ser Lys Asp Lys Phe Lys Leu Tyr Phe Gln Asn Pro Gln
                740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
770                 775                 780

Tyr Ala Lys Cys Leu Gln Lys Ile Asp Lys Asp Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
                820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
850                 855                 860
```

```
Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
            900                 905                 910

Val Asp Lys Leu Val Glu Gly Lys Leu Tyr Met Phe Gln Ile Tyr
        915                 920                 925

Asn Lys Asp Phe Ser Asp Lys Ser His Gly Thr Pro Asn Leu His Thr
    930                 935                 940

Met Tyr Phe Lys Leu Leu Phe Asp Glu Asn Asn His Gly Gln Ile Arg
945                 950                 955                 960

Leu Ser Gly Gly Ala Glu Leu Phe Met Arg Arg Ala Ser Leu Lys Lys
                965                 970                 975

Glu Glu Leu Val Val His Pro Ala Asn Ser Pro Ile Ala Asn Lys Asn
            980                 985                 990

Pro Asp Asn Pro Lys Lys Thr Thr  Thr Leu Ser Tyr Asp  Val Tyr Lys
            995                 1000                1005

Asp Lys  Arg Phe Ser Glu Asp  Gln Tyr Glu Leu His  Ile Pro Ile
    1010                1015                1020

Ala Ile  Asn Lys Cys Pro Lys  Asn Ile Phe Lys Ile  Asn Thr Glu
    1025                1030                1035

Val Arg  Val Leu Leu Lys His  Asp Asp Asn Pro Tyr  Val Ile Gly
    1040                1045                1050

Ile Ala  Arg Gly Glu Arg Asn  Leu Leu Tyr Ile Val  Val Val Asp
    1055                1060                1065

Gly Lys  Gly Asn Ile Val Glu  Gln Tyr Ser Leu Asn  Glu Ile Ile
    1070                1075                1080

Asn Asn  Phe Asn Gly Ile Arg  Ile Lys Thr Asp Tyr  His Ser Leu
    1085                1090                1095

Leu Asp  Lys Lys Glu Lys Glu  Arg Phe Glu Ala Arg  Gln Asn Trp
    1100                1105                1110

Thr Ser  Ile Glu Asn Ile Lys  Glu Leu Lys Ala Gly  Tyr Ile Ser
    1115                1120                1125

Gln Val  Val His Lys Ile Cys  Glu Leu Val Glu Lys  Tyr Asp Ala
    1130                1135                1140

Val Ile  Ala Leu Ala Asp Leu  Asn Ser Gly Phe Lys  Asn Ser Arg
    1145                1150                1155

Val Lys  Val Glu Lys Gln Val  Tyr Gln Lys Phe Glu  Lys Met Leu
    1160                1165                1170

Ile Asp  Lys Leu Asn Tyr Met  Val Asp Lys Lys Ser  Asn Pro Cys
    1175                1180                1185

Ala Thr  Gly Gly Ala Leu Lys  Gly Tyr Gln Ile Thr  Asn Lys Phe
    1190                1195                1200

Glu Ser  Phe Lys Ser Met Ser  Thr Gln Asn Gly Phe  Ile Phe Tyr
    1205                1210                1215

Ile Pro  Ala Trp Leu Thr Ser  Lys Ile Asp Pro Ser  Thr Gly Phe
    1220                1225                1230

Val Asn  Leu Leu Lys Thr Lys  Tyr Thr Ser Ile Ala  Asp Ser Lys
    1235                1240                1245

Lys Phe  Ile Ser Ser Phe Asp  Arg Ile Met Tyr Val  Pro Glu Glu
    1250                1255                1260

Asp Leu  Phe Glu Phe Ala Leu  Asp Tyr Lys Asn Phe  Ser Arg Thr
```

```
           1265                1270                1275

Asp Ala Asp Tyr Ile Lys Lys Trp Lys Leu Tyr Ser Tyr Gly Asn
            1280                1285                1290

Arg Ile Arg Ile Phe Arg Asn Pro Lys Lys Asn Asn Val Phe Asp
        1295                1300                1305

Trp Glu Val Cys Leu Thr Ser Ala Tyr Lys Glu Leu Phe Asn
    1310                1315                1320

Lys Tyr Gly Ile Asn Tyr Gln Gln Gly Asp Ile Arg Ala Leu Leu
        1325                1330                1335

Cys Glu Gln Ser Asp Lys Ala Phe Tyr Ser Ser Phe Met Ala Leu
        1340                1345                1350

Met Ser Leu Met Leu Gln Met Arg Asn Ser Ile Thr Gly Arg Thr
        1355                1360                1365

Asp Val Ala Phe Leu Ile Ser Pro Val Lys Asn Ser Asp Gly Ile
        1370                1375                1380

Phe Tyr Asp Ser Arg Asn Tyr Glu Ala Gln Glu Asn Ala Ile Leu
        1385                1390                1395

Pro Lys Asn Ala Asp Ala Asn Gly Ala Tyr Asn Ile Ala Arg Lys
        1400                1405                1410

Val Leu Trp Ala Ile Gly Gln Phe Lys Lys Ala Glu Asp Glu Lys
        1415                1420                1425

Leu Asp Lys Val Lys Ile Ala Ile Ser Asn Lys Glu Trp Leu Glu
        1430                1435                1440

Tyr Ala Gln Thr Ser Val Lys His Gly Ser Pro Lys Lys Lys Arg
        1445                1450                1455

Lys Val Ser Gly Gly Ser Thr Asn Leu Ser Asp Ile Ile Glu Lys
        1460                1465                1470

Glu Thr Gly Lys Gln Leu Val Ile Gln Glu Ser Ile Leu Met Leu
        1475                1480                1485

Pro Glu Glu Val Glu Glu Val Ile Gly Asn Lys Pro Glu Ser Asp
        1490                1495                1500

Ile Leu Val His Thr Ala Tyr Asp Glu Ser Thr Asp Glu Asn Val
        1505                1510                1515

Met Leu Leu Thr Ser Asp Ala Pro Glu Tyr Lys Pro Trp Ala Leu
        1520                1525                1530

Val Ile Gln Asp Ser Asn Gly Glu Asn Lys Ile Lys Met Leu Ser
        1535                1540                1545

Gly Gly Ser Pro Lys Lys Lys Arg Lys Val
        1550                1555

<210> SEQ ID NO 49
<211> LENGTH: 1558
<212> TYPE: PRT
<213> ORGANISM: Artificial Sequence
<220> FEATURE:
<223> OTHER INFORMATION: Synthetic

<400> SEQUENCE: 49

Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
```

```
                50                  55                  60
Asn Gln Ala Lys Asn Leu Leu Cys Gly Phe Tyr Gly Arg His Ala Glu
 65                  70                  75                  80
Leu Arg Phe Leu Asp Leu Val Pro Ser Leu Gln Leu Asp Pro Ala Gln
                     85                  90                  95
Ile Tyr Arg Val Thr Trp Phe Ile Ser Trp Ser Pro Cys Phe Ser Ala
                100                 105                 110
Gly Cys Ala Gly Glu Val Arg Ala Phe Leu Gln Glu Asn Thr His Val
                115                 120                 125
Arg Leu Arg Ile Phe Ala Ala Arg Ile Phe Asp Tyr Asp Tyr Leu Tyr
                130                 135                 140
Lys Glu Ala Leu Gln Met Leu Arg Asp Ala Gly Ala Gln Val Ser Ile
145                 150                 155                 160
Met Thr Tyr Asp Glu Phe Lys His Cys Trp Asp Thr Phe Val Asp His
                165                 170                 175
Gln Gly Cys Pro Phe Gln Pro Trp Asp Gly Leu Asp Glu His Ser Gln
                180                 185                 190
Ala Leu Ser Gly Arg Leu Arg Ala Ile Leu Gln Asn Gln Gly Asn Ser
                195                 200                 205
Gly Ser Glu Thr Pro Gly Thr Ser Glu Ser Ala Thr Pro Glu Ser Met
210                 215                 220
Ser Lys Leu Glu Lys Phe Thr Asn Cys Tyr Ser Leu Ser Lys Thr Leu
225                 230                 235                 240
Arg Phe Lys Ala Ile Pro Val Gly Lys Thr Gln Glu Asn Ile Asp Asn
                245                 250                 255
Lys Arg Leu Leu Val Glu Asp Glu Lys Arg Ala Glu Asp Tyr Lys Gly
                260                 265                 270
Val Lys Lys Leu Leu Asp Arg Tyr Tyr Leu Ser Phe Ile Asn Asp Val
                275                 280                 285
Leu His Ser Ile Lys Leu Lys Asn Leu Asn Asn Tyr Ile Ser Leu Phe
                290                 295                 300
Arg Lys Lys Thr Arg Thr Glu Lys Glu Asn Lys Glu Leu Glu Asn Leu
305                 310                 315                 320
Glu Ile Asn Leu Arg Lys Glu Ile Ala Lys Ala Phe Lys Gly Asn Glu
                325                 330                 335
Gly Tyr Lys Ser Leu Phe Lys Lys Asp Ile Ile Glu Thr Ile Leu Pro
                340                 345                 350
Glu Phe Leu Asp Asp Lys Asp Glu Ile Ala Leu Val Asn Ser Phe Asn
                355                 360                 365
Gly Phe Thr Thr Ala Phe Thr Gly Phe Phe Asp Asn Arg Glu Asn Met
                370                 375                 380
Phe Ser Glu Glu Ala Lys Ser Thr Ser Ile Ala Phe Arg Cys Ile Asn
385                 390                 395                 400
Glu Asn Leu Thr Arg Tyr Ile Ser Asn Met Asp Ile Phe Glu Lys Val
                405                 410                 415
Asp Ala Ile Phe Asp Lys His Glu Val Gln Glu Ile Lys Glu Lys Ile
                420                 425                 430
Leu Asn Ser Asp Tyr Asp Val Glu Asp Phe Phe Glu Gly Glu Phe Phe
                435                 440                 445
Asn Phe Val Leu Thr Gln Glu Gly Ile Asp Val Tyr Asn Ala Ile Ile
                450                 455                 460
Gly Gly Phe Val Thr Glu Ser Gly Glu Lys Ile Lys Gly Leu Asn Glu
465                 470                 475                 480
```

Tyr Ile Asn Leu Tyr Asn Gln Lys Thr Lys Gln Lys Leu Pro Lys Phe
            485                 490                 495

Lys Pro Leu Tyr Lys Gln Val Leu Ser Asp Arg Glu Ser Leu Ser Phe
        500                 505                 510

Tyr Gly Glu Gly Tyr Thr Ser Asp Glu Glu Val Leu Glu Val Phe Arg
        515                 520                 525

Asn Thr Leu Asn Lys Asn Ser Glu Ile Phe Ser Ser Ile Lys Lys Leu
    530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
            580                 585                 590

His Leu Lys Lys Lys Ala Val Val Thr Glu Lys Tyr Glu Asp Asp Arg
            595                 600                 605

Arg Lys Ser Phe Lys Lys Ile Gly Ser Phe Ser Leu Glu Gln Leu Gln
        610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
            660                 665                 670

Asp Ala Val Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
            740                 745                 750

Phe Met Gly Gly Trp Asp Lys Asp Lys Glu Thr Asp Tyr Arg Ala Thr
755                 760                 765

Ile Leu Arg Tyr Gly Ser Lys Tyr Tyr Leu Ala Ile Met Asp Lys Lys
770                 775                 780

Tyr Ala Lys Cys Leu Gln Lys Ile Asp Lys Asp Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
            820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

```
Glu Glu Gln Gly Tyr Lys Val Ser Phe Ser Ala Ser Lys Lys Glu
            900                 905                 910
Val Asp Lys Leu Val Glu Glu Gly Lys Leu Tyr Met Phe Gln Ile Tyr
        915                 920                 925
Asn Lys Asp Phe Ser Asp Lys Ser His Gly Thr Pro Asn Leu His Thr
    930                 935                 940
Met Tyr Phe Lys Leu Leu Phe Asp Glu Asn Asn His Gly Gln Ile Arg
945                 950                 955                 960
Leu Ser Gly Gly Ala Glu Leu Phe Met Arg Arg Ala Ser Leu Lys Lys
                965                 970                 975
Glu Glu Leu Val Val His Pro Ala Asn Ser Pro Ile Ala Asn Lys Asn
            980                 985                 990
Pro Asp Asn Pro Lys Lys Thr Thr Thr Leu Ser Tyr Asp Val Tyr Lys
        995                 1000                1005
Asp Lys Arg Phe Ser Glu Asp Gln Tyr Glu Leu His Ile Pro Ile
    1010                1015                1020
Ala Ile Asn Lys Cys Pro Lys Asn Ile Phe Lys Ile Asn Thr Glu
    1025                1030                1035
Val Arg Val Leu Leu Lys His Asp Asp Asn Pro Tyr Val Ile Gly
    1040                1045                1050
Ile Ala Arg Gly Glu Arg Asn Leu Leu Tyr Ile Val Val Val Asp
    1055                1060                1065
Gly Lys Gly Asn Ile Val Glu Gln Tyr Ser Leu Asn Glu Ile Ile
    1070                1075                1080
Asn Asn Phe Asn Gly Ile Arg Ile Lys Thr Asp Tyr His Ser Leu
    1085                1090                1095
Leu Asp Lys Lys Glu Lys Glu Arg Phe Glu Ala Arg Gln Asn Trp
    1100                1105                1110
Thr Ser Ile Glu Asn Ile Lys Glu Leu Lys Ala Gly Tyr Ile Ser
    1115                1120                1125
Gln Val Val His Lys Ile Cys Glu Leu Val Glu Lys Tyr Asp Ala
    1130                1135                1140
Val Ile Ala Leu Ala Asp Leu Asn Ser Gly Phe Lys Asn Ser Arg
    1145                1150                1155
Val Lys Val Glu Lys Gln Val Tyr Gln Lys Phe Glu Lys Met Leu
    1160                1165                1170
Ile Asp Lys Leu Asn Tyr Met Val Asp Lys Lys Ser Asn Pro Cys
    1175                1180                1185
Ala Thr Gly Gly Ala Leu Lys Gly Tyr Gln Ile Thr Asn Lys Phe
    1190                1195                1200
Glu Ser Phe Lys Ser Met Ser Thr Gln Asn Gly Phe Ile Phe Tyr
    1205                1210                1215
Ile Pro Ala Trp Leu Thr Ser Lys Ile Asp Pro Ser Thr Gly Phe
    1220                1225                1230
Val Asn Leu Leu Lys Thr Lys Tyr Thr Ser Ile Ala Asp Ser Lys
    1235                1240                1245
Lys Phe Ile Ser Ser Phe Asp Arg Ile Met Tyr Val Pro Glu Glu
    1250                1255                1260
Asp Leu Phe Glu Phe Ala Leu Asp Tyr Lys Asn Phe Ser Arg Thr
    1265                1270                1275
Asp Ala Asp Tyr Ile Lys Lys Trp Lys Leu Tyr Ser Tyr Gly Asn
    1280                1285                1290
Arg Ile Arg Ile Phe Arg Asn Pro Lys Lys Asn Asn Val Phe Asp
```

Trp Glu Glu Val Cys Leu Thr Ser Ala Tyr Lys Glu Leu Phe Asn
   1310                1315                1320

Lys Tyr Gly Ile Asn Tyr Gln Gln Gly Asp Ile Arg Ala Leu Leu
   1325                1330                1335

Cys Glu Gln Ser Asp Lys Ala Phe Tyr Ser Ser Phe Met Ala Leu
   1340                1345                1350

Met Ser Leu Met Leu Gln Met Arg Asn Ser Ile Thr Gly Arg Thr
   1355                1360                1365

Asp Val Ala Phe Leu Ile Ser Pro Val Lys Asn Ser Asp Gly Ile
   1370                1375                1380

Phe Tyr Asp Ser Arg Asn Tyr Glu Ala Gln Glu Asn Ala Ile Leu
   1385                1390                1395

Pro Lys Asn Ala Asp Ala Asn Gly Ala Tyr Asn Ile Ala Arg Lys
   1400                1405                1410

Val Leu Trp Ala Ile Gly Gln Phe Lys Lys Ala Glu Asp Glu Lys
   1415                1420                1425

Leu Asp Lys Val Lys Ile Ala Ile Ser Asn Lys Glu Trp Leu Glu
   1430                1435                1440

Tyr Ala Gln Thr Ser Val Lys His Gly Ser Pro Lys Lys Lys Arg
   1445                1450                1455

Lys Val Ser Gly Gly Ser Thr Asn Leu Ser Asp Ile Ile Glu Lys
   1460                1465                1470

Glu Thr Gly Lys Gln Leu Val Ile Gln Glu Ser Ile Leu Met Leu
   1475                1480                1485

Pro Glu Glu Val Glu Glu Val Ile Gly Asn Lys Pro Glu Ser Asp
   1490                1495                1500

Ile Leu Val His Thr Ala Tyr Asp Glu Ser Thr Asp Glu Asn Val
   1505                1510                1515

Met Leu Leu Thr Ser Asp Ala Pro Glu Tyr Lys Pro Trp Ala Leu
   1520                1525                1530

Val Ile Gln Asp Ser Asn Gly Glu Asn Lys Ile Lys Met Leu Ser
   1535                1540                1545

Gly Gly Ser Pro Lys Lys Lys Arg Lys Val
   1550                1555

<210> SEQ ID NO 50
<211> LENGTH: 1558
<212> TYPE: PRT
<213> ORGANISM: Artificial Sequence
<220> FEATURE:
<223> OTHER INFORMATION: Synthetic

<400> SEQUENCE: 50

Met Pro Lys Lys Lys Arg Lys Val Met Glu Ala Ser Pro Ala Ser Gly
1               5                   10                  15

Pro Arg His Leu Met Asp Pro His Ile Phe Thr Ser Asn Phe Asn Asn
                20                  25                  30

Gly Ile Gly Arg His Lys Thr Tyr Leu Cys Tyr Glu Val Glu Arg Leu
            35                  40                  45

Asp Asn Gly Thr Ser Val Lys Met Asp Gln His Arg Gly Phe Leu His
        50                  55                  60

Asn Gln Ala Lys Asn Leu Leu Cys Gly Phe Tyr Gly Arg His Ala Glu
65                  70                  75                  80

Leu Arg Phe Leu Asp Leu Val Pro Ser Leu Gln Leu Asp Pro Ala Gln

```
            85                  90                  95
Ile Tyr Arg Val Thr Trp Phe Ile Ser Trp Ser Pro Cys Phe Ser Ala
            100                 105                 110

Gly Cys Ala Gly Glu Val Arg Ala Phe Leu Gln Glu Asn Thr His Val
            115                 120                 125

Arg Leu Arg Ile Phe Ala Ala Arg Ile Tyr Asp Asp Tyr Leu Tyr
    130                 135                 140

Lys Glu Ala Leu Gln Met Leu Arg Asp Ala Gly Ala Gln Val Ser Ile
145                 150                 155                 160

Met Thr Tyr Asp Glu Phe Lys His Cys Trp Asp Thr Phe Val Asp His
                165                 170                 175

Gln Gly Cys Pro Phe Gln Pro Trp Asp Gly Leu Asp Glu His Ser Gln
            180                 185                 190

Ala Leu Ser Gly Arg Leu Arg Ala Ile Leu Gln Asn Gln Gly Asn Ser
            195                 200                 205

Gly Ser Glu Thr Pro Gly Thr Ser Glu Ser Ala Thr Pro Glu Ser Met
    210                 215                 220

Ser Lys Leu Glu Lys Phe Thr Asn Cys Tyr Ser Leu Ser Lys Thr Leu
225                 230                 235                 240

Arg Phe Lys Ala Ile Pro Val Gly Lys Thr Gln Glu Asn Ile Asp Asn
                245                 250                 255

Lys Arg Leu Leu Val Glu Asp Glu Lys Arg Ala Glu Asp Tyr Lys Gly
            260                 265                 270

Val Lys Lys Leu Leu Asp Arg Tyr Tyr Leu Ser Phe Ile Asn Asp Val
    275                 280                 285

Leu His Ser Ile Lys Leu Lys Asn Leu Asn Asn Tyr Ile Ser Leu Phe
290                 295                 300

Arg Lys Lys Thr Arg Thr Glu Lys Glu Asn Lys Glu Leu Glu Asn Leu
305                 310                 315                 320

Glu Ile Asn Leu Arg Lys Glu Ile Ala Lys Ala Phe Lys Gly Asn Glu
                325                 330                 335

Gly Tyr Lys Ser Leu Phe Lys Lys Asp Ile Ile Glu Thr Ile Leu Pro
            340                 345                 350

Glu Phe Leu Asp Asp Lys Asp Glu Ile Ala Leu Val Asn Ser Phe Asn
    355                 360                 365

Gly Phe Thr Thr Ala Phe Thr Gly Phe Phe Asp Asn Arg Glu Asn Met
    370                 375                 380

Phe Ser Glu Glu Ala Lys Ser Thr Ser Ile Ala Phe Arg Cys Ile Asn
385                 390                 395                 400

Glu Asn Leu Thr Arg Tyr Ile Ser Asn Met Asp Ile Phe Glu Lys Val
                405                 410                 415

Asp Ala Ile Phe Asp Lys His Glu Val Gln Glu Ile Lys Glu Lys Ile
            420                 425                 430

Leu Asn Ser Asp Tyr Asp Val Glu Asp Phe Phe Glu Gly Glu Phe Phe
    435                 440                 445

Asn Phe Val Leu Thr Gln Glu Gly Ile Asp Val Tyr Asn Ala Ile Ile
    450                 455                 460

Gly Gly Phe Val Thr Glu Ser Gly Glu Lys Ile Lys Gly Leu Asn Glu
465                 470                 475                 480

Tyr Ile Asn Leu Tyr Asn Gln Lys Thr Lys Gln Lys Leu Pro Lys Phe
                485                 490                 495

Lys Pro Leu Tyr Lys Gln Val Leu Ser Asp Arg Glu Ser Leu Ser Phe
            500                 505                 510
```

```
Tyr Gly Glu Gly Tyr Thr Ser Asp Glu Glu Val Leu Glu Val Phe Arg
            515                 520                 525

Asn Thr Leu Asn Lys Asn Ser Glu Ile Phe Ser Ser Ile Lys Lys Leu
        530                 535                 540

Glu Lys Leu Phe Lys Asn Phe Asp Glu Tyr Ser Ser Ala Gly Ile Phe
545                 550                 555                 560

Val Lys Asn Gly Pro Ala Ile Ser Thr Ile Ser Lys Asp Ile Phe Gly
                565                 570                 575

Glu Trp Asn Val Ile Arg Asp Lys Trp Asn Ala Glu Tyr Asp Asp Ile
                580                 585                 590

His Leu Lys Lys Lys Ala Val Val Thr Glu Lys Tyr Glu Asp Asp Arg
            595                 600                 605

Arg Lys Ser Phe Lys Lys Ile Gly Ser Phe Ser Leu Glu Gln Leu Gln
        610                 615                 620

Glu Tyr Ala Asp Ala Asp Leu Ser Val Val Glu Lys Leu Lys Glu Ile
625                 630                 635                 640

Ile Ile Gln Lys Val Asp Glu Ile Tyr Lys Val Tyr Gly Ser Ser Glu
                645                 650                 655

Lys Leu Phe Asp Ala Asp Phe Val Leu Glu Lys Ser Leu Lys Lys Asn
                660                 665                 670

Asp Ala Val Val Ala Ile Met Lys Asp Leu Leu Asp Ser Val Lys Ser
            675                 680                 685

Phe Glu Asn Tyr Ile Lys Ala Phe Phe Gly Glu Gly Lys Glu Thr Asn
        690                 695                 700

Arg Asp Glu Ser Phe Tyr Gly Asp Phe Val Leu Ala Tyr Asp Ile Leu
705                 710                 715                 720

Leu Lys Val Asp His Ile Tyr Asp Ala Ile Arg Asn Tyr Val Thr Gln
                725                 730                 735

Lys Pro Tyr Ser Lys Asp Lys Phe Lys Leu Tyr Phe Gln Asn Pro Gln
                740                 745                 750

Phe Met Gly Gly Trp Asp Lys Asp Lys Glu Thr Asp Tyr Arg Ala Thr
            755                 760                 765

Ile Leu Arg Tyr Gly Ser Lys Tyr Tyr Leu Ala Ile Met Asp Lys Lys
        770                 775                 780

Tyr Ala Lys Cys Leu Gln Lys Ile Asp Lys Asp Asp Val Asn Gly Asn
785                 790                 795                 800

Tyr Glu Lys Ile Asn Tyr Lys Leu Leu Pro Gly Pro Asn Lys Met Leu
                805                 810                 815

Pro Lys Val Phe Phe Ser Lys Lys Trp Met Ala Tyr Tyr Asn Pro Ser
                820                 825                 830

Glu Asp Ile Gln Lys Ile Tyr Lys Asn Gly Thr Phe Lys Lys Gly Asp
            835                 840                 845

Met Phe Asn Leu Asn Asp Cys His Lys Leu Ile Asp Phe Phe Lys Asp
        850                 855                 860

Ser Ile Ser Arg Tyr Pro Lys Trp Ser Asn Ala Tyr Asp Phe Asn Phe
865                 870                 875                 880

Ser Glu Thr Glu Lys Tyr Lys Asp Ile Ala Gly Phe Tyr Arg Glu Val
                885                 890                 895

Glu Glu Gln Gly Tyr Lys Val Ser Phe Glu Ser Ala Ser Lys Lys Glu
            900                 905                 910

Val Asp Lys Leu Val Glu Glu Gly Lys Leu Tyr Met Phe Gln Ile Tyr
        915                 920                 925
```

```
Asn Lys Asp Phe Ser Asp Lys Ser His Gly Thr Pro Asn Leu His Thr
    930             935             940
Met Tyr Phe Lys Leu Leu Phe Asp Glu Asn Asn His Gly Gln Ile Arg
945             950             955             960
Leu Ser Gly Gly Ala Glu Leu Phe Met Arg Arg Ala Ser Leu Lys Lys
            965             970             975
Glu Glu Leu Val Val His Pro Ala Asn Ser Pro Ile Ala Asn Lys Asn
        980             985             990
Pro Asp Asn Pro Lys Lys Thr Thr Thr Leu Ser Tyr Asp Val Tyr Lys
        995             1000            1005
Asp Lys Arg Phe Ser Glu Asp Gln Tyr Glu Leu His Ile Pro Ile
    1010            1015            1020
Ala Ile Asn Lys Cys Pro Lys Asn Ile Phe Lys Ile Asn Thr Glu
    1025            1030            1035
Val Arg Val Leu Leu Lys His Asp Asp Asn Pro Tyr Val Ile Gly
    1040            1045            1050
Ile Ala Arg Gly Glu Arg Asn Leu Leu Tyr Ile Val Val Asp
    1055            1060            1065
Gly Lys Gly Asn Ile Val Glu Gln Tyr Ser Leu Asn Glu Ile Ile
    1070            1075            1080
Asn Asn Phe Asn Gly Ile Arg Ile Lys Thr Asp Tyr His Ser Leu
    1085            1090            1095
Leu Asp Lys Lys Glu Lys Glu Arg Phe Glu Ala Arg Gln Asn Trp
    1100            1105            1110
Thr Ser Ile Glu Asn Ile Lys Glu Leu Lys Ala Gly Tyr Ile Ser
    1115            1120            1125
Gln Val Val His Lys Ile Cys Glu Leu Val Glu Lys Tyr Asp Ala
    1130            1135            1140
Val Ile Ala Leu Ala Asp Leu Asn Ser Gly Phe Lys Asn Ser Arg
    1145            1150            1155
Val Lys Val Glu Lys Gln Val Tyr Gln Lys Phe Glu Lys Met Leu
    1160            1165            1170
Ile Asp Lys Leu Asn Tyr Met Val Asp Lys Lys Ser Asn Pro Cys
    1175            1180            1185
Ala Thr Gly Gly Ala Leu Lys Gly Tyr Gln Ile Thr Asn Lys Phe
    1190            1195            1200
Glu Ser Phe Lys Ser Met Ser Thr Gln Asn Gly Phe Ile Phe Tyr
    1205            1210            1215
Ile Pro Ala Trp Leu Thr Ser Lys Ile Asp Pro Ser Thr Gly Phe
    1220            1225            1230
Val Asn Leu Leu Lys Thr Lys Tyr Thr Ser Ile Ala Asp Ser Lys
    1235            1240            1245
Lys Phe Ile Ser Ser Phe Asp Arg Ile Met Tyr Val Pro Glu Glu
    1250            1255            1260
Asp Leu Phe Glu Phe Ala Leu Asp Tyr Lys Asn Phe Ser Arg Thr
    1265            1270            1275
Asp Ala Asp Tyr Ile Lys Lys Trp Lys Leu Tyr Ser Tyr Gly Asn
    1280            1285            1290
Arg Ile Arg Ile Phe Arg Asn Pro Lys Lys Asn Asn Val Phe Asp
    1295            1300            1305
Trp Glu Glu Val Cys Leu Thr Ser Ala Tyr Lys Glu Leu Phe Asn
    1310            1315            1320
Lys Tyr Gly Ile Asn Tyr Gln Gln Gly Asp Ile Arg Ala Leu Leu
```

-continued

```
            1325                1330                1335

Cys Glu Gln Ser Asp Lys Ala Phe Tyr Ser Ser Phe Met Ala Leu
        1340                1345                1350

Met Ser Leu Met Leu Gln Met Arg Asn Ser Ile Thr Gly Arg Thr
        1355                1360                1365

Asp Val Ala Phe Leu Ile Ser Pro Val Lys Asn Ser Asp Gly Ile
        1370                1375                1380

Phe Tyr Asp Ser Arg Asn Tyr Glu Ala Gln Glu Asn Ala Ile Leu
        1385                1390                1395

Pro Lys Asn Ala Asp Ala Asn Gly Ala Tyr Asn Ile Ala Arg Lys
        1400                1405                1410

Val Leu Trp Ala Ile Gly Gln Phe Lys Lys Ala Glu Asp Glu Lys
        1415                1420                1425

Leu Asp Lys Val Lys Ile Ala Ile Ser Asn Lys Glu Trp Leu Glu
        1430                1435                1440

Tyr Ala Gln Thr Ser Val Lys His Gly Ser Pro Lys Lys Lys Arg
        1445                1450                1455

Lys Val Ser Gly Gly Ser Thr Asn Leu Ser Asp Ile Ile Glu Lys
        1460                1465                1470

Glu Thr Gly Lys Gln Leu Val Ile Gln Glu Ser Ile Leu Met Leu
        1475                1480                1485

Pro Glu Glu Val Glu Glu Val Ile Gly Asn Lys Pro Glu Ser Asp
        1490                1495                1500

Ile Leu Val His Thr Ala Tyr Asp Glu Ser Thr Asp Glu Asn Val
        1505                1510                1515

Met Leu Leu Thr Ser Asp Ala Pro Glu Tyr Lys Pro Trp Ala Leu
        1520                1525                1530

Val Ile Gln Asp Ser Asn Gly Glu Asn Lys Ile Lys Met Leu Ser
        1535                1540                1545

Gly Gly Ser Pro Lys Lys Lys Arg Lys Val
        1550                1555
```

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51
cgagggcccg gttctccagc agg         23

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
cgagggcccg gttctccagc agg         23

<210> SEQ ID NO 53
<211> LENGTH: 23
<212> TYPE: DNA
<213> ORGANISM: Artificial Sequence
<220> FEATURE:
<223> OTHER INFORMATION: Synthetic

<400> SEQUENCE: 53
cgagggtttg gttctccagc agg    23

<210> SEQ ID NO 54
<211> LENGTH: 23
<212> TYPE: DNA
<213> ORGANISM: Artificial Sequence
<220> FEATURE:
<223> OTHER INFORMATION: Synthetic

<400> SEQUENCE: 54
ggcactgcgg ctggaggtgg ggg    23

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
ggcattgcgg ctggaggtgg ggg    23

<210> SEQ ID NO 56
<211> LENGTH: 23
<212> TYPE: DNA
<213> ORGANISM: Artificial Sequence
<220> FEATURE:
<223> OTHER INFORMATION: Synthetic

<400> SEQUENCE: 56
ggcactgcgg ctggaggtgg ggg    23

<210> SEQ ID NO 57
<211> LENGTH: 23
<212> TYPE: DNA
<213> ORGANISM: Artificial Sequence
<220> FEATURE:
<223> OTHER INFORMATION: Synthetic

<400> SEQUENCE: 57
ggcccagact gagcacgtga tgg    23

<210> SEQ ID NO 58
<211> LENGTH: 23
<212> TYPE: DNA
<213> ORGANISM: Artificial Sequence
<220> FEATURE:
<223> OTHER INFORMATION: Synthetic

<400> SEQUENCE: 58
ggcccagact gagcacgtga tgg    23

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
ggcccagact gagcacgtga tgg    23

<210> SEQ ID NO 60
<211> LENGTH: 23

```
<212> TYPE: DNA
<213> ORGANISM: Artificial Sequence
<220> FEATURE:
<223> OTHER INFORMATION: Synthetic

<400> SEQUENCE: 60
ggctcagact gagcacgtga tgg                                            23

<210> SEQ ID NO 61
<211> LENGTH: 23
<212> TYPE: DNA
<213> ORGANISM: Artificial Sequence
<220> FEATURE:
<223> OTHER INFORMATION: Synthetic

<400> SEQUENCE: 61
gagtccgagc agaagaagaa ggg                                            23

<210> SEQ ID NO 62
<211> LENGTH: 23
<212> TYPE: DNA
<213> ORGANISM: Artificial Sequence
<220> FEATURE:
<223> OTHER INFORMATION: Synthetic

<400> SEQUENCE: 62
gagtttgagc agaagaagaa ggg                                            23

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
gagtttgagc agaagaagaa ggg                                            23

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
gagtttgagc agaagaagaa ggg                                            23

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
ggaatccctt ctgcagcacc tgg                                            23

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
``` ggaatcccctt ctgcagcacc tgg                                              23

<210> SEQ ID NO 67
<211> LENGTH: 23
<212> TYPE: DNA
<213> ORGANISM: Artificial Sequence
<220> FEATURE:
<223> OTHER INFORMATION: Synthetic

<400> SEQUENCE: 67
ggaattcctt ctgcagcacc tgg                                               23

<210> SEQ ID NO 68
<211> LENGTH: 23
<212> TYPE: DNA
<213> ORGANISM: Artificial Sequence
<220> FEATURE:
<223> OTHER INFORMATION: Synthetic

<400> SEQUENCE: 68
ggaatccctt ctgcagcacc tgg                                               23

<210> SEQ ID NO 69
<211> LENGTH: 23
<212> TYPE: DNA
<213> ORGANISM: Artificial Sequence
<220> FEATURE:
<223> OTHER INFORMATION: Synthetic

<400> SEQUENCE: 69
gaacacaaag catagactgc ggg                                               23

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
gaatataaag catagactgc ggg                                               23

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
gaatataaag catagactgc ggg                                               23

<210> SEQ ID NO 72
<211> LENGTH: 23
<212> TYPE: DNA
<213> ORGANISM: Artificial Sequence
<220> FEATURE:
<223> OTHER INFORMATION: Synthetic

<400> SEQUENCE: 72
gaatataaag catagactgc ggg                                               23

<210> SEQ ID NO 73
<211> LENGTH: 23
<212> TYPE: DNA
<213> ORGANISM: Artificial Sequence

```
<220> FEATURE:
<223> OTHER INFORMATION: Synthetic

<400> SEQUENCE: 73
ggcccagact gagcacgtga tgg                                             23

<210> SEQ ID NO 74
<211> LENGTH: 23
<212> TYPE: DNA
<213> ORGANISM: Artificial Sequence
<220> FEATURE:
<223> OTHER INFORMATION: Synthetic

<400> SEQUENCE: 74
ggcccagact gagcacgtga tgg                                             23

<210> SEQ ID NO 75
<211> LENGTH: 23
<212> TYPE: DNA
<213> ORGANISM: Artificial Sequence
<220> FEATURE:
<223> OTHER INFORMATION: Synthetic

<400> SEQUENCE: 75
ggcctagact gagcacgtga tgg                                             23

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
ggcctagact gagcacgtga tgg                                             23

<210> SEQ ID NO 77
<211> LENGTH: 23
<212> TYPE: DNA
<213> ORGANISM: Artificial Sequence
<220> FEATURE:
<223> OTHER INFORMATION: Synthetic

<400> SEQUENCE: 77
ggaatccctt ctgcagcacc tgg                                             23

<210> SEQ ID NO 78
<211> LENGTH: 23
<212> TYPE: DNA
<213> ORGANISM: Artificial Sequence
<220> FEATURE:
<223> OTHER INFORMATION: Synthetic

<400> SEQUENCE: 78 ggaattttt ctgcagcacc tgg                                              23

<210> SEQ ID NO 79
<211> LENGTH: 23
<212> TYPE: DNA
<213> ORGANISM: Artificial Sequence
<220> FEATURE:
<223> OTHER INFORMATION: Synthetic

<400> SEQUENCE: 79
ggaattcctt ctgcagcacc tgg                                             23
```

```
<210> SEQ ID NO 80
<211> LENGTH: 23
<212> TYPE: DNA
<213> ORGANISM: Artificial Sequence
<220> FEATURE:
<223> OTHER INFORMATION: Synthetic

<400> SEQUENCE: 80
ggaattcctt ctgcagcacc tgg                                              23

<210> SEQ ID NO 81
<211> LENGTH: 23
<212> TYPE: DNA
<213> ORGANISM: Artificial Sequence
<220> FEATURE:
<223> OTHER INFORMATION: Synthetic

<400> SEQUENCE: 81
gcgcacggtg gcggggtccc agg                                              23

<210> SEQ ID NO 82
<211> LENGTH: 23
<212> TYPE: DNA
<213> ORGANISM: Artificial Sequence
<220> FEATURE:
<223> OTHER INFORMATION: Synthetic

<400> SEQUENCE: 82
aagttcgcta atcccggaac tgg                                              23

<210> SEQ ID NO 83
<211> LENGTH: 23
<212> TYPE: DNA
<213> ORGANISM: Artificial Sequence
<220> FEATURE:
<223> OTHER INFORMATION: Synthetic

<400> SEQUENCE: 83
gtaacgagct gcatccccga ggg                                              23

<210> SEQ ID NO 84
<211> LENGTH: 23
<212> TYPE: DNA
<213> ORGANISM: Artificial Sequence
<220> FEATURE:
<223> OTHER INFORMATION: Synthetic

<400> SEQUENCE: 84
cgagggcccg gttctccagc agg                                              23

<210> SEQ ID NO 85
<211> LENGTH: 23
<212> TYPE: DNA
<213> ORGANISM: Artificial Sequence
<220> FEATURE:
<223> OTHER INFORMATION: Synthetic

<400> SEQUENCE: 85
tcccgcgggt gggccagggc tgg                                              23

<210> SEQ ID NO 86
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 86
gctggcagca agggcggcgc tgg                                              23

<210> SEQ ID NO 87
<211> LENGTH: 23
<212> TYPE: DNA
<213> ORGANISM: Artificial Sequence
<220> FEATURE:
<223> OTHER INFORMATION: Synthetic

<400> SEQUENCE: 87
acccacggcg gggatcaggg tgg                                              23

<210> SEQ ID NO 88
<211> LENGTH: 23
<212> TYPE: DNA
<213> ORGANISM: Artificial Sequence
<220> FEATURE:
<223> OTHER INFORMATION: Synthetic

<400> SEQUENCE: 88
aatgcgggtg caaggcctgc cgg                                              23

<210> SEQ ID NO 89
<211> LENGTH: 23
<212> TYPE: DNA
<213> ORGANISM: Artificial Sequence
<220> FEATURE:
<223> OTHER INFORMATION: Synthetic

<400> SEQUENCE: 89
cgtcgccgat cttcacaggg tgg                                              23

<210> SEQ ID NO 90
<211> LENGTH: 23
<212> TYPE: DNA
<213> ORGANISM: Artificial Sequence
<220> FEATURE:
<223> OTHER INFORMATION: Synthetic

<400> SEQUENCE: 90
ctggcgcaac gctgagcagc tgg                                              23

<210> SEQ ID NO 91
<211> LENGTH: 23
<212> TYPE: DNA
<213> ORGANISM: Artificial Sequence
<220> FEATURE:
<223> OTHER INFORMATION: Synthetic

<400> SEQUENCE: 91
caggcggaca gaagcgcggc tgg                                              23

<210> SEQ ID NO 92
<211> LENGTH: 23
<212> TYPE: DNA
<213> ORGANISM: Artificial Sequence
<220> FEATURE:
<223> OTHER INFORMATION: Synthetic

<400> SEQUENCE: 92
aggcagcaaa tccagtttgc cgg                                              23

<210> SEQ ID NO 93
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 93
ggtcagcgga ctcaccggcc agg                                          23

<210> SEQ ID NO 94
<211> LENGTH: 23
<212> TYPE: DNA
<213> ORGANISM: Artificial Sequence
<220> FEATURE:
<223> OTHER INFORMATION: Synthetic

<400> SEQUENCE: 94
tagctcggag gtcgtggcgc tgg                                          23

<210> SEQ ID NO 95
<211> LENGTH: 23
<212> TYPE: DNA
<213> ORGANISM: Artificial Sequence
<220> FEATURE:
<223> OTHER INFORMATION: Synthetic

<400> SEQUENCE: 95
ggctagcacc agcgctctgt cgg                                          23

<210> SEQ ID NO 96
<211> LENGTH: 23
<212> TYPE: DNA
<213> ORGANISM: Artificial Sequence
<220> FEATURE:
<223> OTHER INFORMATION: Synthetic

<400> SEQUENCE: 96
gcgcacggtg gcggggtccc agg                                          23

<210> SEQ ID NO 97
<211> LENGTH: 23
<212> TYPE: DNA
<213> ORGANISM: Artificial Sequence
<220> FEATURE:
<223> OTHER INFORMATION: Synthetic

<400> SEQUENCE: 97
aagttcgcta atcccggaac tgg                                          23

<210> SEQ ID NO 98
<211> LENGTH: 23
<212> TYPE: DNA
<213> ORGANISM: Artificial Sequence
<220> FEATURE:
<223> OTHER INFORMATION: Synthetic

<400> SEQUENCE: 98
gctggcagca agggcggcgc tgg                                          23

<210> SEQ ID NO 99
<211> LENGTH: 27
<212> TYPE: DNA
<213> ORGANISM: Artificial Sequence
<220> FEATURE:
<223> OTHER INFORMATION: Synthetic

<400> SEQUENCE: 99
```
tttagaagca catcaaggac attctaa                                    27

<210> SEQ ID NO 100
<211> LENGTH: 27
<212> TYPE: DNA
<213> ORGANISM: Artificial Sequence
<220> FEATURE:
<223> OTHER INFORMATION: Synthetic

<400> SEQUENCE: 100
tttagaagca tattaaggac attctaa                                    27

<210> SEQ ID NO 101
<211> LENGTH: 27
<212> TYPE: DNA
<213> ORGANISM: Artificial Sequence
<220> FEATURE:
<223> OTHER INFORMATION: Synthetic

<400> SEQUENCE: 101
tttagaagca tattaaggac attctaa                                    27

<210> SEQ ID NO 102
<211> LENGTH: 27
<212> TYPE: DNA
<213> ORGANISM: Artificial Sequence
<220> FEATURE:
<223> OTHER INFORMATION: Synthetic

<400> SEQUENCE: 102
tttagaagca tattaaggac attctaa                                    27

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
tttagaagca catcaaggac attctaa                                    27

<210> SEQ ID NO 104
<211> LENGTH: 27
<212> TYPE: DNA
<213> ORGANISM: Artificial Sequence
<220> FEATURE:
<223> OTHER INFORMATION: Synthetic

<400> SEQUENCE: 104
tttagaagca tattaaggac attctaa                                    27

<210> SEQ ID NO 105
<211> LENGTH: 27
<212> TYPE: DNA
<213> ORGANISM: Artificial Sequence
<220> FEATURE:
<223> OTHER INFORMATION: Synthetic

<400> SEQUENCE: 105
tttagaagca tattaaggac attctaa                                    27

<210> SEQ ID NO 106
<211> LENGTH: 27
<212> TYPE: DNA

```
<213> ORGANISM: Artificial Sequence
<220> FEATURE:
<223> OTHER INFORMATION: Synthetic

<400> SEQUENCE: 106
tttagaagca cattaaggac attttaa                                        27

<210> SEQ ID NO 107
<211> LENGTH: 27
<212> TYPE: DNA
<213> ORGANISM: Artificial Sequence
<220> FEATURE:
<223> OTHER INFORMATION: Synthetic

<400> SEQUENCE: 107
tttagaagca catcaaggac attctaa                                        27

<210> SEQ ID NO 108
<211> LENGTH: 27
<212> TYPE: DNA
<213> ORGANISM: Artificial Sequence
<220> FEATURE:
<223> OTHER INFORMATION: Synthetic

<400> SEQUENCE: 108
tttagaagca tattaaggac attctaa                                        27

<210> SEQ ID NO 109
<211> LENGTH: 27
<212> TYPE: DNA
<213> ORGANISM: Artificial Sequence
<220> FEATURE:
<223> OTHER INFORMATION: Synthetic

<400> SEQUENCE: 109
tttagaagca tattaaggac attctaa                                        27

<210> SEQ ID NO 110
<211> LENGTH: 27
<212> TYPE: DNA
<213> ORGANISM: Artificial Sequence
<220> FEATURE:
<223> OTHER INFORMATION: Synthetic

<400> SEQUENCE: 110
tttagaagca tattaaggac attctaa                                        27

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
tttagaagca tattaaggac attctaa                                        27

<210> SEQ ID NO 112
<211> LENGTH: 27
<212> TYPE: DNA
<213> ORGANISM: Artificial Sequence
<220> FEATURE:
<223> OTHER INFORMATION: Synthetic

<400> SEQUENCE: 112
tttagaagca cattaaggac attctaa                                        27
```

```
<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
tttagaagca tattaaggac attctaa                                            27

<210> SEQ ID NO 114
<211> LENGTH: 27
<212> TYPE: DNA
<213> ORGANISM: Artificial Sequence
<220> FEATURE:
<223> OTHER INFORMATION: Synthetic

<400> SEQUENCE: 114
tttagaagca tattaaggac attctaa                                            27

<210> SEQ ID NO 115
<211> LENGTH: 27
<212> TYPE: DNA
<213> ORGANISM: Artificial Sequence
<220> FEATURE:
<223> OTHER INFORMATION: Synthetic

<400> SEQUENCE: 115
tttagaagca tattaaggac attctaa                                            27

<210> SEQ ID NO 116
<211> LENGTH: 27
<212> TYPE: DNA
<213> ORGANISM: Artificial Sequence
<220> FEATURE:
<223> OTHER INFORMATION: Synthetic

<400> SEQUENCE: 116
tttagaagca cattaaggac attctaa                                            27

<210> SEQ ID NO 117
<211> LENGTH: 27
<212> TYPE: DNA
<213> ORGANISM: Artificial Sequence
<220> FEATURE:
<223> OTHER INFORMATION: Synthetic

<400> SEQUENCE: 117
tttagaagca cattaaggac attctaa                                            27

<210> SEQ ID NO 118
<211> LENGTH: 27
<212> TYPE: DNA
<213> ORGANISM: Artificial Sequence
<220> FEATURE:
<223> OTHER INFORMATION: Synthetic

<400> SEQUENCE: 118
tttagaagca tataaggac attctaa                                             27

<210> SEQ ID NO 119
<211> LENGTH: 27
<212> TYPE: DNA
<213> ORGANISM: Artificial Sequence
<220> FEATURE:
```

<223> OTHER INFORMATION: Synthetic

<400> SEQUENCE: 119
tttagaagca cattaaggac attctaa                                              27

<210> SEQ ID NO 120
<211> LENGTH: 27
<212> TYPE: DNA
<213> ORGANISM: Artificial Sequence
<220> FEATURE:
<223> OTHER INFORMATION: Synthetic

<400> SEQUENCE: 120
tttagaagca cattaaggac attctaa                                              27

<210> SEQ ID NO 121
<211> LENGTH: 27
<212> TYPE: DNA
<213> ORGANISM: Artificial Sequence
<220> FEATURE:
<223> OTHER INFORMATION: Synthetic

<400> SEQUENCE: 121
tttagaagca tattaaggac attctaa                                              27

<210> SEQ ID NO 122
<211> LENGTH: 27
<212> TYPE: DNA
<213> ORGANISM: Artificial Sequence
<220> FEATURE:
<223> OTHER INFORMATION: Synthetic

<400> SEQUENCE: 122
tttagaagca cattaaggac attctaa                                              27

<210> SEQ ID NO 123
<211> LENGTH: 27
<212> TYPE: DNA
<213> ORGANISM: Artificial Sequence
<220> FEATURE:
<223> OTHER INFORMATION: Synthetic

<400> SEQUENCE: 123
tttagaagca cattaaggac attctaa                                              27

<210> SEQ ID NO 124
<211> LENGTH: 27
<212> TYPE: DNA
<213> ORGANISM: Artificial Sequence
<220> FEATURE:
<223> OTHER INFORMATION: Synthetic

<400> SEQUENCE: 124
tttagaagca tattaaggac attctaa                                              27

<210> SEQ ID NO 125
<211> LENGTH: 27
<212> TYPE: DNA
<213> ORGANISM: Artificial Sequence
<220> FEATURE:
<223> OTHER INFORMATION: Synthetic

<400> SEQUENCE: 125
tttagaagca cattaaggac attctaa                                              27

```
<210> SEQ ID NO 126
<211> LENGTH: 27
<212> TYPE: DNA
<213> ORGANISM: Artificial Sequence
<220> FEATURE:
<223> OTHER INFORMATION: Synthetic

<400> SEQUENCE: 126
tttagaagca cattaaggac attctaa                                          27

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
tttcccctcg tccccttgt gagtacc                                           27

<210> SEQ ID NO 128
<211> LENGTH: 27
<212> TYPE: DNA
<213> ORGANISM: Artificial Sequence
<220> FEATURE:
<223> OTHER INFORMATION: Synthetic

<400> SEQUENCE: 128
tttcccctcg tcccccctgt gagtacc                                          27

<210> SEQ ID NO 129
<211> LENGTH: 27
<212> TYPE: DNA
<213> ORGANISM: Artificial Sequence
<220> FEATURE:
<223> OTHER INFORMATION: Synthetic

<400> SEQUENCE: 129
tttcccctcg tcccccctgt gagtacc                                          27

<210> SEQ ID NO 130
<211> LENGTH: 27
<212> TYPE: DNA
<213> ORGANISM: Artificial Sequence
<220> FEATURE:
<223> OTHER INFORMATION: Synthetic

<400> SEQUENCE: 130
tttcccctcg tcccccctgt gagtacc                                          27

<210> SEQ ID NO 131
<211> LENGTH: 27
<212> TYPE: DNA
<213> ORGANISM: Artificial Sequence
<220> FEATURE:
<223> OTHER INFORMATION: Synthetic

<400> SEQUENCE: 131
tttcccctcg tcccccctgt gagtacc                                          27

<210> SEQ ID NO 132
<211> LENGTH: 27
<212> TYPE: DNA
<213> ORGANISM: Artificial Sequence
<220> FEATURE:
<223> OTHER INFORMATION: Synthetic
```

<400> SEQUENCE: 132
tttcccctcg tccttttgt gagtacc			27

<210> SEQ ID NO 133
<211> LENGTH: 27
<212> TYPE: DNA
<213> ORGANISM: Artificial Sequence
<220> FEATURE:
<223> OTHER INFORMATION: Synthetic

<400> SEQUENCE: 133
tttcccctcg tcccccttgt gagtacc			27

<210> SEQ ID NO 134
<211> LENGTH: 27
<212> TYPE: DNA
<213> ORGANISM: Artificial Sequence
<220> FEATURE:
<223> OTHER INFORMATION: Synthetic

<400> SEQUENCE: 134
tttcccctcg ttttttttgt gagtacc			27

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
tttcccctcg tcccccctgt gagtacc			27

<210> SEQ ID NO 136
<211> LENGTH: 27
<212> TYPE: DNA
<213> ORGANISM: Artificial Sequence
<220> FEATURE:
<223> OTHER INFORMATION: Synthetic

<400> SEQUENCE: 136
tttcccctcg tcccccctgt gagtacc			27

<210> SEQ ID NO 137
<211> LENGTH: 27
<212> TYPE: DNA
<213> ORGANISM: Artificial Sequence
<220> FEATURE:
<223> OTHER INFORMATION: Synthetic

<400> SEQUENCE: 137
tttcccctcg ttttttttgt gagtacc			27

<210> SEQ ID NO 138
<211> LENGTH: 27
<212> TYPE: DNA
<213> ORGANISM: Artificial Sequence
<220> FEATURE:
<223> OTHER INFORMATION: Synthetic

<400> SEQUENCE: 138
tttcccctcg tccttttgt gagtacc			27

<210> SEQ ID NO 139
<211> LENGTH: 27

-continued

<210> SEQ ID NO 140
<211> LENGTH: 27
<212> TYPE: DNA
<213> ORGANISM: Artificial Sequence
<220> FEATURE:
<223> OTHER INFORMATION: Synthetic

<400> SEQUENCE: 139
tttcccctcg tccccctgt gagtacc                                              27

<210> SEQ ID NO 140
<211> LENGTH: 27
<212> TYPE: DNA
<213> ORGANISM: Artificial Sequence
<220> FEATURE:
<223> OTHER INFORMATION: Synthetic

<400> SEQUENCE: 140
tttcccctcg tccccctgt gagtacc                                              27

<210> SEQ ID NO 141
<211> LENGTH: 27
<212> TYPE: DNA
<213> ORGANISM: Artificial Sequence
<220> FEATURE:
<223> OTHER INFORMATION: Synthetic

<400> SEQUENCE: 141
tttcccctcg tccccctgt gagtacc                                              27

<210> SEQ ID NO 142
<211> LENGTH: 27
<212> TYPE: DNA
<213> ORGANISM: Artificial Sequence
<220> FEATURE:
<223> OTHER INFORMATION: Synthetic

<400> SEQUENCE: 142
tttcccctcg tccccctgt gagtacc                                              27

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
tttcccctcg tccccctgt gagtacc                                              27

<210> SEQ ID NO 144
<211> LENGTH: 27
<212> TYPE: DNA
<213> ORGANISM: Artificial Sequence
<220> FEATURE:
<223> OTHER INFORMATION: Synthetic

<400> SEQUENCE: 144
tttcccctcg tttttctgt gagtacc                                              27

<210> SEQ ID NO 145
<211> LENGTH: 27
<212> TYPE: DNA
<213> ORGANISM: Artificial Sequence
<220> FEATURE:
<223> OTHER INFORMATION: Synthetic

<400> SEQUENCE: 145

```
tttcccctcg ttccccctgt gagtacc                                              27

<210> SEQ ID NO 146
<211> LENGTH: 27
<212> TYPE: DNA
<213> ORGANISM: Artificial Sequence
<220> FEATURE:
<223> OTHER INFORMATION: Synthetic

<400> SEQUENCE: 146
tttcccctcg tttttttgt gagtacc                                               27

<210> SEQ ID NO 147
<211> LENGTH: 27
<212> TYPE: DNA
<213> ORGANISM: Artificial Sequence
<220> FEATURE:
<223> OTHER INFORMATION: Synthetic

<400> SEQUENCE: 147
tttcccctcg tccccttgt gagtacc                                               27

<210> SEQ ID NO 148
<211> LENGTH: 27
<212> TYPE: DNA
<213> ORGANISM: Artificial Sequence
<220> FEATURE:
<223> OTHER INFORMATION: Synthetic

<400> SEQUENCE: 148
tttcccctcg tcccccctgt gagtacc                                              27

<210> SEQ ID NO 149
<211> LENGTH: 27
<212> TYPE: DNA
<213> ORGANISM: Artificial Sequence
<220> FEATURE:
<223> OTHER INFORMATION: Synthetic

<400> SEQUENCE: 149
tttcccctcg tcccccctgt gagtacc                                              27

<210> SEQ ID NO 150
<211> LENGTH: 27
<212> TYPE: DNA
<213> ORGANISM: Artificial Sequence
<220> FEATURE:
<223> OTHER INFORMATION: Synthetic

<400> SEQUENCE: 150
tttcccctcg tttttctgt gagtacc                                               27

<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151
tttcccctcg tttttctgt gagtacc                                               27

<210> SEQ ID NO 152
<211> LENGTH: 27
<212> TYPE: DNA
<213> ORGANISM: Artificial Sequence
```

```
<220> FEATURE:
<223> OTHER INFORMATION: Synthetic

<400> SEQUENCE: 152 tttccctcg tttttctgt gagtacc                                              27

<210> SEQ ID NO 153
<211> LENGTH: 27
<212> TYPE: DNA
<213> ORGANISM: Artificial Sequence
<220> FEATURE:
<223> OTHER INFORMATION: Synthetic

<400> SEQUENCE: 153 tttccctcg tccccctgt gagtacc                                              27

<210> SEQ ID NO 154
<211> LENGTH: 27
<212> TYPE: DNA
<213> ORGANISM: Artificial Sequence
<220> FEATURE:
<223> OTHER INFORMATION: Synthetic

<400> SEQUENCE: 154 tttccctcg tccccctgt gagtacc                                              27

<210> SEQ ID NO 155
<211> LENGTH: 27
<212> TYPE: DNA
<213> ORGANISM: Artificial Sequence
<220> FEATURE:
<223> OTHER INFORMATION: Synthetic

<400> SEQUENCE: 155 tttccctcg tccccctgt gagtacc                                              27

<210> SEQ ID NO 156
<211> LENGTH: 27
<212> TYPE: DNA
<213> ORGANISM: Artificial Sequence
<220> FEATURE:
<223> OTHER INFORMATION: Synthetic

<400> SEQUENCE: 156 tttccctcg tttttctgt gagtacc                                              27

<210> SEQ ID NO 157
<211> LENGTH: 27
<212> TYPE: DNA
<213> ORGANISM: Artificial Sequence
<220> FEATURE:
<223> OTHER INFORMATION: Synthetic

<400> SEQUENCE: 157
tttcttctcc cctctgctgg ataccctc                                           27

<210> SEQ ID NO 158
<211> LENGTH: 27
<212> TYPE: DNA
<213> ORGANISM: Artificial Sequence
<220> FEATURE:
<223> OTHER INFORMATION: Synthetic

<400> SEQUENCE: 158
tttcttctcc ttttgctgg ataccctc                                            27
```

```
<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
tttcttctcc tttttgctgg atacctc                                        27

<210> SEQ ID NO 160
<211> LENGTH: 27
<212> TYPE: DNA
<213> ORGANISM: Artificial Sequence
<220> FEATURE:
<223> OTHER INFORMATION: Synthetic

<400> SEQUENCE: 160
tttcttctcc tttttgctgg atacctc                                        27

<210> SEQ ID NO 161
<211> LENGTH: 27
<212> TYPE: DNA
<213> ORGANISM: Artificial Sequence
<220> FEATURE:
<223> OTHER INFORMATION: Synthetic

<400> SEQUENCE: 161
tttcttctcc cctctgctgg atacctc                                        27

<210> SEQ ID NO 162
<211> LENGTH: 27
<212> TYPE: DNA
<213> ORGANISM: Artificial Sequence
<220> FEATURE:
<223> OTHER INFORMATION: Synthetic

<400> SEQUENCE: 162
tttcttctcc tttctgctgg atacctc                                        27

<210> SEQ ID NO 163
<211> LENGTH: 27
<212> TYPE: DNA
<213> ORGANISM: Artificial Sequence
<220> FEATURE:
<223> OTHER INFORMATION: Synthetic

<400> SEQUENCE: 163
tttcttctcc tttttgctgg atacctc                                        27

<210> SEQ ID NO 164
<211> LENGTH: 27
<212> TYPE: DNA
<213> ORGANISM: Artificial Sequence
<220> FEATURE:
<223> OTHER INFORMATION: Synthetic

<400> SEQUENCE: 164
tttcttctcc tttttgctgg atacctc                                        27

<210> SEQ ID NO 165
<211> LENGTH: 27
<212> TYPE: DNA
<213> ORGANISM: Artificial Sequence
<220> FEATURE:
<223> OTHER INFORMATION: Synthetic
```

<400> SEQUENCE: 165
tttcttctcc tttttgctgg atacctc 27

<210> SEQ ID NO 166
<211> LENGTH: 27
<212> TYPE: DNA
<213> ORGANISM: Artificial Sequence
<220> FEATURE:
<223> OTHER INFORMATION: Synthetic

<400> SEQUENCE: 166
tttcttctcc tttttgctgg atacctc 27

<210> SEQ ID NO 167
<211> LENGTH: 27
<212> TYPE: DNA
<213> ORGANISM: Artificial Sequence
<220> FEATURE:
<223> OTHER INFORMATION: Synthetic

<400> SEQUENCE: 167
tttcttctcc tttttgctgg atacctc 27

<210> SEQ ID NO 168
<211> LENGTH: 27
<212> TYPE: DNA
<213> ORGANISM: Artificial Sequence
<220> FEATURE:
<223> OTHER INFORMATION: Synthetic

<400> SEQUENCE: 168
tttcttctcc tttttgctgg atacctc 27

<210> SEQ ID NO 169
<211> LENGTH: 27
<212> TYPE: DNA
<213> ORGANISM: Artificial Sequence
<220> FEATURE:
<223> OTHER INFORMATION: Synthetic

<400> SEQUENCE: 169
tttcttctcc tttttgctgg atacctc 27

<210> SEQ ID NO 170
<211> LENGTH: 27
<212> TYPE: DNA
<213> ORGANISM: Artificial Sequence
<220> FEATURE:
<223> OTHER INFORMATION: Synthetic

<400> SEQUENCE: 170
tttcttctcc tttttgctgg atacctc 27

<210> SEQ ID NO 171
<211> LENGTH: 27
<212> TYPE: DNA
<213> ORGANISM: Artificial Sequence
<220> FEATURE:
<223> OTHER INFORMATION: Synthetic

<400> SEQUENCE: 171
tttcttctcc cttctgctgg atacctc 27

<210> SEQ ID NO 172

<211> LENGTH: 27
<212> TYPE: DNA
<213> ORGANISM: Artificial Sequence
<220> FEATURE:
<223> OTHER INFORMATION: Synthetic

<400> SEQUENCE: 172
tttcttctcc tttttgctgg atacctc                27

<210> SEQ ID NO 173
<211> LENGTH: 27
<212> TYPE: DNA
<213> ORGANISM: Artificial Sequence
<220> FEATURE:
<223> OTHER INFORMATION: Synthetic

<400> SEQUENCE: 173
tttcttctct tttttgctgg atacctc                27

<210> SEQ ID NO 174
<211> LENGTH: 27
<212> TYPE: DNA
<213> ORGANISM: Artificial Sequence
<220> FEATURE:
<223> OTHER INFORMATION: Synthetic

<400> SEQUENCE: 174
tttcttctcc tttttgctgg atacctc                27

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
tttcttctcc cttttgctgg atacctc                27

<210> SEQ ID NO 176
<211> LENGTH: 27
<212> TYPE: DNA
<213> ORGANISM: Artificial Sequence
<220> FEATURE:
<223> OTHER INFORMATION: Synthetic

<400> SEQUENCE: 176
tttcttctct tttttgctgg atacctc                27

<210> SEQ ID NO 177
<211> LENGTH: 27
<212> TYPE: DNA
<213> ORGANISM: Artificial Sequence
<220> FEATURE:
<223> OTHER INFORMATION: Synthetic

<400> SEQUENCE: 177
tttcttctcc cttttgctgg atacctc                27

<210> SEQ ID NO 178
<211> LENGTH: 27
<212> TYPE: DNA
<213> ORGANISM: Artificial Sequence
<220> FEATURE:
<223> OTHER INFORMATION: Synthetic

```
<400> SEQUENCE: 178
tttcttctcc cttttgctgg ataccte                                          27

<210> SEQ ID NO 179
<211> LENGTH: 27
<212> TYPE: DNA
<213> ORGANISM: Artificial Sequence
<220> FEATURE:
<223> OTHER INFORMATION: Synthetic

<400> SEQUENCE: 179
tttcttctcc ttttgctgg ataccte                                           27

<210> SEQ ID NO 180
<211> LENGTH: 27
<212> TYPE: DNA
<213> ORGANISM: Artificial Sequence
<220> FEATURE:
<223> OTHER INFORMATION: Synthetic

<400> SEQUENCE: 180
tttcttctcc cttttgctgg ataccte                                          27

<210> SEQ ID NO 181
<211> LENGTH: 27
<212> TYPE: DNA
<213> ORGANISM: Artificial Sequence
<220> FEATURE:
<223> OTHER INFORMATION: Synthetic

<400> SEQUENCE: 181
tttcttctcc cttttgctgg ataccte                                          27

<210> SEQ ID NO 182
<211> LENGTH: 27
<212> TYPE: DNA
<213> ORGANISM: Artificial Sequence
<220> FEATURE:
<223> OTHER INFORMATION: Synthetic

<400> SEQUENCE: 182
tttcttctct ttttgctgg ataccte                                           27

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
tttcttctcc cttttgctgg ataccte                                          27

<210> SEQ ID NO 184
<211> LENGTH: 27
<212> TYPE: DNA
<213> ORGANISM: Artificial Sequence
<220> FEATURE:
<223> OTHER INFORMATION: Synthetic

<400> SEQUENCE: 184
tttcttctcc ttttgctgg ataccte                                           27
```

What is claimed is:

1. A fusion protein comprising a first fragment comprising an apolipoprotein B mRNA editing enzyme catalytic subunit 3A (APOBEC3A) and a second fragment comprising a clustered regularly interspaced short palindromic repeats (CRISPR)-associated (Cas) protein, wherein the APOBEC3A is a mutant of human APOBEC3A having a mutation selected from the group consisting of D131Y, Y132D, W104A, P134Y and combinations thereof, according to residue numbering in SEQ ID NO:1, wherein the amino acid sequence of the fusion protein is at least 85% identity to SEQ ID NO: 1, and wherein the mutant retains cytidine deaminase activity.

2. The fusion protein of claim 1, further comprising a uracil glycosylase inhibitor (UGI).

3. The fusion protein of claim 1, wherein the mutant human APOBEC3A has mutations selected from the group consisting of Y130F+D131E+Y132D, Y130F+D131Y+Y132D, W98Y+W104A, W98Y+P134Y, W104A+P134Y, W104A+Y130F, W104A+Y132D, W98Y+W104A+Y130F, W98Y+W104A+Y132D, W104A+Y130F+P134Y, and W104A+Y132D+P134Y, according to residue numbering in SEQ ID NO:1.

4. The fusion protein of claim 1, wherein the human APOBEC3A is human APOBEC3A isoform a or isoform b.

5. The fusion protein of claim 1, wherein the APOBEC3A comprises an amino acid sequence selected from the group consisting of SEQ ID NO: 3-5, 22-23, 25-34.

6. The fusion protein of claim 1, wherein the Cas protein is selected from the group consisting of Streptococcus pyogenes CRISPR-associated protein (SpCas9), Francisella novicida Cas9 (FnCas9), Streptococcus thermophilus CRISPR-1 Cas9 (St1Cas9), Streptococcus thermophilus CRISPR-3 Cas9 (St3Cas9), NmCas9, SaCas9, AsCpf1, LbCpf1, FnCpf1, D1135V/R1335Q/T1337R (VQR) SpCas9, D1135E/R1335Q/T1337R (EQR) SpCas9, D1135V/G1218R/R1335E/T1337R (VRER) SpCas9, E1369R/E1449H/R1556A (RHA) FnCas9, E782K/N968K/R1015H (KKH) Staphylococcus aureus Cas9 (SaCas9), Neisseria meningitidis Cas9 (NmeCas9), Streptococcus thermophilus Cas9 (StCas9), Campylobacter jejuni (CjCas9), Acidaminococcus sp. Cpf1 (AsCpf1), Franscisella novicida Cpf1 (FnCpf1), Smithella sp. Cpf1 (SsCpf1), Porphyromonas crevioricanis Cpf1 (PcCpf1), Butyrivibrio proteoclasticus Cpf1 (BpCpf1), Candidatus Methanoplasma termitum (CmtCpf1), Leptospira inadai Cpf1 (LiCpf1), Porphyromonas macacae Cpf1 (PmCpf1), Parcubacteria bacterium 3310 Cpf1 (Pb3310Cpf1), Parcubacteria bacterium 4417 Cpf1 (Pb4417Cpf1), Butyrivibrio sp. NC3005 Cpf1 (BsCpf1), Eubacterium eligens Cpf1 (EeCpf1), Bacillus hisashii Cas12b (BhCas12b), Alicyclobacillus kakegawensis Cas12b (AkCas12b), Elusimicrobia bacterium Cas12b (EbCas12b), Laceyella sediminis Cas12b (LsCas12b), Ruminococcus flavefaciens Cas13d (RfCas13d), Leptotrichia wadei Cas13a (LwaCas13a), Prevotella sp. Cas13b (PspCas13b), Porphyromonas gulae Cas13b (PguCas13b), Porphyromonas gulae Cas13b (RanCas13b), CasX, and CasY.

7. The fusion protein of claim 1, wherein the Cas protein is a mutant of protein selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, KKH SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, BhCas12b, AkCas12b, EbCas12b, LsCas12b, RfCas13d, LwaCas13a, PspCas13b, PguCas13b, RanCas13b, CasX, and CasY, wherein the mutant retains the DNA-binding capability but does not introduce double strand DNA breaks.

8. The fusion protein of claim 7, wherein the mutant Cas protein is capable of introducing a nick to one of the strands of a double stranded DNA bound by the mutant.

9. The fusion protein of claim 7, wherein the mutant Cas protein comprises an amino acid sequence selected from the group consisting of SEQ ID NO:11, and 37-39.

10. The fusion protein of claim 1, wherein the first fragment is at the N-terminal side of the second fragment.

11. The fusion protein of claim 2, wherein the UGI comprises the amino acid sequence of SEQ ID NO:12 or has at least at least 90% sequence identity to SEQ ID NO:12 and retains the uracil glycosylase inhibition activity.

12. The fusion protein of claim 11, wherein the first fragment is at the N-terminal side of the second fragment which is at the N-terminal side of the UGI.

13. A method of editing a target polynucleotide, comprising contacting to the target polynucleotide a fusion protein of claim 1 and a guide RNA having at least partial sequence complementarity to the target polynucleotide, wherein the editing comprises deamination of a cytosine (C) in the target polynucleotide.

14. The method of claim 13, wherein the C is methylated.

* * * * *